US007262031B2

(12) United States Patent
Lathrop et al.

(10) Patent No.: US 7,262,031 B2
(45) Date of Patent: Aug. 28, 2007

(54) METHOD FOR PRODUCING A SYNTHETIC GENE OR OTHER DNA SEQUENCE

(75) Inventors: Richard H. Lathrop, Irvine, CA (US); G. Wesley Hatfield, Corona del Mar, CA (US)

(73) Assignee: The Regents of the University of California, Oakland, CA (US)

(*) Notice: Subject to any disclaimer, the term of this patent is extended or adjusted under 35 U.S.C. 154(b) by 411 days.

(21) Appl. No.: 10/851,383

(22) Filed: May 21, 2004

(65) Prior Publication Data

US 2004/0235035 A1 Nov. 25, 2004

Related U.S. Application Data

(60) Provisional application No. 60/472,822, filed on May 22, 2003.

(51) Int. Cl.
*C12P 19/24* (2006.01)

(52) U.S. Cl. .................................................... 435/91.2

(58) Field of Classification Search ..................... None
See application file for complete search history.

(56) References Cited

U.S. PATENT DOCUMENTS

| | | | | |
|---|---|---|---|---|
| 6,472,184 | B1 | 10/2002 | Hegemann | |
| 6,586,211 | B1 | 7/2003 | Stahler et al. | |
| 6,673,552 | B2 | 1/2004 | Frey | |
| 2003/0068633 | A1 | 4/2003 | Beishaw et al. | |
| 2003/0162265 | A1 | 8/2003 | Evans et al. | |
| 2003/0215837 | A1* | 11/2003 | Frey et al. | 435/6 |

FOREIGN PATENT DOCUMENTS

| | | |
|---|---|---|
| DE | 44 23 183 | 1/1994 |
| DE | 102 32 507 | 7/2002 |
| WO | WO94/12632 | 9/1994 |
| WO | WO99/11820 | 11/1999 |

OTHER PUBLICATIONS

Jayaraman, Krishna and Shah, Janack, *Nucleic Acids Research*, Symposium Series No. 20 1998 (107-109), "Synthetic gene constructions using improved gene synthesis procedures."

Horton, Robert M., Hunt Henry D., Ho, Steffan N., Pullen, Jeffrey K. and Pease, Larry R., *Department of Immunology and Department of Biochemistry and Molecular Biology, Mayo Clinic*, Dec. 19, 1988, (61-68), "Engineering hybrid genes without the use of restriction enzymes: gene splicing by overlap extension."

Prodromou, Chrisostomos and Pear, Laurence H., *Protein Engineering*, vol. 5, No. 8, (827-829), 1992, "Recursive PCR: a novel technique for total gene synthesis."

Jayaraman, Krishna and Puccini, Christopher J., *Bio Techniques*, vol. 12, No. 3 1992. "A PCR-Mediated Gene Synthesis Strategy Involving the Assembly of Oligonucleotides Representing Only One of the Strands."

Dillon, Patrick J. and Rosen, Craig A., *Methods of Molecular Biology, PCR Protocols, Current Methods and Applications*, vol. 15, Chapter 26, (263-269), 1993, "Use of Polymerase Chain Reaction for the Rapid Construction of Synthetic Genes."

Bambot, Shabbir B. and Russell, Alan J., *PCR Methods and Applications*, vol. 2, No. 3, Feb. 1993, "Efficient Total Gene Synthesis of 1.35-kb Hybrid a-lytic Protease Gene Using the Polymearse Chain Reaction."

Hiltunen, Timo, Raja-Honkala, Maria, Nikkari, Tapio and Yla-Herttuala, Seppo, *University of Tampere, Tampere, Finland*, Accepted Mar. 10, 1994, "Assembly of Humanized Antibody Genes from Synthetic Oligonucleotides Using a Single-Round PCR."

Stemmer, Willem P.C., Crameri, Andreas, Ha, Kim D., Brennan, Thomas M. and Heyneker, Herbert L., *Affymax Research Institute and PhotoGene Laboratories, Inc.*, Jul. 24, 1995 (49-53), "Single-step assembly of a gene and entire plasmid from large numbers of oligodeoxyribonucleotides."

Kobayashi, Norihiro, Soderlind, Eskil and Borrebaeck, Carl A.K., *BioTechniques*, vol. 23, No. 3 (1997), "Analysis of Assembly of Synthetic Antibody Fragments: Expression of Functional scFv with Predefined Specificity."

Casimoro, Danilo R., Wright, Peter E. and Dyson, Jane H., *Structure*, vol. 5, No. 11 (1997), "PCR-based gene synthesis and protein NMR spectroscopy."

SantaLucia, John Jr., *Proc. National Academy of Science USA*, vol. 95, (1460-1465), Feb. 1998, "A unified view of polymer, dumbbell, and oligonucleotid DNA nearest-neighbor therodynamics."

Zucker, M., Mathews, D.H. and Turner, D.H., *RNA Biochemistry and Biotechnology*11-43, 1999, "Algorithms and thermodynamics for RNA Secondary Structure Prediction: A Practical Guide."

Mathews, David H., Sabina, Jeffrey, Zuker, Michael and Turner, Douglas H., *Journal of Molecular Biology*, vol. 288, (911-940), 1999, "Expanded Sequence Dependence of Thermodynamic Parameters Improves Prediction of RNA Secondary Structure."

(Continued)

*Primary Examiner*—Jeffrey Fredman
*Assistant Examiner*—Suchira Pande
(74) *Attorney, Agent, or Firm*—Knobbe, Martens, Olson & Bear, LLP

(57) ABSTRACT

Disclosed herein is a method for synthesizing a desired nucleic acid sequence. The method comprises dividing the desired sequence into a plurality of partially overlapping segments; optimizing the melting temperatures of the overlapping regions of each segment to disfavor hybridization to the overlapping segments which are non-adjacent in the desired sequence; allowing the overlapping regions of single stranded segments which are adjacent to one another in the desired sequence to hybridize to one another under conditions which disfavor hybridization of non-adjacent segments; and filling in, ligating, or repairing the gaps between the overlapping regions, thereby forming a double-stranded DNA with the desired sequence. Also disclosed is a method for preventing errors in the synthesis of the nucleic acid sequence.

43 Claims, 73 Drawing Sheets

OTHER PUBLICATIONS

Martinez-Whithers, Chrislaine, Carpenter, Elisabeth P., Hackett, Fiona, Ely, Barry, Sajid, Mohammed, Grainger, Muni and Blackman, Michael J., *Protein Engineering*, vol. 12, No. 12 (1113-1120), 1999, "PCR-based Gene Synthesis as an Efficient Approach for Expression of the A+ T-rich Malaria Genome."

Lathrop, Richard H., Sazhin, Anton and Sun, Ye, *Genome Informatics* vol. 12 (73-82), 2001, "A Multi-Queue Branch-and-Bound Algorithm for Anytime Optimal Search with Biological Applications."

Hoover, David M. and Lubkowkski, Jacek, *Nucleic Acids Research*, vol. 30, No. 10, 2002, "DNAWorks: An Automated Method for Designing Oligonucleotides for PCR-based Gene Synthesis."

Cello, Jeronimo, Paul, Aniko V., and Wimmer, Eckard, www.sciencemag.org, vol. 297, Aug. 9, 2002, "Chemical Synthesis of Poliovirus cDNA: Generation of Infectious Virus in the Absence of Natural Template."

Smith, Hamilton O., Hutchison, Clyde A. III, Pfannkoch, Cynthia and Venter, J. Craig. *PNAS*, vol. 100, No. 26,k Dec. 23, 2003, "Generating a Synthetic Genome by Whole Genome Assembly: oX174 Bacteriophage from Synthetic Oligonucleotides."

International Search Report in PCT Application No. PCT/US2004/016120; Dated Nov. 24, 2004; in 13 pages.

* cited by examiner

300

| 302 | DIVIDE DNA SEQUENCE INTO SMALL PIECES OF DNA |
| --- | --- |
| 304 | OPTIMIZE SMALL PIECES OF DNA |
| 306 | OBTAIN SMALL PIECES OF DNA |
| 308 | COMBINE PIECES OF DNA |
| 310 | ALLOW PIECES OF DNA TO SELF-ASSEMBLE |
| 312 | EXTEND DNA CONSTRUCT TO FULL-DUPLEX |
| 314 | SELECT DNA LIKELY TO BE CORRECT |
| 316 | REPEAT STEPS 308–314 IN REVERSE ORDER OF DIVISON |

```
M0 A1 D0 S1 Q1 P2 L0 S1 G3 A2 P2 E0 G3 A2 E0 Y0 L1 R2 A2 V0  ; 20
L1 R0 A0 P0 V0 Y0 E0 A1 A1 Q0 V0 T0 P0 L1 Q0 K0 M0 E0 K0 L4  ; 40
S2 S3 R0 L4 D0 N1 V0 I0 L0 V2 K1 R1 E1 D1 R3 Q0 P3 V0 H1 S4  ; 60
F1 K1 L4 R0 G1 A0 Y0 A0 M0 M0 A2 G2 L2 T1 E0 E0 Q0 K0 A1 H1  ; 80
G1 V0 I0 T1 A2 S5 A3 G0 N0 H0 A3 Q1 G1 V0 A0 F1 S1 S1 A3 R3  ;100
L0 G3 V0 K0 A0 L1 I1 V0 M0 P2 T2 A3 T3 A0 D0 I0 K0 V0 D0 A1  ;120
V2 R3 G2 F0 G1 G1 E0 V1 L0 L0 H0 G0 A0 N0 F0 D0 E0 A1 K1 A1  ;140
K1 A0 I1 E1 L4 S1 Q1 Q1 Q0 G2 F1 T1 W0 V0 P1 P1 F1 D0 H0 P0  ;160
M0 V3 I1 A1 G1 Q0 G2 T1 L1 A2 L0 E1 L2 L3 Q1 Q0 D1 A2 H0 L4  ;180
D1 R2 V2 F1 V1 P2 V1 G2 G1 G1 G1 L0 A0 A0 G1 V3 A2 V3 L4 I1  ;200
K1 Q0 L4 M0 P1 Q1 I0 K0 V0 I2 A1 V1 E0 A1 E0 D0 S3 A2 C1 L0  ;220
K1 A1 A2 L3 D0 A1 G3 H1 P2 V2 D0 L0 P0 R0 V0 G2 L0 F0 A2 E0  ;240
G2 V1 A0 V0 K0 R2 I0 G2 D0 E1 T0 F1 R1 L5 C0 Q0 E1 Y0 L2 D1  ;260
D1 I1 I1 T0 V0 D1 S3 D0 A1 I0 C1 A1 A1 M0 K1 D1 L5 F1 E0 D0  ;280
V2 R0 A2 V2 A1 E0 P0 S1 G3 A3 L1 A2 L1 A1 G2 M0 K1 K1 Y1 I0  ;300
A3 L0 H1 N0 I1 R3 G0 E0 R3 L0 A1 H1 I1 L1 S0 G1 A0 N1 V2 N0  ;320
F1 H1 G0 L1 R2 Y0 V0 S1 E1 R0 C0 E1 L0 G0 E0 Q1 R4 E0 A2 L1  ;340
L0 A2 V0 T0 I0 P0 E0 E0 K0 G1 S4 F1 L4 K1 F1 C0 Q0 L0 L1 G3  ;360
G1 R2 S0 V2 T1 E0 F0 N0 Y0 R2 F0 A2 D1 A1 K1 N1 A1 C1 I0 F0  ;380
V0 G1 V0 R5 L2 S0 R5 G3 L2 E1 E1 R1 K1 E1 I0 L3 Q0 M0 L0 N0  ;400
D0 G0 G1 Y0 S0 V0 V0 D1 L0 S0 D1 D1 E0 M0 A3 K0 L5 H1 V3 R1  ;420
Y1 M0 V0 G1 G3 R3 P2 S5 H0 P3 L4 Q0 E1 R3 L0 Y0 S3 F0 E0 F1  ;440
P1 E1 S1 P3 G0 A1 L1 L1 R0 F1 L1 N0 T0 L0 G0 T0 Y0 W0 N1 I1  ;460
S0 L0 F1 H1 Y1 R3 S1 H0 G2 T1 D0 Y1 G2 R0 V1 L0 L0 A0 F0 E1  ;480
L3 G0 D0 H0 E0 P0 D1 F0 E0 T1 R1 L0 N0 E0 L0 G0 Y0 D0 C0 H0  ;500
D0 E1 T0 N0 N0 P3 A1 F0 R0 F1 F1 L4 A2 G0
```

| | 0 | 1 | 2 | 3 | 4 | 5 |
|---|---|---|---|---|---|---|
| A: | GCG | GCC | GCA | GCT | | |
| C: | TGC | TGT | | | | |
| D: | GAT | GAC | | | | |
| E: | GAA | GAG | | | | |
| F: | TTT | TTC | | | | |
| G: | GGC | GGT | GGG | GGA | | |
| H: | CAT | CAC | | | | |
| I: | ATT | ATC | ATA | | | |
| K: | AAA | AAG | | | | |
| L: | CTG | TTA | TTG | CTT | CTC | CTA |
| M: | ATG | | | | | |
| N: | AAC | AAT | | | | |
| P: | CCG | CCA | CCT | CCC | | |
| Q: | CAG | CAA | | | | |
| R: | CGT | CGC | CGG | CGA | AGA | AGG |
| S: | AGC | TCT | AGT | TCC | TCG | TCA |
| T: | ACC | ACG | ACT | ACA | | |
| V: | GTG | GTT | GTC | GTA | | |
| W: | TGG | | | | | |
| Y: | TAT | TAC | | | | |

*FIG. 9*

Strand 0:
{CTATACTGCA} GATGGCCGATTCTCAACCACT [GTCTGGAGCTCCTGAAGGG]
[GTCTGGAGCTCCTGAAGGG] GCAGAATATTTAC [GGGCAGTGTTACGTGCGC]
[GGGCAGTGTTACGTGCGC] CGGTGTATGAA [GCCGCCCAGGTGACCCCG]
[GCCGCCCAGGTGACCCCG] TTACAGAAAATG [GAAAAACTCTCCTCCCGGC]
[GAAAAACTCTCCTCCCGGC] TCGATAATGT [GATTCTGGTCAAGCGCGAGG]
[GATTCTGGTCAAGCGCGAGG] ACCGTCAGCCC [GTGCACTCGTTCAAGCTCC]
[GTGCACTCGTTCAAGCTCC] GTGGTGCCTATGC [GATGATGGCGGGCCTGAC]
[GATGATGGCGGGCCTGAC] GGAAGAACAGAAAG [CCCACGGTGTGATTACGG]
[CCCACGGTGTGATTACGG] CATCAGCAGGCAAC [CATGCTCAAGGTGTGGCG]
[CATGCTCAAGGTGTGGCG] TTCTCTTCTGCTC [GACTGGGAGTGAAAGCGC]
[GACTGGGAGTGAAAGCGC] TGATTGTGATGCCTACAGCTAC {TCGAGAATAC}

*FIG. 11A*

Strand 1:
{CTATACTGCA} GAGTGAAAGCGCTGATTGT [GATGCCTACAGCTACAGCCG]
[GATGCCTACAGCTACAGCCG] ATATTAAAGTG [GATGCGGTGCGTGGCTTCG]
[GATGCGGTGCGTGGCTTCG] GTGGTGAAGTT [CTGCTGCATGGCGCGAAC]
[CTGCTGCATGGCGCGAAC] TTTGATGAAGC [CAAGGCCAAGGCGATCGAGC]
[CAAGGCCAAGGCGATCGAGC] TCTCTCAACAA [CAGGGGTTCACGTGGGTGC]
[CAGGGGTTCACGTGGGTGC] CACCGTTTGAT [CATCCGATGGTCATCGCCGG]
[CATCCGATGGTCATCGCCGG] TCAAGGCAC [GTTAGCGCTGGAGTTGCTTC]
[GTTAGCGCTGGAGTTGCTTC] AACAGGACGCA [CACCTCGACCGGGTCTTCG]
[CACCTCGACCGGGTCTTCG] TTCCTGTTGGGG [GTGGTGGTCTGGCGGCGGG]
[GTGGTGGTCTGGCGGCGGG] GGTAGCAGTACT [CATCAAGCAGCTCATGCC]
[CATCAAGCAGCTCATGCC] ACAAATTAAAGT [GATAGCCGTTGAAGCCTCG]
[GATAGCCGTTGAAGCCTCG] (-3) {TCGAGAATAC}

*FIG. 11B*

Strand 2:
{CTATACTGCA} GCTCATGCCACAAATTAAA [GTGATAGCCGTTGAAGCCG]
[GTGATAGCCGTTGAAGCCG] AAGATTCCGCAT [GCCTGAAGGCCGCACTTG]
[GCCTGAAGGCCGCACTTG] ACGCCGGACATCCA [GTCGACCTGCCGCGCGTG]
[GTCGACCTGCCGCGCGTG] GGGCTGTTTGCA [GAAGGGGTTGCGGTGAAACG]
[GAAGGGGTTGCGGTGAAACG] GATTGGGGAT [GAGACCTTCCGCCTATGCC]
[GAGACCTTCCGCCTATGCC] AGGAGTATTTG [GACGACATCATCACCGTGG]
[GACGACATCATCACCGTGG] ACTCCGATGC [CATTTGTGCCGCCATGAAGG]
[CATTTGTGCCGCCATGAAGG] ACCTATTCGAG [GATGTCCGTGCAGTCGCCG]
[GATGTCCGTGCAGTCGCCG] AACCGTCTGGA [GCTCTCGCACTGGCCGGG]
[GCTCTCGCACTGGCCGGG] ATGAAGAAGTA [CATTGCTCTGCACAACATCCG]
[CATTGCTCTGCACAACATCCG] AGGCGAACGA [CTGGCCCACATCCTGAGC]
[CTGGCCCACATCCTGAGC] {TCGAGAATAC}

*FIG. 11C*

Strand 3:
{CTATACTGCA} GCACAACATCCGAGGCGAACGA [CTGGCCCACATCCTGAGC]
[CTGGCCCACATCCTGAGC] GGTGCGAATGT [CAACTTCCACGGCTTACGG]
[CAACTTCCACGGCTTACGG] TATGTGTCTGAGC [GTTGCGAGCTGGGCGAAC]
[GTTGCGAGCTGGGCGAAC] AACGCGAAGCATTA [CTGGCAGTGACCATTCCG]
[CTGGCAGTGACCATTCCG] GAAGAAAAAGGTT [CGTTCCTCAAGTTCTGCC]
[CGTTCCTCAAGTTCTGCC] AGCTGTTAG [GAGGTCGGAGCGTCACGG]
[GAGGTCGGAGCGTCACGG] AATTTAACTAT [CGGTTTGCAGACGCCAAG]
[CGGTTTGCAGACGCCAAG] AATGCCT [GTATTTTTGTGGGTGTGAGGTTGAG]
[GTATTTTTGTGGGTGTGAGGTTGAG] CAGGG [GATTGGAGGAGCGCAAGGAG]
[GATTGGAGGAGCGCAAGGAG] ATTCTTCA [GATGCTGAACGATGGCGG]
[GATGCTGAACGATGGCGG] TTATAGCGTG [GTGGACCTGAGCGACGACG]
[GTGGACCTGAGCGACGACG] AAATGGC {TCGAGAATAC}

*FIG. 11D*

Strand 4:
{CTATACTGCA} GTTATAGCGTGGTGGACCT [GAGCGACGACGAAATGGC]
[GAGCGACGACGAAATGGC] TAAACTACACGTAC [GCTACATGGTGGGTGGAC]
[GCTACATGGTGGGTGGAC] GACCTTCACAT [CCCCTCCAGGAGCGACTG]
[CCCCTCCAGGAGCGACTG] TATTCCTTTGAATT [CCCAGAGTCTCCCGGCGC]
[CCCAGAGTCTCCCGGCGC] CTTATTACGTTT [CTTAAACACCCTGGGCACC]
[CTTAAACACCCTGGGCACC] TATTGGAATAT [CAGCCTGTTCCACTACCG]
[CAGCCTGTTCCACTACCG] ATCTCACGGCACG [GATTACGGGCGTGTTCTGG]
[GATTACGGGCGTGTTCTGG] CGGCGTTTGAA [CTGGGCGATCATGAACCGG]
[CTGGGCGATCATGAACCGG] ACTTTGAAACG [CGCCTGAACGAACTGGGC]
[CGCCTGAACGAACTGGGC] TATGATTGCCAT [GATGAGACCAACAACCCCGC]
[GATGAGACCAACAACCCCGC] CTTTCGTTT [CTTCCTCGCCGGCTAACTCG]
[CTTCCTCGCCGGCTAACTCG] (-3) {TCGAGAATAC}

*FIG. 11E*

Medium-sized piece Set 0

Forward segments (Watson or plus strand):

Seg-0-0
5'-GGCCGATTCTCAACCTCTGTCTGGAGCACCTGAAGG-3'
(36-mer) 1

Seg-0-2
5'-GGGCAGTGTTACGTGCGCCGGTGTATGAAGCCGCCCAGGTGACCCCG-3'
(47-mer) 2 3

Seg-0-4
5'-GAAAAACTCAGTTCCCGTCTCGATAATGTGATTCTGGTCAAGCGCGAGG-3'
(49-mer) 4 5

Seg-0-6
5'-GTGCACTCGTTCAAGCTCCGTGGTGCGTATGCGATGATGGCAGGGTTGAC-3'
(50-mer) 6 7

Seg-0-8
5'-CCCACGGTGTGATTACGGCATCAGCTGGCAACCATGCTCAAGGTGTGGCG-3'
(50-mer) 8 9

Seg-0-10
5'-CGACTGGGAGTGAAAGCGTTAATCGTGATGCCTACTGCTAC-3'
(41-mer) 10

Reverse complement segments (Crick or minus strand):

Seg-0-1 (rev cmp)
5'-GCGCACGTAACACTGCCCGTAAATATTCTGCTCCTTCAGGTGCTCCAGAC-3'
(50-mer) 2' 1'

Seg-0-3 (rev cmp)
5'-GACGGGAACTGAGTTTTTCCATTTTCTGTAACGGGGTCACCTGGGCGGC-3'
(49-mer) 4' 3'

Seg-0-5 (rev cmp)
5'-GGAGCTTGAACGAGTGCACGGGCTGTCGGTCCTCGCGCTTGACCAGAATC-3'
(50-mer) 6' 5'

Seg-0-7 (rev cmp)
5'-CCGTAATCACACCGTGGGCTTTCTGTTCTTCCGTCAACCCTGCCATCATC-3'
(50-mer) 8' 7'

Seg-0-9 (rev cmp)
5'-CGCTTTCACTCCCAGTCGAGCAGAAGAGAACGCCACACCTTGAGCATG-3'
(48-mer) 10' 9'

*FIG. 12A*

Medium-sized piece Set #1

Forward segments:

Seg-1-0
5'-GAGTGAAAGCGTTAATCGTGATGCCTACTGCTACAGCGG-3'
(39-mer) 11

Seg-1-2
5'-GATGCCGTCCGAGGGTTTGGTGGTGAAGTTCTGCTGCATGGCGCGAAC-3'
(48-mer) 12 13

Seg-1-4
5'-CAAGGCCAAGGCGATCGAGCTCTCTCAACAACAGGGGTTCACGTGGGTGC-3'
(50-mer) 14 15

Seg-1-6
5'-CATCCGATGGTAATCGCCGGTCAGGGGACGTTAGCACTGGAGTTGCTTC-3'
(49-mer) 16 17

Seg-1-8
5'-CATCTCGACCGGGTCTTCGTTCCTGTTGGGGGTGGTGGTCTGGCGGCGGG-3'
(50-mer) 18 19

Seg-1-10
5'-CATCAAGCAGCTCATGCCACAAATTAAAGTGATAGCCGTTGAAGCC-3'
(46-mer) 20

Reverse complement segments:

Seg-1-1 (rev cmp)
5'-CAAACCCTCGGACGGCATCCACTTTAATATCCGCTGTAGCAGTAGGCATC-3'
(50-mer) 12' 11'

Seg-1-3 (rev cmp)
5'-GCTCGATCGCCTTGGCCTTGGCTTCATCAAAGTTCGCGCCATGCAGCAG-3'
(49-mer) 14' 13'

Seg-1-5 (rev cmp)
5'-CCGGCGATTACCATCGGATGATCGAATGGTGGCACCCACGTGAACCCCTG-3'
(50-mer) 16' 15'

Seg-1-7 (rev cmp)
5'-CGAAGACCCGGTCGAGATGTGCGTCCTGTTGAAGCAACTCCAGTGCTAAC-3'
(50-mer) 18' 17'

Seg-1-9 (rev cmp)
5'-GGCATGAGCTGCTTGATGAGTACTGCTACACCCGCCGCCAGACCACCAC-3'
(49-mer) 20' 19'

*FIG. 12B*

Medium-sized piece Set #2

Forward segments
Seg-2-0
5'-GCTCATGCCACAAATTAAAGTGATAGCCGTTGAAGCCG-3'
(38-mer)                              21
Seg-2-2
5'-GTCTGAAGGCCGCACTTGATGCCGGACACCCTGTCGATCTGCCGCGTGTG-3'
(50-mer)     22                         23
Seg-2-4
5'-GAAGGGGTTGCGGTGAAACGGATTGGGGATGAGACCTTCCGCCTATGCC-3'
(49-mer)    24                       25
Seg-2-6
5'-GACGACATCATCACCGTGGACTCCGATGCCATTTGTGCCGCCATGAAGG-3'
(49-mer)   26                        27
Seg-2-8
5'-GATGTCCGTGCAGTCGCCGAACCGTCTGGAGCTTTAGCATTAGCCGGG-3'
(48-mer)     28                      29
Seg-2-10
5'-CATTGCTCTGCACAACATCCGAGGCGAACGACTGGCCCACATCTTAAGC-3'
(49-mer)    30

Reverse complement segments:
Seg-2-1 (rev cmp)
5'-CAAGTGCGGCCTTCAGACATGCGGAATCTTCGGCTTCAACGGCTATCAC-3'
(49-mer)    22'                      21'
Seg-2-3 (rev cmp)
5'-CGTTTCACCGCAACCCCTTCTGCAAACAGCCCCACACGCGGCAGATCGAC-3'
(50-mer)    24'                     23'
Seg-2-5 (rev cmp)
5'-CCACGGTGATGATGTCGTCCAAATACTCCTGGCATAGGCGGAAGGTCTC-3'
(49-mer)    26'                     25'
Seg-2-7 (rev cmp)
5'-CGGCGACTGCACGGACATCTTCGAATAGGTCCTTCATGGCGGCACAAATG-3'
(50-mer)   28'                      27'
Seg-2-9 (rev cmp)
5'-CGGATGTTGTGCAGAGCAATGTACTTCTTCATCCCGGCTAATGCTAAAGC-3'
(50-mer)    30'                     29'

*FIG. 12C*

Medium-sized piece Set #3

Forward segments

Seg-3-0
5'-GCACAACATCCGAGGCGAACGACTGGCCCACATCTTAAGC-3'
(40-mer) 31

Seg-3-2
5'-CAACTTCCACGGCTTACGGTATGTGTCTGAGCGTTGCGAGCTGGGCGAAC-3'
(50-mer) 32 33

Seg-3-4
5'-CTGGCAGTGACCATTCCGGAAGAAAAAGGTTCGTTCCTCAAGTTCTGCC-3'
(49-mer) 34 35

Seg-3-6
5'-GAGGTCGGAGCGTCACGGAATTTAACTATCGGTTTGCAGACGCCAAG-3'
(47-mer) 36 37

Seg-3-8
5'-GTATTTTTGTGGGTGTGAGGTTGAGCAGGGGATTGGAGGAGCGCAAGGAG-3'
(50-mer) 38 39

Seg-3-10
5'-GATGCTGAACGATGGCGGTTATAGCGTGGTGGACCTGAGCGACGACG-3'
(47-mer) 40 41

Reverse complement segments:

Seg-3-1 (rev cmp)
5'-CCGTAAGCCGTGGAAGTTGACATTCGCACCGCTTAAGATGTGGGCCAG-3'
(48-mer) 32' 31'

Seg-3-3 (rev cmp)
5'-CGGAATGGTCACTGCCAGTAATGCTTCTCTTTGTTCGCCCAGCTCGCAAC-3'
(50-mer) 34' 33'

Seg-3-5 (rev cmp)
5'-CCGTGACGCTCCGACCTCCTAACAGCTGGCAGAACTTGAGGAACG-3'
(45-mer) 36' 35'

Seg-3-7 (rev cmp)
5'-CTCAACCTCACACCCACAAAAATACAGGCATTCTTGGCGTCTGCAAACCG-3'
(50-mer) 38' 37'

Seg-3-9 (rev cmp)
5'-CCGCCATCGTTCAGCATCTGAAGAATCTCCTTGCGCTCCTCCAATC-3'
(46-mer) 40' 39'

Seg-3-11 (rev cmp)
5'-GCCATTTCGTCGTCGCTCAGGTCCAC-3'
(26-mer) 41'

*FIG. 12D*

Medium-sized piece Set #4

Forward segments

Seg-4-0
5'-GTTATAGCGTGGTGGACCTGAGCGACGACGAAATGGC-3'
(37-mer) 42

Seg-4-2
5'-GCTACATGGTGGGTGGACGACCTTCACATCCCCTCCAGGAGCGACTG-3'
(47-mer) 43 44

Seg-4-4
5'-CCCAGAGTCTCCCGGCGCCTTATTACGTTTCTTAAACACCCTGGGCACC-3'
(49-mer) 45 46

Seg-4-6
5'-CAGCCTGTTCCACTACCGATCTCATGGGACGGATTACGGGCGTGTTCTGG-3'
(50-mer) 47 48

Seg-4-8
5'-CTTGGCGATCATGAACCGGACTTTGAAACGCGCCTGAACGAACTGGGC-3'
(48-mer) 49 50

Seg-4-10
5'-GATGAGACCAACAACCCCGCCTTTCGTTTCTTCCTCGCAGGCTAA-3'
(45-mer) 51

Reverse complement segments:

Seg-4-1 (rev cmp)
5'-GTCCACCCACCATGTAGCGTACGTGTAGTTTAGCCATTTCGTCGTCGCTC-3'
(50-mer) 43' 42'

Seg-4-3 (rev cmp)
5'-GCGCCGGGAGACTCTGGGAATTCAAAGGAATACAGTCGCTCCTGGAGGGG-3'
(50-mer) 45' 44'

Seg-4-5 (rev cmp)
5'-CGGTAGTGGAACAGGCTGATATTCCAATAGGTGCCCAGGGTGTTTAAG-3'
(48-mer) 47' 46'

Seg-4-7 (rev cmp)
5'-CCGGTTCATGATCGCCAAGCTCAAACGCTGCCAGAACACGCCCGTAATC-3'
(49-mer) 49' 48'

Seg-4-9 (rev cmp)
5'-GCGGGGTTGTTGGTCTCATCATGGCAATCATAGCCCAGTTCGTTCAGGCG-3'
(50-mer) 51' 50'

*FIG. 12E*

Distribution of theoretical melting temperatures for most common codons, variola polymerase-1
solid = correct matches between small segment overlaps
dash-dot = correct matches between medium-sized piece overlaps
dashed = error matches between small segment overlaps
dotted = error matches between medium-sized piece overlaps Distribution of theoretical melting temperatures for designed gene, variola polymerase-1
solid = correct matches between small segment overlaps
dash-dot = correct matches between medium-sized piece overlaps
dashed = error matches between small segment overlaps
dotted = error matches between medium-sized piece overlaps

```
M0 D0 V0 R0 C0 I1 N1 W0 F0 E0 S4 H0 G1 E0 N0 R5 F0 L1 Y0 L0  ; 20
K0 S0 R1 C1 R0 N1 G2 E0 T2 V0 F1 I0 R1 F1 P2 H1 Y1 F0 Y1 Y0  ; 40
V0 V0 T0 D0 E1 I1 Y1 Q0 S0 L1 A1 P3 P1 P2 F1 N0 A3 R0 P2 M0  ; 60
G1 K0 M0 R2 T0 I0 D1 I1 D0 E1 T0 I1 S4 Y1 N0 L0 D1 I1 K1 D0  ; 80
R0 K0 C0 S1 V0 A0 D1 M0 W0 L1 I0 E0 E1 P0 K0 K1 R1 N0 I0 Q0  ;100
N1 A1 T0 M0 D0 E1 F0 L0 N1 I0 S1 W0 F1 Y1 I1 S0 N0 G0 I0 S1  ;120
P0 D0 G3 C0 Y1 S0 L2 D1 D0 Q0 Y0 L4 T1 K0 I1 N0 N0 G2 C0 Y0  ;140
H0 C1 G0 D1 P2 R0 N0 C1 F0 A0 K0 E1 I1 P3 R0 F0 D1 I0 P0 R4  ;160
S0 Y0 L0 F1 L0 D1 I0 E0 C0 H0 F1 D0 K1 K1 F1 P0 S0 V1 F0 I0  ;180
N1 P0 I1 S0 H0 T0 S3 Y0 C1 Y0 I0 D0 L0 S0 G0 K0 R0 L0 L0 F0  ;200
T0 L0 I1 N0 E1 E1 M0 L0 T0 E0 Q1 E0 I1 Q0 E1 A1 V0 D0 R0 G0  ;220
C1 L0 R1 I0 Q0 S3 L2 M0 E1 M0 D0 Y0 E0 R0 E0 L0 V0 L0 C0 S1  ;240
E0 I0 V0 L0 L4 Q1 I1 A1 K0 Q0 L1 L1 E1 L0 T0 F0 D0 Y1 I1 V0  ;260
T1 F1 N0 G0 H1 N0 F1 D0 L0 R2 Y0 I0 T0 N1 R0 L4 E1 L0 L2 T0  ;280
G0 E0 K0 I1 I1 F0 R0 S0 P3 D1 K1 K0 E0 A0 V1 H1 L0 C0 I1 Y0  ;300
E1 R0 N1 Q0 S4 S0 H1 K0 G2 V1 G3 G2 M0 A0 N1 T1 T0 F1 H1 V2  ;320
N1 N1 N1 N1 G0 T0 I0 F0 F1 D1 L0 Y0 S1 F1 I1 Q0 K0 S4 E1 K1  ;340
L3 D0 S1 Y1 K0 L0 D1 S0 I1 S0 K0 N0 A1 F0 S4 C0 M0 G0 K0 V0  ;360
L0 N1 R0 G1 V0 R0 E1 M0 T0 F0 I1 G1 D0 D0 T0 T2 D0 A0 K0 G2  ;380
K0 A0 A3 V0 F0 A0 K1 V2 L4 T0 T3 G0 N1 Y1 V0 T1 V2 D0 D0 I1  ;400
I0 C1 K0 V0 I0 H1 K1 D1 I1 W0 E0 N1 G0 F0 K1 V0 V0 L2 S0 C1  ;420
P0 T2 L0 T0 N0 D1 T1 Y1 K0 L4 S3 F0 G1 K0 D0 D0 V2 D1 L0 A0  ;440
Q0 M0 Y0 K0 D1 Y0 N0 L0 N0 I1 A1 L3 D0 M0 A1 R1 Y0 C0 I1 H1  ;460
D1 A1 C1 L0 C0 Q1 Y1 L0 W0 E1 Y1 Y0 G1 V3 E1 T1 K0 T1 D0 A0  ;480
G1 A1 S1 T0 Y0 V0 L2 P2 Q0 S3 M0 V0 F0 E1 Y0 K0 A0 S0 T1 V0  ;500
I0 K1 G2 P3                                                  ;501-504
(G2 P3 shared w/vpol2 as restriction site)
```

*FIG. 18* smallpox (variola) polymerase-1 designed codon usage dashed line, circles = codon usage in designed v. polymerase-1 solid line, x's = codon usage in E. coli native threonine deaminase for comparison Distribution of theoretical melting temperatures for most common codons, variola polymerase-2
solid = correct matches between small segment overlaps
dash-dot = correct matches between medium-sized piece overlaps
dashed = error matches between small segment overlaps
dotted = error matches between medium-sized piece overlaps Distribution of theoretical melting temperatures for designed gene, variola polymerase-2
solid = correct matches between small segment overlaps
dash-dot = correct matches between medium-sized piece overlaps
dashed = error matches between small segment overlaps
dotted = error matches between medium-sized piece overlaps

```
(G2 P3 shared w/vpol1 as restriction site)
G2 P3 L0 L0 K0 L2 L0 L0 E0 T0 K1 T0 I1 L1 V0 R1 S1 E0 T0 K0  ; 20
Q1 K1 F1 P3 Y0 E0 G0 G1 K0 V1 F0 A1 P0 K1 Q0 K1 M0 F0 S2 N0  ; 40
N0 V2 L0 I1 F0 D1 Y1 N0 S1 L0 Y0 P3 N0 V0 C0 I1 F0 G0 N0 L1  ; 60
S2 P0 E0 T0 L0 V1 G0 V0 V0 V0 S1 S4 N0 R1 L2 E0 E0 E1 I0 N0  ; 80
N0 Q0 L0 L4 L0 Q1 K1 Y1 P0 P0 P1 R0 Y1 I0 T1 V0 H1 C0 E0 P1  ;100
R0 L1 P3 N0 L0 I1 S0 E1 I0 A1 I0 F0 D0 R2 S0 I0 E0 G0 T0 I0  ;120
P0 R0 L1 L0 R4 T0 F0 L0 A1 E1 R0 A0 R0 Y0 K1 K0 M0 L0 K0 Q0  ;140
A0 T0 S2 S1 T1 E0 K0 A1 I1 Y1 D1 S2 M0 Q0 Y1 T0 Y1 K1 I1 I1  ;160
A0 N1 S2 V0 Y0 G0 L2 M0 G1 F0 R1 N0 S1 A1 L2 Y0 S0 Y0 A1 S0  ;180
A3 K1 S2 C1 T0 S2 I0 G0 R0 R0 M0 I1 L0 Y0 L0 E0 S1 V3 L4 N1  ;200
G3 A0 E0 L0 S2 N1 G0 M0 L3 R0 F0 A2 N0 P0 L1 S2 N1 P0 F1 Y1  ;220
M0 D0 D0 R1 D1 I0 N0 P0 I0 V0 K1 T1 S3 L0 P0 I0 D1 Y1 R0 F0  ;240
R1 F1 R5 S2 V2 Y0 G1 D0 T0 D1 S3 V0 F0 T0 E0 I0 D1 S0 Q0 D0  ;260
V1 D1 K0 S2 I0 E1 I2 A0 K1 E1 L0 E0 R0 L0 I1 N0 S1 R0 V0 L0  ;280
F1 N0 N0 F0 K1 I1 E1 F0 E1 A1 V0 Y0 K0 N0 L0 I1 M0 Q0 S0 K1  ;300
K0 K0 Y0 T0 T1 M0 K1 Y0 S0 A0 S2 S1 N0 S3 K0 S2 V0 P0 E1 R0  ;320
I0 N0 K1 G2 T2 S0 E0 T0 R0 R0 D0 V2 S0 K1 F1 H1 K0 N0 M0 I0  ;340
K0 I0 Y1 K1 T0 R0 L2 S0 E0 M0 L1 S2 E0 G0 R2 M0 N0 S0 N0 Q0  ;360
V0 C1 I1 D1 I0 L0 R0 S3 L3 E0 T1 D0 L3 R0 S0 E1 F1 D1 S0 R3  ;380
S1 S0 P0 L2 E0 L0 F1 M0 L1 S0 R1 M0 H1 H1 L2 N0 Y0 K0 S0 A1  ;400
D0 N0 P0 N0 M0 Y1 L0 V0 T0 E1 Y1 N0 K0 N0 N0 P0 E0 T2 I0 E0  ;420
L3 G0 E0 R1 Y1 Y1 F0 A1 Y0 I1 C1 P0 A0 N1 V1 P0 W0 T0 K0 K0  ;440
L4 V0 N0 I1 K1 T1 Y1 E0 T0 I0 I0 D1 R0 S3 F1 K1 L0 G0 S5 D0  ;460
Q0 R1 I0 F0 Y1 E1 V0 Y0 F0 K0 R0 L0 T0 S3 E0 I1 V0 N0 L0 L1  ;480
D0 N0 K1 V0 L0 C0 I0 S1 F0 F0 E0 R1 M0 F0 G0 S0 R4 P0 T0 F1  ;500
Y0 E1 A0                                                     ;501-503
```

*FIG. 22* smallpox (variola) polymerase-2 designed codon usage dashed line, circles = codon usage in designed v. polymerase-2 solid line, x's = codon usage in E. coli native threonine deaminase for comparison Leader-0:
TCCTCGAGCATA [ATGGATGTGCGTTGCATC]

Leader-1:
GACGACGACGACAAGCATATGCTCGAGGAT [ATGGATGTGCGTTGCATC]

*FIG. 24A*

Strand 0:
ATGGATGTGCGTTGCATCAATTGGTTTGAAT [CGCATGGTGAAAACAGG]
[CGCATGGTGAAAACAGG] TTTTTATATCTGAAAA [GCCGCTGTCGTAATGGG]
[GCCGCTGTCGTAATGGG] GAAACTGTGTT [CATTCGCTTCCCTCACTAC]
[CATTCGCTTCCCTCACTAC] TTTTACTATGT [GGTGACCGATGAGATCTACC]
[GGTGACCGATGAGATCTACC] AGAGCTTAGCCCC [CCCACCTTTCAACGCTC]
[CCCACCTTTCAACGCTC] GTCCTATGGGTAAAAT [GCGGACCATTGACATCG]
[GCGGACCATTGACATCG] ATGAGACCATCT [CGTACAACCTGGACATCAAGG]
[CGTACAACCTGGACATCAAGG] ATCGTAAATG [CTCTGTGGCGGACATGTG]
[CTCTGTGGCGGACATGTG] GTTAATTGAA [GAGCCGAAAAAGCGCAAC]
[GAGCCGAAAAAGCGCAAC] ATTCAGAATG [CCACCATGGATGAGTTTCTG]
[CCACCATGGATGAGTTTCTG] AATATTTCTT [GGTTCTACATCAGCAACGGC]
[GGTTCTACATCAGCAACGGC] ATTTCTCCGGATGGATGCTACAGCTTGGAC

*FIG. 24B*

Strand 1:
GGTTCTACATCAGCAACGGCATTTCTCCGGAT [GGATGCTACAGCTTGGAC]
[GGATGCTACAGCTTGGAC] GATCAGTATCT [CACGAAAATCAACAACGGGTG]
[CACGAAAATCAACAACGGGTG] CTATCATTGT [GGCGACCCTCGTAACTG]
[GGCGACCCTCGTAACTG] TTTTGCGAAA [GAGATCCCCCGTTTTGAC]
[GAGATCCCCCGTTTTGAC] ATTCCGAGAA [GCTATCTGTTCCTGGACATTG]
[GCTATCTGTTCCTGGACATTG] AATGCCATTT [CGATAAGAAGTTCCCGAGC]
[CGATAAGAAGTTCCCGAGC] GTTTTTATTAATC [CGATCAGCCATACCTCC]
[CGATCAGCCATACCTCC] TATTGTTATATTGAT [CTGAGCGGCAAACGTCTG]
[CTGAGCGGCAAACGTCTG] CTGTTTACCCT [GATCAACGAGGAGATGCTGAC]
[GATCAACGAGGAGATGCTGAC] CGAACAAGAAAT [CCAGGAGGCCGTGGATC]
[CCAGGAGGCCGTGGATC] GTGGCTGTCTGC [GCATTCAGTCCTTGATGGAG]
[GCATTCAGTCCTTGATGGAG] ATGGATTATGAACGTGAACTGGTGCTGTGC

*FIG. 24C*

Strand 2:
GCATTCAGTCCTTGATGGAGATGGATTATGAAC [GTGAACTGGTGCTGTGC]
[GTGAACTGGTGCTGTGC] TCTGAAATTGTGCT [GCTCCAAATCGCCAAAC]
[GCTCCAAATCGCCAAAC] AGTTATTAGA [GCTGACCTTTGATTACATCGTG]
[GCTGACCTTTGATTACATCGTG] ACGTTCAACG [GCCACAACTTCGATCTGC]
[GCCACAACTTCGATCTGC] GGTATATTACCAATC [GTCTCGAGCTGTTGACC]
[GTCTCGAGCTGTTGACC] GGCGAAAAAATCAT [CTTTCGTAGCCCCGACAAG]
[CTTTCGTAGCCCCGACAAG] AAAGAAGCGGTT [CACCTGTGCATCTATGAGC]
[CACCTGTGCATCTATGAGC] GTAATCAGTC [GAGCCACAAAGGGGTTG]
[GAGCCACAAAGGGGTTG] GAGGGATGGC [GAATACGACCTTCCACGTC]
[GAATACGACCTTCCACGTC] AATAATAATAATGGCACCATTTTTTTCGACC

*FIG. 24D*

Strand 3:
GAATACGACCTTCCACGTCAATAATAATAAT [GGCACCATTTTTTTCGACC]
[GGCACCATTTTTTTCGACC] TGTATTCTTT [CATCCAGAAATCGGAGAAGC]
[CATCCAGAAATCGGAGAAGC] TTGATTCTTA [CAAACTGGACAGCATCAGC]
[CAAACTGGACAGCATCAGC] AAAAACGCCTTTTC [GTGCATGGGCAAAGTGC]
[GTGCATGGGCAAAGTGC] TGAATCGTGGT [GTGCGTGAGATGACCTTTATC]
[GTGCGTGAGATGACCTTTATC] GGTGATGATA [CCACTGATGCGAAAGGG]
[CCACTGATGCGAAAGGG] AAAGCGGCTGT [GTTTGCGAAGGTCCTCACC]
[GTTTGCGAAGGTCCTCACC] ACAGGCAATTA [CGTGACGGTCGATGATATC]
[CGTGACGGTCGATGATATC] ATTTGTAAAGT [GATTCACAAGGACATCTGGG]
[GATTCACAAGGACATCTGGG] AAAATGGCTTTAAGGTGGTGTTGAGCTGTC

*FIG. 24E*

Strand 4:
GATTCACAAGGACATCTGGGAAAATGGCTTTAA [GGTGGTGTTGAGCTGTC]
[GGTGGTGTTGAGCTGTC] CGACTCTGACCAA [CGACACGTACAAACTCTCC]
[CGACACGTACAAACTCTCC] TTTGGTAAAGAT [GATGTCGACCTGGCGCAG]
[GATGTCGACCTGGCGCAG] ATGTATAAAGA [CTATAACCTGAACATCGCCC]
[CTATAACCTGAACATCGCCC] TTGATATGGC [CCGCTATTGCATCCACG]
[CCGCTATTGCATCCACG] ACGCCTGTCT [GTGCCAATACCTGTGGGAGTAC]
[GTGCCAATACCTGTGGGAGTAC] TATGGTGTAGA [GACGAAAACGGATGCGG]
[GACGAAAACGGATGCGG] GTGCCTCTAC [CTATGTGTTGCCTCAGTCC]
[CTATGTGTTGCCTCAGTCC] ATGGTGTTTGA [GTATAAAGCGAGCACGGTG]
[GTATAAAGCGAGCACGGTG] ATTAAGGGGCCC

*FIG. 24F*

Trailer-0:
[CGGTGATTAAGGGGCCC] TATGGCTGCCGC

Trailer-1:
[CGGTGATTAAGGGGCCC] TACCCATACGATGTTCCGGATTACGCTTAA

*FIG. 24G*

Leader-0:
TCCTCGAGCATA [GGGCCCCTGCTGAAATTG]

Leader-1:
GACGACGACGACAAGCATATGCTCGAGGAT [GGGCCCCTGCTGAAATTG]

FIG. 25A

Strand 0:
GGGCCCCTGCTGAAATTGCTGCTGGAAACCAA [GACCATCTTAGTGCGCTC]
[GACCATCTTAGTGCGCTC] TGAAACCAAACAAAA [GTTCCCCTATGAAGGCG]
[GTTCCCCTATGAAGGCG] GTAAAGTTTTTG [CCCCGAAGCAGAAGATG]
[CCCCGAAGCAGAAGATG] TTTAGTAACAA [CGTCCTGATCTTTGACTACAAC]
[CGTCCTGATCTTTGACTACAAC] TCTCTGTATC [CCAACGTGTGCATCTTTG]
[CCAACGTGTGCATCTTTG] GCAACTTAAGTCCG [GAAACCCTGGTTGGCGTG]
[GAAACCCTGGTTGGCGTG] GTGGTGTCTTC [GAACCGCTTGGAAGAAGAG]
[GAACCGCTTGGAAGAAGAG] ATTAACAACCAG [CTGCTCCTGCAAAAGTACC]
[CTGCTCCTGCAAAAGTACC] CGCCGCCACGTTA [CATTACGGTGCACTGCG]
[CATTACGGTGCACTGCG] AACCACGTTTACC [CAACCTGATCAGCGAGATTG]
[CAACCTGATCAGCGAGATTG] CCATTTTTGATC [GGAGCATTGAAGGCACC]
[GGAGCATTGAAGGCACC] ATTCCGCGTTTACTGAGAACCTTTCTGGCCGAG

FIG. 25B

Strand 1:
GGAGCATTGAAGGCACCATTCCGCGTTTACTGA [GAACCTTTCTGGCCGAG]
[GAACCTTTCTGGCCGAG] CGTGCGCGTTATAA [GAAAATGCTGAAACAGGCG]
[GAAAATGCTGAAACAGGCG] ACCAGTTCTA [CGGAAAAAGCCATCTACGAC]
[CGGAAAAAGCCATCTACGAC] AGTATGCAGTA [CACCTACAAGATCATCGCG]
[CACCTACAAGATCATCGCG] AATAGTGTGTATG [GCTTGATGGGTTTTCGC]
[GCTTGATGGGTTTTCGC] AACTCTGCCTTGTATA [GCTATGCCAGCGCTAAG]
[GCTATGCCAGCGCTAAG] AGTTGTACCAGTATTG [GCCGTCGTATGATCCTG]
[GCCGTCGTATGATCCTG] TATCTGGAATCTGTA [CTCAATGGAGCGGAACTG]
[CTCAATGGAGCGGAACTG] AGTAATGGCATG [CTTCGTTTTGCAAACCCG]
[CTTCGTTTTGCAAACCCG] TTAAGTAATC [CGTTCTACATGGATGATCGC]
[CGTTCTACATGGATGATCGC] GACATTAACC [CGATTGTGAAGACGTCCC]
[CGATTGTGAAGACGTCCC] TGCCGATTGACTACCGTTTTCGCTTCAGG

FIG. 25C

Strand 2:
CGATTGTGAAGACGTCCCTGCCGATTGA [CTACCGTTTTCGCTTCAGG]
[CTACCGTTTTCGCTTCAGG] AGTGTCTATG [GTGATACCGACTCCGTG]
[GTGATACCGACTCCGTG] TTTACCGAAATT [GACAGCCAGGATGTTGAC]
[GACAGCCAGGATGTTGAC] AAAAGTATTGA [GATAGCGAAGGAGCTGG]
[GATAGCGAAGGAGCTGG] AACGTCTGAT [CAACTCTCGTGTGCTGTTC]
[CAACTCTCGTGTGCTGTTC] AACAACTTTAA [GATCGAGTTTGAGGCCG]
[GATCGAGTTTGAGGCCG] TGTATAAAAA [CCTGATCATGCAGAGCAAG]
[CCTGATCATGCAGAGCAAG] AAAAAATATAC [CACGATGAAGTATAGCGCG]
[CACGATGAAGTATAGCGCG] AGTTCTAACTC [CAAAAGTGTGCCGGAGC]
[CAAAAGTGTGCCGGAGC] GTATTAACAAGGGGACTAGCGAAACCC

FIG. 25D

Strand 3:
CAAAAGTGTGCCGGAGCGTATTAACAA [GGGGACTAGCGAAACCC]
[GGGGACTAGCGAAACCC] GTCGTGATGT [CAGCAAGTTCCACAAAAACATG]
[CAGCAAGTTCCACAAAAACATG] ATTAAAATTTA [CAAGACCCGTTTGAGCG]
[CAAGACCCGTTTGAGCG] AAATGTTAAGTGAAGG [CCGGATGAACAGCAACC]
[CCGGATGAACAGCAACC] AGGTGTGTAT [CGACATTCTGCGTTCCC]
[CGACATTCTGCGTTCCC] TTGAAACGGAT [CTTCGTAGCGAGTTCGAC]
[CTTCGTAGCGAGTTCGAC] AGCCGATCTA [GCCCGTTGGAACTGTTC]
[GCCCGTTGGAACTGTTC] ATGTTAAGCC [GCATGCACCACTTGAAC]
[GCATGCACCACTTGAAC] TATAAAAGCGC [CGATAACCCGAACATGTACC]
[CGATAACCCGAACATGTACC] TGGTGACCGAGTACAACAAAAACAACCCGG

FIG. 25E

Strand 4:
CGATAACCCGAACATGTACCTGGTGACCGA [GTACAACAAAAACAACCCGG]
[GTACAACAAAAACAACCCGG] AAACTATTGAA [CTTGGCGAACGCTACTAC]
[CTTGGCGAACGCTACTAC] TTTGCCTATATCTGT [CCGGCGAATGTTCCGTG]
[CCGGCGAATGTTCCGTG] GACCAAAAAACT [CGTGAACATCAAGACGTACG]
[CGTGAACATCAAGACGTACG] AAACCATTATTGA [CCGTTCCTTCAAGCTGG]
[CCGTTCCTTCAAGCTGG] GCTCAGATCA [GCGCATTTTTTACGAGGTG]
[GCGCATTTTTTACGAGGTG] TATTTTAAACGT [CTGACCTCCGAAATCGTG]
[CTGACCTCCGAAATCGTG] AACCTGTTAGATAA [CAAGGTGCTGTGCATTTC]
[CAAGGTGCTGTGCATTTC] TTTTTTTGAACG [CATGTTTGGCAGCAGACCG]
[CATGTTTGGCAGCAGACCG] ACCTTCTATGAGGCG

FIG. 25F

Trailer-0:
[CGACCTTCTATGAGGCG] TATGGCTGCCGC

Trailer-1:
[CGACCTTCTATGAGGCG] TACCCATACGATGTTCCGGATTACGCTTAA

FIG. 25G

Intermediate Fragment Set #0

Forward segments (Watson or plus strand):

1Seg-0-00
5'-ATGGATGTGCGTTGCATCAATTGGTTTGAATCGCATGGTGAAAACAGG-3'
(48-mer) 1

1Seg-0-02
5'-GCCGCTGTCGTAATGGGGAAACTGTGTTCATTCGCTTCCCTCACTAC-3'
(47-mer) 2 3

1Seg-0-04
5'-GGTGACCGATGAGATCTACCAGAGCTTAGCCCCCCCACCTTTCAACGCTC-3'
(50-mer) 4 5

1Seg-0-06
5'-GCGGACCATTGACATCGATGAGACCATCTCGTACAACCTGGACATCAAGG-3'
(50-mer) 6 7

1Seg-0-08
5'CTCTGTGGCGGACATGTGGTTAATTGAAGAGCCGAAAAAGCGCAAC-3'
(46-mer) 8 9

1Seg-0-10
5'-CCACCATGGATGAGTTTCTGAATATTTCTTGGTTCTACATCAGCAACGGC-3'
(50-mer) 10 11

Reverse complement segments (Crick or minus strand):

1Seg-0-01 (rev cmp)
5'-CCCATTACGACAGCGGCTTTTCAGATATAAAAACCTGTTTTCACCATGCG-3'
(50-mer) 2' 1'

1Seg-0-03 (rev cmp)
5'-GGTAGATCTCATCGGTCACCACATAGTAAAAGTAGTGAGGGAAGCGAATG-3'
(50-mer) 4' 3'

1Seg-0-05 (rev cmp)
5'-CGATGTCAATGGTCCGCATTTTACCCATAGGACGAGCGTTGAAAGGTGGG-3'
(50-mer) 6' 5'

1Seg-0-07 (rev cmp)
5'-CACATGTCCGCCACAGAGCATTTACGATCCTTGATGTCCAGGTTGTACG-3'
(49-mer) 8' 7'

1Seg-0-9 (rev cmp)
5'-CAGAAACTCATCCATGGTGGCATTCTGAATGTTGCGCTTTTTCGGCTC-3'
(48-mer) 10' 9'

1Seg-0-11(rev cmp)
5'-GTCCAAGCTGTAGCATCCATCCGGAGAAAT GCCGTTGCTGATGTAGAACC-3'
(50-mer) 12' 11'/12'

*FIG. 26A*

Intermediate Fragment Set #1

Forward segments:

1Seg-1-00
5'-GGTTCTACATCAGCAACGGCATTTCTCCGGATGGATGCTACAGCTTGGAC-3'
(50-mer) 12

1Seg-1-02
5'-CACGAAAATCAACAACGGGTGCTATCATTGTGGCGACCCTCGTAACTG-3'
(48-mer) 13 14

1Seg-1-04
5'-GAGATCCCCCGTTTTGACATTCCGAGAAGCTATCTGTTCCTGGACATTG-3'
(49-mer 13 14

1Seg-1-06
5'-CGATAAGAAGTTCCCGAGCGTTTTTATTAATCCGATCAGCCATACCTCC-3'
(49-mer) 15 16

1Seg-1-08
5'-CTGAGCGGCAAACGTCTGCTGTTTACCCTGATCAACGAGGAGATGCTGAC-3'
(50-mer) 17 18

1Seg-1-10
5'-CCAGGAGGCCGTGGATCGTGGCTGTCTGCGCATTCAGTCCTTGATGGAG-3'
(49-mer) 19 20

Reverse complement segments:

1Seg-1-01 (rev cmp)
5'-CACCCGTTGTTGATTTTCGTGAGATACTGATCGTCCAAGCTGTAGCATCC-3'
(50-mer) 13' 12'

1Seg-1-03 (rev cmp)
5'-GTCAAAACGGGGGATCTCTTTCGCAAAACAGTTACGAGGGTCGCC-3'
(50-mer) 14' 15'

1Seg-1-05 (rev cmp)
5'-GCTCGGGAACTTCTTATCGAAATGGCATTCAATGTCCAGGAACAGATAGC-3'
(50-mer) 17' 16'

1Seg-1-07 (rev cmp)
5'-CAGACGTTTGCCGCTCAGATCAATATAACAATAGGAGGTATGGCTGATCG-3'
(49-mer) 19' 18'

1Seg-1-09 (rev cmp)
5'-GATCCACGGCCTCCTGGATTTCTTGTTCGGTCAGCATCTCCTCGTTGATC-3'
(48-mer) 21' 20'

1Seg-1-11 (rev cmp)
5'-GCACAGCACCAGTTCACGTTCATAATCCAT CTCCATCAAGGACTGAATGC-3'
(50-mer) 23' 22'/23'

*FIG. 26B*

Intermediate Fragment Set #2

Forward segments

1Seg-2-00
5'-GCATTCAGTCCTTGATGGAGATGGATTATGAACGTGAACTGGTGCTGTGC-3'
(50-mer) 23

1Seg-2-02
5'-GCTCCAAATCGCCAAACAGTTATTAGAGCTGACCTTTGATTACATCGTG-3'
(49-mer) 24 25

1Seg-2-04
5'-GCCACAACTTCGATCTGCGGTATATTACCAATCGTCTCGAGCTGTTGACC-3'
(50-mer) 26 27

1Seg-2-06
5'-CTTTCGTAGCCCCGACAAGAAAGAAGCGGTTCACCTGTGCATCTATGAGC-3'
(50-mer) 28 29

1Seg-2-08
5'-GAGCCACAAAGGGGTTGGAGGGATGGCGAATACGACCTTCCACGTC-3'
(46-mer) 30 31

Reverse complement segments:

1Seg-2-01 (rev cmp)
5'-GTTTGGCGATTTGGAGCAGCACAATTTCAGAGCACAGCACCAGTTCAC-3'
(48-mer) 24' 23'

1Seg-2-03 (rev cmp)
5'-GCAGATCGAAGTTGTGGCCGTTGAACGTCACGATGTAATCAAAGGTCAGC-3'
(50-mer) 26' 25'

1Seg-2-05 (rev cmp)
5'-CTTGTCGGGGCTACGAAAGATGATTTTTTCGCCGGTCAACAGCTCGAGAC-3'
(50-mer) 28' 27'

1Seg-2-07 (rev cmp)
5'-CAACCCCTTTGTGGCTCGACTGATTACGCTCATAGATGCACAGGTG-3'
(46-mer) 30' 29'

1Seg-2-09 (rev cmp)
5'-GGTCGAAAAAAATGGTGCCATTATTATTATT GACGTGGAAGGTCGTATTC-3'
(50-mer) 32' 31'/32'

*FIG. 26C*

Intermediate Fragment Set #3

Forward segments

1Seg-3-00
5'-GAATACGACCTTCCACGTCAATAATAATAATGGCACCATTTTTTTCGACC-3'
(50-mer) 32

1Seg-3-02
5'-CATCCAGAAATCGGAGAAGCTTGATTCTTACAAACTGGACAGCATCAGC-3'
(49-mer) 33 34

1Seg-3-04
5'-GTGCATGGGCAAAGTGCTGAATCGTGGTGTGCGTGAGATGACCTTTATC-3'
(49-mer) 35 36

1Seg-3-06
5'-CCACTGATGCGAAAGGGAAAGCGGCTGTGTTTGCGAAGGTCCTCACC-3'
(47-mer) 37 38

1Seg-3-08
5'-CGTGACGGTCGATGATATCATTTGTAAAGTGATTCACAAGGACATCTGGG-3'
(50-mer) 39 40

Reverse complement segments:

1Seg-3-01 (rev cmp)
5'-GCTTCTCCGATTTCTGGATGAAAGAATACAGGTCGAAAAAAATGGTGCC-3'
(49-mer) 33' 32'

1Seg-3-03 (rev cmp)
5'-GCACTTTGCCCATGCACGAAAAGGCGTTTTTGCTGATGCTGTCCAGTTTG-3'
(50-mer) 35' 34'

1Seg-3-05 (rev cmp)
5'-CCCTTTCGCATCAGTGGTATCATCACCGATAAAGGTCATCTCACGCAC-3'
(48-mer) 37' 36'

1Seg-3-07 (rev cmp)
5'-GATATCATCGACCGTCACGTAATTGCCTGTGGTGAGGACCTTCGCAAAC-3'
(49-mer) 39' 38'

1Seg-3-09 (rev cmp)
5'-GACAGCTCAACACCACCTTAAAGCCATTTT CCCAGATGTCCTTGTGAATC-3'
(50-mer) 41' 40'/41'

*FIG. 26D*

Intermediate Fragment Set #4

Forward segments

1Seg-4-00
5'-GATTCACAAGGACATCTGGGAAAATGGCTTTAAGGTGGTGTTGAGCTGTC-3'
(50-mer) 41

1Seg-4-02
5'-CGACACGTACAAACTCTCCTTTGGTAAAGATGATGTCGACCTGGCGCAG-3'
(49-mer) 42 43

1Seg-4-04
5'-CTATAACCTGAACATCGCCCTTGATATGGCCCGCTATTGCATCCACG-3'
(47-mer) 44 45

1Seg-4-06
5'-GTGCCAATACCTGTGGGAGTACTATGGTGTAGAGACGAAAACGGATGCGG-3'
(50-mer) 46 47

1Seg-4-08
5'-CTATGTGTTGCCTCAGTCCATGGTGTTTGAGTATAAAGCGAGCACGGTG-3'
(49-mer) 48 49

Reverse complement segments:

1Seg-4-01 (rev cmp)
5'-GGAGAGTTTGTACGTGTCGTTGGTCAGAGTCGGACAGCTCAACACCACC-3'
(49-mer) 42' 41'

1Seg-4-03 (rev cmp)
5'-GGGCGATGTTCAGGTTATAGTCTTTATACATCTGCGCCAGGTCGACATC-3'
(49-mer) 44' 43'

1Seg-4-05 (rev cmp)
5'-GTACTCCCACAGGTATTGGCACAGACAGGCGTCGTGGATGCAATAGCGG-3'
(49-mer) 46' 45'

1Seg-4-07 (rev cmp)
5'-GGACTGAGGCAACACATAGGTAGAGGCACCCGCATCCGTTTTCGTC-3'
(46-mer) 48' 47'

1Seg-4-09 (rev cmp)
5'-GGGCCCCTTAATCACCGTGCTCGCTTTATAC-3'
(31-mer) 49'

*FIG. 26E*

Intermediate Fragment Set #0

Forward segments (Watson or plus strand):

2Seg-0-00
5'-GGGCCCCTGCTGAAATTGCTGCTGGAAACCAAGACCATCTTAGTGCGCTC-3'
(50-mer) 1

2Seg-0-02
5'-GTTCCCCTATGAAGGCGGTAAAGTTTTTGCCCCGAAGCAGAAGATG-3'
(46-mer) 2 3

2Seg-0-04
5'-CGTCCTGATCTTTGACTACAACTCTCTGTATCCCAACGTGTGCATCTTTG-3'
(50-mer) 4 5

2Seg-0-06
5'-GAAACCCTGGTTGGCGTGGTGGTGTCTTCGAACCGCTTGGAAGAAGAG-3'
(48-mer) 6 7

2Seg-0-08
5'-CTGCTCCTGCAAAAGTACCCGCCGCCACGTTACATTACGGTGCACTGCG-3'
(49-mer) 8 9

2Seg-0-10
5'-CAACCTGATCAGCGAGATTGCCATTTTTGATCGGAGCATTGAAGGCACC-3'
(49-mer) 10 11

Reverse complement segments (Crick or minus strand):

2Seg-0-01 (rev cmp)
5'-CGCCTTCATAGGGGAACTTTTGTTTGGTTTCAGAGCGCACTAAGATGGTC-3'
(50-mer) 2' 1'

2Seg-0-03 (rev cmp)
5'-GTTGTAGTCAAAGATCAGGACGTTGTTACTAAACATCTTCTGCTTCGGGG-3'
(50-mer) 4' 3'

2Seg-0-05 (rev cmp)
5'-CACGCCAACCAGGGTTTCCGGACTTAAGTTGCCAAAGATGCACACGTTGG-3'
(50-mer) 6' 5'

2Seg-0-07 (rev cmp)
5'-GGTACTTTTGCAGGAGCAGCTGGTTGTTAATCTCTTCTTCCAAGCGGTTC-3'
(50-mer) 8' 7'

2Seg-0-9 (rev cmp)
5'-CAATCTCGCTGATCAGGTTGGGTAAACGTGGTTCGCAGTGCACCGTAATG-3'
(50-mer) 10' 9'

2Seg-0-11(rev cmp)
5'-CTCGGCCAGAAAGGTTCTCAGTAAACGCGGAAT GGTGCCTTCAATGCTCC-3'
(50-mer) 12' 11'/12'

*FIG. 27A*

Intermediate Fragment Set #1

Forward segments:

2Seg-1-00
5'-GGAGCATTGAAGGCACCATTCCGCGTTTACTGAGAACCTTTCTGGCCGAG-3'
(50-mer) 12

2Seg-1-02
5'-GAAAATGCTGAAACAGGCGACCAGTTCTACGGAAAAAGCCATCTACGAC-3'
(49-mer) 13 14

2Seg-1-04
5'-CACCTACAAGATCATCGCGAATAGTGTGTATGGCTTGATGGGTTTTCGC-3'
(49-mer) 15 16

2Seg-1-06
5'-GCTATGCCAGCGCTAAGAGTTGTACCAGTATTGGCCGTCGTATGATCCTG-3'
(50-mer) 17 18

2Seg-1-08
5'-CTCAATGGAGCGGAACTGAGTAATGGCATGCTTCGTTTTGCAAACCCG-3'
(48-mer) 19 20

2Seg-1-10
5'-CGTTCTACATGGATGATCGCGACATTAACCCGATTGTGAAGACGTCCC-3'
(48-mer) 21 22

Reverse complement segments:

2Seg-1-01 (rev cmp)
5'-CGCCTGTTTCAGCATTTTCTTATAACGCGCACGCTCGGCCAGAAAGGTTC-3'
(50-mer) 13' 12'

2Seg-1-03 (rev cmp)
5'-CGCGATGATCTTGTAGGTGTACTGCATACTGTCGTAGATGGCTTTTTCCG-3'
(50-mer) 15' 14'

2Seg-1-05 (rev cmp)
5'-CTTAGCGCTGGCATAGCTATACAAGGCAGAGTTGCGAAAACCCATCAAGC-3'
(50-mer) 17' 16'

2Seg-1-07 (rev cmp)
5'-CAGTTCCGCTCCATTGAGTACAGATTCCAGATACAGGATCATACGACGGC-3'
(50-mer) 19' 18'

2Seg-1-09 (rev cmp)
5'-GCGATCATCCATGTAGAACGGATTACTTAACGGGTTTGCAAAACGAAG-3'
(48-mer) 21' 20'

2Seg-1-11 (rev cmp)
5'-CCTGAAGCGAAAACGGTAGTCAATCGGCA GGGACGTCTTCACAATCG-3'
(47-mer) 23' 22'/23'

*FIG. 27B*

Intermediate Fragment Set #2

Forward segments

2Seg-2-00
5'-CGATTGTGAAGACGTCCCTGCCGATTGACTACCGTTTTCGCTTCAGG-3'
(47-mer) 23

2Seg-2-02
5'-GTGATACCGACTCCGTGTTTACCGAAATTGACAGCCAGGATGTTGAC-3'
(47-mer) 24 25

2Seg-2-04
5'-GATAGCGAAGGAGCTGGAACGTCTGATCAACTCTCGTGTGCTGTTC-3'
(46-mer) 26 27

2Seg-2-06
5'-GATCGAGTTTGAGGCCGTGTATAAAAACCTGATCATGCAGAGCAAG-3'
(46-mer) 28 29

2Seg-2-08
5'-CACGATGAAGTATAGCGCGAGTTCTAACTCCAAAAGTGTGCCGGAGC-3'
(47-mer) 30 31

Reverse complement segments:

2Seg-2-01 (rev cmp)
5'-CACGGAGTCGGTATCACCATAGACACTCCTGAAGCGAAAACGGTAG-3'
(46-mer) 24' 23'

2Seg-2-03 (rev cmp)
5'-CCAGCTCCTTCGCTATCTCAATACTTTTGTCAACATCCTGGCTGTC-3'
(46-mer) 26' 25'

2Seg-2-05 (rev cmp)
5'-CGGCCTCAAACTCGATCTTAAAGTTGTTGAACAGCACACGAGAGTTG-3'
(47-mer) 28' 27'

2Seg-2-07 (rev cmp)
5'-CGCGCTATACTTCATCGTGGTATATTTTTTCTTGCTCTGCATGATCAGG-3'
(49-mer) 30' 29'

2Seg-2-09 (rev cmp)
5'-GGGTTTCGCTAGTCCCCTTGTTAATA CGCTCCGGCACACTTTTG-3'
(44-mer) 32' 31'/32'

*FIG. 27C*

Intermediate Fragment Set #3

Forward segments
2Seg-3-00
5'-CAAAAGTGTGCCGGAGCGTATTAACAAGGGGACTAGCGAAACCC-3'
(44-mer) 32
2Seg-3-02
5'-CAGCAAGTTCCACAAAAACATGATTAAAATTTACAAGACCCGTTTGAGCG-3'
(50-mer) 33 34
2Seg-3-04
5'-CCGGATGAACAGCAACCAGGTGTGTATCGACATTCTGCGTTCCC-3'
(44-mer) 35 36
2Seg-3-06
5'-CTTCGTAGCGAGTTCGACAGCCGATCTAGCCCGTTGGAACTGTTC-3'
(45-mer) 37 38
2Seg-3-08
5'-GCATGCACCACTTGAACTATAAAAGCGCCGATAACCCGAACATGTACC-3'
(48-mer) 39 40

Reverse complement segments:
2Seg-3-01 (rev cmp)
5'-CATGTTTTTGTGGAACTTGCTGACATCACGACGGGTTTCGCTAGTCCCC-3'
(49-mer) 33' 32'
2Seg-3-03 (rev cmp)
5'-GGTTGCTGTTCATCCGGCCTTCACTTAACATTTCGCTCAAACGGGTCTTG-3'
(50-mer) 35' 34'
2Seg-3-05 (rev cmp)
5'-GTCGAACTCGCTACGAAGATCCGTTTCAAGGGAACGCAGAATGTCG-3'
(46-mer) 37' 36'
2Seg-3-07 (rev cmp)
5'-GTTCAAGTGGTGCATGCGGCTTAACATGAACAGTTCCAACGGGC-3'
(44-mer) 39' 38'
2Seg-3-09 (rev cmp)
5'-CCGGGTTGTTTTTGTTGTACTCGGTCACCA GGTACATGTTCGGGTTATCG-3'
(50-mer) 41' 40'/41'

*FIG. 27D*

Intermediate Fragment Set #4

Forward segments
2Seg-4-00
5'-CGATAACCCGAACATGTACCTGGTGACCGAGTACAACAAAAACAACCCGG-3'
(50-mer)           41
2Seg-4-02
5'-CTTGGCGAACGCTACTACTTTGCCTATATCTGTCCGGCGAATGTTCCGTG-3'
(50-mer) 42                                 43
2Seg-4-04
5'-CGTGAACATCAAGACGTACGAAACCATTATTGACCGTTCCTTCAAGCTGG-3'
(50-mer)   44                           45
2Seg-4-06
5'-GCGCATTTTTTACGAGGTGTATTTTAAACGTCTGACCTCCGAAATCGTG-3'
(49-mer)  46     47
2Seg-4-08
5'-CAAGGTGCTGTGCATTTCTTTTTTTGAACGCATGTTTGGCAGCAGACCG-3'
(49-mer)   48                        49

Reverse complement segments:
2Seg-4-01 (rev cmp)
5'-GTAGTAGCGTTCGCCAAGTTCAATAGTTTCCGGGTTGTTTTTGTTGTAC-3'
(49-mer) 42'                      41'
2Seg-4-03 (rev cmp)
5'-CGTACGTCTTGATGTTCACGAGTTTTTTGGTCCACGGAACATTCGCCGG-3'
(49-mer)   44'                       43'
2Seg-4-05 (rev cmp)
5'-CACCTCGTAAAAAATGCGCTGATCTGAGCCCAGCTTGAAGGAACGG-3'
(46-mer)    46'                      45'
2Seg-4-07 (rev cmp)
5'-GAAATGCACAGCACCTTGTTATCTAACAGGTTCACGATTTCGGAGGTCAG-3'
(50-mer) 48'                          47'
2Seg-4-09 (rev cmp)
5'-CGCCTCATAGAAGGTCGGTCTGCTGCCAAACATG-3'
(34-mer)                49'

*FIG. 27E*

Lane 1: 10 µl fragment 0, 384 bp
Lane 2: 10 µl fragment 1, 383 bp
Lane 3: 10 µl fragment 2, 324 bp
Lane 4: 10 µl fragment 3, 320 bp
Lane 5: 10 µl fragment 4, 301 bp
Lane 6: 10 µl 1 kb Plus Ladder Lane 1: 10 µl fragment 0, 390 bp
Lane 2: 10 µl fragment 1, 389 bp
Lane 3: 10 µl fragment 2, 303 bp
Lane 4: 10 µl fragment 3, 308 bp
Lane 5: 10 µl fragment 4, 310 bp
Lane 6: 10 µl 1 kb Plus Ladder Lane 1: 10ul Part I with 1lead-01 1trail-57
Lane 2: 10ul Part I with 1lead-02 1trail-58
Lane 3: 10ul Part II with 2lead-01 2trail-57
Lane 4: 10ul Part II with 2-lead-02 2trail-58
Lane 5: 10 µl 1 kb Plus Ladder Distribution of theoretical melting temperatures for most common codons, threonine deaminase by direct self-assembly
solid = correct matches between small segment overlaps
dashed = error matches between small segment overlaps Distribution of theoretical melting temperatures for designed gene, threonine deaminase by direct self-assembly
solid = correct matches between small segment overlaps
dashed = error matches between small segment overlaps

| | | | | | | | | | | | | | | | | | | | | |
|---|---|---|---|---|---|---|---|---|---|---|---|---|---|---|---|---|---|---|---|---|
| M0 | A0 | D0 | S1 | Q0 | P0 | L2 | S1 | G1 | A1 | P0 | E0 | G0 | A0 | E1 | Y0 | L3 | R2 | A0 | V3 | ; 20 |
| L0 | R3 | A3 | P1 | V0 | Y0 | E0 | A1 | A2 | Q0 | V0 | T0 | P0 | L0 | Q1 | K0 | M0 | E1 | K0 | L0 | ; 40 |
| S0 | S3 | R0 | L0 | D0 | N0 | V2 | I1 | L0 | V2 | K0 | R1 | E0 | D0 | R0 | Q0 | P0 | V1 | H1 | S0 | ; 60 |
| F1 | K0 | L0 | R1 | G2 | A1 | Y0 | A3 | M0 | M0 | A0 | G0 | L1 | T1 | E0 | E1 | Q0 | K0 | A2 | H0 | ; 80 |
| G0 | V1 | I0 | T0 | A0 | S1 | A2 | G0 | N0 | H0 | A2 | Q0 | G2 | V3 | A0 | F0 | S1 | S2 | A0 | R0 | ;100 |
| L1 | G0 | V0 | K0 | A0 | L2 | I1 | V0 | M0 | P0 | T0 | A2 | T0 | A3 | D0 | I1 | K0 | V2 | D0 | A1 | ;120 |
| V0 | R0 | G0 | F0 | G0 | G3 | E0 | V0 | L0 | L1 | H1 | G0 | A2 | N0 | F1 | D0 | E0 | A2 | K0 | A1 | ;140 |
| K0 | A0 | I1 | E0 | L0 | S1 | Q0 | Q0 | Q0 | G2 | F0 | T0 | W0 | V1 | P0 | P0 | F1 | D0 | H0 | P0 | ;160 |
| M0 | V0 | I0 | A3 | G1 | Q0 | G0 | T2 | L0 | A0 | L1 | E0 | L0 | L4 | Q0 | Q1 | D0 | A1 | H1 | L0 | ;180 |
| D0 | R0 | V0 | F0 | V0 | P0 | V3 | G1 | G3 | G3 | G0 | L3 | A3 | A2 | G3 | V2 | A2 | V0 | L0 | I1 | ;200 |
| K0 | Q0 | L2 | M0 | P0 | Q0 | I1 | K1 | V1 | I0 | A1 | V0 | E0 | A1 | E1 | D0 | S0 | A1 | C1 | L0 | ;220 |
| K0 | A0 | A0 | L1 | D0 | A3 | G1 | H0 | P0 | V2 | D0 | L0 | P1 | R0 | V3 | G0 | L0 | F0 | A0 | E0 | ;240 |
| G1 | V3 | A0 | V0 | K1 | R0 | I0 | G0 | D1 | E0 | T0 | F0 | R2 | L0 | C0 | Q0 | E0 | Y0 | L4 | D1 | ;260 |
| D1 | I1 | I1 | T0 | V1 | D1 | S0 | D0 | A0 | I0 | C1 | A1 | A0 | M0 | K0 | D1 | L0 | F1 | E0 | D0 | ;280 |
| V0 | R0 | A0 | V3 | A3 | E0 | P1 | S2 | G1 | A2 | L1 | A0 | L2 | A1 | G0 | M0 | K0 | K1 | Y1 | I0 | ;300 |
| A1 | L2 | H1 | N0 | I0 | R0 | G0 | E0 | R1 | L0 | A1 | H0 | I1 | L0 | S2 | G3 | A1 | N0 | V2 | N0 | ;320 |
| F1 | H0 | G0 | L0 | R0 | Y1 | V1 | S0 | E0 | R2 | C1 | E0 | L0 | G0 | E1 | Q1 | R0 | E0 | A0 | L4 | ;340 |
| L0 | A1 | V1 | T0 | I1 | P1 | E1 | E1 | K1 | G0 | S0 | F0 | L0 | K0 | F0 | C0 | Q0 | L0 | L1 | G2 | ;360 |
| G0 | R0 | S0 | V2 | T0 | E0 | F1 | N0 | Y1 | R1 | F0 | A1 | D0 | A0 | K0 | N1 | A0 | C0 | I0 | F1 | ;380 |
| V0 | G0 | V2 | R0 | L0 | S3 | R0 | G0 | L0 | E0 | E1 | R1 | K1 | E1 | I0 | L0 | Q0 | M0 | L0 | N0 | ;400 |
| D0 | G1 | G1 | Y0 | S3 | V0 | V0 | D0 | L4 | S0 | D1 | D0 | E0 | M0 | A1 | K1 | L0 | H0 | V0 | R1 | ;420 |
| Y0 | M0 | V0 | G2 | G1 | R0 | P0 | S2 | H1 | P0 | L2 | Q0 | E0 | R1 | L2 | Y1 | S0 | F1 | E1 | F0 | ;440 |
| P0 | E1 | S1 | P2 | G1 | A2 | L0 | L1 | R1 | F1 | L0 | N0 | T0 | L0 | G2 | T1 | Y1 | W0 | N0 | I1 | ;460 |
| S0 | L0 | F0 | H1 | Y0 | R1 | S3 | H0 | G1 | T2 | D1 | Y1 | G1 | R2 | V2 | L0 | A3 | A0 | F0 | E0 | ;480 |
| L0 | G2 | D1 | H1 | E0 | P0 | D1 | F1 | E0 | T0 | R1 | L0 | N0 | E0 | L1 | G0 | Y1 | D1 | C0 | H0 | ;500 |
| D1 | E0 | T0 | N0 | N0 | P0 | A0 | F0 | R1 | F0 | F0 | L0 | A2 | G2 | | | | | | | ;514 |

*FIG. 34* threonine deaminase by direct self-assembly, designed codon usage dashed line, circles = codon usage in designed threonine deaminase by direct self-assembly solid line, x's = codon usage in E. coli native threonine deaminase for comparison

[ATGGCGGATTCTCAGCCGTTGTCTGGTGCCCCG]
[ATGGCGGATTCTCAGCCGTTGTCTGGTGCCCCG] [GAAGGCGCGGAGTATCTTCGGGCGGTA]
[GAAGGCGCGGAGTATCTTCGGGCGGTA] [CTGCGAGCTCCAGTGTATGAAGCCGCACA]
[CTGCGAGCTCCAGTGTATGAAGCCGCACA] [GGTGACCCCGCTGCAAAAAATGGAGAAACTG]
[GGTGACCCCGCTGCAAAAAATGGAGAAACTG] [AGCTCCCGTCTGGATAACGTCATCCTGGT]
[AGCTCCCGTCTGGATAACGTCATCCTGGT] [CAAACGCGAAGATCGTCAGCCGGTTCACAGC]
[CAAACGCGAAGATCGTCAGCCGGTTCACAGC] [TTCAAACTGCGCGGGGCCTATGCTATGAT]
[TTCAAACTGCGCGGGGCCTATGCTATGAT] [GGCGGGCTTAACGGAAGAGCAGAAAGCACAT]
[GGCGGGCTTAACGGAAGAGCAGAAAGCACAT] [GGCGTTATTACCGCGTCTGCAGGCAACCA]
[GGCGTTATTACCGCGTCTGCAGGCAACCA] [TGCACAGGGGGTAGCGTTTTCTAGTGCGCGT]
[TGCACAGGGGGTAGCGTTTTCTAGTGCGCGT] [TTAGGCGTGAAAGCGTTGATCGTGATGCC]
[TTAGGCGTGAAAGCGTTGATCGTGATGCC] [GACCGCAACCGCTGATATCAAAGTCGATGCC]
[GACCGCAACCGCTGATATCAAAGTCGATGCC] [GTGCGTGGCTTTGGCGGAGAAGTGCTGTT]
[GTGCGTGGCTTTGGCGGAGAAGTGCTGTT] [ACACGGCGCAAACTTCGATGAAGCAAAAGCC]
[ACACGGCGCAAACTTCGATGAAGCAAAAGCC] [AAAGCGATCGAACTGTCTCAGCAGCAGGG]
[AAAGCGATCGAACTGTCTCAGCAGCAGGG] [GTTTACCTGGGTTCCGCCGTTCGATCATCCG]
[GTTTACCTGGGTTCCGCCGTTCGATCATCCG] [ATGGTGATTGCTGGTCAGGGCACTCTGGC]
[ATGGTGATTGCTGGTCAGGGCACTCTGGC] [GTTAGAACTGCTCCAGCAAGATGCCCACC]
[GTTAGAACTGCTCCAGCAAGATGCCCACC] [TGGATCGTGTGTTTGTGCCGGTAGGTG]
[TGGATCGTGTGTTTGTGCCGGTAGGTG] [GAGGAGGCCTTGCTGCAGGAGTCGCAG]
[GAGGAGGCCTTGCTGCAGGAGTCGCAG] [TGCTGATCAAACAGTTGATGCCGCAGATCAAGG]
[TGCTGATCAAACAGTTGATGCCGCAGATCAAGG] [TTATTGCCGTGGAAGCCGAGGATAGCG]
[TTATTGCCGTGGAAGCCGAGGATAGCG] [CCTGTCTGAAAGCGGCGTTAGATGCTGGTCATC]
[CCTGTCTGAAAGCGGCGTTAGATGCTGGTCATC] [CGGTCGATCTGCCACGTGTAGGCCTGT]
[CGGTCGATCTGCCACGTGTAGGCCTGT] [TTGCGGAAGGTGTAGCGGTGAAGCGTATTGGCG]
[TTGCGGAAGGTGTAGCGGTGAAGCGTATTGGCG] [ACGAAACCTTTCGGCTGTGCCAGGAAT]
[ACGAAACCTTTCGGCTGTGCCAGGAAT] [ATCTCGACGACATCATCACCGTTGACAGCGAT]
[ATCTCGACGACATCATCACCGTTGACAGCGAT] [GCGATTTGTGCCGCGATGAAAGACCTGT]
[GCGATTTGTGCCGCGATGAAAGACCTGT] [TCGAAGATGTGCGTGCGGTAGCTGAACCAAGT]
[TCGAAGATGTGCGTGCGGTAGCTGAACCAAGT] [GGTGCATTAGCGTTGGCCGGCATGAAAA]
[GGTGCATTAGCGTTGGCCGGCATGAAAA] [AGTACATTGCCTTGCACAACATTCGTGGCGAA]
[AGTACATTGCCTTGCACAACATTCGTGGCGAA] [CGCCTGGCCCATATCCTGAGTGGAGCCA]
[CGCCTGGCCCATATCCTGAGTGGAGCCA] [ACGTCAACTTCCATGGCCTGCGTTACG]
[ACGTCAACTTCCATGGCCTGCGTTACG] [TTAGCGAACGGTGTGAACTGGGCGAGC]
[TTAGCGAACGGTGTGAACTGGGCGAGC] [AACGTGAAGCGCTCCTGGCCGTTACCA]
[AACGTGAAGCGCTCCTGGCCGTTACCA] [TCCCAGAGGAGAAGGGCAGCTTTCTGA]
[TCCCAGAGGAGAAGGGCAGCTTTCTGA] [AATTTTGCCAGCTGTTAGGGGGCCGTA]
[AATTTTGCCAGCTGTTAGGGGGCCGTA] [GCGTCACCGAATTCAACTACCGCTTTGCCGAT]
[GCGTCACCGAATTCAACTACCGCTTTGCCGAT] [GCGAAAAATGCGTGCATTTTCGTGGGCG]
[GCGAAAAATGCGTGCATTTTCGTGGGCG] [TCCGTCTGTCCCGTGGCCTGGAAGAGC]
[TCCGTCTGTCCCGTGGCCTGGAAGAGC] [GCAAGGAGATTCTGCAGATGCTGAACGATGGT]
[GCAAGGAGATTCTGCAGATGCTGAACGATGGT] [GGTTATTCCGTGGTGGATCTCAGCGACG]
[GGTTATTCCGTGGTGGATCTCAGCGACG] [ATGAAATGGCCAAGCTGCATGTGCGCT]
[ATGAAATGGCCAAGCTGCATGTGCGCT] [ATATGGTGGGGGGTCGTCCGAGTCACC]
[ATATGGTGGGGGGTCGTCCGAGTCACC] [CGTTGCAGGAACGCTTGTACAGCTTCGA]
[CGTTGCAGGAACGCTTGTACAGCTTCGA] [GTTTCCGGAGTCTCCTGGTGCACTGTT]
[GTTTCCGGAGTCTCCTGGTGCACTGTT] [ACGCTTCCTGAACACCCTGGGGACGTA]
[ACGCTTCCTGAACACCCTGGGGACGTA] [CTGGAACATCAGCCTGTTTCACTATCGCTCCC]
[CTGGAACATCAGCCTGTTTCACTATCGCTCCC] [ATGGTACTGACTACGGTCGGGTCCTGG]
[ATGGTACTGACTACGGTCGGGTCCTGG] [CTGCGTTTGAACTGGGGGACCACGAAC]
[CTGCGTTTGAACTGGGGGACCACGAAC] [CGGACTTCGAAACCCGCCTGAACGAATT]
[CGGACTTCGAAACCCGCCTGAACGAATT] [AGGCTACGACTGCCATGACGAAACCAACAAC]
[AGGCTACGACTGCCATGACGAAACCAACAAC] [CCGGCGTTTCGCTTTTTTCTGGCAGGG]
[CCGGCGTTTCGCTTTTTTCTGGCAGGG]

*FIG. 36*

Gene Leaders (1) Gene Leader-0
5'-TCCTCGAGCATAATGGCGGATTCTCAGCCGTTGTCTGGTGCCCCG-3'
(45-mer)
(2) Gene Leader-0 Prefix (rev cmp)
5'-TATGCTCGAGGA-3'
(12-mer)
(3) Gene Leader-1
5'-GACGACGACGACAAGCATATGCTCGAGGATATGGCGGATTCTCAGCCGTTGTCTGGTGCCCCG-3'
(63-mer)
(4) Gene Leader-1 Prefix (rev cmp)
5'-ATCCTCGAGCATATGCTTGTCGTCGTCGTC-3'
(30-mer)

*FIG. 37A*

(5) Seg-0-0
5'-ATGGCGGATTCTCAGCCGTTGTCTGGTGCCCCG-3'
(33-mer)
(6) Seg-0-1 (rev cmp)
5'-TACCGCCCGAAGATACTCCGCGCCTTCCGGGGCACCAGACAACGGCTGAGAATCCGCCAT-3'
(60-mer)
(7) Seg-0-2
5'-GAAGGCGCGGAGTATCTTCGGGCGGTACTGCGAGCTCCAGTGTATGAAGCCGCACA-3'
(56-mer)
(8) Seg-0-3 (rev cmp)
5'-CAGTTTCTCCATTTTTTGCAGCGGGGTCACCTGTGCGGCTTCATACACTGGAGCTCGCAG-3'
(60-mer)
(9) Seg-0-4
5'-GGTGACCCCGCTGCAAAAAATGGAGAAACTGAGCTCCCGTCTGGATAACGTCATCCTGGT-3'
(60-mer)
(10) Seg-0-5 (rev cmp)
5'-GCTGTGAACCGGCTGACGATCTTCGCGTTTGACCAGGATGACGTTATCCAGACGGGAGCT-3'
(60-mer)
(11) Seg-0-6
5'-CAAACGCGAAGATCGTCAGCCGGTTCACAGCTTCAAACTGCGCGGGGCCTATGCTATGAT-3'
(60-mer)
(12) Seg-0-7 (rev cmp)
5'-ATGTGCTTTCTGCTCTTCCGTTAAGCCCGCCATCATAGCATAGGCCCCGCGCAGTTTGAA-3'
(60-mer)
(13) Seg-0-8
5'-GGCGGGCTTAACGGAAGAGCAGAAAGCACATGGCGTTATTACCGCGTCTGCAGGCAACCA-3'
(60-mer)
(14) Seg-0-9 (rev cmp)
5'-ACGCGCACTAGAAAACGCTACCCCCTGTGCATGGTTGCCTGCAGACGCGGTAATAACGCC-3'
(60-mer)
(15) Seg-0-10
5'-TGCACAGGGGGTAGCGTTTTCTAGTGCGCGTTTAGGCGTGAAAGCGTTGATCGTGATGCC-3'
(60-mer)
(16) Seg-0-11 (rev cmp)
5'-GGCATCGACTTTGATATCAGCGGTTGCGGTCGGCATCACGATCAACGCTTTCACGCCTAA-3'
(60-mer)
(17) Seg-0-12
5'-GACCGCAACCGCTGATATCAAAGTCGATGCCGTGCGTGGCTTTGGCGGAGAAGTGCTGTT-3'
(60-mer)
(18) Seg-0-13 (rev cmp)
5'-GGCTTTTGCTTCATCGAAGTTTGCGCCGTGTAACAGCACTTCTCCGCCAAAGCCACGCAC-3'
(60-mer)
(19) Seg-0-14
5'-ACACGGCGCAAACTTCGATGAAGCAAAAGCCAAAGCGATCGAACTGTCTCAGCAGCAGGG-3'
(60-mer)

*FIG. 37B*

(20) Seg-0-15 (rev cmp)
5'-CGGATGATCGAACGGCGGAACCCAGGTAAACCCCTGCTGCTGAGACAGTTCGATCGCTTT-3'
(60-mer)
(21) Seg-0-16
5'-GTTTACCTGGGTTCCGCCGTTCGATCATCCGATGGTGATTGCTGGTCAGGGCACTCTGGC-3'
(60-mer)
(22) Seg-0-17 (rev cmp)
5'-GGTGGGCATCTTGCTGGAGCAGTTCTAACGCCAGAGTGCCCTGACCAGCAATCACCAT-3'
(58-mer)
(23) Seg-0-18
5'-GTTAGAACTGCTCCAGCAAGATGCCCACCTGGATCGTGTGTTTGTGCCGGTAGGTG-3'
(56-mer)
(24) Seg-0-19 (rev cmp)
5'-CTGCGACTCCTGCAGCAAGGCCTCCTCCACCTACCGGCACAAACACACGATCCA-3'
(54-mer)
(25) Seg-0-20
5'-GAGGAGGCCTTGCTGCAGGAGTCGCAGTGCTGATCAAACAGTTGATGCCGCAGATCAAGG-3'
(60-mer)
(26) Seg-0-21 (rev cmp)
5'-CGCTATCCTCGGCTTCCACGGCAATAACCTTGATCTGCGGCATCAACTGTTTGATCAGCA-3'
(60-mer)
(27) Seg-0-22
5'-TTATTGCCGTGGAAGCCGAGGATAGCGCCTGTCTGAAAGCGGCGTTAGATGCTGGTCATC-3'
(60-mer)
(28) Seg-0-23 (rev cmp)
5'-ACAGGCCTACACGTGGCAGATCGACCGGATGACCAGCATCTAACGCCGCTTTCAGACAGG-3'
(60-mer)
(29) Seg-0-24
5'-CGGTCGATCTGCCACGTGTAGGCCTGTTTGCGGAAGGTGTAGCGGTGAAGCGTATTGGCG-3'
(60-mer)
(30) Seg-0-25 (rev cmp)
5'-ATTCCTGGCACAGCCGAAAGGTTTCGTCGCCAATACGCTTCACCGCTACACCTTCCGCAA-3'
(60-mer)
(31) Seg-0-26
5'-ACGAAACCTTTCGGCTGTGCCAGGAATATCTCGACGACATCATCACCGTTGACAGCGAT-3'
(59-mer)
(32) Seg-0-27 (rev cmp)
5'-ACAGGTCTTTCATCGCGGCACAAATCGCATCGCTGTCAACGGTGATGATGTCGTCGAGAT-3'
(60-mer)

*FIG. 37C*

(33) Seg-0-28
5'-GCGATTTGTGCCGCGATGAAAGACCTGTTCGAAGATGTGCGTGCGGTAGCTGAACCAAGT-3'
(60-mer)
(34) Seg-0-29 (rev cmp)
5'-TTTTCATGCCGGCCAACGCTAATGCACCACTTGGTTCAGCTACCGCACGCACATCTTCGA-3'
(60-mer)
(35) Seg-0-30
5'-GGTGCATTAGCGTTGGCCGGCATGAAAAAGTACATTGCCTTGCACAACATTCGTGGCGAA-3'
(60-mer)
(36) Seg-0-31 (rev cmp)
5'-TGGCTCCACTCAGGATATGGGCCAGGCGTTCGCCACGAATGTTGTGCAAGGCAATGTACT-3'
(60-mer)
(37) Seg-0-32
5'-CGCCTGGCCCATATCCTGAGTGGAGCCAACGTCAACTTCCATGGCCTGCGTTACG-3'
(55-mer)
(38) Seg-0-33 (rev cmp)
5'-GCTCGCCCAGTTCACACCGTTCGCTAACGTAACGCAGGCCATGGAAGTTGACGT-3'
(54-mer)
(39) Seg-0-34
5'-TTAGCGAACGGTGTGAACTGGGCGAGCAACGTGAAGCGCTCCTGGCCGTTACCA-3'
(54-mer)
(40) Seg-0-35 (rev cmp)
5'-TCAGAAAGCTGCCCTTCTCCTCTGGGATGGTAACGGCCAGGAGCGCTTCACGTT-3'
(54-mer)
(41) Seg-0-36
5'-TCCCAGAGGAGAAGGGCAGCTTTCTGAAATTTTGCCAGCTGTTAGGGGGCCGTA-3'
(54-mer)
(42) Seg-0-37 (rev cmp)
5'-ATCGGCAAAGCGGTAGTTGAATTCGGTGACGCTACGGCCCCCTAACAGCTGGCAAAATT-3'
(59-mer)
(43) Seg-0-38
5'-GCGTCACCGAATTCAACTACCGCTTTGCCGATGCGAAAAATGCGTGCATTTTCGTGGGCG-3'
(60-mer)
(44) Seg-0-39 (rev cmp)
5'-GCTCTTCCAGGCCACGGGACAGACGGACGCCCACGAAAATGCACGCATTTTTCGC-3'
(55-mer)
(45) Seg-0-40
5'-TCCGTCTGTCCCGTGGCCTGGAAGAGCGCAAGGAGATTCTGCAGATGCTGAACGATGGT-3'
(59-mer)

*FIG. 37D*

(46) Seg-0-41 (rev cmp)
5'-CGTCGCTGAGATCCACCACGGAATAACCACCATCGTTCAGCATCTGCAGAATCTCCTTGC-3'
(60-mer)
(47) Seg-0-42
5'-GGTTATTCCGTGGTGGATCTCAGCGACGATGAAATGGCCAAGCTGCATGTGCGCT-3'
(55-mer)
(48) Seg-0-43 (rev cmp)
5'-GGTGACTCGGACGACCCCCCACCATATAGCGCACATGCAGCTTGGCCATTTCAT-3'
(54-mer)
(49) Seg-0-44
5'-ATATGGTGGGGGGTCGTCCGAGTCACCCGTTGCAGGAACGCTTGTACAGCTTCGA-3'
(55-mer)
(50) Seg-0-45 (rev cmp)
5'-AACAGTGCACCAGGAGACTCCGGAAACTCGAAGCTGTACAAGCGTTCCTGCAACG-3'
(55-mer)
(51) Seg-0-46
5'-GTTTCCGGAGTCTCCTGGTGCACTGTTACGCTTCCTGAACACCCTGGGGACGTA-3'
(54-mer)
(52) Seg-0-47 (rev cmp)
5'-GGGAGCGATAGTGAAACAGGCTGATGTTCCAGTACGTCCCCAGGGTGTTCAGGAAGCGT-3'
(59-mer)
(53) Seg-0-48
5'-CTGGAACATCAGCCTGTTTCACTATCGCTCCCATGGTACTGACTACGGTCGGGTCCTGG-3'
(59-mer)
(54) Seg-0-49 (rev cmp)
5'-GTTCGTGGTCCCCCAGTTCAAACGCAGCCAGGACCCGACCGTAGTCAGTACCAT-3'
(54-mer)
(55) Seg-0-50
5'-CTGCGTTTGAACTGGGGGACCACGAACCGGACTTCGAAACCCGCCTGAACGAATT-3'
(55-mer)
(56) Seg-0-51 (rev cmp)
5'-GTTGTTGGTTTCGTCATGGCAGTCGTAGCCTAATTCGTTCAGGCGGGTTTCGAAGTCCG-3'
(59-mer)
(57) Seg-0-52
5'-AGGCTACGACTGCCATGACGAAACCAACAACCCGGCGTTTCGCTTTTTTCTGGCAGGG-3'
(58-mer)
(58) Seg-0-53 (rev cmp)
5'-CCCTGCCAGAAAAAAGCGAAACGCCGG-3'
(27-mer)

*FIG. 37E*

Gene Trailers

(59) Gene Trailer-0 (rev cmp)
5'-GCGGCAGCCATATTACCCTGCCAGAAAAAAGCGAAACGCCGG-3'
(42-mer)
(60) Gene Trailer-0 Suffix
5'-TAATATGGCTGCCGC-3'
(15-mer)
(61) Gene Trailer-1 (rev cmp)
5'-TTAAGCGTAATCCGGAACATCGTATGGGTACCCTGCCAGAAAAAAGCGAAACGCCGG-3'
(57-mer)
(62) Gene Trailer-1 Suffix
5'-TACCCATACGATGTTCCGGATTACGCTTAA-3'
(30-mer)

FIG. 37F

Gene Leaders

1) Gene Leader-0
5'-CTATATCTAGCATATGTCATTCATGGACCAG-3'
31-mer

FIG. 40A

Strand 0

2) Seg-0-0
5'-ATGTCATTCATGGACCAGATTCCGGGCGGGGGTAAC-3'
36-mer
3) Seg-0-1 (rev cmp)
5'-GCAAACATTCTACTGGCAATTTAGGATAGTTACCCCCGCCCGGAATC-3'
47-mer
4) Seg-0-2
5'-GCCAGTAGAATGTTTGCCGAATTTTCCCATTCAACCAAGTCTGACC-3'
46-mer
5) Seg-0-3 (rev cmp)
5'-GTTTGTGGCTATCGTTTCTCCCGCGAAAGGTCAGACTTGGTTGAATG-3'
47-mer
6) Seg-0-4
5'-GAAACGATAGCCACAAACTGAAGAATTTCATTAGCGAGATTATGCTCAAC-3'
50-mer
7) Seg-0-5 (rev cmp)
5'-CATCGTTAGGCCAAGAGATCATCGACATGTTGAGCATAATCTCGCTAATG-3'
50-mer
8) Seg-0-6
5'-CTCTTGGCCTAACGATGCGTCTAGAATTGTGTACTGCCGTCGTCATTTAC-3'
50-mer
9) Seg-0-7 (rev cmp)
5'-CAAAGTCATTAGCCCACTGAGCAGCTGGATTAAGTAAATGACGACGGCAG-3'
50-mer
10) Seg-0-8
5'-GTGGGCTAATGACTTTGTGCAAGAACAGGGTATTCTCGAGATTACGTTCG-3'
50-mer
11) Seg-0-9 (rev cmp)
5'-GTTGATACAGCCCCTGGATAAATGTATCGAACGTAATCTCGAGAATAC-3'
48-mer

FIG. 40B

Strand 1

12) Seg-1-0
5'-GTATTCTCGAGATTACGTTCGATACATTTATCCAGGGGCTGTATCAAC-3'
48-mer
13) Seg-1-1 (rev cmp)
5'-GATTTTATTGATATCAGGCGGTTTATAAAAGTGTTGATACAGCCCCTGG-3'
49-mer
14) Seg-1-2
5'-CCGCCTGATATCAATAAAATCTTTAACGCCATCACGCAGCTGTCCGAGGC-3'
50-mer
15) Seg-1-3 (rev cmp)
5'-CCGTTGATTCAGACGTTCAATGCCTAATTTTGCCTCGGACAGCTGCGTG-3'
49-mer
16) Seg-1-4
5'-GAACGTCTGAATCAACGGTTTCGGAAAATTTGGGATCGCATGCCACCAG-3'
49-mer
17) Seg-1-5 (rev cmp)
5'-CATAATTGCGGCCTTTTCTGTCATGAAATCTGGTGGCATGCGATCC-3'
46-mer
18) Seg-1-6
5'-GAAAAGGCCGCAATTATGACGTATACCCGGTTACTGACGAAAGAGACC-3'
48-mer
19) Seg-1-7 (rev cmp)
5'-CTCCGGCTTATGCATACGTACAATATTATAGGTCTCTTTCGTCAGTAAC-3'
49-mer
20) Seg-1-8
5'-GTATGCATAAGCCGGAGACCCTGAAAGATGCGATGGAGGAAGCCTACCAG-3'
50-mer
21) Seg-1-9 (rev cmp)
5'-CAGGGAAGAATCGTTCGGTAAGGGCAGTGGTCTGGTAGGCTTCCTCCATC-3'
50-mer

*FIG. 40C*

Strand 2

22) Seg-2-0
5'-GATGGAGGAAGCCTACCAGACCACTGCCCTTACCGAACGATTCTTCCCTG-3'
50-mer
23) Seg-2-1 (rev cmp)
5'-GATGGTATCTCCGTCCGCGTCCAGTTCAAAGCCAGGGAAGAATCGTTCG-3'
49-mer
24) Seg-2-2
5'-CGGACGGAGATACCATCATAGGCGCAACCACTCACTTGCAGGAAGAGTAC-3'
50-mer
25) Seg-2-3 (rev cmp)
5'-CAGGTTATCTTCCGAATCGTAATCAGAATCGTACTCTTCCTGCAAGTGAG-3'
50-mer
26) Seg-2-4
5'-CGATTCGGAAGATAACCTGACCCAAAATGGCTACGTTCACACTGTTAGG-3'
49-mer
27) Seg-2-5 (rev cmp)
5'-GCTCATGGGCTTATTGTATGAACGACGGGTCCTAACAGTGTGAACGTAG-3'
49-mer
28) Seg-2-6
5'-CATACAATAAGCCCATGAGCAACCATCGGAACCGCAGAAACAACAACCCG-3'
50-mer
29) Seg-2-7 (rev cmp)
5'-GCACAGACGGTTTTTGATGCATTCTTCTCGGCTCGGGTTGTTGTTTCTGC-3'
50-mer
30) Seg-2-8
5'-CATCAAAAACCGTCTGTGCTTTTATTGTAAGAAAGAAGGCCATCGACTG-3'
49-mer
31) Seg-2-9 (rev cmp)
5'-GAGCTTGCTTTACGGGCACGGCATTCATTCAGTCGATGGCCTTCTTTC-3'
48-mer
32) Seg-2-10
5'-GCCCGTAAAGCAAGCTCTAACCGTAGC-3'
27-mer
33) Strand-2-trailer (rev cmp)
5'-GCTACGGTTAGAGCTTG-3'
17-mer

*FIG. 40D*

Gene Trailers

34) Gene Trailer-0 (rev cmp)
5'-GTATTGGATCCTTATTAGCTACGGTTAGAGCTTG-3'
34-mer

*FIG. 40E*

```
CTATATCTAGCATATGACCATCACCCCGGAAACCTCTCGCCCGATCGACA ;    0-  49
CCGAATCTTGGAAATCTTACTACAAATCCGACCCGCTGTGCTCTGCTGTT ;   50-  99
CTGATCCACATGAAAGAACTGACCCAGCACAACGTTACCCCAGAAGACAT ;  100- 149
GTCCGCTTTCCGCTCCTATCAGAAAAAGCTGGAACTGTCTGAGACCTTCC ;  150- 199
GTAAAAACTACTCCCTGGAGGACGAAATGATCTACTACCAAGATCGCCTG ;  200- 249
GTTGTACCGATTAAACAACAAAATGCTGTCATGCGTCTGTATCACGATCA ;  250- 299
CACTCTGTTTGGTGGTCACTTTGGCGTAACCGTTACCCTGGCGAAAATCT ;  300- 349
CTCCGATCTACTATTGGCCGAAACTGCAGCACTCTATCATCCAGTACATC ;  350- 399
CGTACCTGCGTTCAGTGCCAGCTGATCAAATCTCACCGCCCACGTCTGCA ;  400- 449
TGGTCTCCTGCAACCGCTCCCGATCGCTGAAGGTCGTTGGCTGGACATCT ;  450- 499
CTATGGACTTCGTTACTGGTTTGCCGCCGACCTCTAACAACCTGAACATG ;  500- 549
ATCCTGGTGGTGGTGGACCGCTTCTCTAAACGTGCTCACTTCATCGCTAC ;  550- 599
CCGAAAAACCCTGGACGCGACTCAGCTGATCGACCTGCTCTTCCGTTACA ;  600- 649
TCTTCTCTTACCATGGCTTCCCGCGTACCATCACCTCTGACCGTGACGTT ;  650- 699
CGTATGACTGCGGACAAATACCAAGAACTGACCAAACGTCTGGGTATCAA ;  700- 749
ATCTACCATGTCTTCCGCTAACCACCCGCAGACTGATGGTCAATCCGAGC ;  750- 799
GTACCATTCAGACCCTGAACCGTCTCCTGCGTGCGTATGCGTCTACCAAC ;  800- 849
ATCCAGAACTGGCACGTTTACCTTCCGCAAATTGAATTCGTTTACAACTC ;  850- 899
CACTCCGACTCGTACTCTGGGTAAATCTCCGTTCGAAATCGACCTGGGTT ;  900- 949
ACCTGCCAAACACTCCGGCGATCAAATCTGACGATGAAGTTAACGCTCGT ;  950- 999
TCCTTCACCGCTGTTGAACTGGCTAAACACCTGAAGGCGCTGACCATCCA ;1000-1049
GACCAAAGAACAGCTGGAACACGCGCAGATCGAAATGGAAACCAACAACA ;1050-1099
ACCAGCGTCGCAAACCACTGCTGTTGAATATTGGTGATCATGTTCTGGTA ;1100-1149
CACCGTGATGCCTACTTCAAAAAAGGTGCGTACATGAAAGTTCAGCAGAT ;1150-1199
CTACGTTGGTCCATTCCGTGTCGTTAAGAAAATCAATGACAACGCGTATG ;1200-1249
AACTGGACCTGAACTCGCATAAGAAGAAGCACCGTGTGATCAACGTTCAG ;1250-1299
TTTCTGAAAAAATTTGTTTACCGTCCGGATGCGTACCCGAAAAACAAACC ;1300-1349
GATCTCTTCTACCGAACGCATCAAACGAGCTCACGAAGTTACCGCGCTGA ;1350-1399
TCGGCATCGACACCACCCACAAAACCTATCTGTGCCACATGCAGGACGTT ;1400-1449
GACCCGACCCTGTCCGTTGAATACTCCGAAGCTGAATTCTGCCAGATCCC ;1450-1499
AGAGCGTACCCGTCGTTCTATCCTGGCGAACTTCCGTCAGCTGTACGAAA ;1500-1549
CCCAAGACAACCCTGAACGTGAAGAAGATGTTGTTTCCCAGAACGAAATC ;1550-1599
TGCCAGTACGACAACACCTCTCCGTAATAAGGATCCAATAC          ;1600-1640
```

*FIG. 44*

Leader-0:
CTATATCTAGCATATG [ACCATCACCCCGGAAACCTCTCGCCCGATC]

FIG. 45A

Strand 0:
[ACCATCACCCCGGAAACCTCTCGCC]
[ACCATCACCCCGGAAACCTCTCGCC] [CGATCGACACCGAATCTTGGAAATC]
[CGATCGACACCGAATCTTGGAAATC] [TTACTACAAATCCGACCCGCTGTGC]
[TTACTACAAATCCGACCCGCTGTGC] [TCTGCTGTTCTGATCCACATGAAAG]
[TCTGCTGTTCTGATCCACATGAAAG] [AACTGACCCAGCACAACGTTACCC]
[AACTGACCCAGCACAACGTTACCC] [CAGAAGACATGTCCGCTTTCC]
[CAGAAGACATGTCCGCTTTCC] [GCTCCTATCAGAAAAAGCTGGAACT]
[GCTCCTATCAGAAAAAGCTGGAACT] GTCTGAGACCTTCCGTAAAAACT

FIG. 45B

Strand 1:
GCTCCTATCAGAAAAAGCTGGAACT [GTCTGAGACCTTCCGTAAAAACT]
[GTCTGAGACCTTCCGTAAAAACT] [ACTCCCTGGAGGACGAAATGATCTACT]
[ACTCCCTGGAGGACGAAATGATCTACT] [ACCAAGATCGCCTGGTTGTACCG]
[ACCAAGATCGCCTGGTTGTACCG] [ATTAAACAACAAAATGCTGTCATGCG]
[ATTAAACAACAAAATGCTGTCATGCG] [TCTGTATCACGATCACACTCTGTT]
[TCTGTATCACGATCACACTCTGTT] [TGGTGGTCACTTTGGCGTAACCGTTA]
[TGGTGGTCACTTTGGCGTAACCGTTA] [CCCTGGCGAAAATCTCTCCGATCT]
[CCCTGGCGAAAATCTCTCCGATCT] ACTATTGGCCGAAACTGCAGCACTCT

FIG. 45C

Strand 2:
CCCTGGCGAAAATCTCTCCGATCT [ACTATTGGCCGAAACTGCAGCACTCT]
[ACTATTGGCCGAAACTGCAGCACTCT] [ATCATCCAGTACATCCGTACCTGC]
[ATCATCCAGTACATCCGTACCTGC] [GTTCAGTGCCAGCTGATCAAATCTCA]
[GTTCAGTGCCAGCTGATCAAATCTCA] [CCGCCCACGTCTGCATGGTCTCCT]
[CCGCCCACGTCTGCATGGTCTCCT] [GCAACCGCTCCCGATCGCTGAAGGTC]
[GCAACCGCTCCCGATCGCTGAAGGTC] [GTTGGCTGGACATCTCTATGGACT]
[GTTGGCTGGACATCTCTATGGACT] [TCGTTACTGGTTTGCCGCCGACC]
[TCGTTACTGGTTTGCCGCCGACC] TCTAACAACCTGAACATGATCCTGGTG

FIG. 45D

Strand 3:
TCGTTACTGGTTTGCCGCCGACC [TCTAACAACCTGAACATGATCCTGGTG]
[TCTAACAACCTGAACATGATCCTGGTG] [GTGGTGGACCGCTTCTCTAAACG]
[GTGGTGGACCGCTTCTCTAAACG] [TGCTCACTTCATCGCTACCCGAAAAAC]
[TGCTCACTTCATCGCTACCCGAAAAAC] [CCTGGACGCGACTCAGCTGATCG]
[CCTGGACGCGACTCAGCTGATCG] [ACCTGCTCTTCCGTTACATCTTCTCTT]
[ACCTGCTCTTCCGTTACATCTTCTCTT] [ACCATGGCTTCCCGCGTACCATC]
[ACCATGGCTTCCCGCGTACCATC] [ACCTCTGACCGTGACGTTCGTATGACT]
[ACCTCTGACCGTGACGTTCGTATGACT] GCGGACAAATACCAAGAACTGAC

FIG. 45E

Strand 4:
ACCTCTGACCGTGACGTTCGTATGACT [GCGGACAAATACCAAGAACTGAC]
[GCGGACAAATACCAAGAACTGAC] [CAAACGTCTGGGTATCAAATCTACCAT]
[CAAACGTCTGGGTATCAAATCTACCAT] [GTCTTCCGCTAACCACCCGCAGA]
[GTCTTCCGCTAACCACCCGCAGA] [CTGATGGTCAATCCGAGCGTACCATTC]
[CTGATGGTCAATCCGAGCGTACCATTC] [AGACCCTGAACCGTCTCCTGCGT]
[AGACCCTGAACCGTCTCCTGCGT] [GCGTATGCGTCTACCAACATCCAGAAC]
[GCGTATGCGTCTACCAACATCCAGAAC] [TGGCACGTTTACCTTCCGCAAAT]
[TGGCACGTTTACCTTCCGCAAAT] TGAATTCGTTTACAACTCCACTCCGAC

*FIG. 45F*

Strand 5:
TGGCACGTTTACCTTCCGCAAAT [TGAATTCGTTTACAACTCCACTCCGAC]
[TGAATTCGTTTACAACTCCACTCCGAC] [TCGTACTCTGGGTAAATCTCCGT]
[TCGTACTCTGGGTAAATCTCCGT] [TCGAAATCGACCTGGGTTACCTGCCAA]
[TCGAAATCGACCTGGGTTACCTGCCAA] [ACACTCCGGCGATCAAATCTGAC]
[ACACTCCGGCGATCAAATCTGAC] [GATGAAGTTAACGCTCGTTCCTTCACC]
[GATGAAGTTAACGCTCGTTCCTTCACC] [GCTGTTGAACTGGCTAAACACCT]
[GCTGTTGAACTGGCTAAACACCT] [GAAGGCGCTGACCATCCAGACCAAAGA]
[GAAGGCGCTGACCATCCAGACCAAAGA] ACAGCTGGAACACGCGCAGATCG

*FIG. 45G*

Strand 6:
GAAGGCGCTGACCATCCAGACCAAAGA [ACAGCTGGAACACGCGCAGATCG]
[ACAGCTGGAACACGCGCAGATCG] [AAATGGAAACCAACAACAACCAGCGTC]
[AAATGGAAACCAACAACAACCAGCGTC] [GCAAACCACTGCTGTTGAATATT]
[GCAAACCACTGCTGTTGAATATT] [GGTGATCATGTTCTGGTACACCGTGAT]
[GGTGATCATGTTCTGGTACACCGTGAT] [GCCTACTTCAAAAAAGGTGCGTA]
[GCCTACTTCAAAAAAGGTGCGTA] [CATGAAAGTTCAGCAGATCTACGTTGG]
[CATGAAAGTTCAGCAGATCTACGTTGG] [TCCATTCCGTGTCGTTAAGAAAA]
[TCCATTCCGTGTCGTTAAGAAAA] TCAATGACAACGCGTATGAACTGG

*FIG. 45H*

Strand 7:
TCCATTCCGTGTCGTTAAGAAAA [TCAATGACAACGCGTATGAACTGG]
[TCAATGACAACGCGTATGAACTGG] [ACCTGAACTCGCATAAGAAGAAGCAC]
[ACCTGAACTCGCATAAGAAGAAGCAC] [CGTGTGATCAACGTTCAGTTTCTG]
[CGTGTGATCAACGTTCAGTTTCTG] [AAAAAATTTGTTTACCGTCCGGATG]
[AAAAAATTTGTTTACCGTCCGGATG] [CGTACCCGAAAAACAAACCGATCTC]
[CGTACCCGAAAAACAAACCGATCTC] TTCTACCGAACGCATCAAACGAGCT

*FIG. 45I*

Strand 8:
CGTACCCGAAAAACAAACCGATCTC [TTCTACCGAACGCATCAAACGAGCT]
[TTCTACCGAACGCATCAAACGAGCT] [CACGAAGTTACCGCGCTGATCGGCA]
[CACGAAGTTACCGCGCTGATCGGCA] [TCGACACCACCCACAAAACCTATCT]
[TCGACACCACCCACAAAACCTATCT] [GTGCCACATGCAGGACGTTGACCCG]
[GTGCCACATGCAGGACGTTGACCCG] [ACCCTGTCCGTTGAATACTCCGAAG]
[ACCCTGTCCGTTGAATACTCCGAAG] CTGAATTCTGCCAGATCCCAGAGCG

*FIG. 45J*

Strand 9:
ACCCTGTCCGTTGAATACTCCGAAG [CTGAATTCTGCCAGATCCCAGAGCG]
[CTGAATTCTGCCAGATCCCAGAGCG] [TACCCGTCGTTCTATCCTGGCGAAC]
[TACCCGTCGTTCTATCCTGGCGAAC] [TTCCGTCAGCTGTACGAAACCCAAG]
[TTCCGTCAGCTGTACGAAACCCAAG] [ACAACCCTGAACGTGAAGAAGA]
[ACAACCCTGAACGTGAAGAAGA] [TGTTGTTTCCCAGAACGAAATCTG]
[TGTTGTTTCCCAGAACGAAATCTG] [CCAGTACGACAACACCTCTCCG]
[CCAGTACGACAACACCTCTCCG]

*FIG. 45K*

Trailer-0:
[GAAATCTGCCAGTACGACAACACCTCTCCG] TAATAAGGATCCAATAC

*FIG. 45L*

Gene Leaders

1) Gene Leader-0
5'-CTATATCTAGCATATGACCATCACCCCGGAAACCTCTCGCCCGATC-3'
46-mer

FIG. 46A

Strand 0

2) Seg-0-0
5'-ACCATCACCCCGGAAACCTCTCGCC-3'
25-mer
3) Seg-0-1 (rev cmp)
5'-GATTTCCAAGATTCGGTGTCGATCGGGCGAGAGGTTTCCGGGGTGATGGT-3'
50-mer
4) Seg-0-2
5'-CGATCGACACCGAATCTTGGAAATCTTACTACAAATCCGACCCGCTGTGC-3'
50-mer
5) Seg-0-3 (rev cmp)
5'-CTTTCATGTGGATCAGAACAGCAGAGCACAGCGGGTCGGATTTGTAGTAA-3'
50-mer
6) Seg-0-4
5'-TCTGCTGTTCTGATCCACATGAAAGAACTGACCCAGCACAACGTTACCC-3'
49-mer
7) Seg-0-5 (rev cmp)
5'-GGAAAGCGGACATGTCTTCTGGGGTAACGTTGTGCTGGGTCAGTT-3'
45-mer
8) Seg-0-6
5'-CAGAAGACATGTCCGCTTTCCGCTCCTATCAGAAAAAGCTGGAACT-3'
46-mer
9) Seg-0-7 (rev cmp)
5'-AGTTTTTACGGAAGGTCTCAGACAGTTCCAGCTTTTTCTGATAGGAGC-3'
48-mer

FIG. 46B

Strand 1

10) Seg-1-0
5'-GCTCCTATCAGAAAAAGCTGGAACTGTCTGAGACCTTCCGTAAAAACT-3'
48-mer
11) Seg-1-1 (rev cmp)
5'-AGTAGATCATTTCGTCCTCCAGGGAGTAGTTTTTACGGAAGGTCTCAGAC-3'
50-mer
12) Seg-1-2
5'-ACTCCCTGGAGGACGAAATGATCTACTACCAAGATCGCCTGGTTGTACCG-3'
50-mer
13) Seg-1-3 (rev cmp)
5'-CGCATGACAGCATTTTGTTGTTTAATCGGTACAACCAGGCGATCTTGGT-3'
49-mer
14) Seg-1-4
5'-ATTAAACAACAAAATGCTGTCATGCGTCTGTATCACGATCACACTCTGTT-3'
50-mer
15) Seg-1-5 (rev cmp)
5'-TAACGGTTACGCCAAAGTGACCACCAAACAGAGTGTGATCGTGATACAGA-3'
50-mer
16) Seg-1-6
5'-TGGTGGTCACTTTGGCGTAACCGTTACCCTGGCGAAAATCTCTCCGATCT-3'
50-mer
17) Seg-1-7 (rev cmp)
5'-AGAGTGCTGCAGTTTCGGCCAATAGTAGATCGGAGAGATTTTCGCCAGGG-3'
50-mer

*FIG. 46C*

Strand 2

18) Seg-2-0
5'-CCCTGGCGAAAATCTCTCCGATCTACTATTGGCCGAAACTGCAGCACTCT-3'
50-mer
19) Seg-2-1 (rev cmp)
5'-GCAGGTACGGATGTACTGGATGATAGAGTGCTGCAGTTTCGGCCAATAGT-3'
50-mer
20) Seg-2-2
5'-ATCATCCAGTACATCCGTACCTGCGTTCAGTGCCAGCTGATCAAATCTCA-3'
50-mer
21) Seg-2-3 (rev cmp)
5'-AGGAGACCATGCAGACGTGGGCGGTGAGATTTGATCAGCTGGCACTGAAC-3'
50-mer
22) Seg-2-4
5'-CCGCCCACGTCTGCATGGTCTCCTGCAACCGCTCCCGATCGCTGAAGGTC-3'
50-mer
23) Seg-2-5 (rev cmp)
5'-AGTCCATAGAGATGTCCAGCCAACGACCTTCAGCGATCGGGAGCGGTTGC-3'
50-mer
24) Seg-2-6
5'-GTTGGCTGGACATCTCTATGGACTTCGTTACTGGTTTGCCGCCGACC-3'
47-mer
25) Seg-2-7 (rev cmp)
5'-CACCAGGATCATGTTCAGGTTGTTAGAGGTCGGCGGCAAACCAGTAACGA-3'
50-mer

*FIG. 46D*

Strand 3

26) Seg-3-0
5'-TCGTTACTGGTTTGCCGCCGACCTCTAACAACCTGAACATGATCCTGGTG-3'
50-mer
27) Seg-3-1 (rev cmp)
5'-CGTTTAGAGAAGCGGTCCACCACCACCAGGATCATGTTCAGGTTGTTAGA-3'
50-mer
28) Seg-3-2
5'-GTGGTGGACCGCTTCTCTAAACGTGCTCACTTCATCGCTACCCGAAAAAC-3'
50-mer
29) Seg-3-3 (rev cmp)
5'-CGATCAGCTGAGTCGCGTCCAGGGTTTTTCGGGTAGCGATGAAGTGAGCA-3'
50-mer
30) Seg-3-4
5'-CCTGGACGCGACTCAGCTGATCGACCTGCTCTTCCGTTACATCTTCTCTT-3'
50-mer
31) Seg-3-5 (rev cmp)
5'-GATGGTACGCGGGAAGCCATGGTAAGAGAAGATGTAACGGAAGAGCAGGT-3'
50-mer
32) Seg-3-6
5'-ACCATGGCTTCCCGCGTACCATCACCTCTGACCGTGACGTTCGTATGACT-3'
50-mer
33) Seg-3-7 (rev cmp)
5'-GTCAGTTCTTGGTATTTGTCCGCAGTCATACGAACGTCACGGTCAGAGGT-3'
50-mer

*FIG. 46E*

Strand 4

34) Seg-4-0
5'-ACCTCTGACCGTGACGTTCGTATGACTGCGGACAAATACCAAGAACTGAC-3'
50-mer
35) Seg-4-1 (rev cmp)
5'-ATGGTAGATTTGATACCCAGACGTTTGGTCAGTTCTTGGTATTTGTCCGC-3'
50-mer
36) Seg-4-2
5'-CAAACGTCTGGGTATCAAATCTACCATGTCTTCCGCTAACCACCCGCAGA-3'
50-mer
37) Seg-4-3 (rev cmp)
5'-GAATGGTACGCTCGGATTGACCATCAGTCTGCGGGTGGTTAGCGGAAGAC-3'
50-mer
38) Seg-4-4
5'-CTGATGGTCAATCCGAGCGTACCATTCAGACCCTGAACCGTCTCCTGCGT-3'
50-mer
39) Seg-4-5 (rev cmp)
5'-GTTCTGGATGTTGGTAGACGCATACGCACGCAGGAGACGGTTCAGGGTCT-3'
50-mer
40) Seg-4-6
5'-GCGTATGCGTCTACCAACATCCAGAACTGGCACGTTTACCTTCCGCAAAT-3'
50-mer
41) Seg-4-7 (rev cmp)
5'-GTCGGAGTGGAGTTGTAAACGAATTCAATTTGCGGAAGGTAAACGTGCCA-3'
50-mer

*FIG. 46F*

Strand 5

42) Seg-5-0
5'-TGGCACGTTTACCTTCCGCAAATTGAATTCGTTTACAACTCCACTCCGAC-3'
50-mer
43) Seg-5-1 (rev cmp)
5'-ACGGAGATTTACCCAGAGTACGAGTCGGAGTGGAGTTGTAAACGAATTCA-3'
50-mer
44) Seg-5-2
5'-TCGTACTCTGGGTAAATCTCCGTTCGAAATCGACCTGGGTTACCTGCCAA-3'
50-mer
45) Seg-5-3 (rev cmp)
5'-GTCAGATTTGATCGCCGGAGTGTTTGGCAGGTAACCCAGGTCGATTTCGA-3'
50-mer
46) Seg-5-4
5'-ACACTCCGGCGATCAAATCTGACGATGAAGTTAACGCTCGTTCCTTCACC-3'
50-mer
47) Seg-5-5 (rev cmp)
5'-AGGTGTTTAGCCAGTTCAACAGCGGTGAAGGAACGAGCGTTAACTTCATC-3'
50-mer
48) Seg-5-6
5'-GCTGTTGAACTGGCTAAACACCTGAAGGCGCTGACCATCCAGACCAAAGA-3'
50-mer
49) Seg-5-7 (rev cmp)
5'-CGATCTGCGCGTGTTCCAGCTGTTCTTTGGTCTGGATGGTCAGCGCCTTC-3'
50-mer

*FIG. 46G*

Strand 6

50) Seg-6-0
5'-GAAGGCGCTGACCATCCAGACCAAAGAACAGCTGGAACACGCGCAGATCG-3'
50-mer
51) Seg-6-1 (rev cmp)
5'-GACGCTGGTTGTTGTTGGTTTCCATTTCGATCTGCGCGTGTTCCAGCTGT-3'
50-mer
52) Seg-6-2
5'-AAATGGAAACCAACAACAACCAGCGTCGCAAACCACTGCTGTTGAATATT-3'
50-mer
53) Seg-6-3 (rev cmp)
5'-ATCACGGTGTACCAGAACATGATCACCAATATTCAACAGCAGTGGTTTGC-3'
50-mer
54) Seg-6-4
5'-GGTGATCATGTTCTGGTACACCGTGATGCCTACTTCAAAAAAGGTGCGTA-3'
50-mer
55) Seg-6-5 (rev cmp)
5'-CCAACGTAGATCTGCTGAACTTTCATGTACGCACCTTTTTTGAAGTAGGC-3'
50-mer
56) Seg-6-6
5'-CATGAAAGTTCAGCAGATCTACGTTGGTCCATTCCGTGTCGTTAAGAAAA-3'
50-mer
57) Seg-6-7 (rev cmp)
5'-CCAGTTCATACGCGTTGTCATTGATTTTCTTAACGACACGGAATGGA-3'
47-mer

*FIG. 46H*

Strand 7

58) Seg-7-0
5'-TCCATTCCGTGTCGTTAAGAAAATCAATGACAACGCGTATGAACTGG-3'
    47-mer
59) Seg-7-1  (rev cmp)
5'-GTGCTTCTTCTTATGCGAGTTCAGGTCCAGTTCATACGCGTTGTCATTGA-3'
    50-mer
60) Seg-7-2
5'-ACCTGAACTCGCATAAGAAGAAGCACCGTGTGATCAACGTTCAGTTTCTG-3'
    50-mer
61) Seg-7-3  (rev cmp)
5'-CATCCGGACGGTAAACAAATTTTTTCAGAAACTGAACGTTGATCACACG-3'
    49-mer
62) Seg-7-4
5'-AAAAAATTTGTTTACCGTCCGGATGCGTACCCGAAAAACAAACCGATCTC-3'
    50-mer
63) Seg-7-5  (rev cmp)
5'-AGCTCGTTTGATGCGTTCGGTAGAAGAGATCGGTTTGTTTTTCGGGTACG-3'
    50-mer

*FIG. 46I*

Strand 8

64) Seg-8-0
5'-CGTACCCGAAAAACAAACCGATCTCTTCTACCGAACGCATCAAACGAGCT-3'
    50-mer
65) Seg-8-1  (rev cmp)
5'-TGCCGATCAGCGCGGTAACTTCGTGAGCTCGTTTGATGCGTTCGGTAGAA-3'
    50-mer
66) Seg-8-2
5'-CACGAAGTTACCGCGCTGATCGGCATCGACACCACCCACAAAACCTATCT-3'
    50-mer
67) Seg-8-3  (rev cmp)
5'-CGGGTCAACGTCCTGCATGTGGCACAGATAGGTTTTGTGGGTGGTGTCGA-3'
    50-mer
68) Seg-8-4
5'-GTGCCACATGCAGGACGTTGACCCGACCCTGTCCGTTGAATACTCCGAAG-3'
    50-mer
69) Seg-8-5  (rev cmp)
5'-CGCTCTGGGATCTGGCAGAATTCAGCTTCGGAGTATTCAACGGACAGGGT-3'
    50-mer

*FIG. 46J*

Strand 9

70) Seg-9-0
5'-ACCCTGTCCGTTGAATACTCCGAAGCTGAATTCTGCCAGATCCCAGAGCG-3'
50-mer
71) Seg-9-1 (rev cmp)
5'-GTTCGCCAGGATAGAACGACGGGTACGCTCTGGGATCTGGCAGAATTCAG-3'
50-mer
72) Seg-9-2
5'-TACCCGTCGTTCTATCCTGGCGAACTTCCGTCAGCTGTACGAAACCCAAG-3'
50-mer
73) Seg-9-3 (rev cmp)
5'-TCTTCTTCACGTTCAGGGTTGTCTTGGGTTTCGTACAGCTGACGGAA-3'
47-mer
74) Seg-9-4
5'-ACAACCCTGAACGTGAAGAAGATGTTGTTTCCCAGAACGAAATCTG-3'
46-mer
75) Seg-9-5 (rev cmp)
5'-CGGAGAGGTGTTGTCGTACTGGCAGATTTCGTTCTGGGAAACAACA-3'
46-mer
76) Seg-9-6
5'-CCAGTACGACAACACCTCTCCG-3'
22-mer
77) Strand-9-trailer (rev cmp)
5'-CGGAGAGGTGTTGTCGTACTG-3'
21-mer

*FIG. 46K*

Gene Trailers

78) Gene Trailer-0 (rev cmp)
5'-GTATTGGATCCTTATTACGGAGAGGTGTTGTCGTACTGGCAGATTTC-3'
47-mer

*FIG. 46L*

METHOD FOR PRODUCING A SYNTHETIC GENE OR OTHER DNA SEQUENCE

CROSS-REFERENCE TO RELATED APPLICATION

This application claims the benefit of U.S. Provisional Patent Application No. 60/472,822, filed on May 22, 2003, the disclosure of which is incorporated by reference.

BACKGROUND OF THE INVENTION

1. Field of the Invention

The present application is generally related to the synthesis of DNA molecules, and more particularly, to the synthesis of a synthetic gene or other DNA sequence.

2. Description of the Related Art

Proteins are an important class of biological molecules that have a wide range of valuable medical, pharmaceutical, industrial, and biological applications. A gene encodes the information necessary to produce a protein according to the genetic code by using three nucleotides (one codon or set of codons) for each amino acid in the protein. An expression vector contains DNA sequences that allow transcription of the gene into mRNA for translation into a protein.

It is often desirable to obtain a synthetic DNA which encodes the protein of interest. DNA can be synthesized accurately in short pieces, say 50 to 80 nucleotides or less. Pieces substantially longer than this become problematic due to cumulative error probability in the synthesis process. Most genes are appreciably longer than 50 to 80 nucleotides, usually by hundreds or thousands of nucleotides. Consequently, direct synthesis is not a convenient method for producing large genes. Currently, large synthetic genes with a desired DNA sequence are manufactured by any one of several methods:

1. If the gene does not contain introns it can be synthesized by PCR directly from genomic DNA. This is feasible for genes of bacteria, lower eukaryotes, and many viruses, but nearly all genes of higher organisms contain introns.

2. A related alternative is to PCR the gene from a full-length cDNA clone. It is time consuming and tedious to isolate and characterize a full-length clone, and full-length cDNA clones are available for only a very small fraction of the genes of any higher organism.

3. Based on the gene sequence inferred from the genomic DNA sequence, short DNA segments of both strands of a gene can be synthesized with overlapping ends. These segments are allowed to anneal and are joined together with DNA ligase. Annealing efficiency and accuracy at the segment junctions is often poor, resulting in low yields.

4. An approach to reduce this problem is to build the gene up in subsections in a step-wise manner. This remains time-consuming, expensive, tedious, and inefficient, because many reactions must be performed.

5. Based on the gene sequence inferred from the genomic DNA sequence, short overlapping duplex DNA segments of the gene can be synthesized that contain compatible end-proximal restriction endonuclease sites. Each fragment can be cut with the appropriate enzyme, annealed, and joined with DNA ligase. In addition to the limitations above, both strands of the gene sequence must be synthesized and this method is dependent on the placement of appropriate restriction sites evenly spaced throughout the gene sequence.

6. Genes have also been assembled by overlap extension of partially overlapping oligonucleotides using DNA-polymerase-catalyzed reactions. The gene is divided into oligonucleotides, each of which partially overlaps and is complementary to the adjacent oligonucleotide(s). The oligonucleotides are allowed to anneal and the resulting DNA construct is extended to the full-length double-stranded gene. See, for example, W. P. C. Stemmer et al. "Single-step assembly of a gene and entire plasmid from large numbers of oligodeoxyribonucleotides" *Gene*, 1995, 164, 49-53 and D. E. Casimiro et al. "PCR-based gene synthesis and protein NMR spectroscopy" *Structure*, 1997, 5, 1407-1412, the disclosures of which are incorporated by reference. Designing the oligonucleotides for gene synthesis by this approach has recently been automated as described in D. M. Hoover & J. Lubkowski "DNA Works: an automated method for designing oligonucleotides for PCR-based gene synthesis" *Nucleic Acids Res*., 2002, 30:10 e43, the disclosure of which is incorporated by reference. The method optimizes codon usage, optionally removes DNA hairpins, and uses a nearest-neighbor model of DNA melting to achieve homogeneous target melting temperatures. The process of removing local DNA hairpins and dimerization from a single DNA oligonucleotide is also referred to by those skilled in the art as "removing DNA secondary structure." The methods described in these references do not globally optimize a melting temperature gap between correct hybridizations and incorrect hybridizations, however.

SUMMARY OF THE INVENTION

The present application provides a method for synthesizing a DNA sequence and the DNA sequences synthesized by the method. A preferred embodiment of the method utilizes the flexibility of the genetic code to achieve melting temperatures that optimize the simultaneous annealing of many gene segments in the desired order, facilitating the assembly of a large strand from many small ones.

In some embodiments, the likelihood of synthesizing the correct DNA sequence from a mixture of correct and incorrect gene segments is increased by determining a property of the DNA sequence or fragment thereof, or of a polypeptide or protein expressed therefrom, or of another molecule derived therefrom in order to ascertain the correctness of the DNA sequence or fragment thereof. Examples of suitable properties include the DNA sequence and the molecular weight of the polypeptide expressed therefrom.

The method in the present application is of practical utility. A number of companies currently offer synthetic gene services. Consequently, a method with improved efficiency is valuable. A partial list of such companies may be generated easily, for example, by performing an Internet search for "custom gene synthesis," "synthetic gene services," or related keywords.

Those skilled in the art will immediately comprehend myriad applications to which the disclosed method may be applied, including: (1) creating de novo "designer" proteins; (2) coupling to automated expression and crystallization facilities; (3) building DNA sequences predicted to express novel protein folds for structural proteomics; (4) building other DNA sequences that do not encode proteins, e.g., as RNA structural templates or DNA nanotechnology components; (5) expressing proteins from a different species in a desired expression vector according to its own codon usage preference; and (6) creating a small synthetic genome by specifying its desired protein sequences and regulatory protein binding sites.

The present application provides a recursive method for synthesizing a gene of arbitrary size, i.e., a double-stranded DNA (dsDNA) sequence that codes for a desired peptide sequence, possibly with flanking regulatory and intergenic sequences extending into other flanking genes. The disclosed method uses sequence degeneracy to achieve melting temperatures that optimize the. simultaneous annealing of many gene segments in the desired order. This optimization is achieved by choosing bases and codons such that, with high probability, incorrect or wrong hybridizations melt at a low temperature and correct or right hybridizations melt at a high temperature, allowing the construction of a large synthetic gene quickly and easily.

The method comprises: (a) hierarchical assembly (b) by high-fidelity techniques such as overlap extension using proof-reading DNA polymerase, ligation, cloning, or other methods, (c) with optimization of the sequences of the component oligonucleotide pieces to facilitate preferential hybridization to the desired adjacent piece(s) and to disfavor undesired hybridizations between other pieces, for example, by exploiting the degeneracy of the genetic code or a regulatory region consensus sequence, (d) to achieve a DNA melting temperature gap between correct (high melting temperature) and incorrect (low melting temperature) hybridizations, and (e) optionally selecting pieces of DNA likely to have the correct DNA sequence for subsequent assembly steps, (f) so that, with high probability correct assemblies will form. Thus, the sequence is designed to encode its own correct self-assembly in a signal superimposed on the coding sequence by using synonymous codon substitutions in a manner friendly to the expression vector.

R. M. Horton et al. "Engineering hybrid genes without the use of restriction enzymes: gene splicing by overlap extension" *Gene*, 1989, 77, 61-68, the disclosure of which is incorporated by reference in its entirety, discloses overlap extension, but does not disclose optimizing overlap regions to facilitate the assembly of pieces in the desired order. In particular, Horton et al. does not disclose the use of informatics to encode the self-assembly of the gene by exploiting sequence degeneracy to achieve high melting temperatures for correct hybridizations and low melting temperatures for incorrect hybridizations.

Accordingly, the present disclosure provides a method for synthesizing a DNA sequence comprising at least the steps of: (i) dividing the DNA sequence recursively into small pieces of DNA, wherein adjacent pieces comprise overlapping regions; (ii) optimizing the sequences of the pieces of DNA resulting from each recursive division to strengthen correct hybridizations and to disrupt incorrect hybridizations; (iii) obtaining the optimized small pieces of DNA, wherein the overlapping regions of any adjacent pieces of single-stranded DNA are complementary; (iv) combining the pieces of DNA derived from the division of the next larger piece of DNA; (v) allowing the pieces of DNA to self-assemble to form a DNA construct comprising single-stranded DNA segments connected by double-stranded overlap regions; (vi) producing the next-larger piece of DNA from the DNA construct; and (vii) repeating steps (iv), (v), and (vi) in reverse order of the recursive division in step (i) to produce the DNA sequence.

The present disclosure further provides a DNA sequence, synthesized according to a method comprising at least the steps of: (i) dividing the DNA sequence recursively into small pieces of DNA, wherein adjacent pieces comprise overlapping regions; (ii) optimizing the sequences of the pieces of DNA resulting from each recursive division to strengthen correct hybridizations and to disrupt incorrect hybridizations; (iii) obtaining the optimized small pieces of DNA, wherein the overlapping regions of any adjacent pieces of single-stranded DNA are complementary; (iv) combining the pieces of DNA derived from the division of the next larger piece of DNA; (v) allowing the pieces of DNA to self-assemble to form a DNA construct comprising single-stranded DNA segments connected by double-stranded overlap regions; (vi) producing the next-larger piece of DNA from the DNA construct; and (vii) repeating steps (iv), (v), and (vi) in reverse order of the recursive division in step (i) to produce the DNA sequence.

In some embodiments, a next-larger piece of DNA produced in step (vi) comprises a mixture of DNA molecules. Some embodiments further comprise a step of selecting a DNA molecule from the mixture likely to have the correct DNA sequence and using the selected DNA molecule in the synthesis of the DNA sequence. In some embodiments, a DNA molecule is separated from the mixture by cloning. In some embodiments, the selection comprises determining a property of selected DNA molecules from the mixture, or of polypeptides expressed therefrom, and selecting a DNA molecule based on a predetermined value for the property. In some embodiments, the selection comprises sequencing a sample of DNA molecules from the mixture and selecting a DNA molecule with the correct DNA sequence. In some embodiments, the selection comprises expressing a polypeptide from each member of a sample of DNA molecules from the mixture, determining the molecular weight of the polypeptide, and selecting a DNA molecule from which a polypeptide with a predetermined molecular weight is expressed. In some embodiments, a start codon and/or stop codon is incorporated into DNA molecule from which a polypeptide is expressed. In some embodiments, the reading frame of the DNA molecule is adjusted with respect to the start codon and/or stop codon. In some embodiments, one or more stop codons is inserted into the expression vector downstream (3') from the gene. In some embodiments, the molecular weight of the polypeptide is determined by electrophoresis.

The present disclosure further provides a method for synthesizing a DNA sequence comprising at least the steps of: (i) dividing the DNA sequence recursively into small pieces of DNA, wherein adjacent pieces comprise overlapping regions; (ii) obtaining the small pieces of DNA, wherein the overlapping regions of any adjacent pieces of single-stranded DNA are complementary; (iii) combining the pieces of DNA derived from the division of the next larger piece of DNA; (iv) allowing the pieces of DNA to self-assemble to form a DNA construct comprising single-stranded DNA segments connected by double-stranded overlap regions; (v) producing the next-larger piece of DNA from the DNA construct; (vi) selecting a next-larger piece of DNA likely to have the correct sequence; and (vii) repeating steps (iii), (iv), (v), and (vi) in reverse order of the recursive division in step (i) to produce the DNA sequence.

The present disclosure further provides a DNA sequence, synthesized according to a method comprising at least the steps of: (i) dividing the DNA sequence recursively into small pieces of DNA, wherein adjacent pieces comprise overlapping regions; (ii) obtaining the small pieces of DNA, wherein the overlapping regions of any adjacent pieces of single-stranded DNA are complementary; (iii) combining the pieces of DNA derived from the division of the next larger piece of DNA; (iv) allowing the pieces of DNA to self-assemble to form a DNA construct comprising single-stranded DNA segments connected by double-stranded overlap regions; (v) producing the next-larger piece of DNA from the DNA construct; (vi) selecting a next-larger piece of DNA likely to have the correct sequence; and (vii) repeating steps (iii), (iv), (v), and (vi) in reverse order of the recursive division in step (i) to produce the DNA sequence.

In some embodiments, the DNA sequence comprises a regulatory sequence. In other embodiments, the synthetic gene has an intergenic sequence. In other embodiments, the DNA sequence has flanking regulatory and intergenic sequences extending into other flanking genes. In other embodiments, the DNA sequence encodes a polypeptide. Preferably, the polypeptide is a portion of a full-length protein. More preferably, the polypeptide is a full-length protein. In some embodiments, the DNA sequence is a synthetic genome comprising multiple flanking encoded polypeptides, their regulatory regions, and intergenic regions.

In a preferred embodiment, the sequence of the DNA sequence is divided into small pieces of DNA in a single division. This embodiment is referred to herein as "direct self-assembly." In another preferred embodiment, the sequence of the synthetic gene is divided into small pieces of DNA in a plurality of divisions. This embodiment is referred to herein as "recursive assembly" or "hierarchical assembly." In one embodiment, the sequence of the synthetic gene is divided into pieces of DNA of about 1,500 bases long or shorter.

The small pieces of DNA are preferably about 60 bases long or shorter, more preferably, about 50 bases long or shorter. Preferably, the overlapping regions comprise from about 6 to about 60 base-pairs, more preferably, from about 14 to about 33 base-pairs.

In a preferred embodiment, optimization is performed by calculating a melting temperature for the pieces of DNA. Preferably, the lowest correct hybridization melting temperature is higher than the highest incorrect hybridization melting temperature. Those skilled in the art will realize that the size of the melting temperature gap is related to the annealing conditions such that a narrower gap may require more stringent annealing conditions in the reassembly step to provide the requisite level of fidelity. Consequently, the temperature gap has no minimum value. Practically, the difference between the lowest-melting correct match and the highest melting incorrect match is at least about 1° C., more preferably, at least about 4° C., more preferably, at least about 8° C., most preferably, at least about 16° C. The wider the temperature gap, the more robust the self-assembly, thereby permitting the use of less stringent annealing conditions. Those skilled in the art will appreciate that optimization may be performed using other parameters or measures related to hybridization propensity, for example, free energy, enthalpy, entropy, or other arithmetic or algebraic combinations of such parameters or measures, to achieve the same effect as melting temperature. Indeed, the melting temperature itself is one such arithmetic or algebraic combination of such parameters or measures. Consequently, in some embodiments, optimization is performed by calculating a parameter related to hybridization propensity for the pieces of DNA, for example, free energy, enthalpy, entropy, and arithmetic or algebraic combinations thereof.

In some embodiments, the pieces of DNA are optimized by permuting silent codon substitutions, for example for a portion encoding a polypeptide. In some embodiments, the pieces of DNA are optimized by taking advantage of the degeneracy in the regulatory region consensus sequence, for example for a regulatory region. In some embodiments, the pieces of DNA are optimized by adjusting boundary points between adjacent pieces of DNA. In some embodiments, the pieces of DNA are optimized by direct base assignment, for example for an intergenic region.

In a preferred embodiment, at least one of the optimized small pieces of DNA is synthetic. In another preferred embodiment, at least one of the optimized small pieces of DNA is single-stranded.

In some embodiments, a single-stranded DNA segment in the DNA construct has a length of zero bases. In some embodiments, a single stranded DNA segment has a length of from about zero bases to about 20 bases.

In a preferred embodiment, the next-larger piece of DNA is produced by cloning the DNA construct and using cellular machinery. Examples of suitable cloning methods include exonuclease III cloning, topoisomerase cloning, restriction enzyme cloning, and homologous recombination cloning. In another preferred embodiment, the next-larger piece of DNA is produced by ligating the DNA construct. In yet anther preferred embodiment, the next-larger piece of DNA is produced by extending the DNA construct by a reaction using a DNA polymerase. Preferably, the DNA polymerase is a proof-reading DNA polymerase.

In a preferred embodiment, a 3' nucleotide in an overlapping region is G or C. Preferably, both 3' nucleotides in an overlapping region are independently G or C. In another preferred embodiment, a 3' nucleotide in an overlapping region is A or T.

In a preferred embodiment, a DNA polymerase primer is mixed with the pieces of DNA derived from the division of the next-larger piece of DNA. In another preferred embodiment, no DNA polymerase primer is combined with the pieces of DNA derived from the division of the next-larger piece of DNA.

In a preferred embodiment, a restriction site is designed into an overlapping region. In another preferred embodiment, the restriction site is digested with a site-specific restriction enzyme.

BRIEF DESCRIPTION OF THE DRAWINGS

FIG. 8 is the final codon assignment for *E. coli* threonine deaminase in EXAMPLE 1. The codon assigned to each amino acid in the protein is shown as "Xn" where "X" is a one-letter amino code and "n" is a codon index.

FIG. 9 is a key that maps an amino acid code and codon index for *E. coli.*

FIG. 11A-FIG. 11E provide an overlap map of the synthesized DNA segments of EXAMPLE 1. Each row corresponds to a short segment of single-stranded DNA that was synthesized directly. The overlaps between short segments are indicated by brackets: [ ].The overlaps between long strands are indicated by braces: { }.

FIG. 12A-FIG. 12E illustrate the synthesized oligonucleotide segments from EXAMPLE 1 with forward and reverse complements indicated. Each row corresponds to a short segment of single-stranded DNA that was synthesized directly. Overlaps between short segments are indicated by underlining and numbering. Each underlined region in a forward segment is the reverse complement of the underlined region having the same number, and vice versa. Reverse complement region numbers are primed.

FIG. 18 is the final codon assignment for variola DNA polymerase-1 in EXAMPLE 2. The codon assigned to each amino acid in the protein is shown as "Xn" where "X" is a one-letter amino code and "n" is a codon index.

FIG. 22 is the final codon assignment for variola DNA polymerase-2 in EXAMPLE. 2. The codon assigned to each amino acid in the protein is shown as "Xn" where "X" one-letter amino code and "n" is a codon index.

FIG. 24A-FIG. 24G are overlap maps for the synthesized DNA segments for variola polymerase-1 of EXAMPLE 2, including DNA polymerase leaders (FIG. 24A) and trailers (FIG. 24G). Each row corresponds to a short segment of single-stranded DNA that was synthesized directly. The overlaps between short segments are indicated by brackets: [ ].

FIG. 25A-FIG. 25G are overlap maps for the synthesized DNA segments for variola polymerase-2 of EXAMPLE 2, including DNA polymerase leaders (FIG. 25A) and trailers (FIG. 25G). Each row corresponds to a short segment of single-stranded DNA that was synthesized directly. The overlaps between short segments are indicated by brackets: [ ].

FIG. 26A-FIG. 26E illustrate the synthesized segments for variola polymerase-1 from EXAMPLE 2 with forward and reverse complement indicated. Each row corresponds to a short segment of single-stranded DNA that was synthesized directly. Overlaps between short segments are indicated by underlining and numbering. Each underlined region in a forward segment is the reverse complement of the underlined region having the same number, and vice versa. Reverse complement region numbers are primed.

FIG. 27A-FIG. 27E illustrate the synthesized segments for variola polymerase-2 from EXAMPLE 2 with forward and reverse complement indicated. Each row corresponds to a short segment of single-stranded DNA that was synthesized directly. Overlaps between short segments are indicated by underlining and numbering. Each underlined region in a forward segment is the reverse complement of the underlined region having the same number, and vice versa. Reverse complement region numbers are primed.

FIG. 34 is the final codon assignment for *E. coli* threonine deaminase in EXAMPLE 3. The codon assigned to each amino acid in the protein is shown as "Xn" where "X" is a one-letter amino code and "n" is a codon index.

FIG. 36 provides an overlap map for the synthesized DNA segments of EXAMPLE 3. Each row corresponds to a short segment of single-stranded DNA that was synthesized directly.

FIG. 37A-FIG. 37F illustrate the synthesized segments from EXAMPLE 3 with forward and reverse complement indicated, including leader (FIG. 37A) and trailer (FIG. 37F) primers. Each row corresponds to a short segment of single-stranded DNA that was synthesized directly. Overlaps between short segments are indicated by underlining and numbering. Each underlined region in a forward segment is the reverse complement of the underlined region having the same number, and vice versa. Reverse complement region numbers are primed.

FIG. 40A-FIG. 40E illustrate the sequences of the gene leader, three intermediate fragments, and gene trailer for the Ty3 GAG3 ORF synthesized in EXAMPLE 4.

FIG. 44 illustrates the sequence for the Ty3 IN gene synthesized in EXAMPLE 5.

FIG. 45A-FIG. 45L provide overlap maps for the leader, ten intermediate fragments, and trailer for the Ty3 IN gene synthesized in EXAMPLE 5.

FIG. 46A-FIG. 46L illustrate the 50 nt oligonucleotides used in the synthesis of the intermediate fragments for the Ty3 IN gene synthesized in EXAMPLE 5.

DETAILED DESCRIPTION OF THE PREFERRED EMBODIMENT

As used herein, the term "DNA" includes both single-stranded and doubled-stranded DNA. The term "piece" may refer to either a real or hypothetical piece of DNA depending on context. A "very large" piece of DNA is longer than about 1,500 bases, a "large" piece of DNA is about 1,500 bases or fewer, a "medium-sized" piece of DNA is about 300 to 350 bases or fewer, and a "short" piece of DNA is about 50 to 60 bases or fewer. Short pieces of DNA are also referred to as "oligonucleotides" by those skilled in the art. It will be appreciated that these numbers are approximate, however, and may vary with different processes or process variations. Although descriptions of preferred embodiments of the disclosed method that follow describe each recursive or hierarchical step as involving pieces of DNA of the same size range—for example, in which all of the pieces of DNA are very large, large, medium-sized, or short—one skilled in the art will appreciate a hierarchical step may involve DNA from more than one size range. A particular step may involve both short and medium-sized pieces of DNA, or even short, medium-sized, and large pieces of DNA.

A "small" or "short" piece of DNA is a DNA segment that can be synthesized, purchased, or is otherwise readily obtained. The term "segment" is also used herein to mean "small piece." Those skilled in the art will understand that the term "synthon" is synonymous with the terms "small piece" and "segment" as used herein, although the term "synthon" is not used herein. The DNA segments used in the Examples that follow are synthetic; however, the disclosed method also comprehends using DNA segments derived from other sources known in the art, for example, from natural sources including viruses, bacteria, fungi, plants, or animals; from transformed cells; from tissue cultures; by cloning; or by PCR amplification of a naturally occurring or engineered sequence. As used herein, a "correct" piece of DNA is a piece of DNA with the correct or desired nucleotide sequence. An "incorrect" piece is one with an incorrect or undesired nucleotide sequence.

Figure 1A:
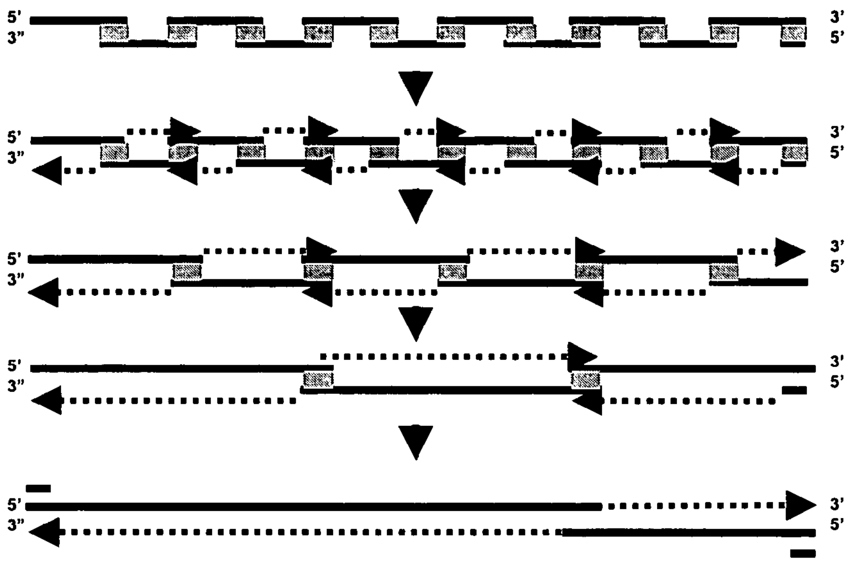
FIG. 1A illustrates an embodiment of the disclosed method for synthesizing a DNA sequence by overlap extension in which a large piece of DNA is divided into five medium-sized pieces.
Figure 1B:
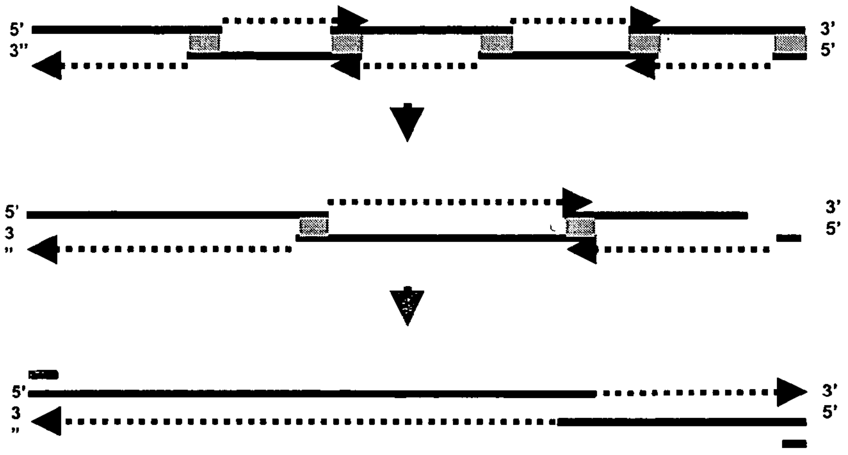
FIG. 1B illustrates an embodiment for the synthesis a DNA sequence by overlap extension in which a medium-sized piece of DNA is divided into 12 short segments.
Figure 2:
FIG. 2 illustrates an embodiment using a direct self-assembled DNA construct, from which a full-length DNA sequence is produced by ligation.

The disclosed method proceeds by a divide-and-conquer strategy (See Aho et al. *The Design and Analysis of Computer Algorithms* Addison-Wesley; Reading, Mass. 1974, the disclosure of which is incorporated by reference in its entirety). A problem that is too large to be solved directly is broken recursively into smaller sub-problems until each is small enough to be solved directly, then the small sub-solutions are combined recursively into a solution to the original problem. Here, a particular full-length gene is too long to synthesize directly. It is broken recursively into smaller overlapping pieces until each is small enough to be synthesized. The gene is then reassembled in the reverse order of the disassembly. The smallest pieces are reassembled into the next larger pieces, which are reassembled into the next larger pieces, and so on and so forth. A reassembly step may be performed by overlap extension using a high-fidelity DNA polymerase as illustrated in FIG. 1A and FIG. 1B, or by ligation as illustrated in FIG. 2. Those skilled in the art will realize that ligation may also be used to reassemble a single strand of DNA using a variation of the DNA construct illustrated in FIG. 2 in which the pieces of DNA that comprise one strand abut, but all of the pieces of DNA comprising the complementary strand do not. Another method for reassembly is cloning into an expression vector and transformation of an appropriate host. Those skilled in the art will understand that many methods of cloning are compatible with the disclosed method, for example, exonuclease III cloning, topoisomerase cloning, restriction enzyme cloning, and homologous recombination cloning.

As discussed in greater detail below, a synthetic oligonucleotide is typically a mixture containing the desired oligonucleotide mixed with incorrect oligonucleotides, that is, oligonucleotides that do not have the desired sequence. As would be apparent to one skilled in the art, synthesizing a gene from such a mixture will likely produce the correct or desired gene in admixture with incorrect genes. One method for synthesizing only the correct gene is to reassemble the gene from pieces of DNA that are likely to have the correct sequences. Consequently, in some embodiments, during the reassembly process, pieces of DNA are selected that are likely to have the correct sequences for use in subsequent reassembly steps. In some embodiments, the criterion for the selection is a property of a reassembled piece of DNA or a polypeptide encoded by and expressed therefrom. In some embodiments, the property is determined from the full-length piece of DNA or polypeptide expressed therefrom. In some embodiments, the property is determined for the complementary strand of DNA or polypeptide expressed therefrom. In some embodiments, the property is determined for a piece of RNA transcribed from the piece of DNA.

Any property indicative of the correctness of the DNA sequence is useful in the method. The likelihood or probability of selecting a correct sequence depends on the property that is measured or determined. In some embodiments, the likelihood approaches certainty. An example of such a property is an experimentally determined nucleotide sequence of the piece of DNA. Any method known in the art for determining a nucleotide sequence may be used, including automated sequencing, manual sequencing, mass spectroscopic sequencing, and the like. In other embodiments, the property indicates that the piece of DNA probably has the correct sequence, but does not confirm the correctness of the sequence. An example of such a property is the molecular weight of a polypeptide encoded by and expressed from the piece of DNA. Any method known in the art for determining the molecular weight of a polypeptide or protein may be used, including gel electrophoresis, mass spectroscopy, and the like.

The term "PCR" as used herein in the context of assembling or reassembling DNA is a PCR or overlap extension reaction, preferably using a proof-reading DNA polymerase ("proof-reading PCR"). The term "direct self-assembly" as used herein in the context of assembling or reassembling DNA is a copy-free method of producing a DNA construct or a DNA construct produced by the method, comprising assembling a large piece of DNA from short synthetic segments in a single step. "Copy-free" means that the method lacks a copy step, such as is found in overlap extension or PCR, thus eliminating the copying errors. In a preferred embodiment, adjacent segments on the same strand abut, i.e., form a nick in the strand. Preferably, the nicks in the self-assembly are repaired by in vitro ligation. In another preferred embodiment, the nicks are repaired in vivo by cellular machinery after cloning.

The method comprises (a) hierarchical assembly (b) by high-fidelity techniques such as overlap extension using proof-reading DNA polymerase, ligation, cloning, or other methods, (c) with optimization of the sequences in the component oligonucleotides to facilitate preferential hybridization to the desired adjacent piece(s) and to disfavor undesired hybridizations to other pieces, for example, by exploiting the degeneracy of the genetic code or a regulatory region consensus sequence, (d) to achieve a DNA melting temperature gap between correct (high melting temperature) and incorrect (low melting temperature) hybridizations, (e) optionally selecting pieces of DNA likely to have the correct DNA sequence for use in the subsequent assembly steps, (f) so that, with high probability correct assemblies will form.

Hierarchical assembly ensures that the complexity at any step, and therefore the possible number of incorrect assemblies, is bounded and manageably small. Overlap extension allows every correctly hybridized 3' end to be extended reliably to a complementary copy of the prefix of its match. Using a high-fidelity DNA polymerase reaction ensures that the copy, with high probability, is correct. Ligation and cloning achieve the same result as overlap extension while avoiding the small but non-zero error rate associated with DNA polymerase reactions. The genetic code degeneracy permits flexibility in silent codon substitutions to strengthen correct matches and disrupt incorrect ones. A broad temperature gap between the highest-melting incorrect hybridization and the lowest-melting correct hybridization means that, with high probability, most incorrect ones have melted and most correct ones have annealed. Selecting gene fragments likely to be correct means that oligonucleotide sequence errors arising from chemical synthesis will be removed or reduced. Consequently, each reassembly reaction, with high probability, produces a correct larger piece of DNA. Errors will occur, of course, but with low probability. Consequently, two or more compensating errors that yield a product of the same molecular weight—i.e., the same band in the final gel—or two or more compensating deletions that provide a product of the same reading frame—i.e., the same or nearly the same encoded amino acid sequence—would correspond to a doubly rare or rarer event.

In optimizing the base sequences, theoretical melting temperatures are calculated for all possible correct and incorrect hybridizations by methods known in the art, for example, using Mfold. Such methods are disclosed, for example, in M. Zuker et al. "Algorithms and thermodynamics for RNA secondary structure prediction: A practical guide." in RNA Biochemistry and *Biotechnology*, Barciszewsld & Clark, eds.; Kluwer: 1999; D. H. Mathews et al. "Expanded sequence dependence of thermodynamic parameters provides robust prediction of RNA secondary structure" *J. Mol. Biol.*, 1999, 288, 910-940; J. Santa-Lucia "A unified view of polymer, dumbbell, and oligonucleotide DNA nearest-neighbor thermodynamics" *Proc. Natl. Acad. Sci. USA*, 1998, 95, 1460-1465; the disclosures all of which are incorporated by reference in their entireties. The figure of merit is the gap between the lowest-melting correct match and the highest-melting incorrect match. Examples of incorrect matches include: (a) hairpins, in which a short segment folds back and hybridizes to itself; (b) dimers, in which a short segment is partially self-complementary; (c) intersegment mismatches, in which part of one short segment is partially complementary to part of a second; (d) and shifted correct matches, in which a misaligned overlap region is partially complementary to another region within the same overlap. Accordingly, in some embodiments, optimization comprises calculating a melting temperature for a single piece of DNA, for example, for a hairpin, in some embodiments, optimization comprises calculating a melting temperature for two pieces of DNA, for example, for an intersegment mismatch. In some embodiments, optimization comprises calculating both types of melting temperatures.

The melting temperature gap is widened by perturbations to the codon assignments, including strengthening correct matches by increasing G-C content in the overlaps and disrupting incorrect matches by choosing non-complementary bases. Codon assignments are varied and the process repeated until the gap is comfortably wide. This process may be performed manually or automated. In a preferred embodiment, the search of possible codon assignments is mapped into an anytime branch and bound algorithm developed for biological applications, which is described in R. H. Lathrop et al. "Multi-Queue Branch-and-Bound Algorithm for Anytime Optimal Search with Biological Applications" in *Proc. Intl. Conf. on Genome Informatics*, Tokyo, Dec. 17-19, 2001 pp. 73-82; in *Genome Informatics* 2001 (*Genome Informatics Series No.* 12), Universal Academy Press, the disclosure of which is incorporated by reference. Those skilled in the art will recognize that other optimization methods could be used, e.g., simulated annealing, genetic algorithms, other branch and bound techniques, hill-climbing, Monte Carlo methods, other search strategies, and the like. Those skilled in the art will further realize that optimizing, i.e., weakening, incorrect matches is functionally equivalent to optimizing, i.e., strengthening, correct matches, and vice versa. Consequently, suitable optimization methods include weakening incorrect matches, strengthening correct matches, and any combination thereof.

Those skilled in the art will realize that the size of the melting temperature gap is related to the annealing conditions such that a narrower gap may require more stringent annealing conditions in the reassembly step to provide the requisite level of fidelity. Consequently, the temperature gap has no minimum value. In some embodiments, the temperature gap is greater than 0° C., at least about 1° C., at least about 2° C., at least about 3° C., at least about 4° C., at least about 5° C., at least about 6° C., at least about 7° C., at about 8° C., at least about 9° C., at least about 10° C., at least about 12° C., at least about 14° C., at least about 16° C., at least about 18° C., or at least about 20° C. Those skilled in the art will understand that, under appropriate annealing conditions, the temperature gap is arbitrarily close to 0° C. Practically, the difference between the lowest-melting correct match and the highest melting incorrect match is at least about 1° C., more preferably, at least about 4° C., more preferably, at least about 8° C., most preferably, at least about 16° C. The wider the temperature gap, the more robust the self-assembly, thereby permitting the use of less stringent annealing conditions.

Those skilled in the art will realize that the temperature gap may be increased by optimizing the division process. For example, the division may be optimized through a nested search strategy, described below. Other appropriate search strategies will be apparent to those skilled in the art.

In an outer search, a temperature variable is initialized to a high temperature, for example, 80° C., then decremented by, for example, one degree at each outer search step. At each outer search step, an inner search is called to see whether it is possible to divide the gene into short pieces such that no overlap region has a melting temperature lower than the current setting of the temperature variable. When the inner search finally succeeds, its corresponding codon assignments are returned from the outer search.

The inner search proceeds via a depth-first search through the possible division points that meet the design constraints, for example, minimum overlap lengths, maximum segment lengths, possible C-G clamps at segment boundaries, and the like. At each inner search step, the overlap region resulting from the most recent candidate division point is used to generate the set of codon assignments that yield the highest self melting temperature for that region. If the highest self-melting temperature is less than the current setting of the, temperature variable the inner search fails. Otherwise it continues to the next step.

While the general DNA melting problem is non-linear because DNA secondary structure can cause non-local elements of the sequence to hybridize, correct matches at the overlap regions are characterized by linear hybridizations among purely local bases. Consequently, for a given subsequence of the gene, linear dynamic programming techniques based on base pairs (nearest neighbors) are used to determine the codon assignment to that subsequence that maximizes its melting temperature.

Thus, the gene is divided into short pieces by finding the division points that maximize the melting temperature of the lowest-melting overlap region, while respecting the design constraints, for example, minimum overlap lengths, maximum segment lengths, possible C-G clamps at segment boundaries, and the like. The codon assignments corresponding to the maximal division points are a better starting codon assignment at the beginning of the design process than are the most common codons.

Those skilled in the art will appreciate that optimization may be performed using other parameters or measures related to hybridization propensity, for example, free energy, enthalpy, entropy, or other arithmetic or algebraic combinations of such parameters or measures, to achieve the same effect as melting temperature. Melting temperature itself is one such arithmetic or algebraic combination of such parameters or measures.

Figure 3:
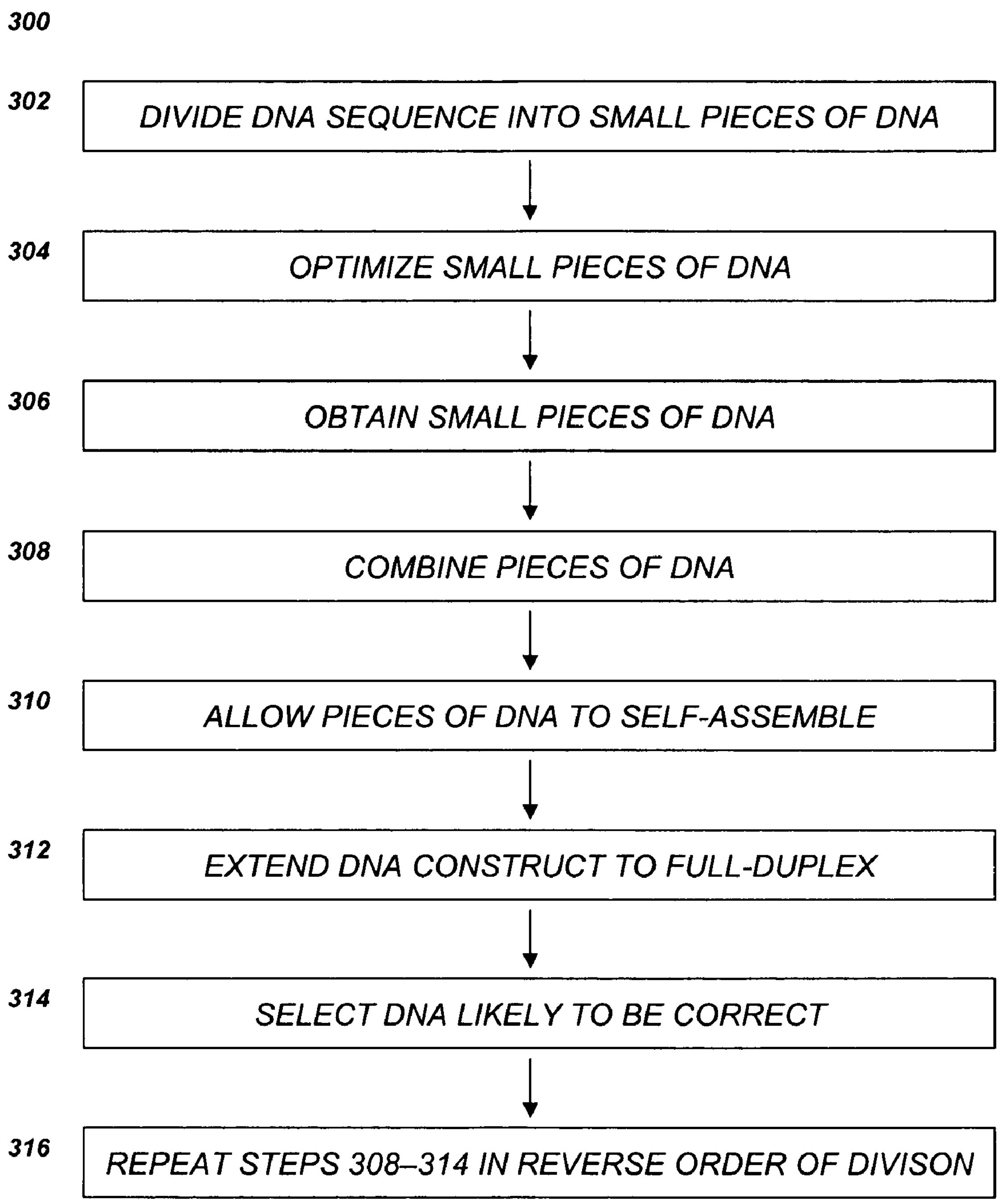
FIG. 3 illustrates an embodiment of the disclosed method for synthesizing a synthetic gene or piece of DNA.

The disclosed method comprises a design or decomposition process and a synthesis or reassembly process. In a preferred embodiment, the synthetic gene is designed according to a method illustrated as method 300 in FIG. 3. In step 302, the DNA sequence or gene is divided into small pieces of DNA or oligonucleotides. In step 304, the small pieces of DNA are optimized. In step 306, the optimized small pieces of DNA are obtained. In step 308, the pieces of DNA derived from one division of each piece of DNA are combined. In step 310, the pieces of DNA are allowed to self-assemble into a DNA construct. In step 312, the DNA construct is extended to full-duplex DNA. In step 314, a property indicative of the likelihood of the correctness of the resulting piece of DNA is determined, and pieces of DNA that are likely to have the correct sequence selected. In step 316, steps 308-314 are repeated in reverse order of the division in step 312 to produce the synthetic gene.

Step 302. The synthetic gene is divided as follows. If the synthetic gene is very large, the DNA sequence is optionally divided into two or more large pieces of DNA of roughly equal size. Adjacent pieces of DNA preferably overlap by a number of nucleotides appropriate to facilitate reassembly. The extent of overlap depends on factors including the particular base sequence, method of reassembly, temperature, and salt concentration, and may be determined by the skilled artisan without undue experimentation. The adjacent pieces of DNA are designed for reassembly by any method or combination of methods known in the art for joining DNA molecules, for example, by ligation or by overlap extension. In some embodiments, the division is optimized to produce pieces of DNA that are more likely to assemble into the desired DNA sequence, as described in greater detail below.

In a preferred embodiment, each large piece is dsDNA and overlaps the adjacent large piece by at least the width of a restriction site (typically from about four to about six bases). Preferably, a restriction site that does not appear elsewhere in either piece is engineered into the DNA sequence of each resulting piece by exploiting the degeneracy of the genetic code as described in greater detail below. Adjacent large pieces are reassembled by cutting with the appropriate restriction enzyme, annealing the adjacent pieces together, and ligating the cut ends together.

In other embodiments, the large pieces of ssDNA or dsDNA are designed such that adjacent pieces of DNA on the same strand abut without a gap, as illustrated in FIG. 2. The DNA is reassembled by annealing and ligation. In a preferred embodiment, the DNA is single-stranded. In some embodiments, the large pieces of DNA are about 3000 bases long. In some embodiments, adjacent large pieces of DNA overlap by about 1500 bases.

In another preferred embodiment, each large piece is ssDNA or dsDNA and directly abuts the adjacent large piece. In this embodiment, primers are then constructed that overlap the abutting ends of the large pieces by from about 25 to about 30 bases or greater, and the abutting large pieces are reassembled by overlap extension.

In yet another preferred embodiment, each large piece is dsDNA with overlapping regions comprising from about 25 to about 30 bases or greater of complementary ssDNA. In this embodiment, the adjacent large pieces are reassembled by hybridization and ligation. In another embodiment, the ssDNA overlaps are designed to leave single-stranded regions flanking the double-stranded overlap region. In this embodiment, the adjacent large pieces are reassembled by overlap extension.

In still another embodiment, each resulting piece is ssDNA and the overlapping regions of adjacent resulting pieces comprise from about 25 to about 33 bases or greater of complementary single-stranded DNA. In some preferred embodiments, the overlapping regions comprise about 75 bases. In this embodiment, the adjacent resulting pieces are reassembled by overlap extension.

In certain embodiments, the large or very large pieces of DNA may be reassembled by cloning using a vector of any type known in the art. Examples of suitable vectors include without limitation, plasmids, cosmids, phagemids, viruses, chromosomes, bacterial artificial chromosomes (BAC), or synthetic chromosomes.

Embodiments using ligation or cloning are preferred in situations in which using DNA polymerase is disfavored, for example, where the DNA is greater than about 3 KB to about 5 KB long.

The method for designing a piece of DNA is described for a large piece of DNA, but is applicable to pieces of DNA of any size. The piece of DNA is divided into overlapping short pieces of DNA that are readily available—that is, small pieces or segments. Preferably, each short piece is small enough to be synthesized readily. This large piece of DNA could be the target DNA sequence or a large piece of DNA derived from the division of a very large piece of DNA as described above.

In a preferred embodiment, the large piece of DNA is designed for "direct self-assembly." In this embodiment, each large piece is divided into from about 50 to about 60 overlapping small pieces of from about 50 to about 60 bases or fewer. Preferably, the adjacent small pieces of DNA from the same strand abut, i.e., hybridize to form a DNA construct with no gaps between the pieces. In this embodiment, the large piece of DNA is preferably reassembled by ligation ("direct self-assembly and ligation"). In an embodiment in which adjacent small pieces from the same strand do not abut, i.e., hybridize to form a DNA construct with single-stranded gaps between the double-stranded overlaps, the large piece of DNA is preferably reassembled by overlap extension. In another embodiment, adjacent small pieces from the same strand abut, i.e., hybridize to form a DNA construct with no single-stranded gaps between the double-stranded overlaps, and the large piece of DNA is reassembled by overlap extension. In another embodiment, a DNA construct with a combination of gaps and no gaps is reassembled by overlap extension. In another preferred embodiment, the large piece of DNA is reassembled by cloning in an expression vector. In this embodiment, the ends of the DNA construct may have any combination of gaps and no gaps. Preferably, the ends of the large piece of DNA are adapted for insertion into an expression vector, for example, complementary to a restriction site in the expression vector.

In another preferred embodiment, the large piece of DNA is designed for "recursive assembly" or "hierarchical assembly." In this embodiment, a large piece of DNA is divided first into about overlapping medium-sized pieces of DNA. In some embodiments, the large piece of DNA is divided into about three to about ten medium-sized pieces of DNA, preferably, about five to about 7 pieces. Each medium-sized piece is then subdivided into overlapping small pieces of DNA, preferably, from about six to about 12 pieces. As described above for direct self-assembly, the DNA pieces at each level of recursion may be designed for reassembly by any combination of methods, including ligation, overlap extension, or cloning. In a preferred embodiment, the DNA pieces are reassembled by overlap extension. One skilled in the art will realize that direct self-assembly is a special case of recursive assembly in which the large piece of DNA is divided in a single step.

Step 304. For the resulting pieces of DNA at each level of recursion, the sequences are optimized to strengthen correct matches (the overlap regions between adjacent pieces of DNA) and to disrupt incorrect matches (all other hybridizations). For example, a DNA sequence in a coding region may be optimized by taking advantage of the genetic code degeneracy. A DNA sequence in a regulatory region may be optimized by taking advantage of the degeneracy in the regulatory region consensus sequence. A DNA sequence outside a coding or regulatory region, i.e., in an intergenic region, may be optimized by direct base assignment.

Some embodiments use no or limited sequence optimization. For example, changes in a nucleotide sequence can change the secondary structure of DNA and RNA. Changes in the secondary structure in RNA viral genomes can affect the viability of the viruses. In some embodiments, no sequence optimization is performed. In other embodiments, selected sequences are optimized as described above and other sequences are not.

In some embodiments, the division described in step 302 is optimized to increase the probability that the pieces of DNA will reassemble into the desired DNA sequence. The boundary points between adjacent pieces of DNA are adjusted to create or to increase a temperature gap, or to disrupt other incorrect hybridizations, for example, hairpins.

Reassembly or synthesis of the synthetic gene is the formal reverse of the division process described in steps 302 and 304.

Step 306. Obtain the optimized small pieces of DNA. Typically, the small pieces of DNA are synthetic. In a preferred embodiment, the small pieces of DNA are single-stranded and overlapping portions of adjacent pieces are complementary.

Step 308. Combine the pieces of DNA derived from one division of each piece of DNA. In a recursive assembly process, the small pieces derived from each medium-sized piece are combined in this step. In the next recursive assembly cycle, the resulting medium-sized pieces derived from each large piece are combined in this step, and so on and so forth. In a direct self-assembly process, the small pieces derived from the large piece of DNA are combined in this step.

Step 310. Allow the DNA segments to self-assemble to form a DNA construct of ssDNA segments connected by double-stranded overlap regions. In embodiments in which pieces of DNA are double-stranded, the pieces are preferably first denatured. Embodiments using overlap extension to reassemble a piece of DNA have single-stranded gaps between the double-stranded overlap regions. Preferably, the single-stranded gaps are from about zero to about 20 bases long. Embodiments using ligation to reassemble a piece of DNA have single-stranded gaps of length zero (i.e., no gap, a nick in the DNA) and the double-stranded overlap regions abut each other. Embodiments using cloning to reassemble a piece of DNA have any combination of gaps and no gaps.

Step 312. Extend the DNA construct to full-duplex dsDNA. In embodiments with single-stranded gaps between the double-stranded overlaps, extension is accomplished using overlap extension, preferably, using a high-fidelity DNA polymerase reaction. In embodiments with no gaps between the double-stranded overlaps, extension is accomplished by ligation. In another preferred embodiment, the self-assembled construct is cloned into an expression vector, and the extension to full-duplex dsDNA is performed by the cellular machinery.

Some embodiments use ssDNA in subsequent steps. ssDNA is produced from the dsDNA using any method known in the art, for example, by denaturing or using nicking enzymes. In some embodiments, the DNA is cloned into a vector that produces ssDNA, for example, bacteriophage M13 or a plasmid containing the M13 origin of DNA replication. M13 is known to roll-off ssDNA into the medium.

Step 314. In some embodiments, a property indicative of the likelihood of correctness of the resulting piece of DNA is optionally determined as disclosed in greater detail below. Pieces of DNA likely to have the correct sequence are selected for subsequent reassembly steps. In some embodiments, the property is determined after the synthetic gene is fully reassembled in order to select a synthetic gene likely to have the correct sequence. In some embodiments, the sequence of the selected synthetic gene is confirmed by sequencing.

Step 316. Repeat, steps 308-314 in reverse order of the division in step 312 to produce the synthetic gene. Those skilled in the art will appreciate that the pieces of DNA identified in the division process may each be synthesized by a different reassembly method. For example, one piece may be synthesized by overlap extension, while a second is synthesized by ligation, and these two pieces reassembled by cloning into an expression vector.

In a preferred embodiment, the disclosed method takes advantage of the fact that the genetic code is sufficiently degenerate to allow codons to be assigned so that, with high probability, wrong hybridizations melt at lower temperatures and correct hybridizations melt at higher temperatures. Consequently, there is an intermediate temperature range within which, with high probability, the product that does form is mostly correct. Because errors occur with low probability, two or more compensating errors that yield a product with the correct molecular weight—i.e., the same band in the final gel—or two or more compensating deletions that yield a product of the same reading frame—i.e., the same or nearly the same encoded amino acid sequence—would correspond to a doubly rare or rarer event.

The final primers, or intermediate primers, or other flanking sequences may contain sequences that allow the synthesized gene to be inserted into an expression vector using various well-known cloning methods, for example, restriction enzymes, homologous recombination, exonuclease cloning, or other methods known in the art, allowing one to build a large synthetic gene quickly and easily.

A problem in some embodiments of the disclosed method is that a synthetic oligonucleotide, or small piece of DNA, typically contains a mixture of the desired DNA sequence ("full-length oligonucleotide") contaminated with sequences with internal point deletions. This problem is referred to herein as the "N−1" problem because oligonucleotides with a single point deletion ("N−1 oligonucleotides") are the most common contaminant in a typical chemical synthesis of oligonucleotides. Furthermore, in some embodiments, the N−1 oligonucleotides are the most problematic because they are more likely to hybridize, and consequently, to provide undesired products, than oligonucleotides with more than one point deletion or mutation. When this mixture of oligonucleotides is used to synthesize medium and large pieces of DNA as disclosed herein, the product pieces of DNA contain a population containing DNA with the desired sequence as well as DNA with errors arising from incorporation of the N−1 oligonucleotides. The N−1 oligonucleotide errors are cumulative and may cause frame-shift mutations, as understood by those skilled in the art.

Figure 4A:
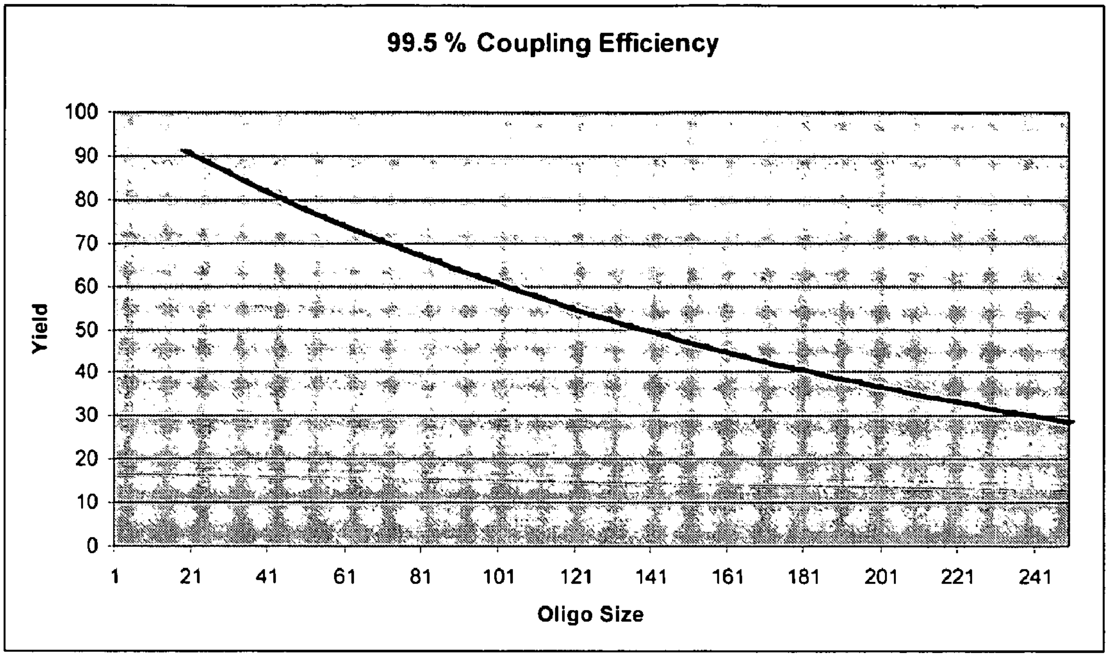
FIG. 4A-FIG. 4C illustrate the yields of full-length oligonucleotide of length 20 to 250 nt, for coupling efficiencies of 99.5%, 99%, and 98%, respectively.
Figure 4B:
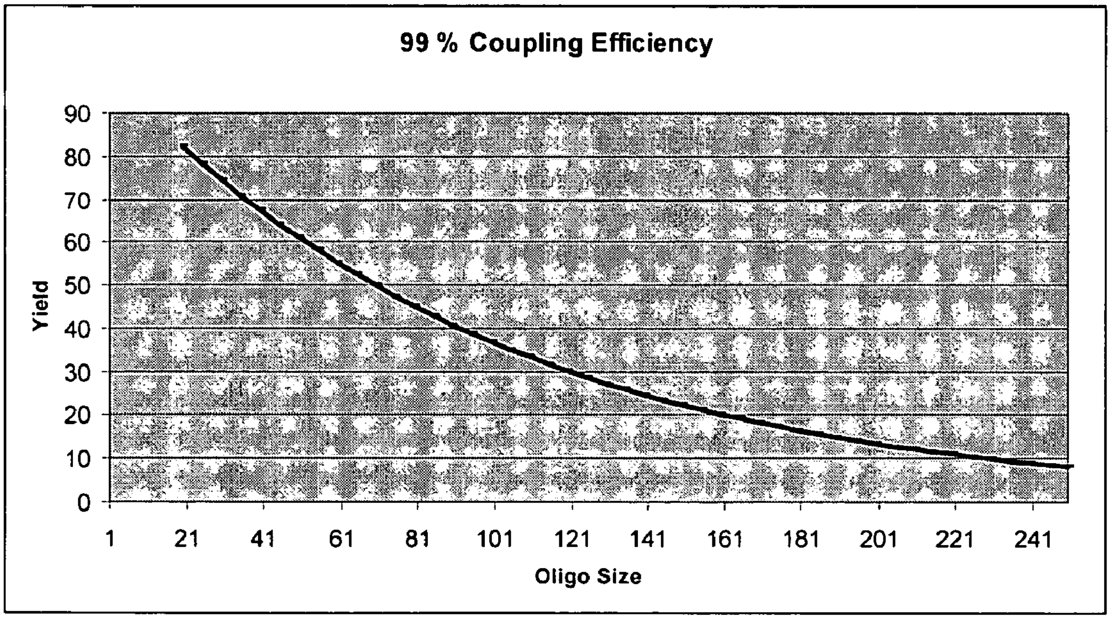
Figure 4C:
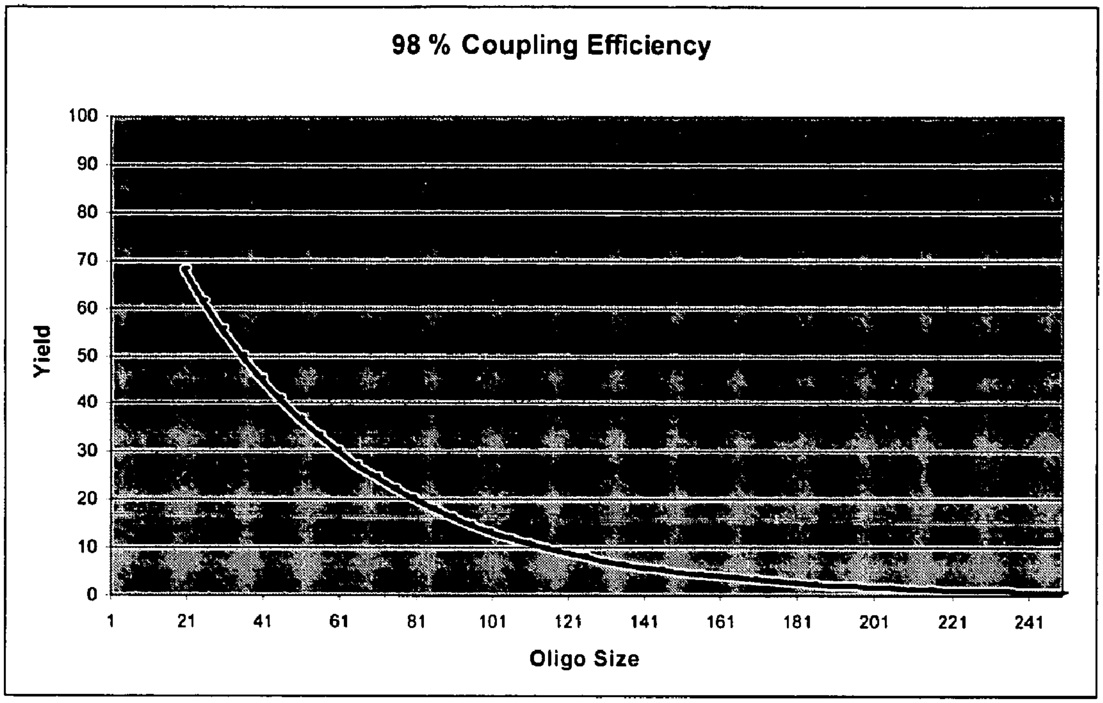

In the chemically synthesized oligonucleotides, the typical coupling efficiency for each nucleotide is from about 98% to about 99.5%, or greater. TABLE I provides the yield of the desired full-length oligonucleotide of length 20 to 250 nt for coupling efficiencies of 99.5%, 99%, and 98%. These results are provided graphically in FIG. 4A-FIG. 4C, respectively. As expected, the probability of synthesizing a correct oligonucleotide decreases with oligonucleotide length and coupling efficiency. Because each of the oligonucleotide pieces used in the construction of the synthetic gene contains some N−1 contaminant, the probability of synthesizing the desired synthetic gene decreases with the length of the synthetic gene.

TABLE I

| | Coupling Efficiency | | |
|---|---|---|---|
| Oligonucleotide Length (nt) | 99.5% | 99% | 98% |
| 20 | 90.916 | 82.617 | 68.123 |
| 25 | 88.665 | 78.568 | 61.578 |
| 30 | 86.471 | 74.717 | 55.662 |
| 35 | 84.311 | 71.055 | 50.314 |
| 40 | 82.243 | 67.573 | 45.480 |
| 45 | 80.208 | 64.261 | 41.11 |
| 50 | 78.222 | 61.112 | 37.16 |
| 55 | 76.286 | 58.117 | 33.59 |
| 60 | 74.398 | 55.268 | 30.363 |
| 65 | 72.557 | 52.56 | 27.445 |
| 70 | 70.761 | 49.984 | 24.808 |
| 75 | 69.009 | 47.534 | 22.425 |
| 80 | 67.301 | 45.204 | 20.27 |
| 85 | 65.635 | 42.989 | 18.323 |
| 90 | 64.011 | 40.882 | 16.562 |
| 95 | 62.427 | 38.878 | 14.971 |
| 100 | 60.881 | 36.973 | 13.533 |
| 110 | 57.905 | 33.438 | 11.057 |
| 115 | 56.472 | 31.799 | 9.995 |
| 120 | 55.074 | 30.240 | 9.034 |
| 130 | 52.381 | 27.239 | 7.382 |
| 140 | 49.821 | 24.734 | 6.031 |
| 150 | 47.385 | 22.369 | 4.928 |
| 160 | 45.068 | 20.23 | 4.027 |
| 170 | 42.865 | 18.296 | 3.29 |
| 180 | 40.769 | 16.546 | 2.688 |
| 190 | 38.776 | 14.964 | 2.196 |
| 200 | 36.88 | 13.533 | 1.795 |
| 210 | 35.08 | 12.24 | 1.47 |
| 220 | 33.36 | 11.07 | 1.19 |
| 230 | 31.73 | 10.01 | 0.98 |
| 240 | 30.18 | 9.05 | 0.8 |
| 250 | 28.7 | 8.19 | 0.65 |

Even in cases in which the desired synthetic gene is synthesized with high probability of correct oligonucleotide order, the desired gene is invariably mixed with many defective genes arising from N−1 oligonucleotides. In many applications, this mixture of correct and defective genes is undesirable. Accordingly, disclosed below is a method for improving the probability of synthesizing the desired gene and/or selecting the desired gene from this mixture.

In some embodiments, the N−1 problem is addressed by assembling the chemically synthesized oligonucleotides using direct self-assembly and ligation, as described above and illustrated in FIG. 2. In embodiments using direct self-assembly and ligation, all of the nucleotides in each oligonucleotide are hybridized, thereby reducing the probability that an N−1 oligonucleotide will be incorporated in the preligation DNA construct. In embodiments using overlap extension, a preextension DNA construct incorporating an oligonucleotide with a deletion in a single stranded region is about as likely as a DNA construct incorporating a correct oligonucleotide. The single-base deletion error rate in double-stranded regions is about 0.3%, while the error rate in single-stranded regions is about 0.5%.

In some embodiments, the N−1 problem is addressed by sampling the population of synthetic DNA molecules and sequencing the sampled molecules. In some embodiments, a random sample from the population of different DNA molecules produced in any of the reassembly steps, including the final step, is sequenced and only those molecules with the correct nucleotide sequence are used in the next reassembly step. The optimum sample size is related to the probability of synthesizing the desired DNA molecule. For example, a synthesis of a 200-nt oligonucleotide or intermediate fragment with a 99.5% coupling efficiency provides about 37% of the correct oligonucleotide. Randomly selecting four oligonucleotides or intermediate fragments from the product mixture provides about an 84% chance of selecting at least one correct oligonucleotide. For a 300 nt oligonucleotide or intermediate fragment at 99.5% coupling efficiency, the correct oligonucleotide makes up about 22% of the product. The probability of selecting at least one correct oligonucleotide or intermediate fragment from a sample of four oligonucleotides from this mixture is about 63%. The probabilities of selecting at least one correct oligonucleotide or intermediate fragment using sample sizes of 1, 4, 6, and 8 for syntheses with coupling efficiencies of 99.5% and 99.7% and oligonucleotide lengths of 250 nt, 300 nt, and 300 nt are provided in TABLE II. As shown in TABLE II, only a modest amount of sequencing is necessary to provide a good probability of selecting a correct oligonucleotide or intermediate fragment.

TABLE II

| Oligonucleotide Length (nt) | Coupling Efficiency | Sample Size 1 | 4 | 6 | 8 |
|---|---|---|---|---|---|
| 200 | 99.5% | 36.7 | 83.9 | 93.6 | 97.4 |
| | 99.7% | 53.7 | 95.4 | 99.0 | 99.7 |
| 250 | 99.5% | 28.6 | 74.0 | 86.7 | 93.2 |
| | 99.7% | 46.0 | 91.5 | 97.5 | 99.3 |
| 300 | 99.5% | 22.2 | 63.4 | 77.9 | 86.6 |
| | 99.7% | 39.4 | 86.5 | 95.0 | 98.2 |

In some embodiments, sampling is performed by cloning the DNA-to-be-sequenced into a suitable vector. Typically, each transformed colony corresponds to one molecule of the synthetic DNA. In some embodiments, a sample of transformed colonies are selected, the DNA sequenced, and DNA with the correct sequence is used in the next hierarchical stage of assembly. The cloning is any type of cloning known in the art. In one embodiment, the cloning is topoisomerase I (TOPO®, Invitrogen) cloning.

The sampling is performed at any of the hierarchical reassembly stages. For example, in some embodiments, an oligonucleotide is sequenced after chemical synthesis. In some embodiments, oligonucleotides or intermediate fragments are assembled into a medium-sized piece of DNA, which is then sequenced. In some embodiments, medium-sized pieces of DNA are assembled into a large piece of DNA, which is then sequenced. In some embodiments, the sampling and sequencing are performed on the medium- or large-sized pieces of DNA, which are synthesized by direct self-assembly and ligation.

In some embodiments, the N−1 problem is addressed by analyzing the polypeptide(s) expressed from a sample from the population of synthetic DNA sequences. The DNA is expressed using any means known in the art, for example, inserting the gene in an expression vector or using a cell-free expression system. In some embodiments, the DNA sequence is cloned in an expression vector and expressed. As discussed above, each clone typically corresponds to one DNA molecule from the population. In some embodiments, the DNA is the full-length synthetic gene. In other embodiments, the DNA is an intermediate fragment. In the case of an intermediate fragment, those skilled in the art will realize that, in some embodiments, the intermediate fragment is designed with (1) a leader that provides a start codon in the correct reading frame, that is, provides an ATG in the DNA and a 0-2 nt filler that adjusts the reading frame in order to express the desired polypeptide, and (2) a trailer that provides one or more stop codons (TAA, TAG, or TGA) in the DNA and a 0-2 nt filler that adjusts the reading frame in order to terminate the desired polypeptide. Typically, the reading frame is the same as for the full-length synthetic gene, although other reading frames are used in some embodiments. Typically, from zero to two bases are inserted into the leader and trailer for adjusting the reading frame. Those skilled in the art will recognize that more than two bases could be used to adjust the reading frame. For example, in some embodiments, the leader and/or trailer encodes additional amino acids, restriction sites, or control sequences. Those skilled in the art will further realize that, in some embodiments, different leaders and/or trailers are used in conjunction with the same piece of DNA in different steps of the method. For example, in some embodiments, the leader and/or trailer used in the expression of a polypeptide from a piece of DNA is different from the leader and/or trailer used in the assembly of that piece of DNA. Some embodiments, provide one or more stop codons downstream (3') of the gene in order to stop the translation of DNA fragments constructed from one or more N−1 oligonucleotides. In some embodiments, the stop codons are engineered into the expression vector. Some embodiments include at least three stop codons downstream (3') of the gene, at least one of each in each of the three possible reading frames. Some embodiments use groups of stop codons instead of single stop codons in each reading frame.

Figure 5:
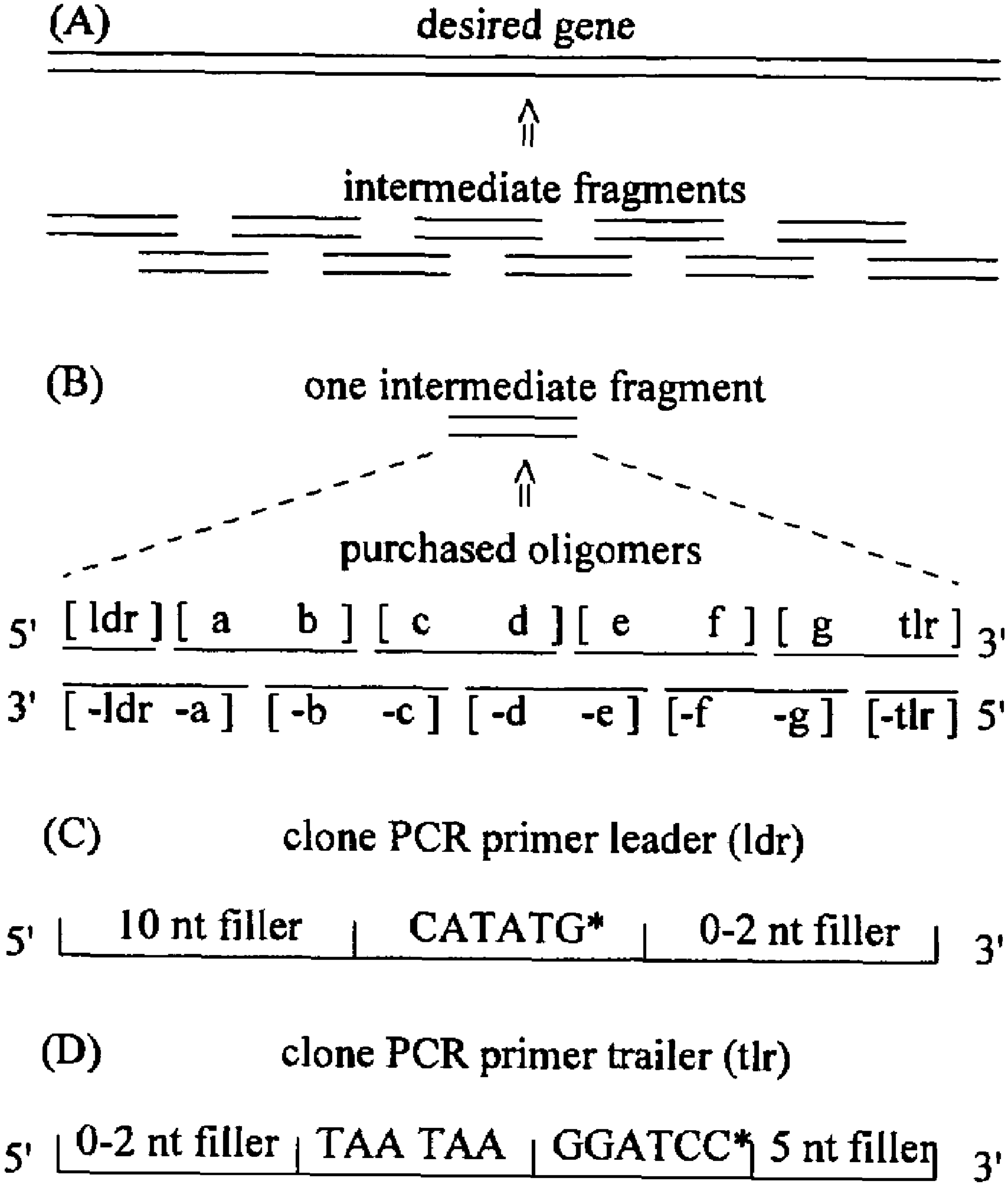
FIG. 5A schematically illustrates an embodiment comprising division and reassembly of a gene from intermediate fragments.
FIG. 5B schematically illustrates an embodiment comprising the division and reassembly of one of the intermediate fragments into oligonucleotides that include leader and trailer sequences.
FIG. 5C schematically illustrates an embodiment of a leader used in the expression of a polypeptide from an intermediate fragment.
FIG. 5D schematically illustrates an embodiment of a trailer used in the expression of a polypeptide from an intermediate fragment.

FIG. 5A-FIG. 5D illustrate an embodiment of the disclosed method in which a polypeptide is expressed from an intermediate fragment in the construction of a synthetic gene. FIG. 5A illustrates schematically the division and construction of a gene into a plurality of intermediate fragments.

FIG. 5B illustrates the division and construction of one of the intermediate fragments. The letters a-g each represents a portion of the sequence of the intermediate fragment. The brackets group these portions into oligonucleotides that are purchased or synthesized. "ldr" and "tlr" represent a leader and trailer, respectively. The corresponding portions of the sequence on the complementary strand are prefixed with a hyphen (-), i.e.,"-ldr," "-a," . . . "-g," and "-tlr." Again, brackets are used to indicate the oligonucleotides.

FIG. 5C is a schematic of leader (ldr) portion illustrated in FIG. 5B. From the 5'-end, the leader comprises a10-nt filler, a CATATG restriction site, and a 0-2-nt filler at the 3'-end. In the illustrated embodiment, the length of the 5'-filler is determined by the requirements of the restriction enzyme. The restriction site is used in cloning the intermediate fragment, and includes an ATG start codon. The 0-2-nt filler adjusts the reading frame of the intermediate fragment relative to the start codon. In some embodiments, the restriction site does not include a start codon. In some embodiments, a start codon is incorporated in the 3'-filler. filler.

FIG. 5D is a schematic of the trailer (tlr) portion illustrated in FIG. 5B. From the 5'-end, the trailer comprises a 0-2-nt filler, a TAATAA stop sequence, a GGATCC restriction site, and a 5-nt filler. The 0-2-nt filler adjusts the reading frame of the stop codon relative to intermediate fragment. TAATAA is a pair of stop codons. Any suitable stop codon is useful. Some embodiments use one stop codon. GGATCC is a restriction site used for cloning the intermediate fragment. The length of the 3'-filler is determined by the requirements of the restriction enzyme. Those skilled in the art will understand that, in other embodiments, the leader and/or trailer use a different combination of fillers, restriction sites, start codon, and/or stop codons. In some embodiments, the intermediate fragment comprises a start and/or stop codon and the leader and/or trailer does not include the codon. For example, in the case of a synthetic gene, the gene typically includes both a start and stop codon. Similarly, those skilled in the art will understand that in some embodiments, the leader and/or trailer does not comprise a restriction site. Some embodiments of the leader and/or trailer do not use a 5'- and/or a 3'-filler.

A polypeptide expressed from a clone with an N−1 defect will be defective. The expressed peptide is analyzed using any means known in the art, for example, gel electrophoresis, capillary electrophoresis, two-dimensional electrophoresis, isoelectric focusing, spectroscopy, mass spectroscopy, NMR spectroscopy, chemically, ligand binding, enzymatic cleavage, or a functional or immunological assay. A clone that expresses the correct peptide is free from N−1 defects.

In some embodiments, the expressed polypeptide is analyzed using gel electrophoresis, which separates polypeptides by molecular weight. Of the 64 possible DNA codons, 3 are stop codons. Consequently, the frame-shift caused by a point deletion is likely to generate a new stop codon, resulting in a prematurely truncated polypeptide, the molecular weight of which is determined using gel electrophoresis. A clone that provides a full-length polypeptide is likely to have the desired sequence, while one that provides a truncated polypeptide is likely to have at least one point deletion. In some embodiments, a clone with an N−1 defect or defects produces a polypeptide that is too long, because the N−1 defect results in a frame-shift that causes the terminating stop codon(s) to be ignored (read through). In some embodiments, such a polypeptide that is too long will be terminated by a stop codon engineered into the expression vector downstream (3') of the gene. As discussed above, some embodiments comprise three groups of stop codons, one group in each possible reading frame. In these embodiments, the molecular weight of the expressed polypeptide is higher than expected.

In some embodiments, analysis of the expressed polypeptide is used to narrow the sample of clones that are then sequenced. In these embodiments, the analysis of the expressed polypeptide is used to identify and to eliminate clearly defective (e.g., truncated or too long) DNA clones. The remaining clones are then sequenced. In these embodiments, the expression and analysis is a semi- or nonrandom selection method, in contrast to the random selection method described above. In some embodiments, the expressed polypeptide is analyzed by gel electrophoresis. In some cases, gel electrophoresis does not distinguish a defective polypeptide from the correct polypeptide. For example, in some cases a DNA sequence with an N−1 defect generates a defective polypeptide that, to within the resolution of the electrophoresis conditions, has the same molecular weight as the correct polypeptide. This scenario can arise where the defective DNA sequence fortuitously expresses a defective polypeptide similar in molecular weight to the correct polypeptide, for example, where the point defect is near the end of the clone. In another scenario, the clone has 3N point deletions that do not generate a new stop codon. As discussed above, the defective polypeptide is most likely shorter than the correct polypeptide. A defective polypeptide closer in molecular weight to the correct polypeptide than the resolution of the electrophoresis experiment is not distinguished. Given the resolving ability of gel electrophoresis, selecting a correct clone using the method is highly probable. The probability is further improved using an analytical technique with higher resolution, for example, capillary electrophoresis or mass spectroscopy. In some cases, all of the clones selected for sequencing in the gene expression screen have the correct sequence, indicating the reliability of this selection method. Furthermore, expressing a gene and determining the molecular weight of the expressed polypeptide is typically faster and/or less expensive than the equivalent amount of DNA sequencing. In some embodiments intermediate fragments are selected by estimating the molecular weight of the expressed polypeptide only, and DNA sequencing is reserved only for the final gene construct, and even then only after its molecular weight of a polypeptide expressed from the final gene has been estimated to be correct.

In some embodiments, all of the expressed polypeptides that are analyzed are defective, for example, truncated. In these embodiments, an analysis of the defective polypeptides indicates the location of the defect in the DNA sequence. The gene is then resynthesized using this information. In embodiments using multiple hierarchical synthesis steps, only some of the pieces of DNA are resynthesized, for example, an intermediate fragment containing the defect. In some embodiments, the offending fragment is divided in a different way and/or reoptimized, as discussed above. In some embodiments a different clone is chosen to replace the offending fragment.

The method described herein provides a quick, easy, and inexpensive method for constructing a synthetic DNA gene that encodes any desired protein or any other desired nucleic acid. A first example provided herein describes a two-step recursive assembly of a gene encoding *E. coli* threonine deaminase, a protein with 514 amino acid residues (1,542 coding bases). A second example describes a three-step recursive assembly of a gene encoding the smallpox (variola) DNA polymerase, a protein with 1,005 amino acid residues (3,015 coding bases). A third example describes a direct self-assembly of a synthetic *E. coli* threonine deaminase gene, with reassembly by cloning into an expression vector. A fourth example describes a two-step recursive assembly with sampling and sequencing of the 876 bp Ty3 GAG3 gene, which encodes the Gag3p polyprotein. Ty3 is a retrotransposon in *Saccharomyces cerevisiae*. A fifth example describes a two-step recursive assembly with sampling and sequencing for the 1640 bp Ty3 integrase ("Ty3

IN") gene. Accordingly, it will be appreciated that the method described herein may be used to construct any desired nucleic acid sequence or any desired gene.

*E. coli* threonine deaminase was chosen arbitrarily because (1) its size is comparable to most proteins, demonstrating wide applicability, (2) it assembles into a homotetramer, demonstrating protein-protein interactions, (3) its allosteric properties easily can be assessed for correct folding and assembly, and (4) in part by whim for old times sake because its structure and properties was the Ph. D. thesis project of one of us. See, Hatfield & Ray "Coupling of slow processes to steady state reactions" *J. Biol. Chem.*, 1970, 245(7), 1753-4; Hatfield, Ray, & Umbarger "Threonine deaminase from *Bacillus subtilis*. III. Pre-steady state kinetic properties." *J. Biol. Chem.*, 1970, 245(7), 1748-53; Hatfield & Umbarger "Threonine deaminase from *Bacillus subtilis*. II. The steady state kinetic properties." *J. Biol. Chem.*, 1970, 245(7), 1742-7; Hatfield & Umbarger "Threonine deaminase from *Bacillus subtilis*. I. Purification of the enzyme." *J. Biol. Chem.*, 1970, 245(7), 1736-41.

Smallpox (variola) DNA polymerase was chosen because (1) it is larger than most proteins, demonstrating wide applicability, and (2) current events render it of special interest. In particular, the ability to synthesize de novo a gene from a pathogenic organism permits study without actual use of the pathogen. Examples of such studies include regulation of gene expression, drug development, vaccine development, and the like. Because the pathogen is never used, there is no chance of exposure, either accidental or intentional. Moreover, the sequence of the synthetic gene may be modified to optimize expression in the selected, non-pathogenic organism.

Ty3 was chosen because of its resemblance to retroviruses. GAG3 encodes Gag3p, a 38 kDa polyprotein that is processed into a 26 kDa capsid and 9 kDa nucleocapsid that assemble into virus-like particles (VLP). Ty3 IN is implicated in the retrovirus-like integration of Ty3 in the *S. cerevisiae* genome.

Preferred embodiments of the disclosed method are illustrated in the following Examples. In these Examples, the terms "Medium-sized piece" and "Intermediate Fragment" are used interchangeably.

EXAMPLE 1

*E. coli* Threonine Deaminase by Two-step Recursive Decomposition and Overlap Extension Assembly EXAMPLE 1 illustrates the synthesis of an *E. coli* threonine deaminase gene by a two-step hierarchical decomposition and reassembly by overlap extension. *E. coli* threonine deaminase is a protein with 514 amino acid residues (1,542 coding bases).

Design

The sequence design method permuted synonymous (silent) codon assignments to each amino acid in the desired protein sequence. Each synonymous codon change results in a different artificial gene sequence that encodes the same protein. Because *E. coli* was the desired expression vector, the initial codon assignment was to pair each amino acid with its most frequent codon according to *E. coli* genomic codon usage statistics. Subsequently, the codon assignments were perturbed as described below. The final codon assignment implied a final DNA sequence to be achieved biochemically.

In this two-step hierarchical decomposition, the gene was divided first into five overlapping medium-sized pieces (in the present example, not longer than 340 bases, overlap not shorter than 33 bases), then each medium-sized piece was divided into several overlapping short segments (in the present example not longer than 50 bases, overlap not shorter than 18 bases). All overlaps were lengthened if necessary to include a terminal C or G for priming efficiency.

Figure 6:
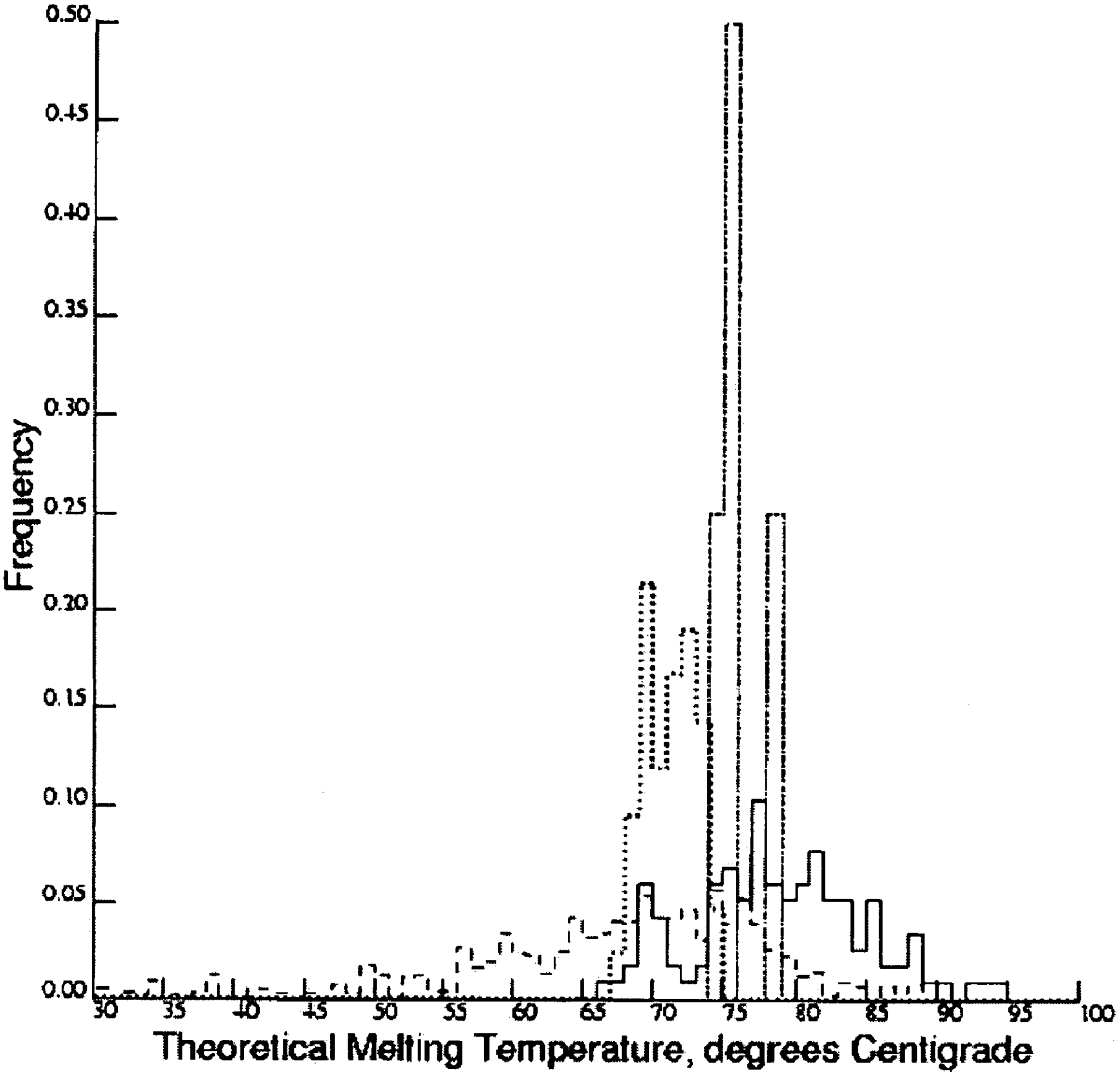
FIG. 6 illustrates the distribution of melting temperatures for the initial codon assignment for *E. coli* threonine deaminase in EXAMPLE 1. (solid) Correct matches between small segment overlaps. (dash-dot) Correct matches between long strand overlaps. (dashed) Incorrect matches between small segments. (dotted) Incorrect matches between long strands.
Figure 7:
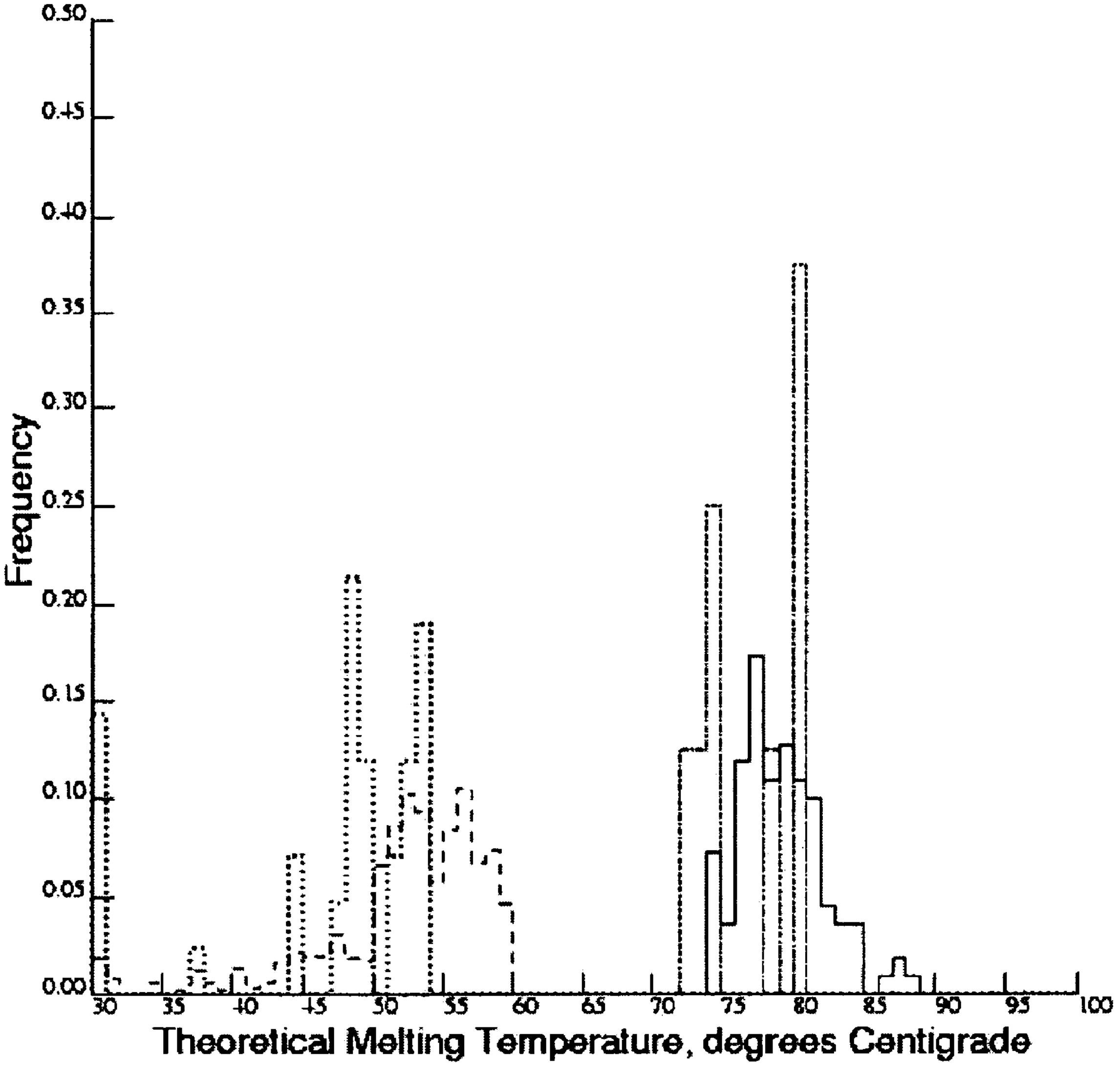
FIG. 7 illustrates the distribution of melting temperatures after the final codon assignment for *E. coli* threonine deaminase in EXAMPLE 1.

Theoretical melting temperatures were calculated with Mfold for all possible correct and incorrect hybridizations of the medium-sized and short pieces of DNA using the most common codons. The results are illustrated in FIG. 6. The gap between the lowest-melting correct match and the highest-melting incorrect match was increased by perturbing the codon assignments as described above. Theoretical melting temperatures for the optimized sequences are illustrated in FIG. 7. In the present example, the gap was at least 10° C.

The final codon assignment to every amino acid in the threonine deaminase protein sequence is provided in FIG. 8 (SEQ. ID. NO.: 1). FIG. 9 is the codon assignment key for *E. coli*. FIG. 8 forms the basis for FIG. 7, FIG. 10, and FIG. 11A-FIG. 11D. The initial codon assignment (column 0 in FIG. 9) forms the basis for FIG. 6.

Figure 10:
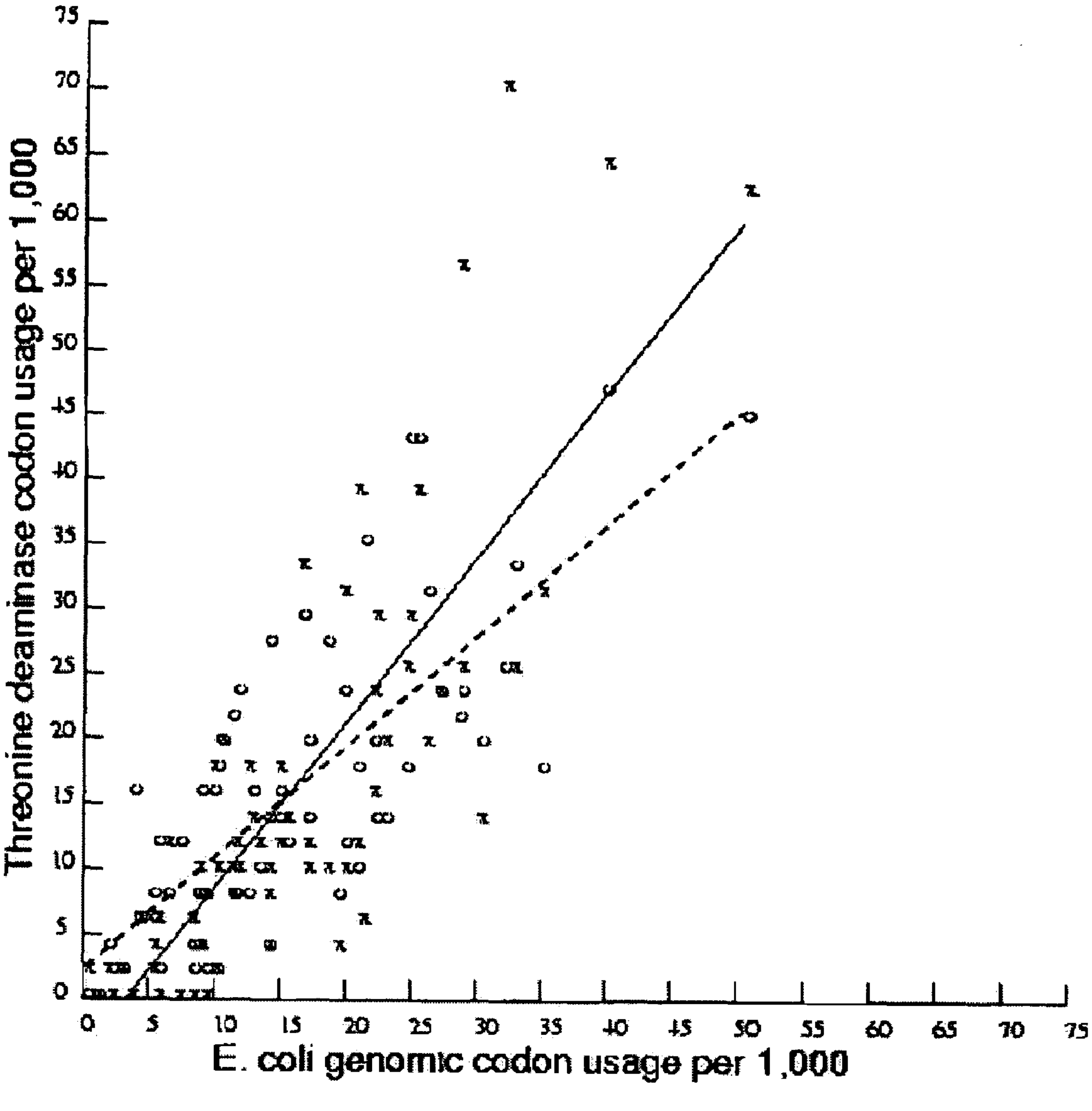
FIG. 10 illustrates the codon usage for the synthetic *E. coli* threonine deaminase sequence from EXAMPLE 1 vs. the codon usage in the *E. coli* genome. Each codon is shown as a point in which the x-coordinate is its usage per 1,000 in *E. coli* and the y-coordinate is its usage per 1,000 in threonine deaminase. (x, solid line) Usage in native threonine deaminase. (o, dashed line) Usage in the synthetic gene.

The design objectives may be achieved without excessive use of rare codons as illustrated in FIG. 10. The codon usage in the present example (open circles and dashed line) is shown as a function of genomic codon usage in *E. coli*. The correlation coefficient of codon usage here with codon usage in *E. coli* is 0.76. For comparison, the native codon usage in natural threonine deaminase is also shown (x's and solid line). The correlation coefficient of native codon usage with codon usage in *E. coli* is 0.81. The native usage is better than, but comparable to, the designed.

The resulting DNA sequence was decomposed into the short overlapping segments shown in the overlap maps illustrated in FIG. 11A-FIG. 11E. The overlaps between short segments are indicated by brackets: [ ]. The overlaps between long strands are indicated by braces: { }. In the depiction of strands 1 and 4, three bases preceding the (−3) are the same bases as the first three bases shown after the (−3) in order to clearly illustrate the overlaps. These bases are not repeated in the actual DNA sequences. SEQ. ID. NO.: 2-SEQ. ID. NO.: 12 correspond to the sequences that comprise strand 0 (FIG. 11A), SEQ. ID. NO.: 13-SEQ. ID. NO.: 24 correspond to the sequences that comprise strand 1 (FIG. 11B), SEQ. ID. NO.: 25-SEQ. ID. NO.: 36 correspond to the sequences that comprise strand 2 (FIG. 11C), SEQ. ID. NO.: 37-SEQ. ID. NO.: 48 correspond to the sequences that comprise strand 3 (FIG. 11D), and SEQ. ID. NO.: 49-SEQ. ID. NO.: 60 correspond to the sequences that comprise strand 4 (FIG. 11E). As is described in greater detail below, each short segment was synthesized directly and assembled into the five medium-sized pieces of DNA in five parallel reactions. In a second stage, the five medium-sized pieces were assembled into the synthetic gene. The segments shown in FIG. 11A-FIG. 11E plus the various primers for overlap extension totaled 72 synthesized segments with a total of 3,093 nucleotides.

Synthesis

The target DNA sequence of the synthetic *E. coli* L-threonine deaminase gene has 1,542 bases. In the present example, the target DNA sequence was decomposed into a set of five medium-sized pieces, each medium-sized piece overlapping the adjacent medium-sized piece by at least 33 bases. In turn, each medium-sized piece was decomposed into "sets" of 11 or 12 small, single-stranded DNA segments, which overlapped the adjacent segment by from 18 to 50 bases. The five medium-sized pieces are designated "Medium-sized piece 0" through "Medium-sized piece 4" herein. The small single-stranded DNA segments that make up the medium-sized pieces are designated as "Seg," medium-sized piece number, and segment number, where the segment number starts at 0 starting at the 5'-end of the forward segment. Note that the numbering for both the medium-sized pieces and the segments begins at zero. For example, the first segment of Medium-sized piece 0 is "Seg-0-0"; the seventh segment of Medium-sized piece 4 is "Seg-4-6. " The segments and primers were commercially synthesized by Illumina, Inc., San Diego, Calif.

FIG. 12A-FIG. 12E illustrate the single-stranded DNA segments used to construct Medium-sized piece 0 through Medium-sized piece 4, respectively. For each segment, the region that overlaps the adjacent complementary strand is underlined and numbered. Overlaps identified by primed numbers are complementary to the corresponding unprimed overlaps. For example, sequence 1 is complementary to sequence 1' of the adjacent complementary strand, while sequence 2 is complementary to sequence 2', and so forth. SEQ. ID. NO.: 61-SEQ. ID. NO.: 71 correspond to Seg-0-0, Seg-0-1, Seg-0-2 . . . Seg-0-10 illustrated in FIG. 12A, respectively. Similarly, SEQ. ID. NO.: 72-SEQ. ID. NO.: 82 correspond to Seg-1-0 through Seg-1-10 (FIG. 12B), SEQ. ID. NO.: 83-SEQ. ID. NO.: 93 correspond to Seg-2-0 through Seg-2-10 (FIG. 12C), SEQ. ID. NO.: 94-SEQ. ID. NO.: 105 correspond to Seg-3-0 through Seg-3-11 (FIG. 12D), and SEQ. ID. NO.: 106-SEQ. ID. NO.: 116 correspond to Seg-4-0 through Seg-4-10 (FIG. 12E).

Leader and Trailer Primers

For Medium-sized piece 0, the first segment, Seg-0-0, serves as the leader primer for overlap extension. The trailer primer (reverse complement) is 5'-GTAGCAGTAGGCATCAC-3' (17-mer, SEQ. ID. NO.: 117). For Medium-sized piece 1, segment Seg-1-0 serves as the leader primer and the trailer primer is 5'-GGCTTCAACGGCTATCAC-3' (18-mer, SEQ. ID. NO.: 118). For Medium-sized piece 2, segment Seg-2-0 serves as the leader primer and the trailer primer is 5'-GCTTAAGATGTGGGCCAG-3' (18-mer, SEQ. ID. NO.: 119). For medium-sized piece 3, Seg-3-0 serves as the leader primer and Seg-3-11 serves as the trailer primer. For Medium-sized piece 4, segment Seg-4-0 serves as the leader primer and the trailer primer is 5'-TTAGCCTGCGAGGAAGAAAC-3' (20-mer, SEQ. ID. NO.: 120). Those skilled in the art will appreciate that the segments may be designed such that no added primers are used, as for Medium-sized piece 3, such that one added primer is used, as for Medium-sized pieces 0-2, and 4, or such that two added primers are used, not illustrated. In particular, if an even number of segments is used, the segments may be designed such that no added primers are needed where the first segment serves as the leader primer and the last segment serves as the trailer primer. It will also be appreciated that different flanking sequences may be added easily to these leaders and trailers.

Assembly of the Five Medium-Sized Pieces

Figure 13:
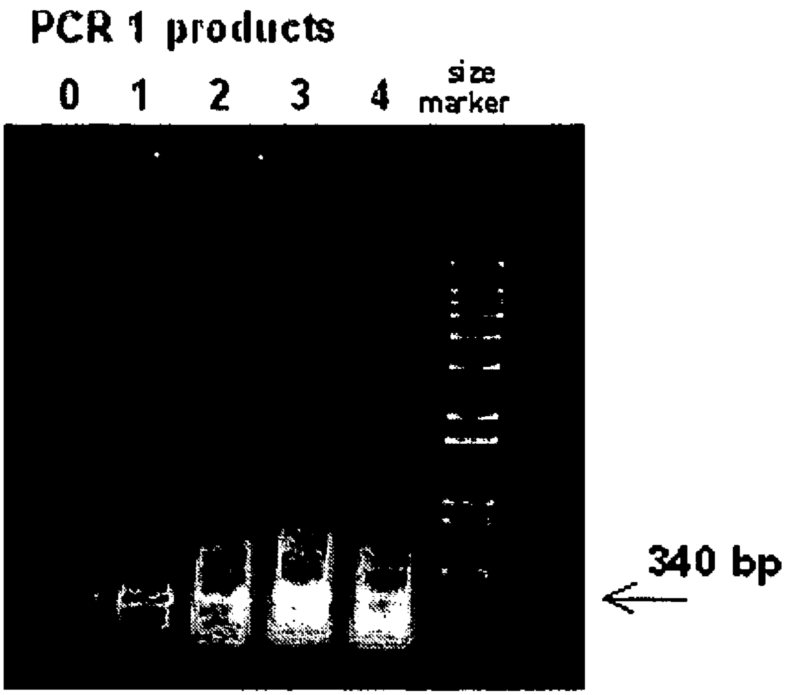
FIG. 13 is a gel of the products of the first set of overlap extension reactions in EXAMPLE 1.

First Overlap Extension Reactions. The five Medium-sized pieces were constructed in parallel by overlap extension and PCR from the appropriate set of single-stranded DNA sequences. The reaction mixture is provided in TABLE III and the thermocycler conditions in TABLE IV. The products of the overlap extension reactions were separated on a 1% agarose gel, shown in FIG. 13.

TABLE III

| Reagent | Quantity |
|---|---|
| Roche High Fidelity PCR Master, Vial #1 (Product # 2140314) | 25.0 μL |
| Synthetic oligonucleotide mix * | 1.0 μL |
| Leader primer, 50 μM | 0.5 μL |
| Trailer primer, 50 μM | 0.5 μL |
| Sterile water, Roche (molecular biology grade) | 23.0 μL |

* For each of the synthetic oligonucleotide sets (0–4), the forward and reverse complement synthetic oligonucleotides were mixed in equal amounts to a final concentration of 27.5 ng/μL.

TABLE IV

| Step | Conditions |
|---|---|
| 1. | 94° C. for 5 minutes for initial denaturation, |
| 2. 25 cycles of: | 94° C. for 1 minute |
| | 45° C. for 30 seconds |
| | 65° C. for 5 minutes |
| 3. | 65° C. for 10 minutes for final extension |

Figure 14:
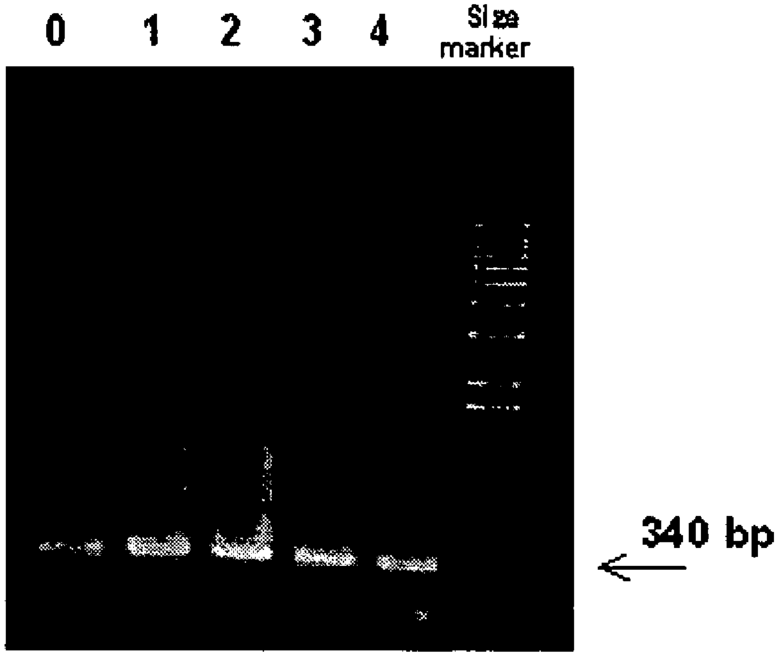
FIG. 14 is a gel of the products of the PCR reactions in EXAMPLE 1.

PCR Reaction (enrichment). Each Medium-sized piece was separately enriched by PCR using the reaction mixture provided in TABLE V and the thermocycler conditions provided in TABLE VI. The products of the PCR reactions were separated on a 1% agarose gel shown in FIG. 14.

TABLE V

| Reagent | Quantity |
|---|---|
| Roche High Fidelity PCR Master, Vial #1 (Product # 2140314) | 25.0 μL |
| 1:50 dilution of first overlap extension reaction product | 1.0 μL |
| Leader primer, 50 μM | 0.5 μL |
| Trailer primer, 50 μM | 0.5 μL |
| Sterile water, Roche (molecular biology grade) | 23.0 μL |

TABLE VI

| Step | Conditions |
|---|---|
| 1. | 94° C. for 5 minutes for initial denaturation, |
| 2. 25 cycles of: | 94° C. for 1 minute |
| | 45° C. for 30 seconds |
| | 65° C. for 5 minutes |
| 3. | 65° C. for 10 minutes for final extension |

Assembly of the Five Medium-Sized Pieces into a Full Length Gene

Figure 15:
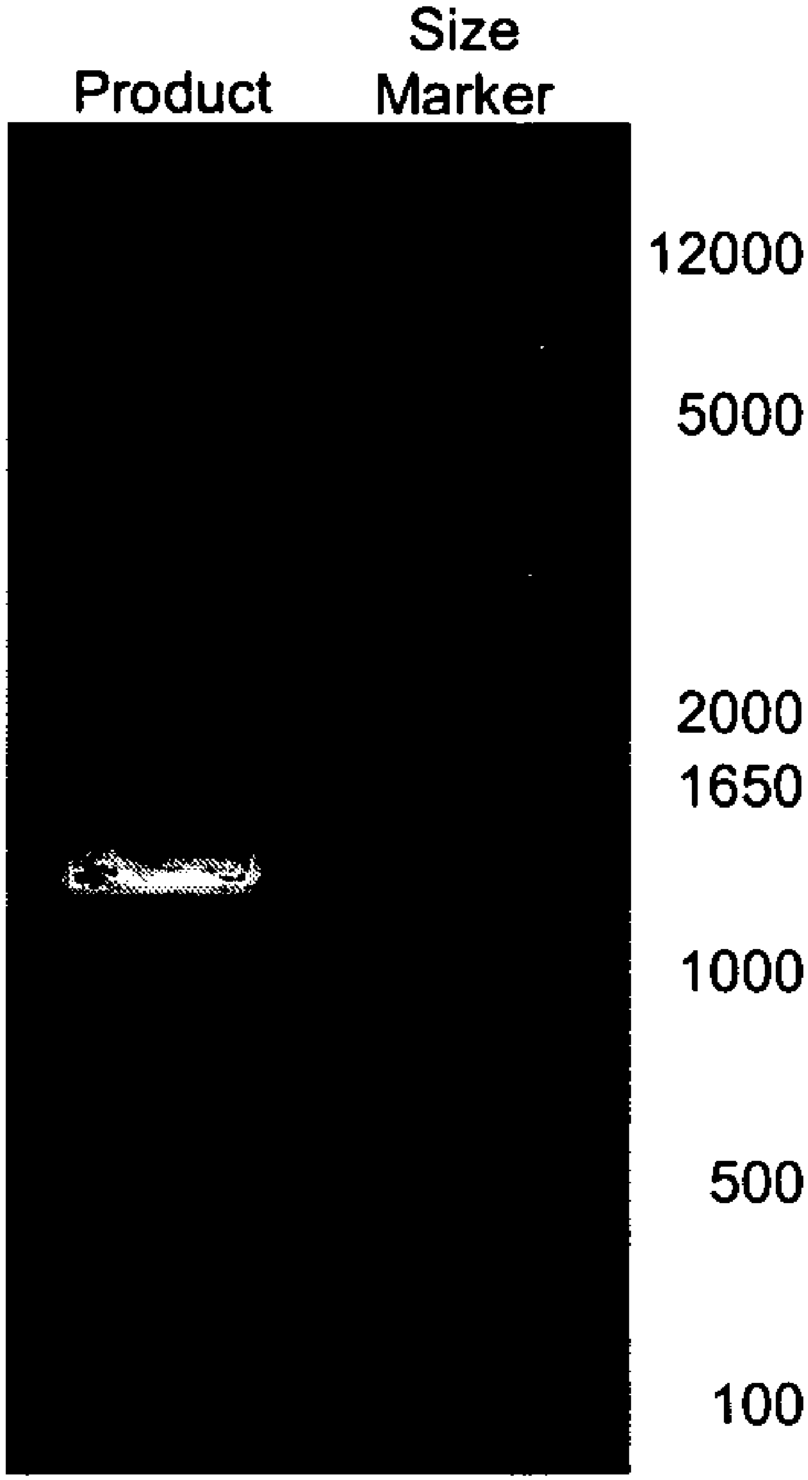
FIG. 15 is a gel of the products of the second overlap extension reaction in EXAMPLE 1.

Second Overlap Extension Reaction. The synthetic threonine deaminase gene was constructed from the five medium-sized pieces from the PCR reactions using the reaction mixture provided in TABLE VII and the thermocycler conditions provided in TABLE VIII. After the reaction was complete, product was run on a 1.2% agarose gel (FIG. 15) and the band corresponding to the threonine deaminase gene was purified from the gel with GENECLEAN® (BIO101 Systems®, Qbiogene) DNA purification system. The purified gene was further purified with phenol-chloroform (1:1) and chloroform-isoamyl alcohol (24:1). The aqueous layer was ethanol precipitated with glycogen, and the precipitate resuspended in water and digested with NdeI and BamHI. Those skilled in the art will appreciate that other restriction sites could be incorporated in the synthetic gene.

TABLE VII

| Reagent | Quantity |
|---|---|
| PCR Reaction Product, Medium-sized piece 0 | 2.0 μL |
| PCR Reaction Product, Medium-sized piece 1 | 2.0 μL |
| PCR Reaction Product, Medium-sized piece 2 | 2.0 μL |
| PCR Reaction Product, Medium-sized piece 3 | 2.0 μL |
| PCR Reaction Product, Medium-sized piece 4 | 2.0 μL |
| Leader primer, 50 μM [1] | 1.0 μL |
| Trailer primer, 50 μM [2] | 1.0 μL |
| Sterile water, Roche (molecular biology grade) | 13.0 μL |
| Roche High Fidelity PCR Master, Vial #1 (Product # 2140314) [3] | 25.0 μL |

[1] Forty-five base pair leader primer with NdeI endonuclease restriction enzyme site (bold): 5'-CTATATCTAGCATATGGCCGATTCT-CAACCTCTGTCTGGAGCACC-3' (SEQ. ID. NO.: 121).
[2] Forty-five base pair trailer primer (reverse complement) with BamHI endonuclease restriction enzyme site (bold): 5'-GTATTGGATCCTTAGC-CTGCGAGGAAGAAACGAAAGGCGGGGTTG-3' (SEQ. ID. NO.: 122).
[3] High fidelity PCR reagent containing Tgo DNA Polymerase and Taq DNA Polymerase in Tris-HCl, 100 mM; $(NH_4)_2SO_4$,44 mM; $MgCl_2$, 3 mM; dATP, dCTP, dGTP, dTTP (each 0.4 mM).

TABLE VIII

| Step | Conditions |
|---|---|
| 1. | 94° C. for 5 minutes for initial denaturation, |
| 2. 20 cycles of: | 94° C. for 1 minute |
| | 60° C. for 30 seconds |
| | 65° C. for 10 minutes |
| 3. | 65° C. for 10 minutes for final extension |

Ligation and Expression

Directional cloning is performed on the purified threonine deaminase gene. pET14b Expression vector (Novagen) is cleaved with BamHI and NdeI generating compatible termini to the threonine deaminase. The threonine deaminase insert is ligated into the vector and this is used to transform into BL21 DE3 electro competent cells.

EXAMPLE 2 variola DNA Polymerase by Three-step Recursive Decomposition and Overlap Extension Assembly EXAMPLE 2 illustrates the synthesis of a variola DNA polymerase gene by a three-step hierarchical decomposition and reassembly by overlap extension. variola DNA polymerase is a protein with 1,005 amino acid residues (3,015 coding bases). variola DNA polymerase is also referred to as "Varpol" and "vpol" herein.

Design

Because the variola DNA polymerase gene was intended for expression in *E. coli*, codon selection considerations were similar to those used in the design of *E. coli* threonine deaminase described in EXAMPLE 1.

The three-step hierarchical decomposition was performed as follows. First, the gene was divided into two large pieces of about 1,500 bases. The first large piece is designated herein as "Part I" or "polymerase-1." The second large piece is referred to herein as "Part II" or "polymerase-2. " Parts I and II were designed with complementary ApaI sites to allow their reassembly by ligation. Second, each large piece was divided into five overlapping medium-sized pieces (Intermediate Fragments), in the present example, not longer than 340 bases, with overlaps not shorter than 33 bases. Third, each medium-sized piece was divided into several overlapping short segments, in the present example not longer than 50 bases, with overlaps not shorter than 18 bases. All overlaps were lengthened if necessary to include a terminal C or G for DNA polymerase priming efficiency.

Figure 16:
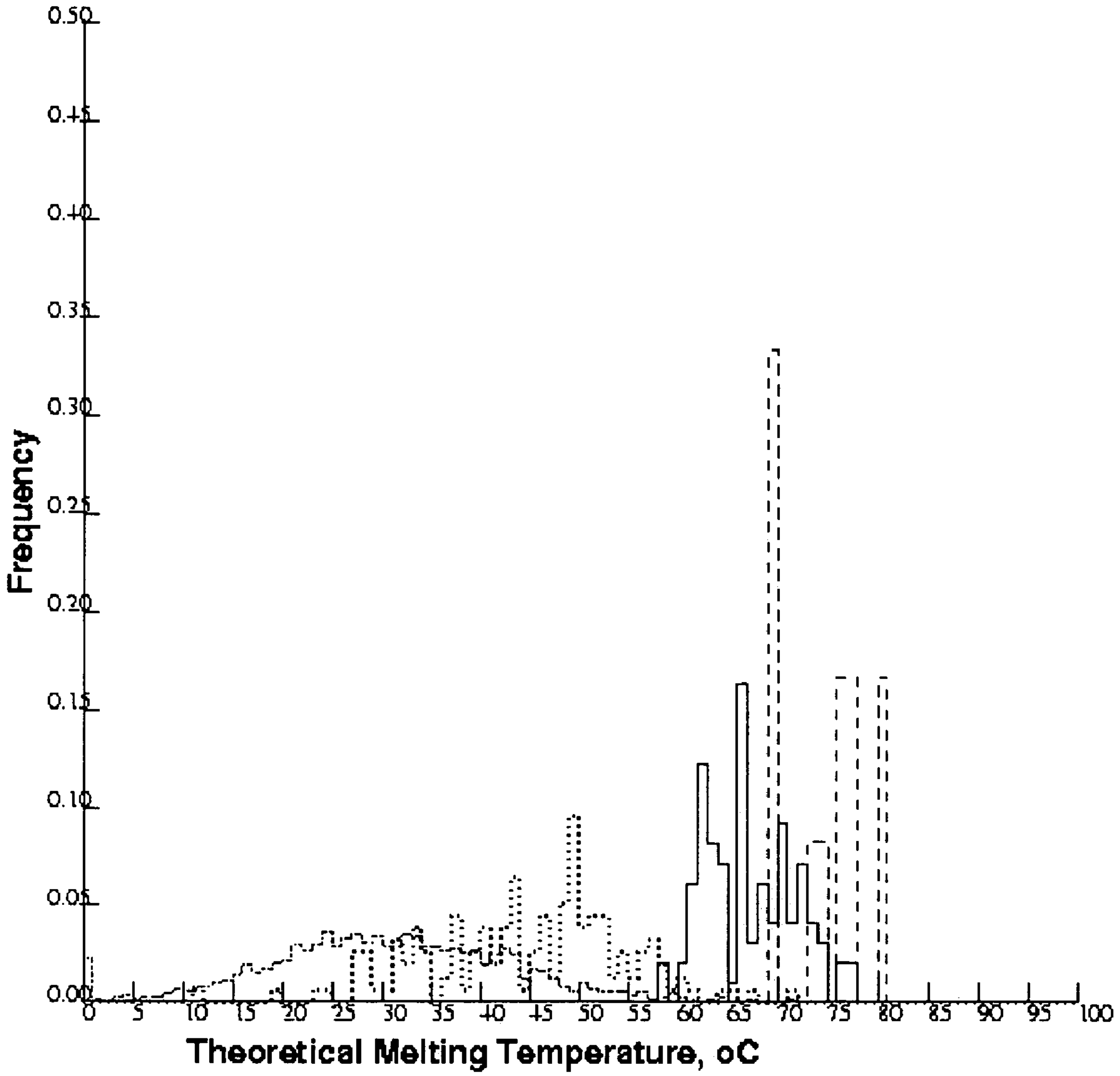
FIG. 16 illustrates the distribution of melting temperatures for the initial codon assignment for variola DNA polymerase-1 in EXAMPLE 2. (solid) Correct matches between small segment overlaps. (dash-dot) Correct matches between long strand overlaps. (dashed) Incorrect matches between small segments. (dotted) Incorrect matches between long stands.
Figure 17:
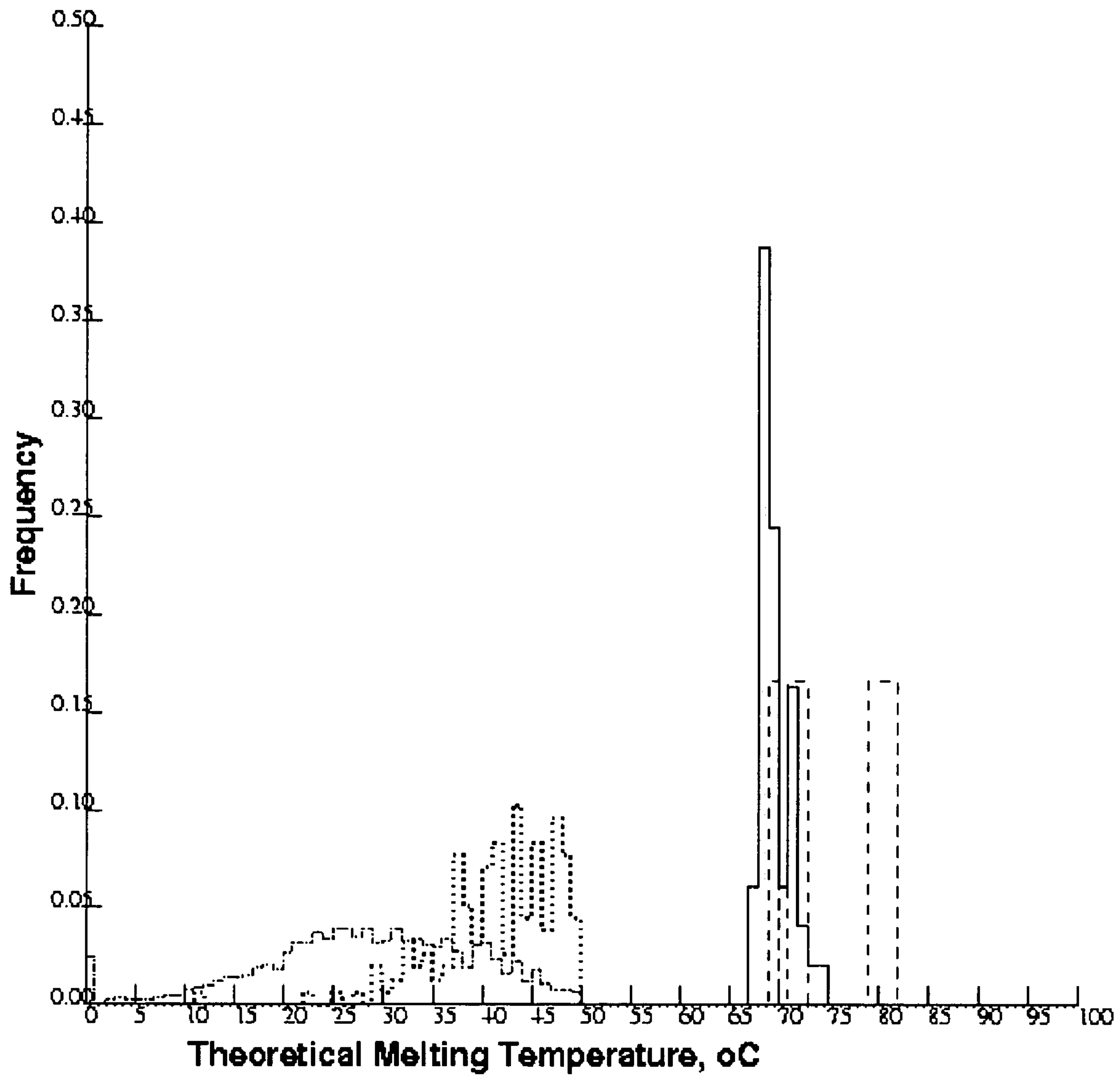
FIG. 17 illustrates the distribution of melting temperatures after the final condon assignment for variola DNA polymerase-1 in EXAMPLE 2.
Figure 19:
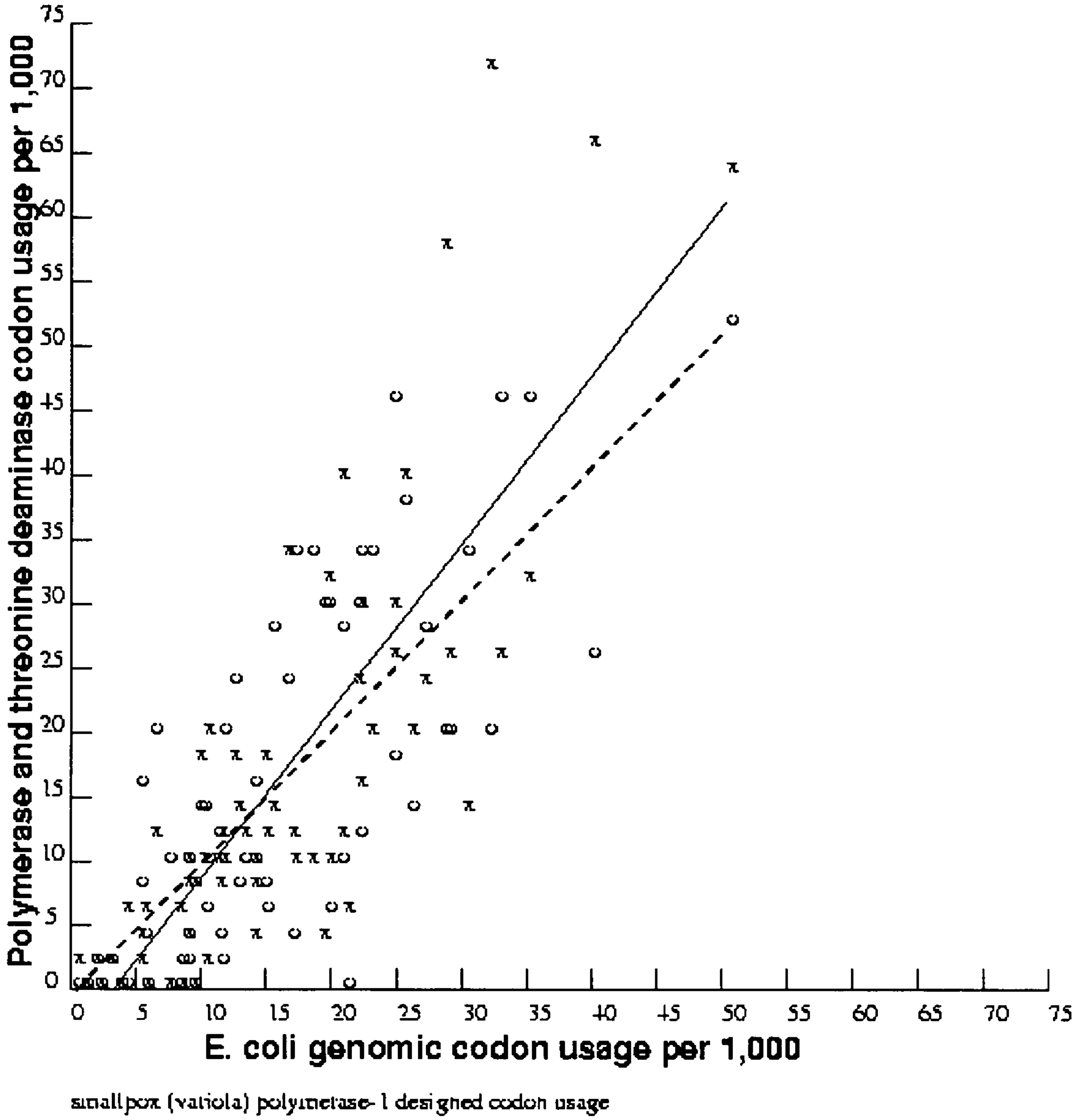
FIG. 19 illustrates the codon usage for the synthetic variola DNA polymerase-sequence from EXAMPLE 2 vs. the codon usage in the *E. coli* genome. Each as a point in which the x-coordinate is its usage per 1,000 in *E. coli* and the y-coodinates is its usage per 1,000 in threonine deaminase. (x, solid line) Usage in native threonine deaminase. (o, dashed line) Usage in the synthetic gene.

The sequences of the DNA pieces were perturbed to provide a suitable gap between the lowest-melting correct match and the highest-melting wrong match. Theoretical melting temperatures were calculated as described in EXAMPLE 1. For Part I of the gene, the melting temperatures of the correct and incorrect matches for the small and medium-sized pieces for the most common *E. coli* codons are provided in FIG. 16 and for the designed sequence in FIG. 17. The designed DNA sequence is provided in FIG. 18 (SEQ. ID. NO.: 123), which is based on the codon key in FIG. 9 of EXAMPLE 1. A comparison of the codon usage in the designed Part I sequence compared to the codon usage in native *E. coli* threonine deaminase is provided in FIG. 19, illustrating the similarity in codon frequency.

Figure 20:
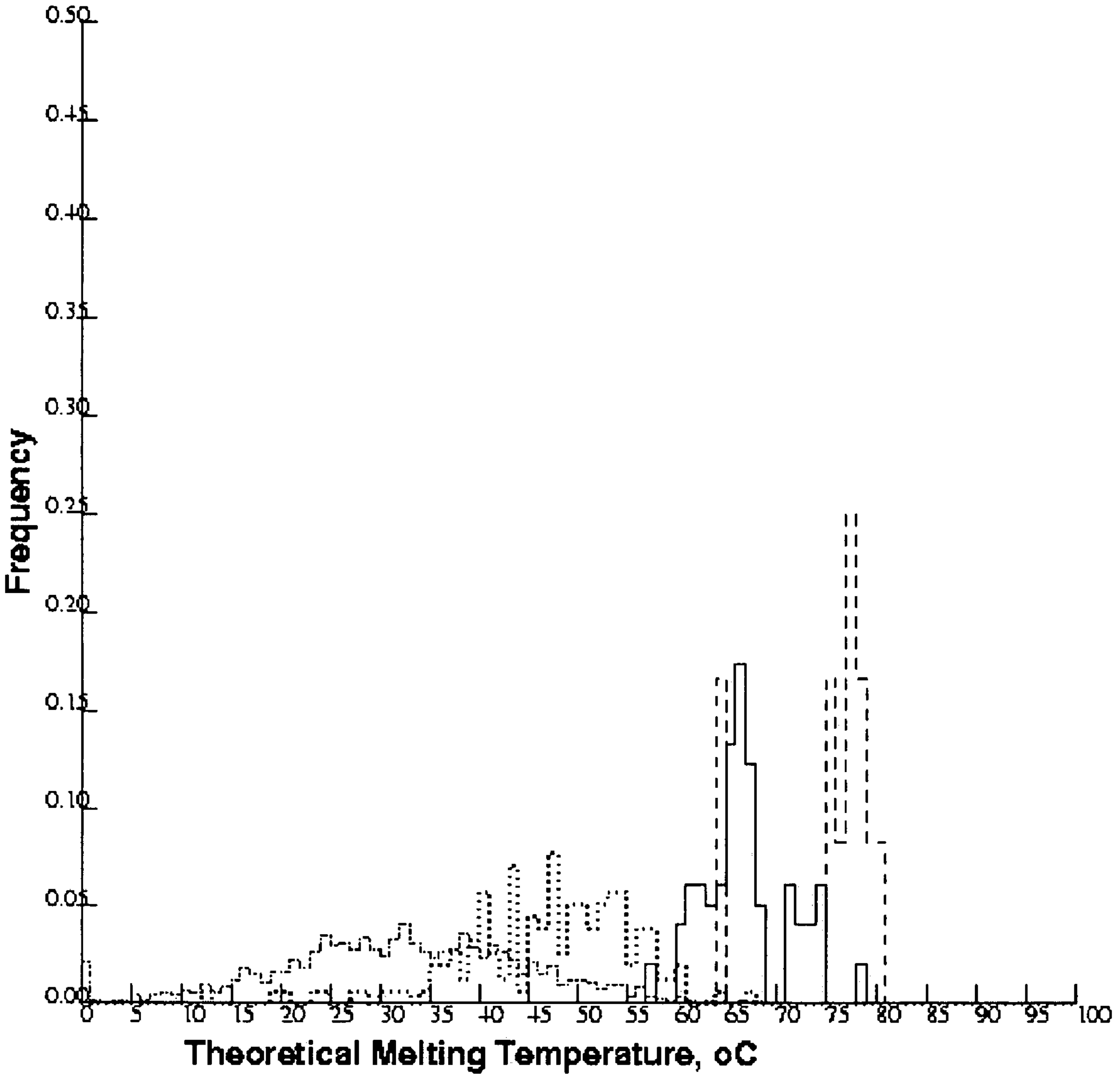
FIG. 20 illustrates the distribution of melting temperatures at the initial codon assignment for variola DNA polymerase-2 in EXAMPLE 2. (solid) Correct matches segment overlaps. (dash-dot) Correct matches between long strand overlaps. (dashed) incorrect matches between small segments. (dotted) Incorrect matches between long
Figure 21:
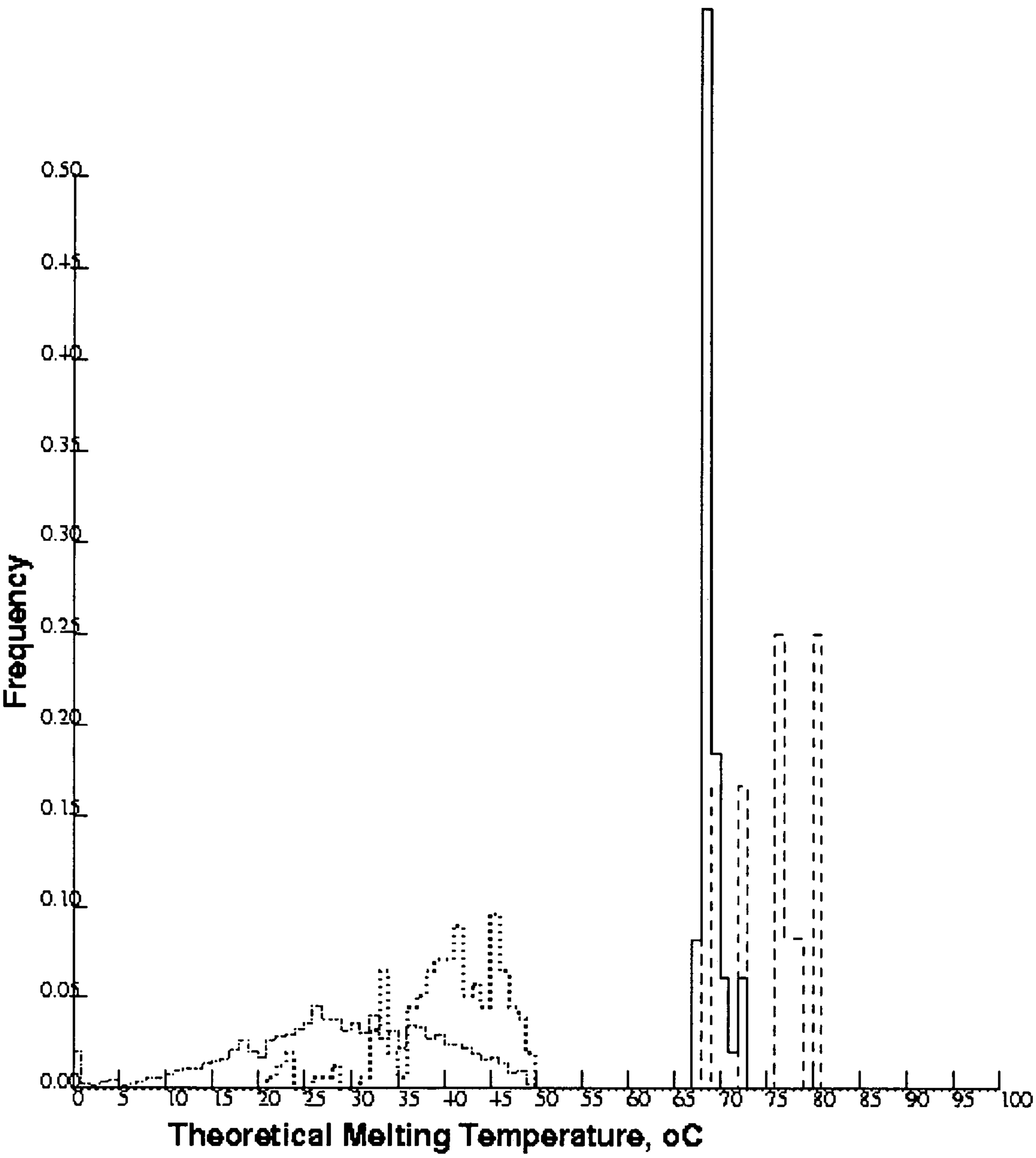
FIG. 21 illustrates the distribution of melting temperatures after the final codon assignment for variola DNA polymerase-2 in EXAMPLE 2.
Figure 23:
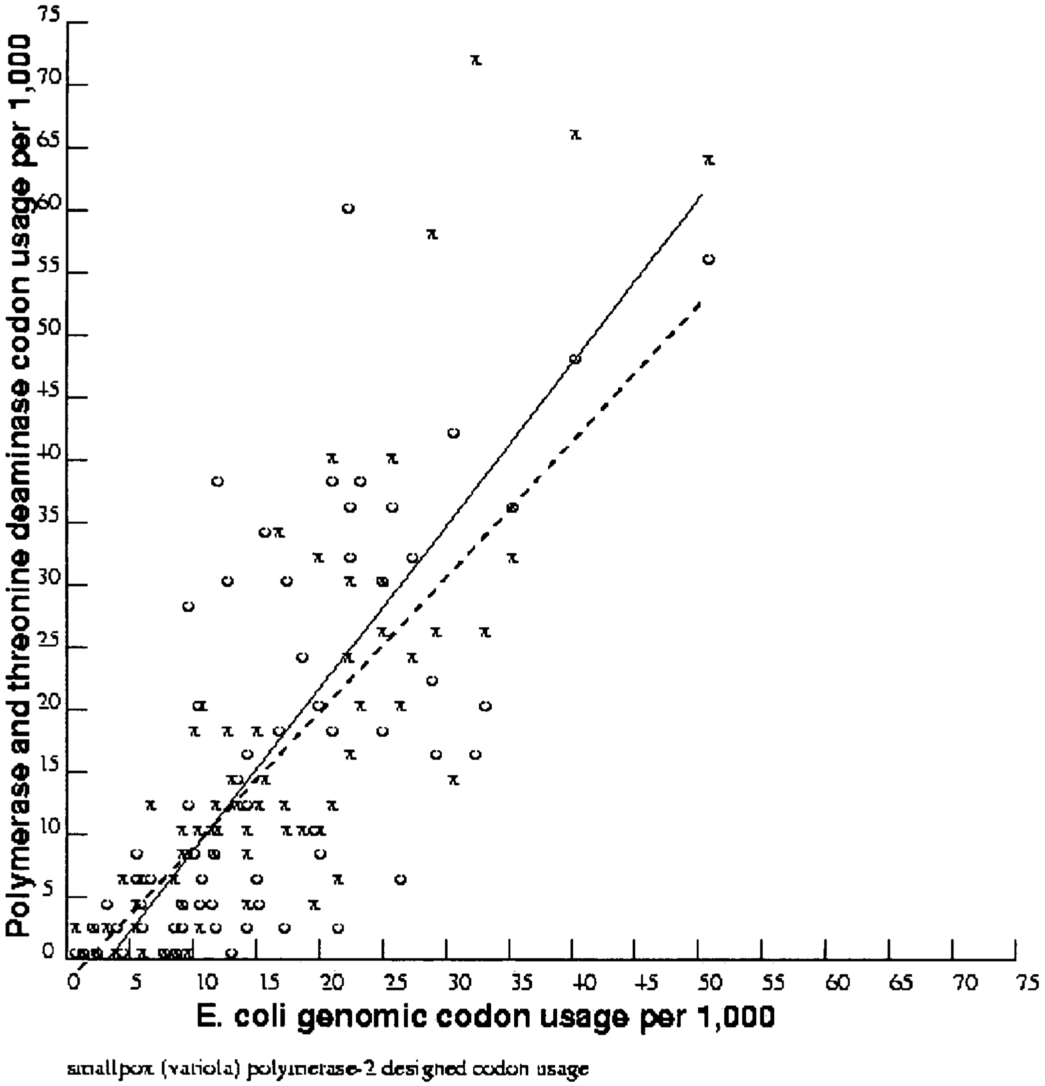
FIG. 23 illustrates the codon usage for the synthetic variola DNA polymerase-2 sequence from EXAMPLE 2 vs. the codon usage in the *E. coli* genome. Each codon is shown as a point in which the x-coordinate is its usage per 1,000 in *E. coli* and the y-coordinate is its usage per 1,000 in threonine deaminase. (x, solid line) Usage in native threonine deaminase. (o, dashed line) Usage in the synthetic gene.

Theoretical melting temperatures for the small and medium-sized pieces of Part II of the variola DNA polymerase gene are provided in FIG. 20 for the most common codons of *E. coli*, and for the designed sequences in FIG. 21. The designed sequence for Part II is provided in FIG. 22 (SEQ. ID. NO.: 124), which is based on the codon key in FIG. 9 of EXAMPLE 1. A comparison of the codon usage of native *E. coli* threonine deaminase with the designed sequence of Part II is provided in FIG. 23, illustrating the similarity in codon frequency.

Overlap maps for the overlapping short segments used to build each of the five Intermediate Fragments (medium-sized pieces) 0-4, leaders, and trailers that make up Part I of the variola DNA polymerase gene are provided in FIG. 24A-FIG. 24G. SEQ. ID. NO.: 125 corresponds to leader-0 (FIG. 24A), SEQ. ID. NO.: 126 corresponds to leader-1 (FIG. 24A), SEQ. ID. NO.: 127-SEQ. ID. NO.: 138 correspond to strand-0 (FIG. 24B), SEQ. ID. NO.: 139-SEQ. ID. NO.: 150 correspond to strand-1 (FIG. 24C), SEQ. ID. NO.: 151-SEQ. ID. NO.: 160 correspond to strand-2 (FIG. 24D), SEQ. ID. NO.: 161-SEQ. ID. NO.: 170 correspond to strand-3 (FIG. 24E), SEQ. ID. NO.: 171-SEQ. ID. NO.: 180 correspond to strand-4 (FIG. 24F), SEQ. ID. NO.: 181 corresponds to trailer-0 (FIG. 24G), SEQ. ID. NO.: 182 corresponds to trailer-1 (FIG. 24G). As is described in greater detail below, each short segment shown in FIG. 24A-FIG. 24G was synthesized directly and assembled into the five Intermediate Fragments in five parallel reactions, then in a second stage, the five Intermediate Fragments were assembled into Part I of the variola DNA polymerase gene.

Overlap maps for the overlapping short segments used to build each of the five Intermediate Fragments 0-4, leaders, and trailers that make up Part II of the variola DNA polymerase gene are provided in FIG. 25A-FIG. 25G. SEQ. ID. NO.: 183 corresponds to leader-0 (FIG. 25A), SEQ. ID. NO.: 184 corresponds to leader-1 (FIG. 25A), SEQ. ID. NO.: 185-SEQ. ID. NO.: 196 correspond to strand-0 (FIG. 25B), SEQ. ID. NO.: 197-SEQ. ID. NO.: 208 correspond to strand-1 (FIG. 25C), SEQ. ID. NO.: 209-SEQ. ID. NO.: 218 correspond to strand-2 (FIG. 25D), SEQ. ID. NO.: 219-SEQ. ID. NO.: 228 correspond to strand-3 (FIG. 25E), SEQ. ID. NO.: 229-SEQ. ID. NO.: 238 correspond to strand-4 (FIG. 25F), SEQ. ID. NO.: 239 corresponds to trailer-0 (FIG. 25G), SEQ. ID. NO.: 240 corresponds to trailer-1 (FIG. 24G). As is described in greater detail below, each short segment shown in FIG. 25A-FIG. 25G was synthesized directly and assembled into the five Intermediate Fragments in five parallel reactions, then in a second stage, the five Intermediate Fragments were assembled into Part II of the variola DNA polymerase gene.

Biochemistry

The variola DNA polymerase gene was assembled in the reverse order of the design process: first, the assembly of the ten Intermediate Fragments (five each for Parts I and II of the variola DNA polymerase gene); second, the assembly of the two 1500 bp large pieces, Parts I and II (which combined make up the full length gene); and finally, ApaI digestion of Part I (in the segment 1Seg-4-09) and Part II (in the segment 2Seg-2-00) to generate compatible flanking termini, allowing the two large pieces to be ligated together to generate the full-length variola DNA polymerase gene.

variola DNA polymerase Part I. Each of the five Intermediate Fragments 0-4 that make up Part I was assembled from synthetic oligonucleotide sets of alternating strand specificity that overlap one another. The sequences of the short ssDNA segments used to construct each of the Intermediate Fragments are provided in FIG. 26A-FIG. 26E. Overlaps between adjacent segments are indicated by underlining and identifying numbers beneath the underlined regions. Overlaps identified with primed numbers are complementary to the corresponding unprimed overlaps. SEQ. ID. NO.: 241-SEQ. ID. NO.: 252 correspond to 1Seg-0-00 through 1Seg-0-11 (FIG. 26A), SEQ. ID. NO.: 253-SEQ. ID. NO.: 264 correspond to 1Seg-1-00 through 1Seg-1-11 (FIG. 26B), SEQ. ID. NO.: 265-SEQ. ID. NO.: 274 correspond to 1Seg-2-00 through 1Seg-2-09 (FIG. 26C), SEQ. ID. NO.: 275-SEQ. ID: NO.: 284 correspond to 1Seg-3-00 through 1Seg-3-09 (FIG. 26D), and SEQ. ID. NO.: 285-SEQ. ID. NO.: 294 correspond to 1Seg-4-00 through 1Seg-4-09 (FIG. 26E).

For each of the Intermediate Fragments, the first segment (1Seg-0-00, 1Seg-1-00, 1Seg-2-00, 1Seg-3-00, and 1Seg-4-00) serves as the leader primer for overlap extension. The last segment (1Seg-0-11, 1Seg-1-11, 1Seg-2-09, 1Seg-3-09, and 1Seg-4-09) serves as the trailer primer.

variola DNA polymerase Part II. Each of the five Intermediate Fragments 0-4 that make up Part II was assembled from synthetic oligonucleotide sets of alternating strand specificity that overlap one another. The sequences of the short ssDNA segments used to construct each of the Intermediate Fragments are provided in FIG. 27A-FIG. 27E. Overlaps between adjacent segments are indicated by underlining and identifying numbers beneath the underlined regions. Overlaps identified with primed numbers are complementary to the corresponding unprimed overlaps. SEQ. ID. NO.: 295-SEQ. ID. NO.: 306 correspond to 2Seg-0-00 through 2Seg-0-11 (FIG. 27A), SEQ. ID. NO.: 307-SEQ. ID. NO.: 318 correspond to 2Seg-1-00 through 2Seg-1-11 (FIG. 27B), SEQ. ID. NO.: 319-SEQ. ID. NO.: 328 correspond to 2Seg-2-00 through 2Seg-2-09 (FIG. 27C), SEQ. ID. NO.: 329-SEQ. ID. NO.: 338 correspond to 2Seg-3-00 through 2Seg-3-09 (FIG. 27D), and SEQ. ID. NO.: 339-SEQ. ID. NO.: 348 correspond to 2Seg-4-00 through 2Seg-4-09 (FIG. 27E).

For each of the Intermediate Fragments, the first segment (2Seg-0-00, 2Seg-1-00, 2Seg-2-00, 2Seg-3-00, and 2Seg-4-00) serves as the leader primer for overlap extension. The last segment (2Seg-0-11, 2Seg-1-11, 2Seg-2-09, 2Seg-3-09, and 2Seg-4-09) serves as the trailer primer.

Assembly of the Five Intermediate Fragments into Large Pieces Part I and Part II Each Intermediate Fragment was separately constructed in a first overlap extension reaction from the appropriate set of ssDNA sequences provided in FIG. 26A-FIG. 26E and FIG. 27A-FIG. 27E. The reaction mixture for each reaction is provided in TABLE IX and the thermocycler program in TABLE X. The "synthetic oligonucleotide mix" entry in TABLE IX is a 27.5 ng/μL mixture of equal amounts of each of the forward and reverse complement synthetic oligonucleotides for a particular Intermediate Fragment.

TABLE IX

| Reagent | Quantity |
|---|---|
| Roche High Fidelity PCR Master, Vial #1 (Product # 2140314) | 25.0 μL |
| Synthetic oligonucleotide mix * | 1.0 μL |
| Leader primer, 50 μM | 0.5 μL |
| Trailer primer, 50 μM | 0.5 μL |
| Sterile water, Roche (molecular biology grade) | 23.0 μL |

* For each of the synthetic oligonucleotide sets (0–4), the forward and reverse complement synthetic oligonucleotides were mixed in equal amounts to a final concentration of 27.5 ng/μL.

TABLE X

| Step | Conditions |
|---|---|
| 1. | 94° C. for 5 minutes for initial denaturation, |
| 2. 20 cycles of: | 94° C. for 1 minute |
| | 50° C. for 30 seconds |
| | 65° C. for 5 minutes |
| 3. | 65° C. for 10 minutes for final extension |

Figure 28:
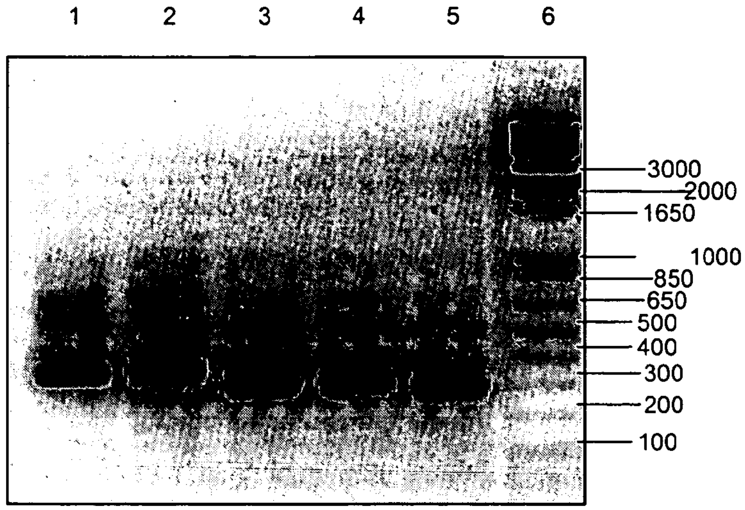
FIG. 28 is a gel of fragments 0-4, which make up variola DNA polymerase-1 from EXAMPLE 2.
Figure 29:
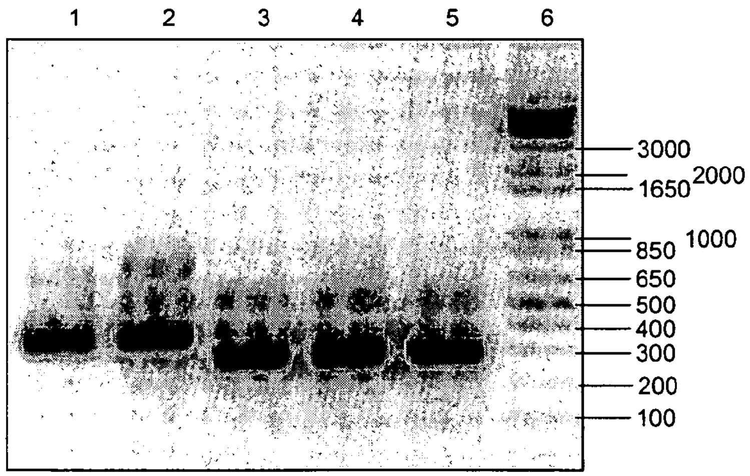
FIG. 29 is a gel of fragments 5-9, which make up variola DNA polymerase-2 from EXAMPLE 2.

The products of these reactions were separated on 1% agarose gels as shown in FIG. 28 for Part I of the variola DNA polymerase gene and FIG. 29 for Part II.

Assembly of the Intermediate Fragments into Full Length Part I and Part II of the Variola DNA Polymerase Gene Parts I and II of the variola DNA polymerase gene were assembled in a second overlap extension reaction of their constituent Intermediate Fragment sets using the reaction mixture provided in TABLE XI and the thermocycler program provided in TABLE XII.

TABLE XI

| Reagent | Quantity |
|---|---|
| Intermediate Fragment 0 * | 0.5 μL |
| Intermediate Fragment 1 * | 0.5 μL |
| Intermediate Fragment 2 * | 0.5 μL |
| Intermediate Fragment 3 * | 0.5 μL |
| Intermediate Fragment 4 * | 0.5 μL |
| Leader primer, 50 μM | 1.0 μL |
| Trailer primer, 50 μM | 1.0 μL |
| Sterile water, Roche (molecular biology grade) | 20.5 μL |
| Roche High Fidelity PCR Master, Vial #1 (Product # 2140314) | 25.0 μL |

* Taken directly from overlap extension reactions (FIG. 28 and FIG. 29)

For the construction of Part I of the variola DNA polymerase gene, two overlap extension reactions were performed using the two different sets of primers illustrated in FIG. 24A and FIG. 24G. The first reaction used the thirty base 1 lead-01 leader (5'-TCCTCGAGCATAAT GGATGT-GCGTTGCATC-3', SEQ. ID. NO.: 125) and the twenty-nine base 1trail-57 trailer (5'-GCGGCAGCCA TAGGGCCCCT-TAATCACCG-3', SEQ. ID. NO.: 349). The second reaction used the forty-eight base 1 lead-02 leader 5'-GACGAC-GACGACAAGCATATGCTCGAGGATA TGGATGT-GCGTTGCATC-3', SEQ. ID. NO.: 126) and the forty-seven base 1trail-58 trailer (5'-TTAAGCGTAATCCGGAA-CATCGTATGGGTAGGGCCCCTTAATCACCG-3', SEQ. ID. NO.: 350).

For the construction of Part II of the variola DNA polymerase gene, two overlap extension reactions were performed using two different sets of primers illustrated in FIG. 25A and FIG. 25G. The first reaction used the thirty base 2lead-01 leader (5'-TCCTCGAGCATAGGGCCCCTGCT-GAAATTG-3', SEQ. ID. NO.: 183) and the twenty-nine base 2trail-57 trailer (5'-GCGGCAGCCATACGCCTCATA-GAAGGTCG-3', SEQ. ID. NO.: 351). The second reaction used the forty-eight base 2lead-02 leader (5'-GACGAC-GACGACAAGCATATGCTCGAGGATG GGCCCCT-GCTGAAATTG-3', SEQ. ID. NO.: 184) and the forty-seven base 2trail-58 trailer (5'-TTAAGCGTA ATCCGGAA-CATCGTATGGGTACGCCTCATAGAAGGTCG-3', SEQ. ID. NO.: 352).

TABLE XII

| Step | Conditions |
|---|---|
| 1. | 94° C. for 5 minutes for initial denaturation, |
| 2. 20 cycles of: | 94° C. for 1 minute |
| | 60° C. for 30 seconds |
| | 65° C. for 10 minutes |
| 3. | 65° C. for 10 minutes for final extension |

Figure 30:
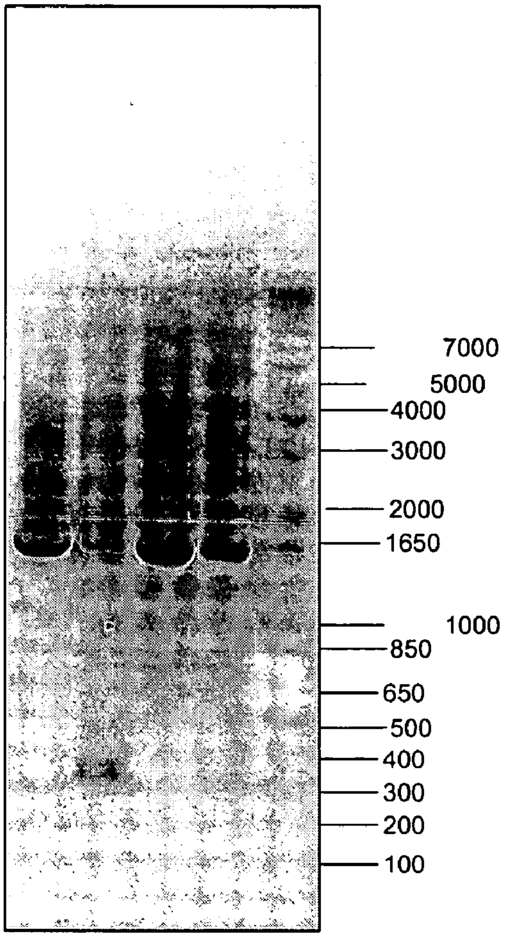
FIG. 30 is a gel of Parts I and II of variola DNA polymerase from EXAMPLE 2.

The products of these reactions were separated on a 1% agarose gel, which is illustrated in FIG. 30.

Ligation of Part I and Part II to Generate the Full Length Variola DNA Polymerase Gene (3000 bp)

The DNA from the lanes corresponding to Parts I and II of the variola DNA polymerase gene was purified using GENECLEAN® (BIO101 Systems®, Qbiogene) DNA purification system. The two fragments were separately digested overnight with ApaI (Boehringer Mannheim), purified on a 1% agarose gel, and purified using GENECLEAN®.

Figure 31:
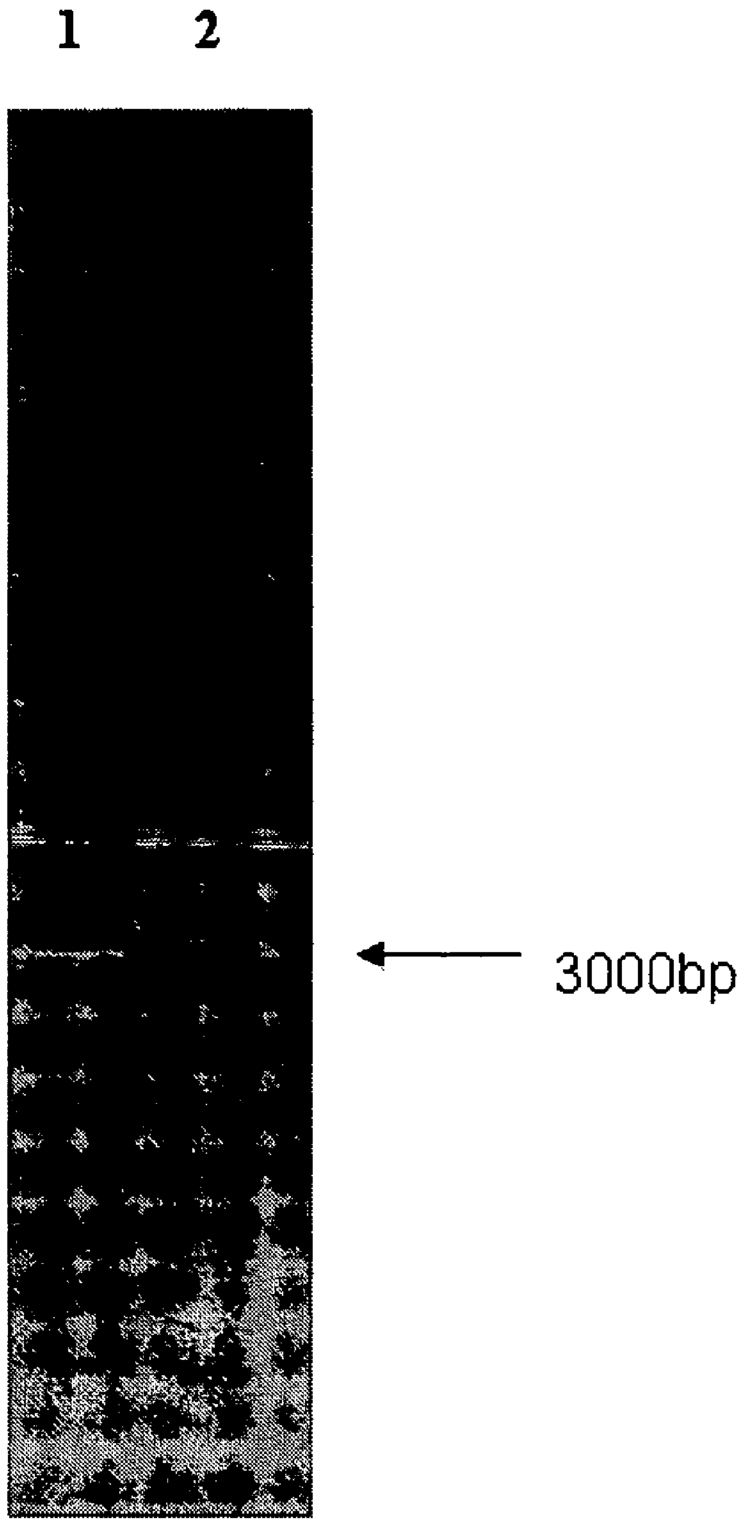
FIG. 31 is a gel of the ligation product of Parts I and II of variola DNA polymerase from EXAMPLE 2.

Parts I and II were ligated for 1.25 hr at ambient temperature under the conditions provided in TABLE XIII. The products were quantified by fluorometry. Ligation was confirmed by PCR using the 1lead-01 and 2 trail-57 primers, the product of which was isolated on a 1% agarose gel, shown in FIG. 31. The PCR product was run in lane 1 and 1 kB Plus ladder in lane 2.

TABLE XIII

| Reagent | Quantity |
|---|---|
| Water | 15 μL |
| Part I (22 ng/μL) | 1 μL |
| Part II (22 ng/μL) | 1 μL |
| T4 10X ligation buffer | 2 μL |
| T4 ligase (400 U/μL) | 1 μL |

EXAMPLE 3

*E. coli* Threonine Deaminase by One-step Hierarchical Decomposition and Ligation EXAMPLE 3 illustrates the synthesis of an *E. coli* threonine deaminase gene by dividing the gene in a one-step hierarchical decomposition and synthesizing the gene by the direct self-assembly method.

Design

In the one-step hierarchical decomposition, the gene was divided directly into 54-overlapping short segments, in the present example not longer than about 60 bases, overlap not shorter than about 27 bases. Because the gene was designed for reassembly by ligation, the adjacent short segments on the same strand abut, i.e., with no single-stranded gaps between the double-stranded overlaps. The overlaps were not designed to terminate in a G or C.

Figure 32:
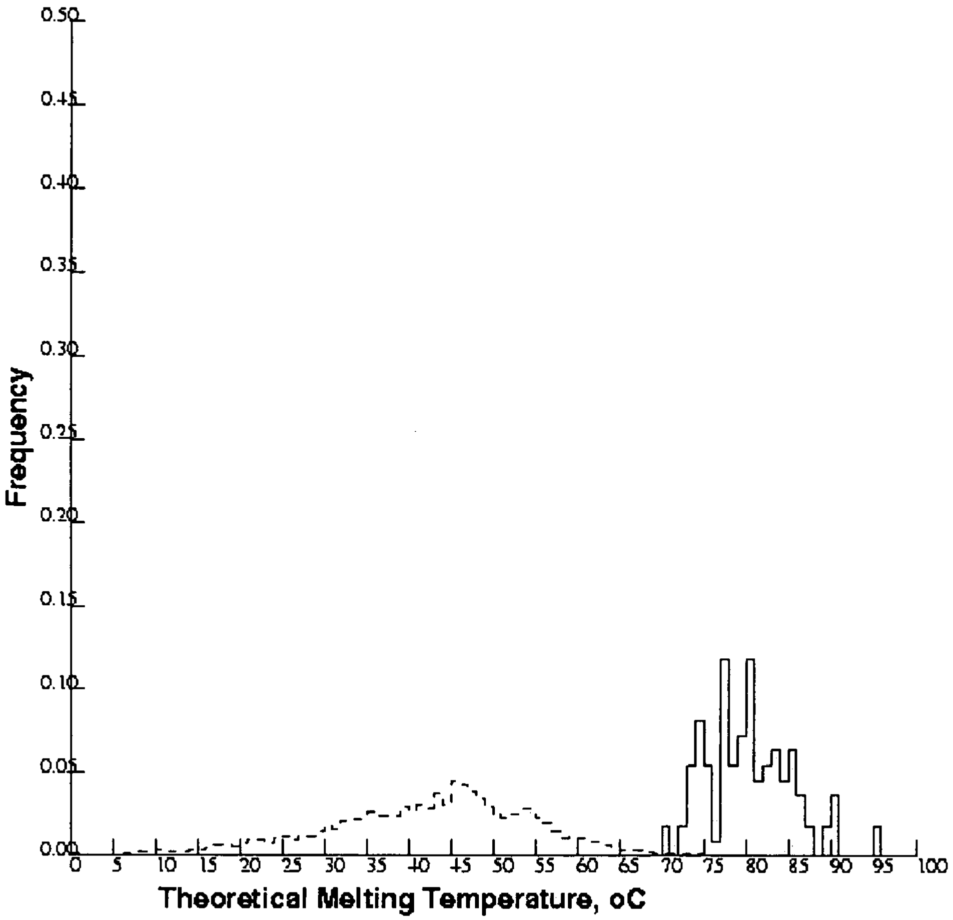
FIG. 32 illustrates the distribution of melting temperatures for the initial codon assignment for *E. coli* threonine deaminase in EXAMPLE 3. (solid) Correct matches between small segment overlaps. (dashed) Incorrect matches between small segments.
Figure 33:
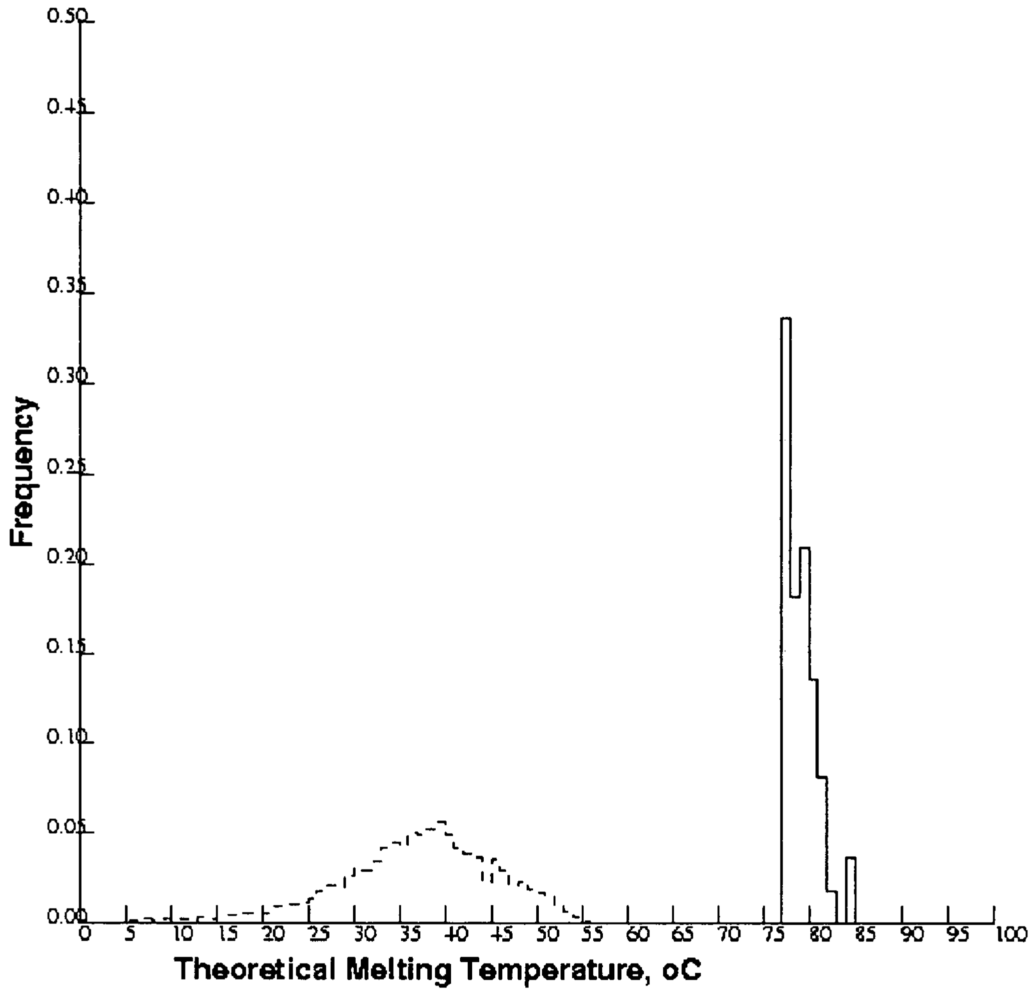
FIG. 33 illustrates the distribution of melting temperatures after the final codon assignment for *E. coli* threonine deaminase in EXAMPLE 3.
Figure 35:
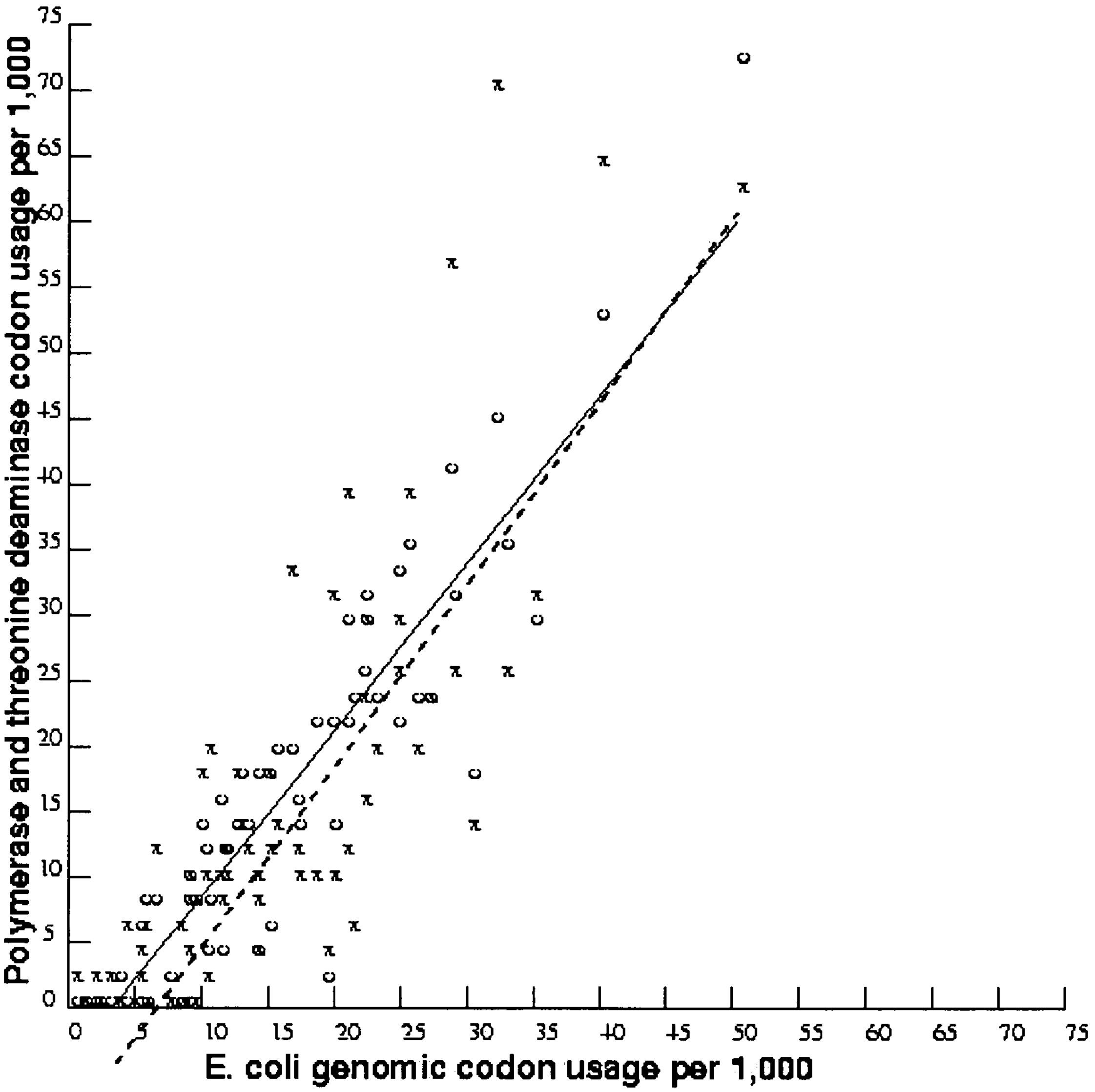
FIG. 35 illustrates the codon usage for the synthetic *E. coli* threonine deaminase sequence from EXAMPLE 3 vs. the codon usage in the *E. coli* genome. Each codon is shown as a point in which the x-coordinate is its usage per 1,000 in *E. coli* and the y-coordinate is its usage per 1,000 in threonine deaminase. (x, solid line) Usage in native threonine deaminase. (o, dashed line) Usage in the synthetic gene.

Theoretical melting temperatures were calculated as described in EXAMPLE 1. The distribution of calculated melting temperatures of the short segments using the most common *E. coli* codons is provided in FIG. 32. The codons were permuted to increase the gap in the melting temperatures as described above, resulting in the calculated melting temperatures for the final short segments provided in FIG. 33. The calculated temperature gap in this example was 21.6° C. (77.1° C.-55.5° C.). The final sequence for the synthetic *E. coli* threonine deaminase gene is provided in FIG. 34 (SEQ. ID. NO.: 353) using the codon key from FIG. 9 of EXAMPLE 1. A comparison of the codon usage of the designed threonine deaminase gene compared with that of the native gene is illustrated in FIG. 35, indicating the similarity in codon frequency.

The resulting DNA sequence was decomposed into the 54 short overlapping segments shown in an overlap map in FIG. 36 (SEQ. ID. NO.: 354-SEQ. ID. NO.: 407). Each short segment in FIG. 36 was synthesized directly and assembled into the synthetic gene in one reaction step.

Biochemistry

The threonine deaminase gene was assembled in two steps by direct self-assembly. The sequences of the leaders, short ssDNA segments, and trailers are provided in FIG. 37A-FIG. 37F. SEQ. ID. NO.: 408-SEQ. ID. NO.: 411 correspond to the gene leaders illustrated in FIG. 37A, SEQ. ID. NO.: 412-SEQ. ID. NO.: 465 correspond to Seg-0-0 through Seg-0-53 (FIG. 37B-FIG. 37E), and SEQ. ID. NO.: 466-SEQ. ID. NO.: 469 correspond to the gene trailers illustrated in FIG. 37F. Overlaps between adjacent segments are not indicated. The DNA segments were purchased from a commercial source.

The threonine deaminase gene was first divided into four Medium-sized pieces of equal size, which were each reassembled by direct self-assembly and ligation, then the four Medium-sized pieces were combined and ligated into the full-length gene.

Direct Self-Assembly of the Four Medium-Sized Pieces

Each of the four Medium-sized pieces was constructed in parallel as follows.

Annealing Reaction. The short segments were first annealed in a thermocycler to form DNA constructs corresponding to the Medium-sized pieces. Each medium-sized piece was divided into two parts, a forward strand and a reverse strand. For each strand, a 20 μL solution of the short segments corresponding to each strand at a concentration of 0.825 μM was treated with 800 U of T4 polynucleotide kinase. The kinased, short segments corresponding to the forward and reverse strands of each Medium-sized piece were mixed together. A phenol extraction was performed on the mixture, followed by an ethanol precipitation and a 70% ethanol wash. The pellet was resuspended in 7.8 μL of 1× TE, from which a solution detailed in TABLE XIV was prepared. The concentration of each short segment was 1.65 μM in this solution. This solution was placed in a thermocycler, which was programmed as described in TABLE XV.

TABLE XIV

| Reagent | Quantity |
| --- | --- |
| Synthetic oligonucleotide mix | 7.8 μL |
| NaCl, 5 M | 0.2 μL |
| MgCl2, 1 M | 1.0 μL |
| Nuclease free water | 1.0 μL |

TABLE XV

| Step | Conditions |
| --- | --- |
| 1. | 94° C. for 5 minutes for initial denaturation, |
| 2. | 80° C. for 1 minute |
| 3. | Cool to 55° C. at 0.5° C./min |
| 4. | 4° C. |

Figure 38:
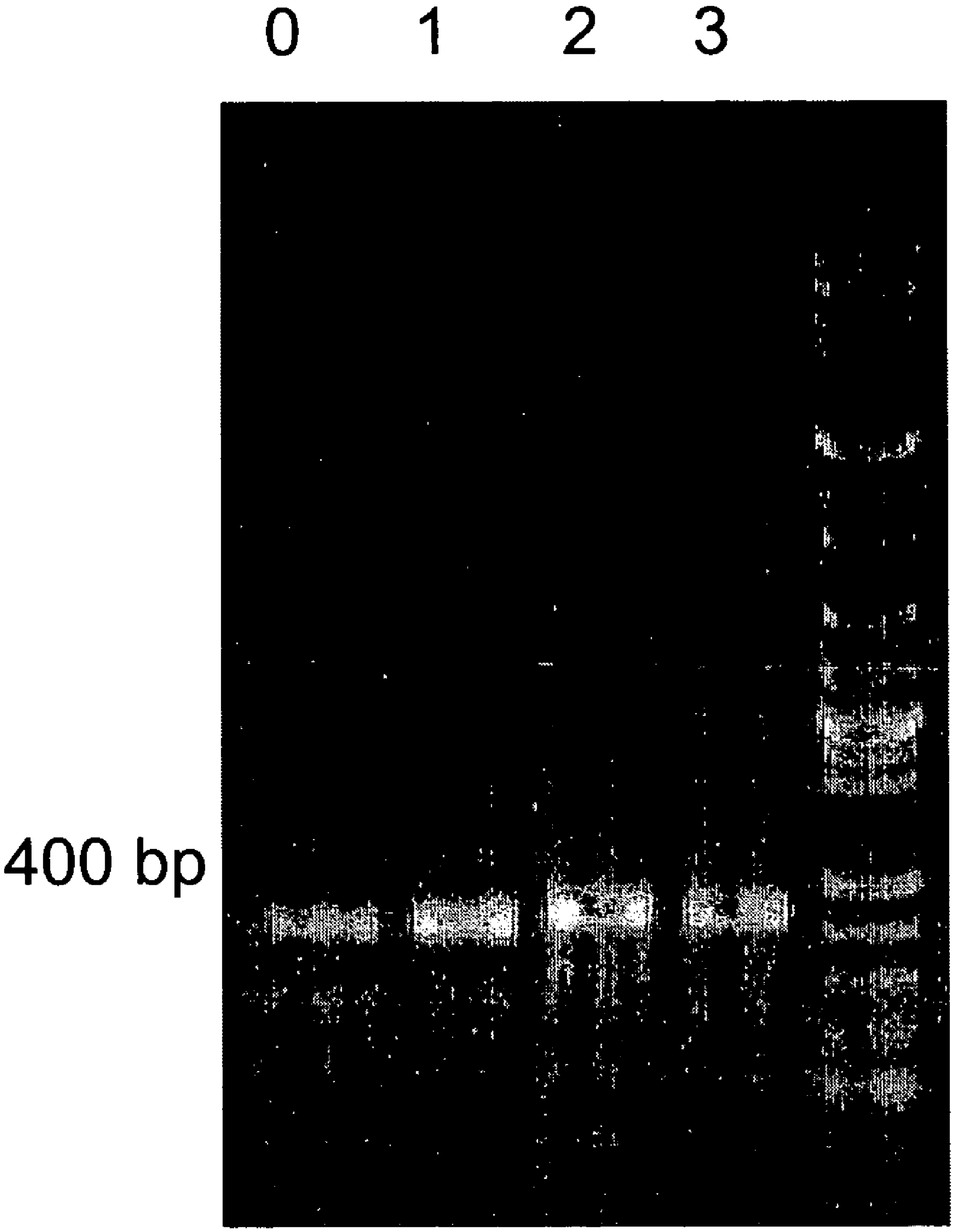
FIG. 38 is a gel of the four Medium-sized pieces synthesized by direct self-assembly and ligation in EXAMPLE 3.

Ligation Reaction. Each Medium-sized piece was produced by ligation of the corresponding DNA construct synthesized in the annealing reaction, described above. The reaction mixture provided in TABLE XVI was maintained at 16° C. overnight. An agarose gel of the resulting four Medium-sized pieces is provided in FIG. 38.

TABLE XVI

| Reagent | Quantity |
| --- | --- |
| DNA construct solution from annealing reaction | 10.0 μL |
| T4 DNA Ligase, 400 U/mL | 2.0 μL |
| 10X Ligase Buffer | 2.0 μL |
| Nuclease free water | 6.0 μL |

Assembly of the Four Medium-Sized Pieces into the Threonine Deaminase Gene

Figure 39:
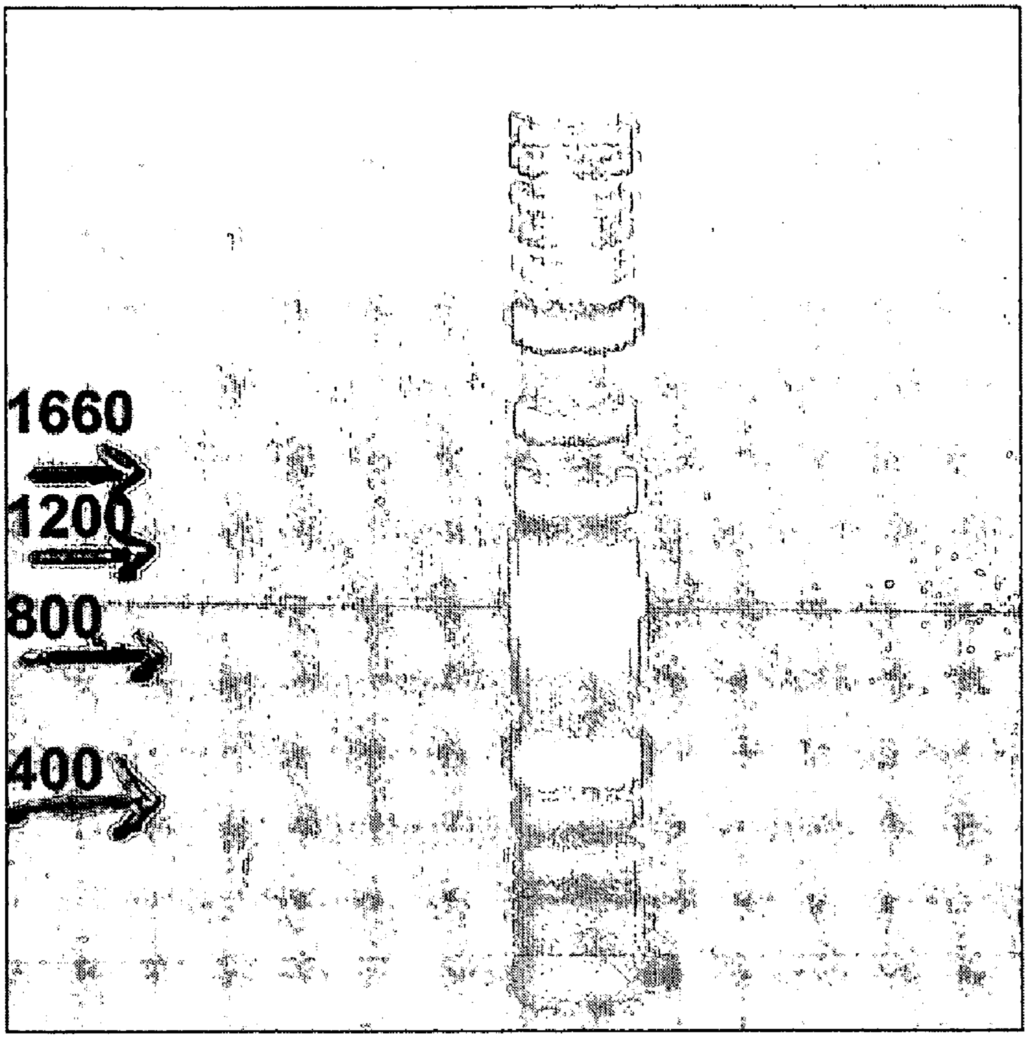
FIG. 39 is a gel of the threonine deaminase gene synthesized by ligation of the four Medium-sized pieces in EXAMPLE 3.

Each Medium-sized piece was isolated from the gel using GENECLEAN® (BIO101 Systems®, Qbiogene) DNA purification system. A ligation reaction mixture containing the four Medium-sized pieces is provided in TABLE XVII. The ligation reaction was performed at 16° C. overnight. An agarose gel of the products, including the full-length threonine deaminase gene, is provided in FIG. 39.

TABLE XVII

| Reagent | Quantity |
| --- | --- |
| DNA construct solution from annealing reaction | 10.0 μL |
| T4 DNA Ligase, 400 U/mL | 2.0 μL |
| 10X Ligase Buffer | 2.0 μL |
| Nuclease free water | 6.0 μL |

At this point the assembled gene may be stored at 4° C. or cloned into expression vector pET14b (Novagen) by ExoIII digestion. The threonine deaminase gene is designed to have 12 bp 3'-end overhangs which are compatible to 5'-overhang regions of the pET14b vector after it has been treated with ExoIII for 1 minute at 14° C. The insert and vector are ligated by mixing and heating, followed by cooling to a temperature below Tm for the overlapping regions of the insert and vector. The annealed fragments are transformed into an *E. coli* host at 37° C.

EXAMPLE 4

Ty3 GAG3 by Two-step Recursive Decomposition with Sampling and Sequencing

EXAMPLE 4 illustrates the synthesis of GAG3 by two-step recursive decomposition with sampling and sequencing. The GAG3 open reading frame (ORF) is 876 bp long.

GAG3 ORF was divided into three overlapping intermediate fragments for reassembly by overlap extension. FIG. 40A-FIG. 40E illustrate the sequences of the gene leader, Fragments 0-2, and gene trailer. Fragment 0 was 307 bp, Fragment 1 was 324 bp, and Fragment 2 was 343 bp. Each intermediate fragment overlapped the adjacent one by 38 nt. Each intermediate fragment was divided into 10 oligonucleotides (50 nt) for reassembly by overlap extension. Adjacent oligonucleotides overlapped by about 19 bps. Collectively, the assembled sequence encoded both strands of each of the intermediate fragments. SEQ. ID. NO.: 470 corresponds to gene leader-0 (FIG. 40A), SEQ. ID. NO.: 471-SEQ. ID. NO.: 480 correspond to Seg-0-0 through Seg-0-9 (FIG. 40B), SEQ. ID. NO.: 481-SEQ. ID. NO.: 490 correspond to Seg-1-0 through Seg-1-9 (FIG. 40C), SEQ. ID. NO.: 491-SEQ. ID. NO.: 501 correspond to Seg-2-0 through Seg-2-10 (FIG. 40D), SEQ. ID. NO.: 502 corresponds to strand 2 trailer (FIG. 40D), and SEQ. ID. NO.: 503 corresponds to gene trailer-0 (FIG. 40E).

Figure 41:
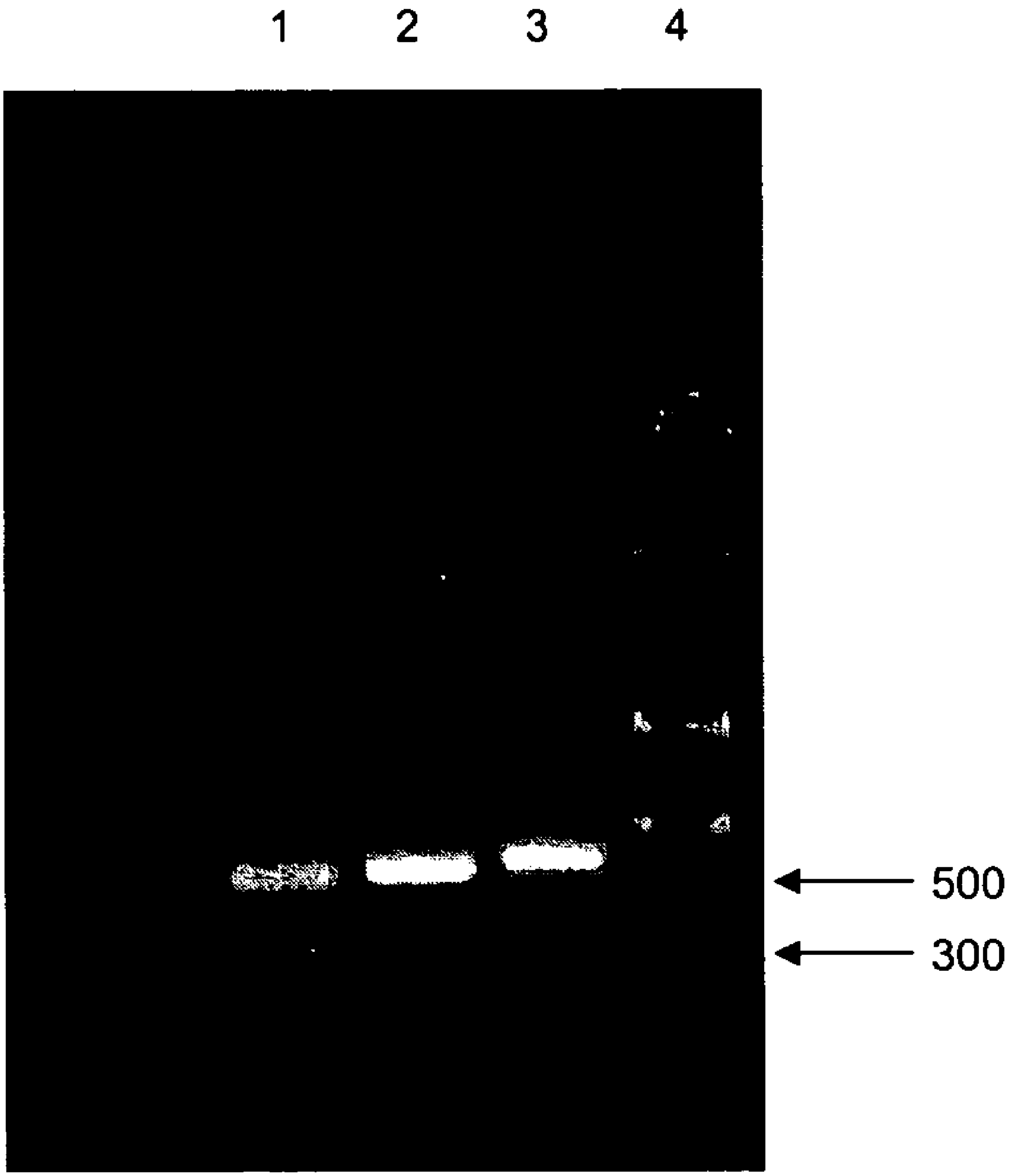
FIG. 41 is an agarose gel of the three intermediate fragments of the Ty3 GAG3 synthesized in EXAMPLE 4.

In the assembly of the intermediate fragments, the oligonucleotides were mixed to a final concentration of 0.1 μM with a proofreading DNA polymerase (Proofstart®, Qiagen) and appropriate leader and trailer sequences. FIG. 41 is an agarose gel showing the products of these reactions. Fragment 0 is in lane 1, Fragment 1 in lane 2, and Fragment 2 in lane 3. Lane 4 contains a 2-Log DNA molecular weight ladder (New England Biolabs).

The intermediate fragments were each cloned using a blunt-end ligation procedure (pCR-Blunt II-TOPO® vector, Invitrogen). Four clones of each intermediate fragment were sequenced and correct sequence was selected. The selected sequences were amplified out of the vector by high-fidelity PCR using a proofreading DNA polymerase (Proofstart® DNA polymerase, Qiagen).

Figure 42:
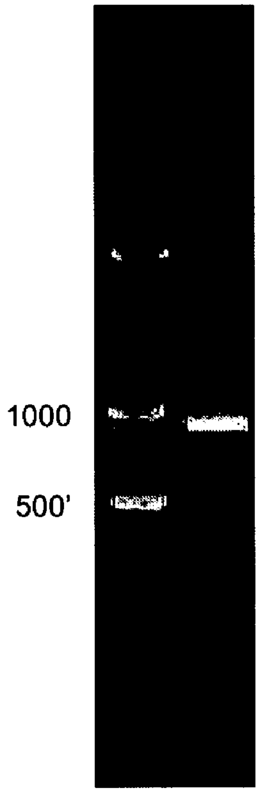
FIG. 42 is an agarose gel of the Ty3 GAG3 gene synthesized in EXAMPLE 4.

The intermediate fragments were mixed and extended to full-duplex DNA as described for the oligonucleotides. FIG. 42 is an agarose gel of the full-length GAG3 gene. The identity and accuracy of the gene was verified by sequencing both strands of the DNA product.

Figure 43:
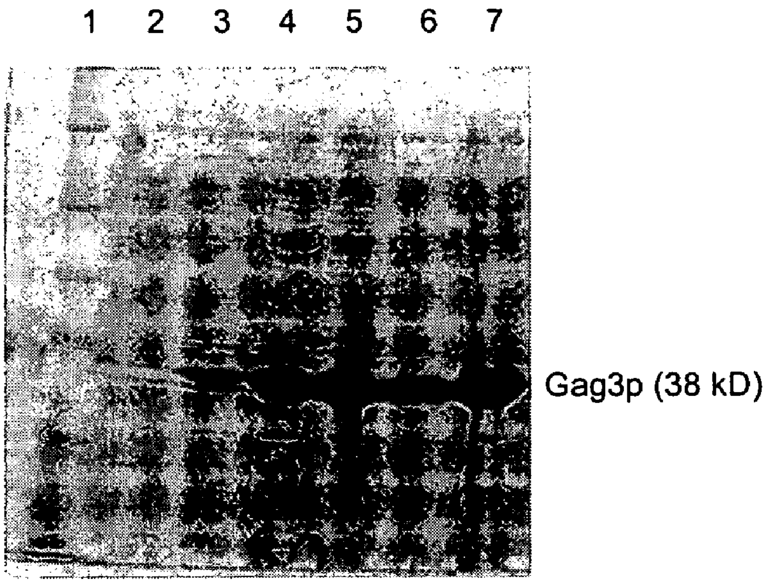
FIG. 43 is an SDS-PAGE gel of the Ty3 Gag3p polyprotein produced in EXAMPLE 4.

The synthetic GAG3 gene was cloned into the pET-3a plasmid (Novagen) using NdeI and BamHI endonuclease restriction sites designed in the 5' and 3' PCR gene primers. The resulting plasmid contained the entire GAG3 gene under the control of an inducible T7 promoter, and a bacterial ribosome-binding site (Shine-Dalgarno sequence). The BL21(DE3) pLysS strain of *E. coli* (Novagen) was transformed with the plasmid. T7 RNA polymerase expression was induced using host-encoded isopropyl-1-thio-β-D-galactopyranoside at a concentration of 0.4 mM. At 30 min intervals, cells were harvested by centrifugation and sonicated. FIG. 43 is an SDS-PAGE gel of the sonicate stained with Coomassie indicating the expression of Gag3p.

EXAMPLE 5

Ty3 IN Gene by Two-step Recursive Decomposition with Sampling and Sequencing

EXAMPLE 5 illustrates the synthesis of the Ty3 IN gene by a two-step recursive decomposition with sampling and sequencing. The Ty3 IN gene is 1640 bp long and is illustrated in FIG. 44 (SEQ. ID. NO.: 504).

The Ty3 IN gene was divided into ten intermediate fragments for reassembly by overlap extension. Overlap maps for the leader, ten intermediate fragments, and trailer are provided in FIG. 45A-FIG. 45L: leader (FIG. 45A, SEQ. ID. NO.: 505), Fragment 0 (196 bp, FIG. 45B, SEQ. ID. NO.: 506-SEQ. ID. NO.: 513), Fragment 1 (224 bp, FIG. 45C, SEQ. ID. NO.: 514-SEQ. ID. NO.: 521), Fragment 2 (224 bp, FIG. 45D, SEQ. ID. NO.: 522-SEQ. ID. NO.: 529), Fragment 3 (223 bp, FIG. 45E, SEQ. ID. NO.: 530-SEQ. ID. NO.: 537), Fragment 4 (227 bp, FIG. 45F, SEQ. ID. NO.: 538-SEQ. ID. NO.: 545), Fragment 5 (223 bp, FIG. 45G, SEQ. ID. NO.: 546-SEQ. ID. NO.: 553), Fragment 6 (224 bp, FIG. 45H, SEQ. ID. NO.: 554-SEQ. ID. NO.: 561), Fragment 7 (172 bp, FIG. 45I, SEQ. ID. NO.: 562-SEQ. II). NO.: 567), Fragment 8 (175 bp, FIG. 45J, SEQ. ID. NO.: 568-SEQ. ID. NO.: 573), Fragment 9 (174 bp, FIG. 45K, SEQ. ID. NO.: 574-SEQ. ID. NO.: 580), and trailer (FIG. 45L, SEQ. ID. NO.: 581). Each of the intermediate fragments was divided into 50 nt oligonucleotides for reassembly by direct self-assembly illustrated in FIG. 46A-FIG. 46L. SEQ. ID. NO.: 582 corresponds to the gene leader (FIG. 46A), SEQ. ID. NO.: 583-SEQ. ID. NO.: 590 correspond to Seg-0-0 through Seg-0-7 (FIG. 46B), SEQ. ID. NO.: 591-SEQ. ID. NO.: 598 correspond to Seg-1-0 through Seg-1-7 (FIG. 46C), SEQ. ID. NO.: 599-SEQ. ID. NO.: 606 correspond to Seg-2-0 through Seg-2-7 (FIG. 46D), SEQ. ID. NO.: 607-SEQ. ID. NO.: 614 correspond to Seg-3-0 through Seg-3-7 (FIG. 46E), SEQ. ID. NO.: 615-SEQ. ID. NO.: 622 correspond to Seg-4-0 through Seg-4-7 (FIG. 46F), SEQ. ID. NO.: 623-SEQ. ID. NO.: 630 correspond to Seg-5-0 through Seg-5-7 (FIG. 46G), SEQ. ID. NO.: 631-SEQ. ID. NO.: 638 correspond to Seg-6-0 through Seg-6-7 (FIG. 46H), SEQ. ID. NO.: 639-SEQ. ID. NO.: 644 correspond to Seg-7-0 through Seg-7-5 (FIG. 46I), SEQ. ID. NO.: 645-SEQ. ID. NO.: 650 correspond to Seg-8-0 through Seg-8-5 (FIG. 46J), SEQ. ID. NO.: 651-SEQ. ID. NO.: 657 correspond to Seg-9-0 through Seg-9-6 (FIG. 46K), SEQ. ID. NO.: 658 corresponds to the strand 9 trailer (FIG. 46K), and SEQ. ID. NO.: 659 corresponds to the gene trailer (FIG. 46L).

Figure 47:
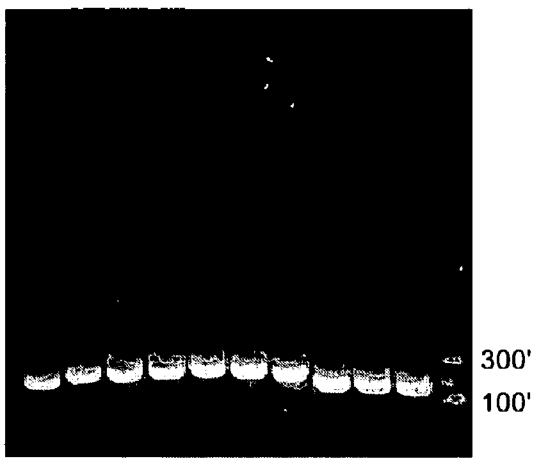
FIG. 47 is an agarose gel of the ten intermediate fragments of the Ty3 IN gene synthesized in EXAMPLE 5.
Figure 48:
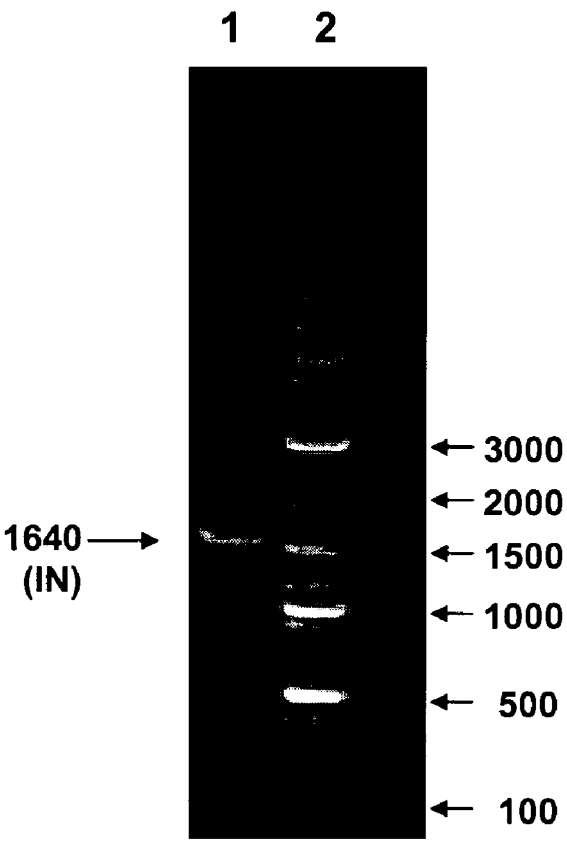
FIG. 48 is an agarose gel of a TY3 IN gene synthesized in EXAMPLE 5.
Figure 49:
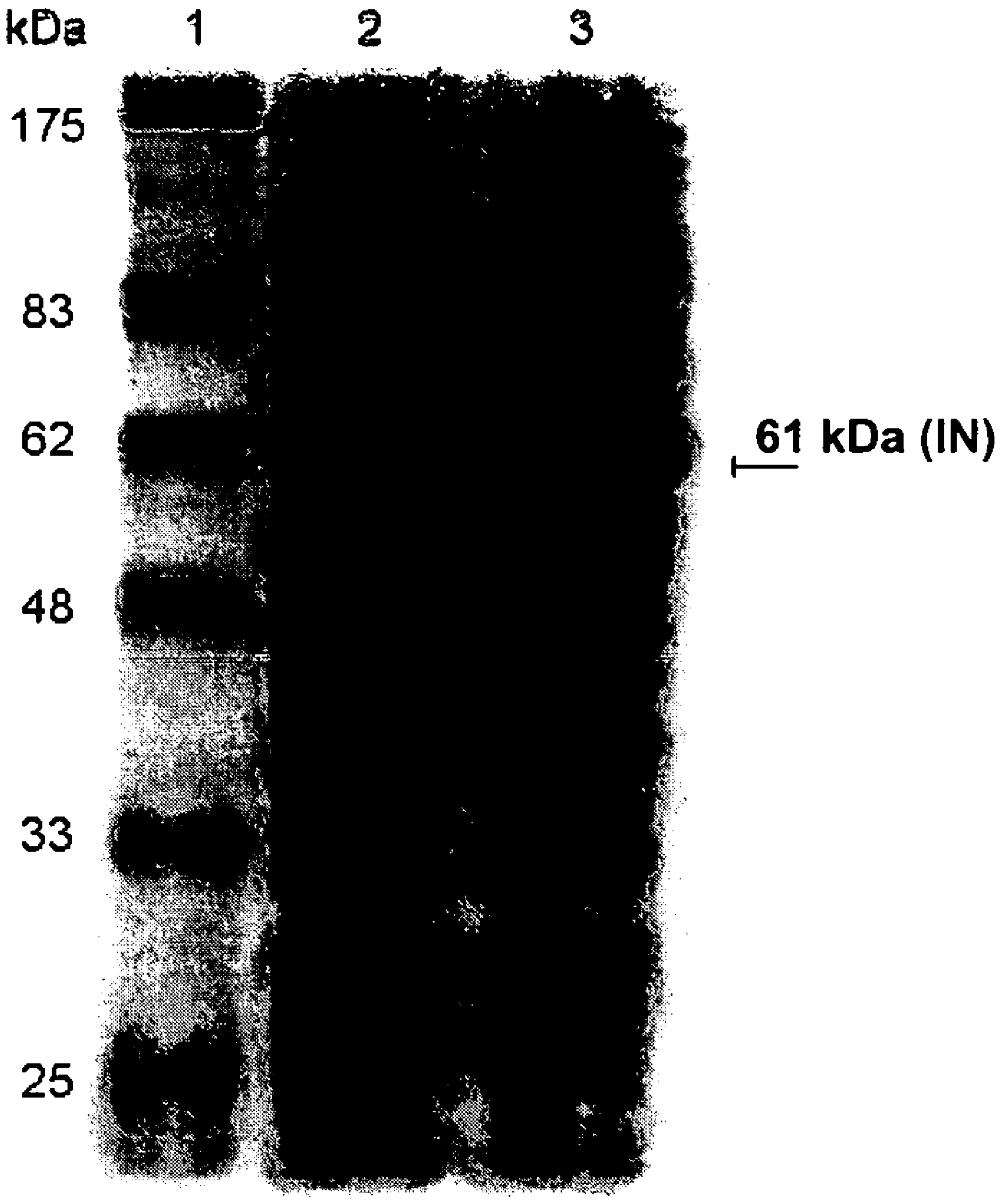
FIG. 49 is an SDS-PAGE gel of a TY3 IN protein synthesized in EXAMPLE 5.

The ten intermediate fragments were separately assembled from the oligonucleotides, cloned, and sequenced as described in EXAMPLE 4. FIG. 47 is an agarose gel showing the products of the ten intermediate fragment reactions. The ten intermediate fragments were reassembled into the Ty3 IN gene using overlap extension as described in EXAMPLE 4. An agarose gel of the product is provided in FIG. 48. Lane 1 is the synthetic Ty3 IN gene, and lane 2, DNA size markers. The synthetic TY3 IN gene was cloned and expressed as described in EXAMPLE 4. An SDS-PAGE gel of the Coomassie stained TY3 IN protein is provided in FIG. 49. Lane 1 contains molecular weight markers; lane 2, uninduced cellular extract; and lane 3, induced cellular extract.

The embodiments illustrated and described herein are provided as examples of certain preferred embodiments. Various changes and modifications can be made to the embodiments presented herein by those skilled in the art without departure from the disclosure.

What is claimed is:

1. A method of synthesizing a DNA sequence encoding a polypeptide, comprising:

(i) dividing the DNA sequence recursively into small pieces of DNA, wherein adjacent pieces comprise overlapping regions, wherein the division results in at least 3 pieces of DNA;

(ii) optimizing the sequences of the pieces of DNA resulting from each recursive division in silico by silent codon permutation to strengthen correct hybridizations between adjacent pieces of DNA and to disrupt incorrect hybridizations between all other pieces of DNA resulting from that division;

(iii) obtaining the optimized small pieces of DNA, wherein the overlapping regions of any adjacent pieces of single-stranded DNA are complementary;

(iv) combining the pieces of DNA derived from the division of the next-larger piece of DNA;

(v) allowing the pieces of DNA to self-assemble to form a DNA construct comprising single-stranded DNA segments connected by double-stranded overlap regions;

(vi) producing the next-larger piece of DNA from the DNA construct; and (vii) repeating steps (iv), (v), and (vi) in reverse order of the recursive division in step (i) to produce the DNA sequence.

2. The method of claim 1, wherein a next-larger piece of DNA comprises a mixture of DNA molecules, the method further comprising:

selecting a DNA molecule from the mixture likely to have the correct DNA sequence, and using the selected DNA molecule in the synthesis of the DNA sequence.

3. The method of claim 2, wherein a DNA molecule is separated from the mixture by cloning.

4. The method of claim 2, wherein the selection comprises sequencing a sample of DNA molecules from the mixture and selecting a DNA molecule with the desired DNA sequence.

5. The method of claim 2, wherein the selection comprises expressing a polypeptide from each member of a sample of DNA molecules from the mixture, determining the molecular weight of the polypeptide, and selecting a DNA molecule from which a polypeptide with a predetermined molecular weight is expressed.

6. The method of claim 5, wherein a start codon and/or a stop codon is incorporated into the DNA molecule from which a polypeptide is expressed.

7. The method of claim 6, wherein the reading frame of the DNA molecule is adjusted with respect to the start codon and/or stop codon.

8. The method of claim 5, wherein each member of the sample of DNA molecules is inserted into an expression vector, and wherein the expression vector comprises a stop codon downstream from the inserted DNA molecule.

9. The method of claim 5, wherein the molecular weight of the polypeptide is determined by electrophoresis.

10. The method of claim 1, wherein the DNA sequence comprises a regulatory sequence.

11. The method of claim 1, wherein the DNA sequence comprises an intergenic sequence.

12. The method of claim 1, wherein the DNA sequence encodes a polypeptide.

13. The method of claim 12, wherein the polypeptide is a full-length protein.

14. The method of claim 1, wherein dividing the DNA sequence into small pieces of DNA is performed in a single division.

15. The method of claim 1, wherein dividing the DNA sequence into small pieces of DNA is performed in a plurality of divisions.

16. The method of claim 15, wherein the DNA sequence is divided into pieces of DNA of about 1,500 bases long or shorter.

17. The method of claim 1, wherein the small pieces of DNA are about 60 bases long or shorter.

18. The method of claim 17, wherein the small pieces of DNA are about 50 bases long or shorter.

19. The method of claim 1, wherein the overlapping regions comprise from about 6 to about 60 base-pairs.

20. The method of claim 1, wherein optimizing comprises calculating a melting temperature for the pieces of DNA.

21. The method of claim 1, wherein optimizing comprises calculating a parameter related to hybridization propensity for the pieces of DNA.

22. The method of claim 21, wherein the parameter is selected from the group consisting of free energy, enthalpy, entropy, and arithmetic or algebraic combinations thereof.

23. The method of claim 20, wherein the melting temperature of the lowest melting correct hybridization is at least 1° C. higher than the melting temperature of the highest melting incorrect hybridization.

24. The method of claim 20, wherein the melting temperature of the lowest melting correct hybridization is at least 4° C. higher than the melting temperature of the highest melting incorrect hybridization.

25. The method of claim 20, wherein the melting temperature of the lowest melting correct hybridization is at least 8° C. higher than the melting temperature of the highest melting incorrect hybridization.

26. The method of claim 20, wherein the melting temperature of the lowest melting correct hybridization is at least 16° C. higher than the melting temperature of the highest melting incorrect hybridization.

27. The method of claim 1, wherein optimizing comprises taking advantage of the degeneracy in the regulatory region consensus sequence.

28. The method of claim 1, wherein optimizing comprises direct base assignment.

29. The method of claim 1, wherein optimizing comprises adjusting boundary points between adjacent pieces of DNA.

30. The method of claim 1, wherein at least one of the optimized small pieces of DNA is synthetic.

31. The method of claim 1, wherein at least one of the optimized small pieces of DNA is single-stranded.

32. The method of claim 1, wherein a single-stranded DNA segment has a length of from about zero bases to about 20 bases.

33. The method of claim 1, wherein the next-larger piece of DNA is produced by cloning the DNA construct.

34. The method of claim 33, wherein the cloning is selected from the group consisting of exonuclease III cloning, topoisomerase cloning, restriction enzyme cloning, and homologous recombination cloning.

35. The method of claim 1, wherein the next-larger piece of DNA is produced by ligating the DNA construct.

36. The method of claim 1, wherein the next-larger piece of DNA is produced by extending the DNA construct by a reaction using DNA polymerase.

37. The method of claim 36, wherein the DNA polymerase is a proof-reading DNA polymerase.

38. The method of claim 36, further comprising mixing a DNA polymerase primer with the pieces of DNA derived from the division of the next-larger piece of DNA.

39. The method of claim 1, further comprising designing a restriction site into an overlapping region.

40. The method of claim 39, further comprising digesting the restriction site with a site-specific restriction enzyme.

41. The method of claim 1, in which the DNA sequence is divided into at least 6 small pieces of DNA.

42. A method for identifying a set of smaller DNAs suitable for assembly into a larger DNA, where the larger DNA encodes a desired polypeptide, comprising:

optimizing in silico a set of at least 6 smaller DNAs for assembly together to create the larger DNA, wherein adjacent smaller DNAs comprise overlapping regions, wherein the optimizing comprises permuting silent codons to strengthen correct hybridizations between adjacent pieces of the smaller DNAs and to disrupt all incorrect hybridizations between members of the set, to create a gap between melting temperatures of the lowest melting correct hybridization and the highest melting incorrect hybridization.

43. The method of claim 42, wherein the set comprises at least 12 smaller DNAs.

* * * * *

UNITED STATES PATENT AND TRADEMARK OFFICE

CERTIFICATE OF CORRECTION

PATENT NO. : 7,262,031 B2
APPLICATION NO. : 10/851383
DATED : August 28, 2007
INVENTOR(S) : Richard H. Lathrop et al.

It is certified that error appears in the above-identified patent and that said Letters Patent is hereby corrected as shown below:

Title page, col. 1 (Other Publications), line 1, delete "Janack," and insert --Janak,--;

Title page, col. 1 (Other Publications), line 16, delete "of" and insert --in--;

Title page, col. 2 (Other Publications), line 6, delete "Polymearse" and insert --Polymerase--;

Title page, col. 2 (Other Publications), line 25, delete "oligonucleotid" and insert --oligonucleotide--;

Title page, col. 2 (Other Publications), line 25, delete "therodynamics."" and insert --thermodynamics."--;

Title Page 2, col. 1 (Other Publications), line 1, delete "Whithers," and insert --Withers,--;

Title Page 2, col. 2 (Other Publications), line 6, delete "Craig." and insert --Craig,--;

Col. 7, line 47, delete "stands." and insert --strands.--;

Col. 7, line 49, delete "condon" and insert --codon--;

Col. 7, line 57, delete "as" and insert --codon is shown as--;

Col. 7, line 59, delete "y-coodinates" and insert --y-coordinates--;

Col. 7, line 64, after "matches" insert --between small--;

Col. 7, line 66, delete "incorrect" and insert --Incorrect--;

Col. 7, line 67, after "long" insert --strands.--;

Col. 8, line 5, delete "EXAMPLE. 2." and insert --EXAMPLE 2.--;

UNITED STATES PATENT AND TRADEMARK OFFICE

CERTIFICATE OF CORRECTION

PATENT NO. : 7,262,031 B2 
APPLICATION NO. : 10/851383
DATED : August 28, 2007
INVENTOR(S) : Richard H. Lathrop et al.

It is certified that error appears in the above-identified patent and that said Letters Patent is hereby corrected as shown below:

Col. 8, line 6, after "“X”" insert --is a--;

Col. 13, line 14, after “7°C.,” delete “at” and insert --at least--;

Col. 13, line 50, delete “the,” and insert --the--;

Col. 17, line 29, delete “Repeat,” and insert --Repeat--;

Col. 21, line 12, below “3’-filler.” delete “filler.”;

Col. 25, line 13, delete "“Seg-4-6.”" and insert --“Seg-4-6.”-- (consider space);

Col. 27, line 62, delete "“polymerase-2.”" and insert --“polymerase-2.”-- (consider space); and Col. 35, line 22, delete “II).” and insert --ID.--.

Signed and Sealed this

Fourth Day of March, 2008

JON W. DUDAS
*Director of the United States Patent and Trademark Office*

```
SEQUENCE LISTING

<160> NUMBER OF SEQ ID NOS: 659

<210> SEQ ID NO 1
<211> LENGTH: 1542
<212> TYPE: DNA
<213> ORGANISM: Artificial Sequence
<220> FEATURE:
<223> OTHER INFORMATION: Synthetic DNA

<400> SEQUENCE: 1

atggccgatt ctcaacctct gtctggagca cctgaaggag cagaatattt acgggcagtg     60

ttacgtgcgc cggtgtatga agccgcccag gtgaccccgt tacagaaaat ggaaaaactc    120

agttcccgtc tcgataatgt gattctggtc aagcgcgagg accgacagcc cgtgcactcg    180

ttcaagctcc gtggtgcgta tgcgatgatg gcagggttga cggaagaaca gaaagcccac    240

ggtgtgatta cggcatcagc tggcaaccat gctcaaggtg tggcgttctc ttctgctcga    300

ctgggagtga aagcgttaat cgtgatgcct actgctacag cggatattaa agtggatgcc    360

gtccgagggt ttggtggtga agttctgctg catggcgcga actttgatga agccaaggcc    420

aaggcgatcg agctctctca acaacagggg ttcacgtggg tgccaccatt cgatcatccg    480

atggtaatcg ccggtcaggg gacgttagca ctggagttgc ttcaacagga cgcacatctc    540

gaccgggtct tcgttcctgt tgggggtggt ggtctggcgg cgggtgtagc agtactcatc    600

aagcagctca tgccacaaat taaagtgata gccgttgaag ccgaagattc cgcatgtctg    660
```

-continued aaggccgcac ttgatgccgg acaccctgtc gatctgccgc gtgtggggct gtttgcagaa 720
ggggttgcgg tgaaacggat tggggatgag accttccgcc tatgccagga gtatttggac 780
gacatcatca ccgtggactc cgatgccatt tgtgccgcca tgaaggacct attcgaagat 840
gtccgtgcag tcgccgaacc gtctggagct ttagcattag ccgggatgaa gaagtacatt 900
gctctgcaca acatccgagg cgaacgactg gcccacatct taagcggtgc gaatgtcaac 960
ttccacggct tacggtatgt gtctgagcgt tgcgagctgg gcgaacaaag agaagcatta 1020
ctggcagtga ccattccgga agaaaaaggt tcgttcctca agttctgcca gctgttagga 1080
ggtcggagcg tcacggaatt taactatcgg tttgcagacg ccaagaatgc ctgtattttt 1140
gtgggtgtga ggttgagcag gggattggag gagcgcaagg agattcttca gatgctgaac 1200
gatggcggtt atagcgtggt ggacctgagc gacgacgaaa tggctaaact acacgtacgc 1260
tacatggtgg gtggacgacc ttcacatccc ctccaggagc gactgtattc ctttgaattc 1320
ccagagtctc ccggcgcctt attacgtttc ttaaacaccc tgggcaccta ttggaatatc 1380
agcctgttcc actaccgatc tcatgggacg gattacgggc gtgttctgct ggcgtttgag 1440
cttggcgatc atgaaccgga ctttgaaacg cgcctgaacg aactgggcta tgattgccat 1500
gatgagacca acaaccccgc ctttcgtttc ttcctcgcag gc 1542

<210> SEQ ID NO 2
<211> LENGTH: 50
<212> TYPE: DNA
<213> ORGANISM: Artificial Sequence
<220> FEATURE:
<223> OTHER INFORMATION: Synthetic DNA

<400> SEQUENCE: 2
ctatactgca gatggccgat tctcaaccac tgtctggagc tcctgaaggg 50

<210> SEQ ID NO 3
<211> LENGTH: 50
<212> TYPE: DNA
<213> ORGANISM: Artificial Sequence
<220> FEATURE:
<223> OTHER INFORMATION: Synthetic DNA

<400> SEQUENCE: 3
gtctggagct cctgaagggg cagaatattt acgggcagtg ttacgtgcgc 50

<210> SEQ ID NO 4
<211> LENGTH: 47
<212> TYPE: DNA
<213> ORGANISM: Artificial Sequence
<220> FEATURE:
<223> OTHER INFORMATION: Synthetic DNA

<400> SEQUENCE: 4
gggcagtgtt acgtgcgccg gtgtatgaag ccgcccaggt gaccccg 47

<210> SEQ ID NO 5
<211> LENGTH: 49
<212> TYPE: DNA
<213> ORGANISM: Artificial Sequence
<220> FEATURE:
<223> OTHER INFORMATION: Synthetic DNA

<400> SEQUENCE: 5
gccgcccagg tgaccccgtt acagaaaatg gaaaaactct cctcccggc 49

-continued

<210> SEQ ID NO 6
<211> LENGTH: 49
<212> TYPE: DNA
<213> ORGANISM: Artificial Sequence
<220> FEATURE:
<223> OTHER INFORMATION: Synthetic DNA

<400> SEQUENCE: 6
gaaaaactct cctcccggct cgataatgtg attctggtca agcgcgagg 49

<210> SEQ ID NO 7
<211> LENGTH: 50
<212> TYPE: DNA
<213> ORGANISM: Artificial Sequence
<220> FEATURE:
<223> OTHER INFORMATION: Synthetic DNA

<400> SEQUENCE: 7
gattctggtc aagcgcgagg accgtcagcc cgtgcactcg ttcaagctcc 50

<210> SEQ ID NO 8
<211> LENGTH: 50
<212> TYPE: DNA
<213> ORGANISM: Artificial Sequence
<220> FEATURE:
<223> OTHER INFORMATION: Synthetic DNA

<400> SEQUENCE: 8
gtgcactcgt tcaagctccg tggtgcctat gcgatgatgg cgggcctgac 50

<210> SEQ ID NO 9
<211> LENGTH: 50
<212> TYPE: DNA
<213> ORGANISM: Artificial Sequence
<220> FEATURE:
<223> OTHER INFORMATION: Synthetic DNA

<400> SEQUENCE: 9
gatgatggcg ggcctgacgg aagaacagaa agcccacggt gtgattacgg 50

<210> SEQ ID NO 10
<211> LENGTH: 50
<212> TYPE: DNA
<213> ORGANISM: Artificial Sequence
<220> FEATURE:
<223> OTHER INFORMATION: Synthetic DNA

<400> SEQUENCE: 10
cccacggtgt gattacggca tcagcaggca accatgctca aggtgtggcg 50

<210> SEQ ID NO 11
<211> LENGTH: 49
<212> TYPE: DNA
<213> ORGANISM: Artificial Sequence
<220> FEATURE:
<223> OTHER INFORMATION: Synthetic DNA

<400> SEQUENCE: 11
catgctcaag gtgtggcgtt ctcttctgct cgactgggag tgaaagcgc 49

<210> SEQ ID NO 12
<211> LENGTH: 50
<212> TYPE: DNA
<213> ORGANISM: Artificial Sequence
<220> FEATURE:
<223> OTHER INFORMATION: Synthetic DNA -continued

<400> SEQUENCE: 12
gactgggagt gaaagcgctg attgtgatgc ctacagctac tcgagaatac 50

<210> SEQ ID NO 13
<211> LENGTH: 49
<212> TYPE: DNA
<213> ORGANISM: Artificial Sequence
<220> FEATURE:
<223> OTHER INFORMATION: Synthetic DNA

<400> SEQUENCE: 13
ctatactgca gagtgaaagc gctgattgtg atgcctacag ctacagccg 49

<210> SEQ ID NO 14
<211> LENGTH: 50
<212> TYPE: DNA
<213> ORGANISM: Artificial Sequence
<220> FEATURE:
<223> OTHER INFORMATION: Synthetic DNA

<400> SEQUENCE: 14
gatgcctaca gctacagccg atattaaagt ggatgcggtg cgtggcttcg 50

<210> SEQ ID NO 15
<211> LENGTH: 48
<212> TYPE: DNA
<213> ORGANISM: Artificial Sequence
<220> FEATURE:
<223> OTHER INFORMATION: Synthetic DNA

<400> SEQUENCE: 15
gatgcggtgc gtggcttcgg tggtgaagtt ctgctgcatg gcgcgaac 48

<210> SEQ ID NO 16
<211> LENGTH: 49
<212> TYPE: DNA
<213> ORGANISM: Artificial Sequence
<220> FEATURE:
<223> OTHER INFORMATION: Synthetic DNA

<400> SEQUENCE: 16
ctgctgcatg gcgcgaactt tgatgaagcc aaggccaagg cgatcgagc 49

<210> SEQ ID NO 17
<211> LENGTH: 50
<212> TYPE: DNA
<213> ORGANISM: Artificial Sequence
<220> FEATURE:
<223> OTHER INFORMATION: Synthetic DNA

<400> SEQUENCE: 17
caaggccaag gcgatcgagc tctctcaaca acaggggttc acgtgggtgc 50

<210> SEQ ID NO 18
<211> LENGTH: 50
<212> TYPE: DNA
<213> ORGANISM: Artificial Sequence
<220> FEATURE:
<223> OTHER INFORMATION: Synthetic DNA

<400> SEQUENCE: 18
caggggttca cgtgggtgcc accgtttgat catccgatgg tcatcgccgg 50

<210> SEQ ID NO 19

-continued

<211> LENGTH: 49
<212> TYPE: DNA
<213> ORGANISM: Artificial Sequence
<220> FEATURE:
<223> OTHER INFORMATION: Synthetic DNA

<400> SEQUENCE: 19
catccgatgg tcatcgccgg tcaaggcacg ttagcgctgg agttgcttc 49

<210> SEQ ID NO 20
<211> LENGTH: 50
<212> TYPE: DNA
<213> ORGANISM: Artificial Sequence
<220> FEATURE:
<223> OTHER INFORMATION: Synthetic DNA

<400> SEQUENCE: 20
gttagcgctg gagttgcttc aacaggacgc acacctcgac cgggtcttcg 50

<210> SEQ ID NO 21
<211> LENGTH: 50
<212> TYPE: DNA
<213> ORGANISM: Artificial Sequence
<220> FEATURE:
<223> OTHER INFORMATION: Synthetic DNA

<400> SEQUENCE: 21
cacctcgacc gggtcttcgt tcctgttggg ggtggtggtc tggcggcggg 50

<210> SEQ ID NO 22
<211> LENGTH: 49
<212> TYPE: DNA
<213> ORGANISM: Artificial Sequence
<220> FEATURE:
<223> OTHER INFORMATION: Synthetic DNA

<400> SEQUENCE: 22
gtggtggtct ggcggcgggg gtagcagtac tcatcaagca gctcatgcc 49

<210> SEQ ID NO 23
<211> LENGTH: 49
<212> TYPE: DNA
<213> ORGANISM: Artificial Sequence
<220> FEATURE:
<223> OTHER INFORMATION: Synthetic DNA

<400> SEQUENCE: 23
catcaagcag ctcatgccac aaattaaagt gatagccgtt gaagcctcg 49

<210> SEQ ID NO 24
<211> LENGTH: 26
<212> TYPE: DNA
<213> ORGANISM: Artificial Sequence
<220> FEATURE:
<223> OTHER INFORMATION: Synthetic DNA

<400> SEQUENCE: 24
gatagccgtt gaagcctcga gaatac 26

<210> SEQ ID NO 25
<211> LENGTH: 48
<212> TYPE: DNA
<213> ORGANISM: Artificial Sequence
<220> FEATURE:
<223> OTHER INFORMATION: Synthetic DNA

<400> SEQUENCE: 25

-continued ctatactgca gctcatgcca caaattaaag tgatagccgt tgaagccg 48

<210> SEQ ID NO 26
<211> LENGTH: 49
<212> TYPE: DNA
<213> ORGANISM: Artificial Sequence
<220> FEATURE:
<223> OTHER INFORMATION: Synthetic DNA

<400> SEQUENCE: 26
gtgatagccg ttgaagccga agattccgca tgcctgaagg ccgcacttg 49

<210> SEQ ID NO 27
<211> LENGTH: 50
<212> TYPE: DNA
<213> ORGANISM: Artificial Sequence
<220> FEATURE:
<223> OTHER INFORMATION: Synthetic DNA

<400> SEQUENCE: 27
gcctgaaggc cgcacttgac gccggacatc cagtcgacct gccgcgcgtg 50

<210> SEQ ID NO 28
<211> LENGTH: 50
<212> TYPE: DNA
<213> ORGANISM: Artificial Sequence
<220> FEATURE:
<223> OTHER INFORMATION: Synthetic DNA

<400> SEQUENCE: 28
gtcgacctgc cgcgcgtggg gctgtttgca gaaggggttg cggtgaaacg 50

<210> SEQ ID NO 29
<211> LENGTH: 49
<212> TYPE: DNA
<213> ORGANISM: Artificial Sequence
<220> FEATURE:
<223> OTHER INFORMATION: Synthetic DNA

<400> SEQUENCE: 29
gaaggggttg cggtgaaacg gattggggat gagaccttcc gcctatgcc 49

<210> SEQ ID NO 30
<211> LENGTH: 49
<212> TYPE: DNA
<213> ORGANISM: Artificial Sequence
<220> FEATURE:
<223> OTHER INFORMATION: Synthetic DNA

<400> SEQUENCE: 30
gagaccttcc gcctatgcca ggagtatttg gacgacatca tcaccgtgg 49

<210> SEQ ID NO 31
<211> LENGTH: 49
<212> TYPE: DNA
<213> ORGANISM: Artificial Sequence
<220> FEATURE:
<223> OTHER INFORMATION: Synthetic DNA

<400> SEQUENCE: 31
gacgacatca tcaccgtgga ctccgatgcc atttgtgccg ccatgaagg 49

<210> SEQ ID NO 32
<211> LENGTH: 50
<212> TYPE: DNA

-continued

<213> ORGANISM: Artificial Sequence
<220> FEATURE:
<223> OTHER INFORMATION: Synthetic DNA

<400> SEQUENCE: 32
catttgtgcc gccatgaagg acctattcga ggatgtccgt gcagtcgccg 50

<210> SEQ ID NO 33
<211> LENGTH: 48
<212> TYPE: DNA
<213> ORGANISM: Artificial Sequence
<220> FEATURE:
<223> OTHER INFORMATION: Synthetic DNA

<400> SEQUENCE: 33
gatgtccgtg cagtcgccga accgtctgga gctctcgcac tggccggg 48

<210> SEQ ID NO 34
<211> LENGTH: 50
<212> TYPE: DNA
<213> ORGANISM: Artificial Sequence
<220> FEATURE:
<223> OTHER INFORMATION: Synthetic DNA

<400> SEQUENCE: 34
gctctcgcac tggccgggat gaagaagtac attgctctgc acaacatccg 50

<210> SEQ ID NO 35
<211> LENGTH: 49
<212> TYPE: DNA
<213> ORGANISM: Artificial Sequence
<220> FEATURE:
<223> OTHER INFORMATION: Synthetic DNA

<400> SEQUENCE: 35
cattgctctg cacaacatcc gaggcgaacg actggcccac atcctgagc 49

<210> SEQ ID NO 36
<211> LENGTH: 28
<212> TYPE: DNA
<213> ORGANISM: Artificial Sequence
<220> FEATURE:
<223> OTHER INFORMATION: Synthetic DNA

<400> SEQUENCE: 36
ctggcccaca tcctgagctc gagaatac 28

<210> SEQ ID NO 37
<211> LENGTH: 50
<212> TYPE: DNA
<213> ORGANISM: Artificial Sequence
<220> FEATURE:
<223> OTHER INFORMATION: Synthetic DNA

<400> SEQUENCE: 37
ctatactgca gcacaacatc cgaggcgaac gactggccca catcctgagc 50

<210> SEQ ID NO 38
<211> LENGTH: 48
<212> TYPE: DNA
<213> ORGANISM: Artificial Sequence
<220> FEATURE:
<223> OTHER INFORMATION: Synthetic DNA

<400> SEQUENCE: 38
ctggcccaca tcctgagcgg tgcgaatgtc aacttccacg gcttacgg 48

-continued

<210> SEQ ID NO 39
<211> LENGTH: 50
<212> TYPE: DNA
<213> ORGANISM: Artificial Sequence
<220> FEATURE:
<223> OTHER INFORMATION: Synthetic DNA

<400> SEQUENCE: 39
caacttccac ggcttacggt atgtgtctga gcgttgcgag ctgggcgaac 50

<210> SEQ ID NO 40
<211> LENGTH: 50
<212> TYPE: DNA
<213> ORGANISM: Artificial Sequence
<220> FEATURE:
<223> OTHER INFORMATION: Synthetic DNA

<400> SEQUENCE: 40
gttgcgagct gggcgaacaa cgcgaagcat tactggcagt gaccattccg 50

<210> SEQ ID NO 41
<211> LENGTH: 49
<212> TYPE: DNA
<213> ORGANISM: Artificial Sequence
<220> FEATURE:
<223> OTHER INFORMATION: Synthetic DNA

<400> SEQUENCE: 41
ctggcagtga ccattccgga agaaaaaggt tcgttcctca agttctgcc 49

<210> SEQ ID NO 42
<211> LENGTH: 45
<212> TYPE: DNA
<213> ORGANISM: Artificial Sequence
<220> FEATURE:
<223> OTHER INFORMATION: Synthetic DNA

<400> SEQUENCE: 42
cgttcctcaa gttctgccag ctgttaggag gtcggagcgt cacgg 45

<210> SEQ ID NO 43
<211> LENGTH: 47
<212> TYPE: DNA
<213> ORGANISM: Artificial Sequence
<220> FEATURE:
<223> OTHER INFORMATION: Synthetic DNA

<400> SEQUENCE: 43
gaggtcggag cgtcacggaa tttaactatc ggtttgcaga cgccaag 47

<210> SEQ ID NO 44
<211> LENGTH: 50
<212> TYPE: DNA
<213> ORGANISM: Artificial Sequence
<220> FEATURE:
<223> OTHER INFORMATION: Synthetic DNA

<400> SEQUENCE: 44
cggtttgcag acgccaagaa tgcctgtatt tttgtgggtg tgaggttgag 50

<210> SEQ ID NO 45
<211> LENGTH: 50
<212> TYPE: DNA
<213> ORGANISM: Artificial Sequence
<220> FEATURE:

-continued

<223> OTHER INFORMATION: Synthetic DNA

<400> SEQUENCE: 45
gtatttttgt gggtgtgagg ttgagcaggg gattggagga gcgcaaggag 50

<210> SEQ ID NO 46
<211> LENGTH: 46
<212> TYPE: DNA
<213> ORGANISM: Artificial Sequence
<220> FEATURE:
<223> OTHER INFORMATION: Synthetic DNA

<400> SEQUENCE: 46
gattggagga gcgcaaggag attcttcaga tgctgaacga tggcgg 46

<210> SEQ ID NO 47
<211> LENGTH: 47
<212> TYPE: DNA
<213> ORGANISM: Artificial Sequence
<220> FEATURE:
<223> OTHER INFORMATION: Synthetic DNA

<400> SEQUENCE: 47
gatgctgaac gatggcggtt atagcgtggt ggacctgagc gacgacg 47

<210> SEQ ID NO 48
<211> LENGTH: 36
<212> TYPE: DNA
<213> ORGANISM: Artificial Sequence
<220> FEATURE:
<223> OTHER INFORMATION: Synthetic DNA

<400> SEQUENCE: 48
gtggacctga gcgacgacga aatggctcga gaatac 36

<210> SEQ ID NO 49
<211> LENGTH: 47
<212> TYPE: DNA
<213> ORGANISM: Artificial Sequence
<220> FEATURE:
<223> OTHER INFORMATION: Synthetic DNA

<400> SEQUENCE: 49
ctatactgca gttatagcgt ggtggacctg agcgacgacg aaatggc 47

<210> SEQ ID NO 50
<211> LENGTH: 50
<212> TYPE: DNA
<213> ORGANISM: Artificial Sequence
<220> FEATURE:
<223> OTHER INFORMATION: Synthetic DNA

<400> SEQUENCE: 50
gagcgacgac gaaatggcta aactacacgt acgctacatg gtgggtggac 50

<210> SEQ ID NO 51
<211> LENGTH: 47
<212> TYPE: DNA
<213> ORGANISM: Artificial Sequence
<220> FEATURE:
<223> OTHER INFORMATION: Synthetic DNA

<400> SEQUENCE: 51
gctacatggt gggtggacga ccttcacatc ccctccagga gcgactg 47

-continued

<210> SEQ ID NO 52
<211> LENGTH: 50
<212> TYPE: DNA
<213> ORGANISM: Artificial Sequence
<220> FEATURE:
<223> OTHER INFORMATION: Synthetic DNA

<400> SEQUENCE: 52
cccctccagg agcgactgta ttcctttgaa ttcccagagt ctcccggcgc 50

<210> SEQ ID NO 53
<211> LENGTH: 49
<212> TYPE: DNA
<213> ORGANISM: Artificial Sequence
<220> FEATURE:
<223> OTHER INFORMATION: Synthetic DNA

<400> SEQUENCE: 53
cccagagtct cccggcgcct tattacgttt cttaaacacc ctgggcacc 49

<210> SEQ ID NO 54
<211> LENGTH: 48
<212> TYPE: DNA
<213> ORGANISM: Artificial Sequence
<220> FEATURE:
<223> OTHER INFORMATION: Synthetic DNA

<400> SEQUENCE: 54
cttaaacacc ctgggcacct attggaatat cagcctgttc cactaccg 48

<210> SEQ ID NO 55
<211> LENGTH: 50
<212> TYPE: DNA
<213> ORGANISM: Artificial Sequence
<220> FEATURE:
<223> OTHER INFORMATION: Synthetic DNA

<400> SEQUENCE: 55
cagcctgttc cactaccgat ctcacggcac ggattacggg cgtgttctgg 50

<210> SEQ ID NO 56
<211> LENGTH: 49
<212> TYPE: DNA
<213> ORGANISM: Artificial Sequence
<220> FEATURE:
<223> OTHER INFORMATION: Synthetic DNA

<400> SEQUENCE: 56
gattacgggc gtgttctggc ggcgtttgaa ctgggcgatc atgaaccgg 49

<210> SEQ ID NO 57
<211> LENGTH: 48
<212> TYPE: DNA
<213> ORGANISM: Artificial Sequence
<220> FEATURE:
<223> OTHER INFORMATION: Synthetic DNA

<400> SEQUENCE: 57
ctgggcgatc atgaaccgga ctttgaaacg cgcctgaacg aactgggc 48

<210> SEQ ID NO 58
<211> LENGTH: 50
<212> TYPE: DNA
<213> ORGANISM: Artificial Sequence
<220> FEATURE:
<223> OTHER INFORMATION: Synthetic DNA -continued

<400> SEQUENCE: 58
cgcctgaacg aactgggcta tgattgccat gatgagacca acaaccccgc 50

<210> SEQ ID NO 59
<211> LENGTH: 49
<212> TYPE: DNA
<213> ORGANISM: Artificial Sequence
<220> FEATURE:
<223> OTHER INFORMATION: Synthetic DNA

<400> SEQUENCE: 59
gatgagacca acaaccccgc ctttcgtttc ttcctcgccg gctaactcg 49

<210> SEQ ID NO 60
<211> LENGTH: 27
<212> TYPE: DNA
<213> ORGANISM: Artificial Sequence
<220> FEATURE:
<223> OTHER INFORMATION: Synthetic DNA

<400> SEQUENCE: 60
cttcctcgcc ggctaactcg agaatac 27

<210> SEQ ID NO 61
<211> LENGTH: 36
<212> TYPE: DNA
<213> ORGANISM: Artificial Sequence
<220> FEATURE:
<223> OTHER INFORMATION: Synthetic DNA

<400> SEQUENCE: 61
ggccgattct caacctctgt ctggagcacc tgaagg 36

<210> SEQ ID NO 62
<211> LENGTH: 50
<212> TYPE: DNA
<213> ORGANISM: Artificial Sequence
<220> FEATURE:
<223> OTHER INFORMATION: Synthetic DNA

<400> SEQUENCE: 62
gcgcacgtaa cactgcccgt aaatattctg ctccttcagg tgctccagac 50

<210> SEQ ID NO 63
<211> LENGTH: 47
<212> TYPE: DNA
<213> ORGANISM: Artificial Sequence
<220> FEATURE:
<223> OTHER INFORMATION: Synthetic DNA

<400> SEQUENCE: 63
gggcagtgtt acgtgcgccg gtgtatgaag ccgcccaggt gaccccg 47

<210> SEQ ID NO 64
<211> LENGTH: 49
<212> TYPE: DNA
<213> ORGANISM: Artificial Sequence
<220> FEATURE:
<223> OTHER INFORMATION: Synthetic DNA

<400> SEQUENCE: 64
gacgggaact gagtttttcc attttctgta acggggtcac ctgggcggc 49

<210> SEQ ID NO 65
<211> LENGTH: 49

-continued

<212> TYPE: DNA
<213> ORGANISM: Artificial Sequence
<220> FEATURE:
<223> OTHER INFORMATION: Synthetic DNA

<400> SEQUENCE: 65
gaaaaactca gttcccgtct cgataatgtg attctggtca agcgcgagg 49

<210> SEQ ID NO 66
<211> LENGTH: 50
<212> TYPE: DNA
<213> ORGANISM: Artificial Sequence
<220> FEATURE:
<223> OTHER INFORMATION: Synthetic DNA

<400> SEQUENCE: 66
ggagcttgaa cgagtgcacg ggctgtcggt cctcgcgctt gaccagaatc 50

<210> SEQ ID NO 67
<211> LENGTH: 50
<212> TYPE: DNA
<213> ORGANISM: Artificial Sequence
<220> FEATURE:
<223> OTHER INFORMATION: Synthetic DNA

<400> SEQUENCE: 67
gtgcactcgt tcaagctccg tggtgcgtat gcgatgatgg cagggttgac 50

<210> SEQ ID NO 68
<211> LENGTH: 50
<212> TYPE: DNA
<213> ORGANISM: Artificial Sequence
<220> FEATURE:
<223> OTHER INFORMATION: Synthetic DNA

<400> SEQUENCE: 68
ccgtaatcac accgtgggct ttctgttctt ccgtcaaccc tgccatcatc 50

<210> SEQ ID NO 69
<211> LENGTH: 50
<212> TYPE: DNA
<213> ORGANISM: Artificial Sequence
<220> FEATURE:
<223> OTHER INFORMATION: Synthetic DNA

<400> SEQUENCE: 69
cccacggtgt gattacggca tcagctggca accatgctca aggtgtggcg 50

<210> SEQ ID NO 70
<211> LENGTH: 48
<212> TYPE: DNA
<213> ORGANISM: Artificial Sequence
<220> FEATURE:
<223> OTHER INFORMATION: Synthetic DNA

<400> SEQUENCE: 70
cgctttcact cccagtcgag cagaagagaa cgccacacct tgagcatg 48

<210> SEQ ID NO 71
<211> LENGTH: 41
<212> TYPE: DNA
<213> ORGANISM: Artificial Sequence
<220> FEATURE:
<223> OTHER INFORMATION: Synthetic DNA

<400> SEQUENCE: 71

-continued

```
cgactgggag tgaaagcgtt aatcgtgatg cctactgcta c                          41


<210> SEQ ID NO 72
<211> LENGTH: 39
<212> TYPE: DNA
<213> ORGANISM: Artificial Sequence
<220> FEATURE:
<223> OTHER INFORMATION: Synthetic DNA

<400> SEQUENCE: 72

gagtgaaagc gttaatcgtg atgcctactg ctacagcgg                             39


<210> SEQ ID NO 73
<211> LENGTH: 50
<212> TYPE: DNA
<213> ORGANISM: Artificial Sequence
<220> FEATURE:
<223> OTHER INFORMATION: Synthetic DNA

<400> SEQUENCE: 73

caaaccctcg gacggcatcc actttaatat ccgctgtagc agtaggcatc                 50


<210> SEQ ID NO 74
<211> LENGTH: 48
<212> TYPE: DNA
<213> ORGANISM: Artificial Sequence
<220> FEATURE:
<223> OTHER INFORMATION: Synthetic DNA

<400> SEQUENCE: 74

gatgccgtcc gagggtttgg tggtgaagtt ctgctgcatg gcgcgaac                   48


<210> SEQ ID NO 75
<211> LENGTH: 49
<212> TYPE: DNA
<213> ORGANISM: Artificial Sequence
<220> FEATURE:
<223> OTHER INFORMATION: Synthetic DNA

<400> SEQUENCE: 75

gctcgatcgc cttggccttg gcttcatcaa agttcgcgcc atgcagcag                  49


<210> SEQ ID NO 76
<211> LENGTH: 50
<212> TYPE: DNA
<213> ORGANISM: Artificial Sequence
<220> FEATURE:
<223> OTHER INFORMATION: Synthetic DNA

<400> SEQUENCE: 76

caaggccaag gcgatcgagc tctctcaaca acaggggttc acgtgggtgc                 50


<210> SEQ ID NO 77
<211> LENGTH: 50
<212> TYPE: DNA
<213> ORGANISM: Artificial Sequence
<220> FEATURE:
<223> OTHER INFORMATION: Synthetic DNA

<400> SEQUENCE: 77

ccggcgatta ccatcggatg atcgaatggt ggcacccacg tgaacccctg                 50


<210> SEQ ID NO 78
<211> LENGTH: 49
<212> TYPE: DNA
<213> ORGANISM: Artificial Sequence
```

-continued

<220> FEATURE:
<223> OTHER INFORMATION: Synthetic DNA

<400> SEQUENCE: 78
catccgatgg taatcgccgg tcaggggacg ttagcactgg agttgcttc 49

<210> SEQ ID NO 79
<211> LENGTH: 50
<212> TYPE: DNA
<213> ORGANISM: Artificial Sequence
<220> FEATURE:
<223> OTHER INFORMATION: Synthetic DNA

<400> SEQUENCE: 79
cgaagacccg gtcgagatgt gcgtcctgtt gaagcaactc cagtgctaac 50

<210> SEQ ID NO 80
<211> LENGTH: 50
<212> TYPE: DNA
<213> ORGANISM: Artificial Sequence
<220> FEATURE:
<223> OTHER INFORMATION: Synthetic DNA

<400> SEQUENCE: 80
catctcgacc gggtcttcgt tcctgttggg ggtggtggtc tggcggcggg 50

<210> SEQ ID NO 81
<211> LENGTH: 49
<212> TYPE: DNA
<213> ORGANISM: Artificial Sequence
<220> FEATURE:
<223> OTHER INFORMATION: Synthetic DNA

<400> SEQUENCE: 81
ggcatgagct gcttgatgag tactgctaca cccgccgcca gaccaccac 49

<210> SEQ ID NO 82
<211> LENGTH: 46
<212> TYPE: DNA
<213> ORGANISM: Artificial Sequence
<220> FEATURE:
<223> OTHER INFORMATION: Synthetic DNA

<400> SEQUENCE: 82
catcaagcag ctcatgccac aaattaaagt gatagccgtt gaagcc 46

<210> SEQ ID NO 83
<211> LENGTH: 38
<212> TYPE: DNA
<213> ORGANISM: Artificial Sequence
<220> FEATURE:
<223> OTHER INFORMATION: Synthetic DNA

<400> SEQUENCE: 83
gctcatgcca caaattaaag tgatagccgt tgaagccg 38

<210> SEQ ID NO 84
<211> LENGTH: 49
<212> TYPE: DNA
<213> ORGANISM: Artificial Sequence
<220> FEATURE:
<223> OTHER INFORMATION: Synthetic DNA

<400> SEQUENCE: 84
caagtgcggc cttcagacat gcggaatctt cggcttcaac ggctatcac 49

-continued

<210> SEQ ID NO 85
<211> LENGTH: 50
<212> TYPE: DNA
<213> ORGANISM: Artificial Sequence
<220> FEATURE:
<223> OTHER INFORMATION: Synthetic DNA

<400> SEQUENCE: 85
gtctgaaggc cgcacttgat gccggacacc ctgtcgatct gccgcgtgtg 50

<210> SEQ ID NO 86
<211> LENGTH: 50
<212> TYPE: DNA
<213> ORGANISM: Artificial Sequence
<220> FEATURE:
<223> OTHER INFORMATION: Synthetic DNA

<400> SEQUENCE: 86
cgtttcaccg caacccccttc tgcaaacagc cccacacgcg gcagatcgac 50

<210> SEQ ID NO 87
<211> LENGTH: 49
<212> TYPE: DNA
<213> ORGANISM: Artificial Sequence
<220> FEATURE:
<223> OTHER INFORMATION: Synthetic DNA

<400> SEQUENCE: 87
gaaggggttg cggtgaaacg gattggggat gagaccttcc gcctatgcc 49

<210> SEQ ID NO 88
<211> LENGTH: 49
<212> TYPE: DNA
<213> ORGANISM: Artificial Sequence
<220> FEATURE:
<223> OTHER INFORMATION: Synthetic DNA

<400> SEQUENCE: 88
ccacggtgat gatgtcgtcc aaatactcct ggcataggcg gaaggtctc 49

<210> SEQ ID NO 89
<211> LENGTH: 49
<212> TYPE: DNA
<213> ORGANISM: Artificial Sequence
<220> FEATURE:
<223> OTHER INFORMATION: Synthetic DNA

<400> SEQUENCE: 89
gacgacatca tcaccgtgga ctccgatgcc atttgtgccg ccatgaagg 49

<210> SEQ ID NO 90
<211> LENGTH: 50
<212> TYPE: DNA
<213> ORGANISM: Artificial Sequence
<220> FEATURE:
<223> OTHER INFORMATION: Synthetic DNA

<400> SEQUENCE: 90
cggcgactgc acggacatct tcgaataggt ccttcatggc ggcacaaatg 50

<210> SEQ ID NO 91
<211> LENGTH: 48
<212> TYPE: DNA
<213> ORGANISM: Artificial Sequence
<220> FEATURE:
<223> OTHER INFORMATION: Synthetic DNA -continued

<400> SEQUENCE: 91
gatgtccgtg cagtcgccga accgtctgga gctttagcat tagccggg 48

<210> SEQ ID NO 92
<211> LENGTH: 50
<212> TYPE: DNA
<213> ORGANISM: Artificial Sequence
<220> FEATURE:
<223> OTHER INFORMATION: Synthetic DNA

<400> SEQUENCE: 92
cggatgttgt gcagagcaat gtacttcttc atcccggcta atgctaaagc 50

<210> SEQ ID NO 93
<211> LENGTH: 49
<212> TYPE: DNA
<213> ORGANISM: Artificial Sequence
<220> FEATURE:
<223> OTHER INFORMATION: Synthetic DNA

<400> SEQUENCE: 93
cattgctctg cacaacatcc gaggcgaacg actggcccac atcttaagc 49

<210> SEQ ID NO 94
<211> LENGTH: 40
<212> TYPE: DNA
<213> ORGANISM: Artificial Sequence
<220> FEATURE:
<223> OTHER INFORMATION: Synthetic DNA

<400> SEQUENCE: 94
gcacaacatc cgaggcgaac gactggccca catcttaagc 40

<210> SEQ ID NO 95
<211> LENGTH: 48
<212> TYPE: DNA
<213> ORGANISM: Artificial Sequence
<220> FEATURE:
<223> OTHER INFORMATION: Synthetic DNA

<400> SEQUENCE: 95
ccgtaagccg tggaagttga cattcgcacc gcttaagatg tgggccag 48

<210> SEQ ID NO 96
<211> LENGTH: 50
<212> TYPE: DNA
<213> ORGANISM: Artificial Sequence
<220> FEATURE:
<223> OTHER INFORMATION: Synthetic DNA

<400> SEQUENCE: 96
caacttccac ggcttacggt atgtgtctga gcgttgcgag ctgggcgaac 50

<210> SEQ ID NO 97
<211> LENGTH: 50
<212> TYPE: DNA
<213> ORGANISM: Artificial Sequence
<220> FEATURE:
<223> OTHER INFORMATION: Synthetic DNA

<400> SEQUENCE: 97
cggaatggtc actgccagta atgcttctct ttgttcgccc agctcgcaac 50

<210> SEQ ID NO 98

-continued

<211> LENGTH: 49
<212> TYPE: DNA
<213> ORGANISM: Artificial Sequence
<220> FEATURE:
<223> OTHER INFORMATION: Synthetic DNA

<400> SEQUENCE: 98
ctggcagtga ccattccgga agaaaaaggt tcgttcctca agttctgcc 49

<210> SEQ ID NO 99
<211> LENGTH: 45
<212> TYPE: DNA
<213> ORGANISM: Artificial Sequence
<220> FEATURE:
<223> OTHER INFORMATION: Synthetic DNA

<400> SEQUENCE: 99
ccgtgacgct ccgacctcct aacagctggc agaacttgag gaacg 45

<210> SEQ ID NO 100
<211> LENGTH: 47
<212> TYPE: DNA
<213> ORGANISM: Artificial Sequence
<220> FEATURE:
<223> OTHER INFORMATION: Synthetic DNA

<400> SEQUENCE: 100
gaggtcggag cgtcacggaa tttaactatc ggtttgcaga cgccaag 47

<210> SEQ ID NO 101
<211> LENGTH: 50
<212> TYPE: DNA
<213> ORGANISM: Artificial Sequence
<220> FEATURE:
<223> OTHER INFORMATION: Synthetic DNA

<400> SEQUENCE: 101
ctcaacctca cacccacaaa aatacaggca ttcttggcgt ctgcaaaccg 50

<210> SEQ ID NO 102
<211> LENGTH: 50
<212> TYPE: DNA
<213> ORGANISM: Artificial Sequence
<220> FEATURE:
<223> OTHER INFORMATION: Synthetic DNA

<400> SEQUENCE: 102
gtatttttgt gggtgtgagg ttgagcaggg gattggagga gcgcaaggag 50

<210> SEQ ID NO 103
<211> LENGTH: 46
<212> TYPE: DNA
<213> ORGANISM: Artificial Sequence
<220> FEATURE:
<223> OTHER INFORMATION: Synthetic DNA

<400> SEQUENCE: 103
ccgccatcgt tcagcatctg aagaatctcc ttgcgctcct ccaatc 46

<210> SEQ ID NO 104
<211> LENGTH: 47
<212> TYPE: DNA
<213> ORGANISM: Artificial Sequence
<220> FEATURE:
<223> OTHER INFORMATION: Synthetic DNA

<400> SEQUENCE: 104

-continued gatgctgaac gatggcggtt atagcgtggt ggacctgagc gacgacg 47

<210> SEQ ID NO 105
<211> LENGTH: 26
<212> TYPE: DNA
<213> ORGANISM: Artificial Sequence
<220> FEATURE:
<223> OTHER INFORMATION: Synthetic DNA

<400> SEQUENCE: 105
gccatttcgt cgtcgctcag gtccac 26

<210> SEQ ID NO 106
<211> LENGTH: 37
<212> TYPE: DNA
<213> ORGANISM: Artificial Sequence
<220> FEATURE:
<223> OTHER INFORMATION: Synthetic DNA

<400> SEQUENCE: 106
gttatagcgt ggtggacctg agcgacgacg aaatggc 37

<210> SEQ ID NO 107
<211> LENGTH: 50
<212> TYPE: DNA
<213> ORGANISM: Artificial Sequence
<220> FEATURE:
<223> OTHER INFORMATION: Synthetic DNA

<400> SEQUENCE: 107
gtccacccac catgtagcgt acgtgtagtt tagccatttc gtcgtcgctc 50

<210> SEQ ID NO 108
<211> LENGTH: 47
<212> TYPE: DNA
<213> ORGANISM: Artificial Sequence
<220> FEATURE:
<223> OTHER INFORMATION: Synthetic DNA

<400> SEQUENCE: 108
gctacatggt gggtggacga ccttcacatc ccctccagga gcgactg 47

<210> SEQ ID NO 109
<211> LENGTH: 50
<212> TYPE: DNA
<213> ORGANISM: Artificial Sequence
<220> FEATURE:
<223> OTHER INFORMATION: Synthetic DNA

<400> SEQUENCE: 109
gcgccgggag actctgggaa ttcaaaggaa tacagtcgct cctggagggg 50

<210> SEQ ID NO 110
<211> LENGTH: 49
<212> TYPE: DNA
<213> ORGANISM: Artificial Sequence
<220> FEATURE:
<223> OTHER INFORMATION: Synthetic DNA

<400> SEQUENCE: 110
cccagagtct cccggcgcct tattacgttt cttaaacacc ctgggcacc 49

<210> SEQ ID NO 111
<211> LENGTH: 48
<212> TYPE: DNA

-continued

<213> ORGANISM: Artificial Sequence
<220> FEATURE:
<223> OTHER INFORMATION: Synthetic DNA

<400> SEQUENCE: 111
cggtagtgga acaggctgat attccaatag gtgcccaggg tgtttaag 48

<210> SEQ ID NO 112
<211> LENGTH: 50
<212> TYPE: DNA
<213> ORGANISM: Artificial Sequence
<220> FEATURE:
<223> OTHER INFORMATION: Synthetic DNA

<400> SEQUENCE: 112
cagcctgttc cactaccgat ctcatgggac ggattacggg cgtgttctgg 50

<210> SEQ ID NO 113
<211> LENGTH: 49
<212> TYPE: DNA
<213> ORGANISM: Artificial Sequence
<220> FEATURE:
<223> OTHER INFORMATION: Synthetic DNA

<400> SEQUENCE: 113
ccggttcatg atcgccaagc tcaaacgctg ccagaacacg cccgtaatc 49

<210> SEQ ID NO 114
<211> LENGTH: 48
<212> TYPE: DNA
<213> ORGANISM: Artificial Sequence
<220> FEATURE:
<223> OTHER INFORMATION: Synthetic DNA

<400> SEQUENCE: 114
cttggcgatc atgaaccgga ctttgaaacg cgcctgaacg aactgggc 48

<210> SEQ ID NO 115
<211> LENGTH: 50
<212> TYPE: DNA
<213> ORGANISM: Artificial Sequence
<220> FEATURE:
<223> OTHER INFORMATION: Synthetic DNA

<400> SEQUENCE: 115
gcggggttgt tggtctcatc atggcaatca tagcccagtt cgttcaggcg 50

<210> SEQ ID NO 116
<211> LENGTH: 45
<212> TYPE: DNA
<213> ORGANISM: Artificial Sequence
<220> FEATURE:
<223> OTHER INFORMATION: Synthetic DNA

<400> SEQUENCE: 116
gatgagacca acaaccccgc ctttcgtttc ttcctcgcag gctaa 45

<210> SEQ ID NO 117
<211> LENGTH: 17
<212> TYPE: DNA
<213> ORGANISM: Artificial Sequence
<220> FEATURE:
<223> OTHER INFORMATION: Synthetic DNA

<400> SEQUENCE: 117
gtagcagtag gcatcac 17

-continued

<210> SEQ ID NO 118
<211> LENGTH: 18
<212> TYPE: DNA
<213> ORGANISM: Artificial Sequence
<220> FEATURE:
<223> OTHER INFORMATION: Synthetic DNA

<400> SEQUENCE: 118
ggcttcaacg gctatcac 18

<210> SEQ ID NO 119
<211> LENGTH: 18
<212> TYPE: DNA
<213> ORGANISM: Artificial Sequence
<220> FEATURE:
<223> OTHER INFORMATION: Synthetic DNA

<400> SEQUENCE: 119
gcttaagatg tgggccag 18

<210> SEQ ID NO 120
<211> LENGTH: 20
<212> TYPE: DNA
<213> ORGANISM: Artificial Sequence
<220> FEATURE:
<223> OTHER INFORMATION: Synthetic DNA

<400> SEQUENCE: 120
ttagcctgcg aggaagaaac 20

<210> SEQ ID NO 121
<211> LENGTH: 45
<212> TYPE: DNA
<213> ORGANISM: Artificial Sequence
<220> FEATURE:
<223> OTHER INFORMATION: Synthetic DNA

<400> SEQUENCE: 121
ctatatctag catatggccg attctcaacc tctgtctgga gcacc 45

<210> SEQ ID NO 122
<211> LENGTH: 45
<212> TYPE: DNA
<213> ORGANISM: Artificial Sequence
<220> FEATURE:
<223> OTHER INFORMATION: Synthetic DNA

<400> SEQUENCE: 122
gtattggatc cttagcctgc gaggaagaaa cgaaaggcgg ggttg 45

<210> SEQ ID NO 123
<211> LENGTH: 1512
<212> TYPE: DNA
<213> ORGANISM: Artificial Sequence
<220> FEATURE:
<223> OTHER INFORMATION: Synthetic DNA

<400> SEQUENCE: 123
atggatgtgc gttgcatcaa ttggtttgaa tcgcatggtg aaaacaggtt tttatatctg 60
aaaagccgct gtcgtaatgg ggaaactgtg ttcattcgct tccctcacta cttttactat 120
gtggtgaccg atgagatcta ccagagctta gcccccccac ctttcaacgc tcgtcctatg 180
ggtaaaatgc ggaccattga catcgatgag accatctcgt acaacctgga catcaaggat 240

-continued

```
cgtaaatgct ctgtggcgga catgtggtta attgaagagc cgaaaaagcg caacattcag    300

aatgccacca tggatgagtt tctgaatatt tcttggttct acatcagcaa cggcatttct    360

ccggatggat gctacagctt ggacgatcag tatctcacga aatcaacaa cgggtgctat    420

cattgtggcg accctcgtaa ctgttttgcg aaagagatcc cccgttttga cattccgaga    480

agctatctgt tcctggacat tgaatgccat ttcgataaga agttcccgag cgtttttatt    540

aatccgatca gccatacctc ctattgttat attgatctga gcggcaaacg tctgctgttt    600

accctgatca acgaggagat gctgaccgaa caagaaatcc aggaggccgt ggatcgtggc    660

tgtctgcgca ttcagtcctt gatggagatg gattatgaac gtgaactggt gctgtgctct    720

gaaattgtgc tgctccaaat cgccaaacag ttattagagc tgacctttga ttacatcgtg    780

acgttcaacg gccacaactt cgatctgcgg tatattacca atcgtctcga gctgttgacc    840

ggcgaaaaaa tcatctttcg tagccccgac aagaaagaag cggttcacct gtgcatctat    900

gagcgtaatc agtcgagcca caaaggggtt ggagggatgg cgaatacgac cttccacgtc    960

aataataata atggcaccat ttttttcgac ctgtattctt tcatccagaa atcggagaag   1020

cttgattctt acaaactgga cagcatcagc aaaaacgcct tttcgtgcat gggcaaagtg   1080

ctgaatcgtg gtgtgcgtga gatgaccttt atcggtgatg ataccactga tgcgaaaggg   1140

aaagcggctg tgtttgcgaa ggtcctcacc acaggcaatt acgtgacggt cgatgatatc   1200

atttgtaaag tgattcacaa ggacatctgg gaaaatggct ttaaggtggt gttgagctgt   1260

ccgactctga ccaacgacac gtacaaactc tcctttggta aagatgatgt cgacctggcg   1320

cagatgtata aagactataa cctgaacatc gcccttgata tggcccgcta ttgcatccac   1380

gacgcctgtc tgtgccaata cctgtgggag tactatggtg tagagacgaa aacggatgcg   1440

ggtgcctcta cctatgtgtt gcctcagtcc atggtgtttg agtataaagc gagcacggtg   1500

attaaggggc cc                                                       1512
```

<210> SEQ ID NO 124
<211> LENGTH: 1509
<212> TYPE: DNA
<213> ORGANISM: Artificial Sequence
<220> FEATURE:
<223> OTHER INFORMATION: Synthetic DNA

<400> SEQUENCE: 124

```
gggcccctgc tgaaattgct gctggaaacc aagaccatct tagtgcgctc tgaaaccaaa     60

caaaagttcc cctatgaagg cggtaaagtt tttgccccga agcagaagat gtttagtaac    120

aacgtcctga tctttgacta caactctctg tatcccaacg tgtgcatctt tggcaactta    180

agtccggaaa ccctggttgg cgtggtggtg tcttcgaacc gcttggaaga agagattaac    240

aaccagctgc tcctgcaaaa gtacccgccg ccacgttaca ttacggtgca ctgcgaacca    300

cgtttaccca acctgatcag cgagattgcc atttttgatc ggagcattga aggcaccatt    360

ccgcgtttac tgagaacctt tctggccgag cgtgcgcgtt ataagaaaat gctgaaacag    420

gcgaccagtt ctacggaaaa agccatctac gacagtatgc agtacaccta caagatcatc    480

gcgaatagtg tgtatggctt gatgggtttt cgcaactctg ccttgtatag ctatgccagc    540

gctaagagtt gtaccagtat tggccgtcgt atgatcctgt atctggaatc tgtactcaat    600

ggagcggaac tgagtaatgg catgcttcgt tttgcaaacc cgttaagtaa tccgttctac    660

atggatgatc gcgacattaa cccgattgtg aagacgtccc tgccgattga ctaccgtttt    720

cgcttcagga gtgtctatgg tgataccgac tccgtgttta ccgaaattga cagccaggat    780
```

-continued

```
gttgacaaaa gtattgagat agcgaaggag ctggaacgtc tgatcaactc tcgtgtgctg    840
ttcaacaact ttaagatcga gtttgaggcc gtgtataaaa acctgatcat gcagagcaag    900
aaaaaatata ccacgatgaa gtatagcgcg agttctaact ccaaaagtgt gccggagcgt    960
attaacaagg ggactagcga aacccgtcgt gatgtcagca agttccacaa aaacatgatt   1020
aaaatttaca agacccgttt gagcgaaatg ttaagtgaag gccggatgaa cagcaaccag   1080
gtgtgtatcg acattctgcg ttcccttgaa acggatcttc gtagcgagtt cgacagccga   1140
tctagcccgt tggaactgtt catgttaagc cgcatgcacc acttgaacta taaaagcgcc   1200
gataacccga acatgtacct ggtgaccgag tacaacaaaa acaacccgga aactattgaa   1260
cttggcgaac gctactactt tgcctatatc tgtccggcga atgttccgtg gaccaaaaaa   1320
ctcgtgaaca tcaagacgta cgaaaccatt attgaccgtt ccttcaagct gggctcagat   1380
cagcgcattt tttacgaggt gtattttaaa cgtctgacct ccgaaatcgt gaacctgtta   1440
gataacaagg tgctgtgcat ttcttttttt gaacgcatgt ttggcagcag accgaccttc   1500
tatgaggcg                                                          1509
```

<210> SEQ ID NO 125
<211> LENGTH: 30
<212> TYPE: DNA
<213> ORGANISM: Artificial Sequence
<220> FEATURE:
<223> OTHER INFORMATION: Synthetic DNA

<400> SEQUENCE: 125

```
tcctcgagca taatggatgt gcgttgcatc                                     30
```

<210> SEQ ID NO 126
<211> LENGTH: 48
<212> TYPE: DNA
<213> ORGANISM: Artificial Sequence
<220> FEATURE:
<223> OTHER INFORMATION: Synthetic DNA

<400> SEQUENCE: 126

```
gacgacgacg acaagcatat gctcgaggat atggatgtgc gttgcatc                 48
```

<210> SEQ ID NO 127
<211> LENGTH: 48
<212> TYPE: DNA
<213> ORGANISM: Artificial Sequence
<220> FEATURE:
<223> OTHER INFORMATION: Synthetic DNA

<400> SEQUENCE: 127

```
atggatgtgc gttgcatcaa ttggtttgaa tcgcatggtg aaaacagg                 48
```

<210> SEQ ID NO 128
<211> LENGTH: 50
<212> TYPE: DNA
<213> ORGANISM: Artificial Sequence
<220> FEATURE:
<223> OTHER INFORMATION: Synthetic DNA

<400> SEQUENCE: 128

```
cgcatggtga aaacaggttt ttatatctga aaagccgctg tcgtaatggg               50
```

<210> SEQ ID NO 129
<211> LENGTH: 47
<212> TYPE: DNA

-continued

<213> ORGANISM: Artificial Sequence
<220> FEATURE:
<223> OTHER INFORMATION: Synthetic DNA

<400> SEQUENCE: 129
gccgctgtcg taatggggaa actgtgttca ttcgcttccc tcactac 47

<210> SEQ ID NO 130
<211> LENGTH: 50
<212> TYPE: DNA
<213> ORGANISM: Artificial Sequence
<220> FEATURE:
<223> OTHER INFORMATION: Synthetic DNA

<400> SEQUENCE: 130
cattcgcttc cctcactact tttactatgt ggtgaccgat gagatctacc 50

<210> SEQ ID NO 131
<211> LENGTH: 50
<212> TYPE: DNA
<213> ORGANISM: Artificial Sequence
<220> FEATURE:
<223> OTHER INFORMATION: Synthetic DNA

<400> SEQUENCE: 131
ggtgaccgat gagatctacc agagcttagc ccccccacct ttcaacgctc 50

<210> SEQ ID NO 132
<211> LENGTH: 50
<212> TYPE: DNA
<213> ORGANISM: Artificial Sequence
<220> FEATURE:
<223> OTHER INFORMATION: Synthetic DNA

<400> SEQUENCE: 132
cccacctttc aacgctcgtc ctatgggtaa aatgcggacc attgacatcg 50

<210> SEQ ID NO 133
<211> LENGTH: 50
<212> TYPE: DNA
<213> ORGANISM: Artificial Sequence
<220> FEATURE:
<223> OTHER INFORMATION: Synthetic DNA

<400> SEQUENCE: 133
gcggaccatt gacatcgatg agaccatctc gtacaacctg gacatcaagg 50

<210> SEQ ID NO 134
<211> LENGTH: 49
<212> TYPE: DNA
<213> ORGANISM: Artificial Sequence
<220> FEATURE:
<223> OTHER INFORMATION: Synthetic DNA

<400> SEQUENCE: 134
cgtacaacct ggacatcaag gatcgtaaat gctctgtggc ggacatgtg 49

<210> SEQ ID NO 135
<211> LENGTH: 46
<212> TYPE: DNA
<213> ORGANISM: Artificial Sequence
<220> FEATURE:
<223> OTHER INFORMATION: Synthetic DNA

<400> SEQUENCE: 135
ctctgtggcg gacatgtggt taattgaaga gccgaaaaag cgcaac 46

-continued

<210> SEQ ID NO 136
<211> LENGTH: 48
<212> TYPE: DNA
<213> ORGANISM: Artificial Sequence
<220> FEATURE:
<223> OTHER INFORMATION: Synthetic DNA

<400> SEQUENCE: 136
gagccgaaaa agcgcaacat tcagaatgcc accatggatg agtttctg 48

<210> SEQ ID NO 137
<211> LENGTH: 50
<212> TYPE: DNA
<213> ORGANISM: Artificial Sequence
<220> FEATURE:
<223> OTHER INFORMATION: Synthetic DNA

<400> SEQUENCE: 137
ccaccatgga tgagtttctg aatatttctt ggttctacat cagcaacggc 50

<210> SEQ ID NO 138
<211> LENGTH: 50
<212> TYPE: DNA
<213> ORGANISM: Artificial Sequence
<220> FEATURE:
<223> OTHER INFORMATION: Synthetic DNA

<400> SEQUENCE: 138
ggttctacat cagcaacggc atttctccgg atggatgcta cagcttggac 50

<210> SEQ ID NO 139
<211> LENGTH: 50
<212> TYPE: DNA
<213> ORGANISM: Artificial Sequence
<220> FEATURE:
<223> OTHER INFORMATION: Synthetic DNA

<400> SEQUENCE: 139
ggttctacat cagcaacggc atttctccgg atggatgcta cagcttggac 50

<210> SEQ ID NO 140
<211> LENGTH: 50
<212> TYPE: DNA
<213> ORGANISM: Artificial Sequence
<220> FEATURE:
<223> OTHER INFORMATION: Synthetic DNA

<400> SEQUENCE: 140
ggatgctaca gcttggacga tcagtatctc acgaaaatca acaacgggtg 50

<210> SEQ ID NO 141
<211> LENGTH: 48
<212> TYPE: DNA
<213> ORGANISM: Artificial Sequence
<220> FEATURE:
<223> OTHER INFORMATION: Synthetic DNA

<400> SEQUENCE: 141
cacgaaaatc aacaacgggt gctatcattg tggcgaccct cgtaactg 48

<210> SEQ ID NO 142
<211> LENGTH: 45
<212> TYPE: DNA
<213> ORGANISM: Artificial Sequence
<220> FEATURE:

-continued

<223> OTHER INFORMATION: Synthetic DNA

<400> SEQUENCE: 142
ggcgaccctc gtaactgttt tgcgaaagag atccccgtt ttgac 45

<210> SEQ ID NO 143
<211> LENGTH: 49
<212> TYPE: DNA
<213> ORGANISM: Artificial Sequence
<220> FEATURE:
<223> OTHER INFORMATION: Synthetic DNA

<400> SEQUENCE: 143
gagatccccc gttttgacat tccgagaagc tatctgttcc tggacattg 49

<210> SEQ ID NO 144
<211> LENGTH: 50
<212> TYPE: DNA
<213> ORGANISM: Artificial Sequence
<220> FEATURE:
<223> OTHER INFORMATION: Synthetic DNA

<400> SEQUENCE: 144
gctatctgtt cctggacatt gaatgccatt tcgataagaa gttcccgagc 50

<210> SEQ ID NO 145
<211> LENGTH: 49
<212> TYPE: DNA
<213> ORGANISM: Artificial Sequence
<220> FEATURE:
<223> OTHER INFORMATION: Synthetic DNA

<400> SEQUENCE: 145
cgataagaag ttcccgagcg tttttattaa tccgatcagc catacctcc 49

<210> SEQ ID NO 146
<211> LENGTH: 50
<212> TYPE: DNA
<213> ORGANISM: Artificial Sequence
<220> FEATURE:
<223> OTHER INFORMATION: Synthetic DNA

<400> SEQUENCE: 146
cgatcagcca tacctcctat tgttatattg atctgagcgg caaacgtctg 50

<210> SEQ ID NO 147
<211> LENGTH: 50
<212> TYPE: DNA
<213> ORGANISM: Artificial Sequence
<220> FEATURE:
<223> OTHER INFORMATION: Synthetic DNA

<400> SEQUENCE: 147
ctgagcggca aacgtctgct gtttaccctg atcaacgagg agatgctgac 50

<210> SEQ ID NO 148
<211> LENGTH: 50
<212> TYPE: DNA
<213> ORGANISM: Artificial Sequence
<220> FEATURE:
<223> OTHER INFORMATION: Synthetic DNA

<400> SEQUENCE: 148
gatcaacgag gagatgctga ccgaacaaga aatccaggag gccgtggatc 50

-continued

<210> SEQ ID NO 149
<211> LENGTH: 49
<212> TYPE: DNA
<213> ORGANISM: Artificial Sequence
<220> FEATURE:
<223> OTHER INFORMATION: Synthetic DNA

<400> SEQUENCE: 149
ccaggaggcc gtggatcgtg gctgtctgcg cattcagtcc ttgatggag 49

<210> SEQ ID NO 150
<211> LENGTH: 50
<212> TYPE: DNA
<213> ORGANISM: Artificial Sequence
<220> FEATURE:
<223> OTHER INFORMATION: Synthetic DNA

<400> SEQUENCE: 150
gcattcagtc cttgatggag atggattatg aacgtgaact ggtgctgtgc 50

<210> SEQ ID NO 151
<211> LENGTH: 50
<212> TYPE: DNA
<213> ORGANISM: Artificial Sequence
<220> FEATURE:
<223> OTHER INFORMATION: Synthetic DNA

<400> SEQUENCE: 151
gcattcagtc cttgatggag atggattatg aacgtgaact ggtgctgtgc 50

<210> SEQ ID NO 152
<211> LENGTH: 48
<212> TYPE: DNA
<213> ORGANISM: Artificial Sequence
<220> FEATURE:
<223> OTHER INFORMATION: Synthetic DNA

<400> SEQUENCE: 152
gtgaactggt gctgtgctct gaaattgtgc tgctccaaat cgccaaac 48

<210> SEQ ID NO 153
<211> LENGTH: 49
<212> TYPE: DNA
<213> ORGANISM: Artificial Sequence
<220> FEATURE:
<223> OTHER INFORMATION: Synthetic DNA

<400> SEQUENCE: 153
gctccaaatc gccaaacagt tattagagct gacctttgat tacatcgtg 49

<210> SEQ ID NO 154
<211> LENGTH: 50
<212> TYPE: DNA
<213> ORGANISM: Artificial Sequence
<220> FEATURE:
<223> OTHER INFORMATION: Synthetic DNA

<400> SEQUENCE: 154
gctgaccttt gattacatcg tgacgttcaa cggccacaac ttcgatctgc 50

<210> SEQ ID NO 155
<211> LENGTH: 50
<212> TYPE: DNA
<213> ORGANISM: Artificial Sequence
<220> FEATURE:
<223> OTHER INFORMATION: Synthetic DNA

<400> SEQUENCE: 155
gccacaactt cgatctgcgg tatattacca atcgtctcga gctgttgacc 50

<210> SEQ ID NO 156
<211> LENGTH: 50
<212> TYPE: DNA
<213> ORGANISM: Artificial Sequence
<220> FEATURE:
<223> OTHER INFORMATION: Synthetic DNA

<400> SEQUENCE: 156
gtctcgagct gttgaccggc gaaaaaatca tctttcgtag ccccgacaag 50

<210> SEQ ID NO 157
<211> LENGTH: 50
<212> TYPE: DNA
<213> ORGANISM: Artificial Sequence
<220> FEATURE:
<223> OTHER INFORMATION: Synthetic DNA

<400> SEQUENCE: 157
ctttcgtagc cccgacaaga aagaagcggt tcacctgtgc atctatgagc 50

<210> SEQ ID NO 158
<211> LENGTH: 46
<212> TYPE: DNA
<213> ORGANISM: Artificial Sequence
<220> FEATURE:
<223> OTHER INFORMATION: Synthetic DNA

<400> SEQUENCE: 158
cacctgtgca tctatgagcg taatcagtcg agccacaaag gggttg 46

<210> SEQ ID NO 159
<211> LENGTH: 46
<212> TYPE: DNA
<213> ORGANISM: Artificial Sequence
<220> FEATURE:
<223> OTHER INFORMATION: Synthetic DNA

<400> SEQUENCE: 159
gagccacaaa ggggttggag ggatggcgaa tacgaccttc cacgtc 46

<210> SEQ ID NO 160
<211> LENGTH: 50
<212> TYPE: DNA
<213> ORGANISM: Artificial Sequence
<220> FEATURE:
<223> OTHER INFORMATION: Synthetic DNA

<400> SEQUENCE: 160
gaatacgacc ttccacgtca ataataataa tggcaccatt tttttcgacc 50

<210> SEQ ID NO 161
<211> LENGTH: 50
<212> TYPE: DNA
<213> ORGANISM: Artificial Sequence
<220> FEATURE:
<223> OTHER INFORMATION: Synthetic DNA

<400> SEQUENCE: 161
gaatacgacc ttccacgtca ataataataa tggcaccatt tttttcgacc 50

<210> SEQ ID NO 162
<211> LENGTH: 49

-continued

<212> TYPE: DNA
<213> ORGANISM: Artificial Sequence
<220> FEATURE:
<223> OTHER INFORMATION: Synthetic DNA

<400> SEQUENCE: 162
ggcaccattt ttttcgacct gtattctttc atccagaaat cggagaagc 49

<210> SEQ ID NO 163
<211> LENGTH: 49
<212> TYPE: DNA
<213> ORGANISM: Artificial Sequence
<220> FEATURE:
<223> OTHER INFORMATION: Synthetic DNA

<400> SEQUENCE: 163
catccagaaa tcggagaagc ttgattctta caaactggac agcatcagc 49

<210> SEQ ID NO 164
<211> LENGTH: 50
<212> TYPE: DNA
<213> ORGANISM: Artificial Sequence
<220> FEATURE:
<223> OTHER INFORMATION: Synthetic DNA

<400> SEQUENCE: 164
caaactggac agcatcagca aaaacgcctt ttcgtgcatg ggcaaagtgc 50

<210> SEQ ID NO 165
<211> LENGTH: 49
<212> TYPE: DNA
<213> ORGANISM: Artificial Sequence
<220> FEATURE:
<223> OTHER INFORMATION: Synthetic DNA

<400> SEQUENCE: 165
gtgcatgggc aaagtgctga atcgtggtgt gcgtgagatg acctttatc 49

<210> SEQ ID NO 166
<211> LENGTH: 48
<212> TYPE: DNA
<213> ORGANISM: Artificial Sequence
<220> FEATURE:
<223> OTHER INFORMATION: Synthetic DNA

<400> SEQUENCE: 166
gtgcgtgaga tgacctttat cggtgatgat accactgatg cgaaaggg 48

<210> SEQ ID NO 167
<211> LENGTH: 47
<212> TYPE: DNA
<213> ORGANISM: Artificial Sequence
<220> FEATURE:
<223> OTHER INFORMATION: Synthetic DNA

<400> SEQUENCE: 167
ccactgatgc gaaagggaaa gcggctgtgt ttgcgaaggt cctcacc 47

<210> SEQ ID NO 168
<211> LENGTH: 49
<212> TYPE: DNA
<213> ORGANISM: Artificial Sequence
<220> FEATURE:
<223> OTHER INFORMATION: Synthetic DNA

<400> SEQUENCE: 168

-continued gtttgcgaag gtcctcacca caggcaatta cgtgacggtc gatgatatc 49

<210> SEQ ID NO 169
<211> LENGTH: 50
<212> TYPE: DNA
<213> ORGANISM: Artificial Sequence
<220> FEATURE:
<223> OTHER INFORMATION: Synthetic DNA

<400> SEQUENCE: 169
cgtgacggtc gatgatatca tttgtaaagt gattcacaag gacatctggg 50

<210> SEQ ID NO 170
<211> LENGTH: 50
<212> TYPE: DNA
<213> ORGANISM: Artificial Sequence
<220> FEATURE:
<223> OTHER INFORMATION: Synthetic DNA

<400> SEQUENCE: 170
gattcacaag gacatctggg aaaatggctt taaggtggtg ttgagctgtc 50

<210> SEQ ID NO 171
<211> LENGTH: 50
<212> TYPE: DNA
<213> ORGANISM: Artificial Sequence
<220> FEATURE:
<223> OTHER INFORMATION: Synthetic DNA

<400> SEQUENCE: 171
gattcacaag gacatctggg aaaatggctt taaggtggtg ttgagctgtc 50

<210> SEQ ID NO 172
<211> LENGTH: 49
<212> TYPE: DNA
<213> ORGANISM: Artificial Sequence
<220> FEATURE:
<223> OTHER INFORMATION: Synthetic DNA

<400> SEQUENCE: 172
ggtggtgttg agctgtccga ctctgaccaa cgacacgtac aaactctcc 49

<210> SEQ ID NO 173
<211> LENGTH: 49
<212> TYPE: DNA
<213> ORGANISM: Artificial Sequence
<220> FEATURE:
<223> OTHER INFORMATION: Synthetic DNA

<400> SEQUENCE: 173
cgacacgtac aaactctcct ttggtaaaga tgatgtcgac ctggcgcag 49

<210> SEQ ID NO 174
<211> LENGTH: 49
<212> TYPE: DNA
<213> ORGANISM: Artificial Sequence
<220> FEATURE:
<223> OTHER INFORMATION: Synthetic DNA

<400> SEQUENCE: 174
gatgtcgacc tggcgcagat gtataaagac tataacctga acatcgccc 49

<210> SEQ ID NO 175
<211> LENGTH: 47
<212> TYPE: DNA
<213> ORGANISM: Artificial Sequence -continued
<220> FEATURE:
<223> OTHER INFORMATION: Synthetic DNA

<400> SEQUENCE: 175
ctataacctg aacatcgccc ttgatatggc ccgctattgc atccacg 47

<210> SEQ ID NO 176
<211> LENGTH: 49
<212> TYPE: DNA
<213> ORGANISM: Artificial Sequence
<220> FEATURE:
<223> OTHER INFORMATION: Synthetic DNA

<400> SEQUENCE: 176
ccgctattgc atccacgacg cctgtctgtg ccaatacctg tgggagtac 49

<210> SEQ ID NO 177
<211> LENGTH: 50
<212> TYPE: DNA
<213> ORGANISM: Artificial Sequence
<220> FEATURE:
<223> OTHER INFORMATION: Synthetic DNA

<400> SEQUENCE: 177
gtgccaatac ctgtgggagt actatggtgt agagacgaaa acggatgcgg 50

<210> SEQ ID NO 178
<211> LENGTH: 46
<212> TYPE: DNA
<213> ORGANISM: Artificial Sequence
<220> FEATURE:
<223> OTHER INFORMATION: Synthetic DNA

<400> SEQUENCE: 178
gacgaaaacg gatgcgggtg cctctaccta tgtgttgcct cagtcc 46

<210> SEQ ID NO 179
<211> LENGTH: 49
<212> TYPE: DNA
<213> ORGANISM: Artificial Sequence
<220> FEATURE:
<223> OTHER INFORMATION: Synthetic DNA

<400> SEQUENCE: 179
ctatgtgttg cctcagtcca tggtgtttga gtataaagcg agcacggtg 49

<210> SEQ ID NO 180
<211> LENGTH: 31
<212> TYPE: DNA
<213> ORGANISM: Artificial Sequence
<220> FEATURE:
<223> OTHER INFORMATION: Synthetic DNA

<400> SEQUENCE: 180
gtataaagcg agcacggtga ttaaggggcc c 31

<210> SEQ ID NO 181
<211> LENGTH: 29
<212> TYPE: DNA
<213> ORGANISM: Artificial Sequence
<220> FEATURE:
<223> OTHER INFORMATION: Synthetic DNA

<400> SEQUENCE: 181
cggtgattaa ggggccctat ggctgccgc 29

-continued

<210> SEQ ID NO 182
<211> LENGTH: 47
<212> TYPE: DNA
<213> ORGANISM: Artificial Sequence
<220> FEATURE:
<223> OTHER INFORMATION: Synthetic DNA

<400> SEQUENCE: 182
cggtgattaa ggggccctac ccatacgatg ttccggatta cgcttaa 47

<210> SEQ ID NO 183
<211> LENGTH: 30
<212> TYPE: DNA
<213> ORGANISM: Artificial Sequence
<220> FEATURE:
<223> OTHER INFORMATION: Synthetic DNA

<400> SEQUENCE: 183
tcctcgagca tagggcccct gctgaaattg 30

<210> SEQ ID NO 184
<211> LENGTH: 48
<212> TYPE: DNA
<213> ORGANISM: Artificial Sequence
<220> FEATURE:
<223> OTHER INFORMATION: Synthetic DNA

<400> SEQUENCE: 184
gacgacgacg acaagcatat gctcgaggat gggcccctgc tgaaattg 48

<210> SEQ ID NO 185
<211> LENGTH: 50
<212> TYPE: DNA
<213> ORGANISM: Artificial Sequence
<220> FEATURE:
<223> OTHER INFORMATION: Synthetic DNA

<400> SEQUENCE: 185
gggcccctgc tgaaattgct gctggaaacc aagaccatct tagtgcgctc 50

<210> SEQ ID NO 186
<211> LENGTH: 50
<212> TYPE: DNA
<213> ORGANISM: Artificial Sequence
<220> FEATURE:
<223> OTHER INFORMATION: Synthetic DNA

<400> SEQUENCE: 186
gaccatctta gtgcgctctg aaaccaaaca aaagttcccc tatgaaggcg 50

<210> SEQ ID NO 187
<211> LENGTH: 46
<212> TYPE: DNA
<213> ORGANISM: Artificial Sequence
<220> FEATURE:
<223> OTHER INFORMATION: Synthetic DNA

<400> SEQUENCE: 187
gttcccctat gaaggcggta aagtttttgc cccgaagcag aagatg 46

<210> SEQ ID NO 188
<211> LENGTH: 50
<212> TYPE: DNA
<213> ORGANISM: Artificial Sequence
<220> FEATURE:
<223> OTHER INFORMATION: Synthetic DNA -continued

<400> SEQUENCE: 188
ccccgaagca gaagatgttt agtaacaacg tcctgatctt tgactacaac 50

<210> SEQ ID NO 189
<211> LENGTH: 50
<212> TYPE: DNA
<213> ORGANISM: Artificial Sequence
<220> FEATURE:
<223> OTHER INFORMATION: Synthetic DNA

<400> SEQUENCE: 189
cgtcctgatc tttgactaca actctctgta tcccaacgtg tgcatctttg 50

<210> SEQ ID NO 190
<211> LENGTH: 50
<212> TYPE: DNA
<213> ORGANISM: Artificial Sequence
<220> FEATURE:
<223> OTHER INFORMATION: Synthetic DNA

<400> SEQUENCE: 190
ccaacgtgtg catctttggc aacttaagtc cggaaaccct ggttggcgtg 50

<210> SEQ ID NO 191
<211> LENGTH: 48
<212> TYPE: DNA
<213> ORGANISM: Artificial Sequence
<220> FEATURE:
<223> OTHER INFORMATION: Synthetic DNA

<400> SEQUENCE: 191
gaaaccctgg ttggcgtggt ggtgtcttcg aaccgcttgg aagaagag 48

<210> SEQ ID NO 192
<211> LENGTH: 50
<212> TYPE: DNA
<213> ORGANISM: Artificial Sequence
<220> FEATURE:
<223> OTHER INFORMATION: Synthetic DNA

<400> SEQUENCE: 192
gaaccgcttg gaagaagaga ttaacaacca gctgctcctg caaaagtacc 50

<210> SEQ ID NO 193
<211> LENGTH: 49
<212> TYPE: DNA
<213> ORGANISM: Artificial Sequence
<220> FEATURE:
<223> OTHER INFORMATION: Synthetic DNA

<400> SEQUENCE: 193
ctgctcctgc aaaagtaccc gccgccacgt tacattacgg tgcactgcg 49

<210> SEQ ID NO 194
<211> LENGTH: 50
<212> TYPE: DNA
<213> ORGANISM: Artificial Sequence
<220> FEATURE:
<223> OTHER INFORMATION: Synthetic DNA

<400> SEQUENCE: 194
cattacggtg cactgcgaac cacgtttacc caacctgatc agcgagattg 50

<210> SEQ ID NO 195

-continued

<211> LENGTH: 49
<212> TYPE: DNA
<213> ORGANISM: Artificial Sequence
<220> FEATURE:
<223> OTHER INFORMATION: Synthetic DNA

<400> SEQUENCE: 195
caacctgatc agcgagattg ccatttttga tcggagcatt gaaggcacc 49

<210> SEQ ID NO 196
<211> LENGTH: 50
<212> TYPE: DNA
<213> ORGANISM: Artificial Sequence
<220> FEATURE:
<223> OTHER INFORMATION: Synthetic DNA

<400> SEQUENCE: 196
ggagcattga aggcaccatt ccgcgtttac tgagaacctt tctggccgag 50

<210> SEQ ID NO 197
<211> LENGTH: 50
<212> TYPE: DNA
<213> ORGANISM: Artificial Sequence
<220> FEATURE:
<223> OTHER INFORMATION: Synthetic DNA

<400> SEQUENCE: 197
ggagcattga aggcaccatt ccgcgtttac tgagaacctt tctggccgag 50

<210> SEQ ID NO 198
<211> LENGTH: 50
<212> TYPE: DNA
<213> ORGANISM: Artificial Sequence
<220> FEATURE:
<223> OTHER INFORMATION: Synthetic DNA

<400> SEQUENCE: 198
gaacctttct ggccgagcgt gcgcgttata agaaaatgct gaaacaggcg 50

<210> SEQ ID NO 199
<211> LENGTH: 49
<212> TYPE: DNA
<213> ORGANISM: Artificial Sequence
<220> FEATURE:
<223> OTHER INFORMATION: Synthetic DNA

<400> SEQUENCE: 199
gaaaatgctg aaacaggcga ccagttctac ggaaaaagcc atctacgac 49

<210> SEQ ID NO 200
<211> LENGTH: 50
<212> TYPE: DNA
<213> ORGANISM: Artificial Sequence
<220> FEATURE:
<223> OTHER INFORMATION: Synthetic DNA

<400> SEQUENCE: 200
cggaaaaagc catctacgac agtatgcagt acacctacaa gatcatcgcg 50

<210> SEQ ID NO 201
<211> LENGTH: 49
<212> TYPE: DNA
<213> ORGANISM: Artificial Sequence
<220> FEATURE:
<223> OTHER INFORMATION: Synthetic DNA

<400> SEQUENCE: 201

-continued cacctacaag atcatcgcga atagtgtgta tggcttgatg ggttttcgc 49

<210> SEQ ID NO 202
<211> LENGTH: 50
<212> TYPE: DNA
<213> ORGANISM: Artificial Sequence
<220> FEATURE:
<223> OTHER INFORMATION: Synthetic DNA

<400> SEQUENCE: 202
gcttgatggg ttttcgcaac tctgccttgt atagctatgc cagcgctaag 50

<210> SEQ ID NO 203
<211> LENGTH: 50
<212> TYPE: DNA
<213> ORGANISM: Artificial Sequence
<220> FEATURE:
<223> OTHER INFORMATION: Synthetic DNA

<400> SEQUENCE: 203
gctatgccag cgctaagagt tgtaccagta ttggccgtcg tatgatcctg 50

<210> SEQ ID NO 204
<211> LENGTH: 50
<212> TYPE: DNA
<213> ORGANISM: Artificial Sequence
<220> FEATURE:
<223> OTHER INFORMATION: Synthetic DNA

<400> SEQUENCE: 204
gccgtcgtat gatcctgtat ctggaatctg tactcaatgg agcggaactg 50

<210> SEQ ID NO 205
<211> LENGTH: 48
<212> TYPE: DNA
<213> ORGANISM: Artificial Sequence
<220> FEATURE:
<223> OTHER INFORMATION: Synthetic DNA

<400> SEQUENCE: 205
ctcaatggag cggaactgag taatggcatg cttcgttttg caaacccg 48

<210> SEQ ID NO 206
<211> LENGTH: 48
<212> TYPE: DNA
<213> ORGANISM: Artificial Sequence
<220> FEATURE:
<223> OTHER INFORMATION: Synthetic DNA

<400> SEQUENCE: 206
cttcgttttg caaacccgtt aagtaatccg ttctacatgg atgatcgc 48

<210> SEQ ID NO 207
<211> LENGTH: 48
<212> TYPE: DNA
<213> ORGANISM: Artificial Sequence
<220> FEATURE:
<223> OTHER INFORMATION: Synthetic DNA

<400> SEQUENCE: 207
cgttctacat ggatgatcgc gacattaacc cgattgtgaa gacgtccc 48

<210> SEQ ID NO 208
<211> LENGTH: 47
<212> TYPE: DNA

-continued

<213> ORGANISM: Artificial Sequence
<220> FEATURE:
<223> OTHER INFORMATION: Synthetic DNA

<400> SEQUENCE: 208
cgattgtgaa gacgtccctg ccgattgact accgttttcg cttcagg 47

<210> SEQ ID NO 209
<211> LENGTH: 47
<212> TYPE: DNA
<213> ORGANISM: Artificial Sequence
<220> FEATURE:
<223> OTHER INFORMATION: Synthetic DNA

<400> SEQUENCE: 209
cgattgtgaa gacgtccctg ccgattgact accgttttcg cttcagg 47

<210> SEQ ID NO 210
<211> LENGTH: 46
<212> TYPE: DNA
<213> ORGANISM: Artificial Sequence
<220> FEATURE:
<223> OTHER INFORMATION: Synthetic DNA

<400> SEQUENCE: 210
ctaccgtttt cgcttcagga gtgtctatgg tgataccgac tccgtg 46

<210> SEQ ID NO 211
<211> LENGTH: 47
<212> TYPE: DNA
<213> ORGANISM: Artificial Sequence
<220> FEATURE:
<223> OTHER INFORMATION: Synthetic DNA

<400> SEQUENCE: 211
gtgataccga ctccgtgttt accgaaattg acagccagga tgttgac 47

<210> SEQ ID NO 212
<211> LENGTH: 46
<212> TYPE: DNA
<213> ORGANISM: Artificial Sequence
<220> FEATURE:
<223> OTHER INFORMATION: Synthetic DNA

<400> SEQUENCE: 212
gacagccagg atgttgacaa aagtattgag atagcgaagg agctgg 46

<210> SEQ ID NO 213
<211> LENGTH: 46
<212> TYPE: DNA
<213> ORGANISM: Artificial Sequence
<220> FEATURE:
<223> OTHER INFORMATION: Synthetic DNA

<400> SEQUENCE: 213
gatagcgaag gagctggaac gtctgatcaa ctctcgtgtg ctgttc 46

<210> SEQ ID NO 214
<211> LENGTH: 47
<212> TYPE: DNA
<213> ORGANISM: Artificial Sequence
<220> FEATURE:
<223> OTHER INFORMATION: Synthetic DNA

<400> SEQUENCE: 214
caactctcgt gtgctgttca acaactttaa gatcgagttt gaggccg 47

-continued

<210> SEQ ID NO 215
<211> LENGTH: 46
<212> TYPE: DNA
<213> ORGANISM: Artificial Sequence
<220> FEATURE:
<223> OTHER INFORMATION: Synthetic DNA

<400> SEQUENCE: 215
gatcgagttt gaggccgtgt ataaaaacct gatcatgcag agcaag 46

<210> SEQ ID NO 216
<211> LENGTH: 49
<212> TYPE: DNA
<213> ORGANISM: Artificial Sequence
<220> FEATURE:
<223> OTHER INFORMATION: Synthetic DNA

<400> SEQUENCE: 216
cctgatcatg cagagcaaga aaaaatatac cacgatgaag tatagcgcg 49

<210> SEQ ID NO 217
<211> LENGTH: 47
<212> TYPE: DNA
<213> ORGANISM: Artificial Sequence
<220> FEATURE:
<223> OTHER INFORMATION: Synthetic DNA

<400> SEQUENCE: 217
cacgatgaag tatagcgcga gttctaactc caaaagtgtg ccggagc 47

<210> SEQ ID NO 218
<211> LENGTH: 44
<212> TYPE: DNA
<213> ORGANISM: Artificial Sequence
<220> FEATURE:
<223> OTHER INFORMATION: Synthetic DNA

<400> SEQUENCE: 218
caaaagtgtg ccggagcgta ttaacaaggg gactagcgaa accc 44

<210> SEQ ID NO 219
<211> LENGTH: 44
<212> TYPE: DNA
<213> ORGANISM: Artificial Sequence
<220> FEATURE:
<223> OTHER INFORMATION: Synthetic DNA

<400> SEQUENCE: 219
caaaagtgtg ccggagcgta ttaacaaggg gactagcgaa accc 44

<210> SEQ ID NO 220
<211> LENGTH: 49
<212> TYPE: DNA
<213> ORGANISM: Artificial Sequence
<220> FEATURE:
<223> OTHER INFORMATION: Synthetic DNA

<400> SEQUENCE: 220
ggggactagc gaaacccgtc gtgatgtcag caagttccac aaaaacatg 49

<210> SEQ ID NO 221
<211> LENGTH: 50
<212> TYPE: DNA
<213> ORGANISM: Artificial Sequence
<220> FEATURE:

-continued

<223> OTHER INFORMATION: Synthetic DNA

<400> SEQUENCE: 221
cagcaagttc cacaaaaaca tgattaaaat ttacaagacc cgtttgagcg 50

<210> SEQ ID NO 222
<211> LENGTH: 50
<212> TYPE: DNA
<213> ORGANISM: Artificial Sequence
<220> FEATURE:
<223> OTHER INFORMATION: Synthetic DNA

<400> SEQUENCE: 222
caagacccgt ttgagcgaaa tgttaagtga aggccggatg aacagcaacc 50

<210> SEQ ID NO 223
<211> LENGTH: 44
<212> TYPE: DNA
<213> ORGANISM: Artificial Sequence
<220> FEATURE:
<223> OTHER INFORMATION: Synthetic DNA

<400> SEQUENCE: 223
ccggatgaac agcaaccagg tgtgtatcga cattctgcgt tccc 44

<210> SEQ ID NO 224
<211> LENGTH: 46
<212> TYPE: DNA
<213> ORGANISM: Artificial Sequence
<220> FEATURE:
<223> OTHER INFORMATION: Synthetic DNA

<400> SEQUENCE: 224
cgacattctg cgttcccttg aaacggatct tcgtagcgag ttcgac 46

<210> SEQ ID NO 225
<211> LENGTH: 45
<212> TYPE: DNA
<213> ORGANISM: Artificial Sequence
<220> FEATURE:
<223> OTHER INFORMATION: Synthetic DNA

<400> SEQUENCE: 225
cttcgtagcg agttcgacag ccgatctagc ccgttggaac tgttc 45

<210> SEQ ID NO 226
<211> LENGTH: 44
<212> TYPE: DNA
<213> ORGANISM: Artificial Sequence
<220> FEATURE:
<223> OTHER INFORMATION: Synthetic DNA

<400> SEQUENCE: 226
gcccgttgga actgttcatg ttaagccgca tgcaccactt gaac 44

<210> SEQ ID NO 227
<211> LENGTH: 48
<212> TYPE: DNA
<213> ORGANISM: Artificial Sequence
<220> FEATURE:
<223> OTHER INFORMATION: Synthetic DNA

<400> SEQUENCE: 227
gcatgcacca cttgaactat aaaagcgccg ataacccgaa catgtacc 48

-continued

<210> SEQ ID NO 228
<211> LENGTH: 50
<212> TYPE: DNA
<213> ORGANISM: Artificial Sequence
<220> FEATURE:
<223> OTHER INFORMATION: Synthetic DNA

<400> SEQUENCE: 228
cgataacccg aacatgtacc tggtgaccga gtacaacaaa aacaacccgg 50

<210> SEQ ID NO 229
<211> LENGTH: 50
<212> TYPE: DNA
<213> ORGANISM: Artificial Sequence
<220> FEATURE:
<223> OTHER INFORMATION: Synthetic DNA

<400> SEQUENCE: 229
cgataacccg aacatgtacc tggtgaccga gtacaacaaa aacaacccgg 50

<210> SEQ ID NO 230
<211> LENGTH: 49
<212> TYPE: DNA
<213> ORGANISM: Artificial Sequence
<220> FEATURE:
<223> OTHER INFORMATION: Synthetic DNA

<400> SEQUENCE: 230
gtacaacaaa aacaacccgg aaactattga acttggcgaa cgctactac 49

<210> SEQ ID NO 231
<211> LENGTH: 50
<212> TYPE: DNA
<213> ORGANISM: Artificial Sequence
<220> FEATURE:
<223> OTHER INFORMATION: Synthetic DNA

<400> SEQUENCE: 231
cttggcgaac gctactactt tgcctatatc tgtccggcga atgttccgtg 50

<210> SEQ ID NO 232
<211> LENGTH: 49
<212> TYPE: DNA
<213> ORGANISM: Artificial Sequence
<220> FEATURE:
<223> OTHER INFORMATION: Synthetic DNA

<400> SEQUENCE: 232
ccggcgaatg ttccgtggac caaaaaactc gtgaacatca agacgtacg 49

<210> SEQ ID NO 233
<211> LENGTH: 50
<212> TYPE: DNA
<213> ORGANISM: Artificial Sequence
<220> FEATURE:
<223> OTHER INFORMATION: Synthetic DNA

<400> SEQUENCE: 233
cgtgaacatc aagacgtacg aaaccattat tgaccgttcc ttcaagctgg 50

<210> SEQ ID NO 234
<211> LENGTH: 46
<212> TYPE: DNA
<213> ORGANISM: Artificial Sequence
<220> FEATURE:
<223> OTHER INFORMATION: Synthetic DNA -continued
<400> SEQUENCE: 234
ccgttccttc aagctgggct cagatcagcg cattttttac gaggtg 46

<210> SEQ ID NO 235
<211> LENGTH: 49
<212> TYPE: DNA
<213> ORGANISM: Artificial Sequence
<220> FEATURE:
<223> OTHER INFORMATION: Synthetic DNA
<400> SEQUENCE: 235
gcgcattttt tacgaggtgt attttaaacg tctgacctcc gaaatcgtg 49

<210> SEQ ID NO 236
<211> LENGTH: 50
<212> TYPE: DNA
<213> ORGANISM: Artificial Sequence
<220> FEATURE:
<223> OTHER INFORMATION: Synthetic DNA
<400> SEQUENCE: 236
ctgacctccg aaatcgtgaa cctgttagat aacaaggtgc tgtgcatttc 50

<210> SEQ ID NO 237
<211> LENGTH: 49
<212> TYPE: DNA
<213> ORGANISM: Artificial Sequence
<220> FEATURE:
<223> OTHER INFORMATION: Synthetic DNA
<400> SEQUENCE: 237
caaggtgctg tgcatttctt tttttgaacg catgtttggc agcagaccg 49

<210> SEQ ID NO 238
<211> LENGTH: 34
<212> TYPE: DNA
<213> ORGANISM: Artificial Sequence
<220> FEATURE:
<223> OTHER INFORMATION: Synthetic DNA
<400> SEQUENCE: 238
catgtttggc agcagaccga ccttctatga ggcg 34

<210> SEQ ID NO 239
<211> LENGTH: 29
<212> TYPE: DNA
<213> ORGANISM: Artificial Sequence
<220> FEATURE:
<223> OTHER INFORMATION: Synthetic DNA
<400> SEQUENCE: 239
cgaccttcta tgaggcgtat ggctgccgc 29

<210> SEQ ID NO 240
<211> LENGTH: 47
<212> TYPE: DNA
<213> ORGANISM: Artificial Sequence
<220> FEATURE:
<223> OTHER INFORMATION: Synthetic DNA
<400> SEQUENCE: 240
cgaccttcta tgaggcgtac ccatacgatg ttccggatta cgcttaa 47

<210> SEQ ID NO 241
<211> LENGTH: 48

-continued

<212> TYPE: DNA
<213> ORGANISM: Artificial Sequence
<220> FEATURE:
<223> OTHER INFORMATION: Synthetic DNA

<400> SEQUENCE: 241
atggatgtgc gttgcatcaa ttggtttgaa tcgcatggtg aaaacagg 48

<210> SEQ ID NO 242
<211> LENGTH: 50
<212> TYPE: DNA
<213> ORGANISM: Artificial Sequence
<220> FEATURE:
<223> OTHER INFORMATION: Synthetic DNA

<400> SEQUENCE: 242
cccattacga cagcggcttt tcagatataa aaacctgttt tcaccatgcg 50

<210> SEQ ID NO 243
<211> LENGTH: 47
<212> TYPE: DNA
<213> ORGANISM: Artificial Sequence
<220> FEATURE:
<223> OTHER INFORMATION: Synthetic DNA

<400> SEQUENCE: 243
gccgctgtcg taatggggaa actgtgttca ttcgcttccc tcactac 47

<210> SEQ ID NO 244
<211> LENGTH: 50
<212> TYPE: DNA
<213> ORGANISM: Artificial Sequence
<220> FEATURE:
<223> OTHER INFORMATION: Synthetic DNA

<400> SEQUENCE: 244
ggtagatctc atcggtcacc acatagtaaa agtagtgagg gaagcgaatg 50

<210> SEQ ID NO 245
<211> LENGTH: 50
<212> TYPE: DNA
<213> ORGANISM: Artificial Sequence
<220> FEATURE:
<223> OTHER INFORMATION: Synthetic DNA

<400> SEQUENCE: 245
ggtgaccgat gagatctacc agagcttagc ccccccacct ttcaacgctc 50

<210> SEQ ID NO 246
<211> LENGTH: 50
<212> TYPE: DNA
<213> ORGANISM: Artificial Sequence
<220> FEATURE:
<223> OTHER INFORMATION: Synthetic DNA

<400> SEQUENCE: 246
cgatgtcaat ggtccgcatt ttacccatag gacgagcgtt gaaaggtggg 50

<210> SEQ ID NO 247
<211> LENGTH: 50
<212> TYPE: DNA
<213> ORGANISM: Artificial Sequence
<220> FEATURE:
<223> OTHER INFORMATION: Synthetic DNA

<400> SEQUENCE: 247

-continued gcggaccatt gacatcgatg agaccatctc gtacaacctg gacatcaagg 50

<210> SEQ ID NO 248
<211> LENGTH: 49
<212> TYPE: DNA
<213> ORGANISM: Artificial Sequence
<220> FEATURE:
<223> OTHER INFORMATION: Synthetic DNA

<400> SEQUENCE: 248
cacatgtccg ccacagagca tttacgatcc ttgatgtcca ggttgtacg 49

<210> SEQ ID NO 249
<211> LENGTH: 46
<212> TYPE: DNA
<213> ORGANISM: Artificial Sequence
<220> FEATURE:
<223> OTHER INFORMATION: Synthetic DNA

<400> SEQUENCE: 249
ctctgtggcg gacatgtggt taattgaaga gccgaaaaag cgcaac 46

<210> SEQ ID NO 250
<211> LENGTH: 48
<212> TYPE: DNA
<213> ORGANISM: Artificial Sequence
<220> FEATURE:
<223> OTHER INFORMATION: Synthetic DNA

<400> SEQUENCE: 250
cagaaactca tccatggtgg cattctgaat gttgcgcttt ttcggctc 48

<210> SEQ ID NO 251
<211> LENGTH: 50
<212> TYPE: DNA
<213> ORGANISM: Artificial Sequence
<220> FEATURE:
<223> OTHER INFORMATION: Synthetic DNA

<400> SEQUENCE: 251
ccaccatgga tgagtttctg aatatttctt ggttctacat cagcaacggc 50

<210> SEQ ID NO 252
<211> LENGTH: 50
<212> TYPE: DNA
<213> ORGANISM: Artificial Sequence
<220> FEATURE:
<223> OTHER INFORMATION: Synthetic DNA

<400> SEQUENCE: 252
gtccaagctg tagcatccat ccggagaaat gccgttgctg atgtagaacc 50

<210> SEQ ID NO 253
<211> LENGTH: 50
<212> TYPE: DNA
<213> ORGANISM: Artificial Sequence
<220> FEATURE:
<223> OTHER INFORMATION: Synthetic DNA

<400> SEQUENCE: 253
ggttctacat cagcaacggc atttctccgg atggatgcta cagcttggac 50

<210> SEQ ID NO 254
<211> LENGTH: 50
<212> TYPE: DNA
<213> ORGANISM: Artificial Sequence -continued
<220> FEATURE:
<223> OTHER INFORMATION: Synthetic DNA

<400> SEQUENCE: 254
cacccgttgt tgattttcgt gagatactga tcgtccaagc tgtagcatcc 50

<210> SEQ ID NO 255
<211> LENGTH: 48
<212> TYPE: DNA
<213> ORGANISM: Artificial Sequence
<220> FEATURE:
<223> OTHER INFORMATION: Synthetic DNA

<400> SEQUENCE: 255
cacgaaaatc aacaacgggt gctatcattg tggcgaccct cgtaactg 48

<210> SEQ ID NO 256
<211> LENGTH: 45
<212> TYPE: DNA
<213> ORGANISM: Artificial Sequence
<220> FEATURE:
<223> OTHER INFORMATION: Synthetic DNA

<400> SEQUENCE: 256
gtcaaaacgg gggatctctt tcgcaaaaca gttacgaggg tcgcc 45

<210> SEQ ID NO 257
<211> LENGTH: 49
<212> TYPE: DNA
<213> ORGANISM: Artificial Sequence
<220> FEATURE:
<223> OTHER INFORMATION: Synthetic DNA

<400> SEQUENCE: 257
gagatccccc gttttgacat tccgagaagc tatctgttcc tggacattg 49

<210> SEQ ID NO 258
<211> LENGTH: 50
<212> TYPE: DNA
<213> ORGANISM: Artificial Sequence
<220> FEATURE:
<223> OTHER INFORMATION: Synthetic DNA

<400> SEQUENCE: 258
gctcgggaac ttcttatcga aatggcattc aatgtccagg aacagatagc 50

<210> SEQ ID NO 259
<211> LENGTH: 49
<212> TYPE: DNA
<213> ORGANISM: Artificial Sequence
<220> FEATURE:
<223> OTHER INFORMATION: Synthetic DNA

<400> SEQUENCE: 259
cgataagaag ttcccgagcg tttttattaa tccgatcagc catacctcc 49

<210> SEQ ID NO 260
<211> LENGTH: 50
<212> TYPE: DNA
<213> ORGANISM: Artificial Sequence
<220> FEATURE:
<223> OTHER INFORMATION: Synthetic DNA

<400> SEQUENCE: 260
cagacgtttg ccgctcagat caatataaca ataggaggta tggctgatcg 50

-continued

<210> SEQ ID NO 261
<211> LENGTH: 50
<212> TYPE: DNA
<213> ORGANISM: Artificial Sequence
<220> FEATURE:
<223> OTHER INFORMATION: Synthetic DNA

<400> SEQUENCE: 261
ctgagcggca aacgtctgct gtttaccctg atcaacgagg agatgctgac 50

<210> SEQ ID NO 262
<211> LENGTH: 50
<212> TYPE: DNA
<213> ORGANISM: Artificial Sequence
<220> FEATURE:
<223> OTHER INFORMATION: Synthetic DNA

<400> SEQUENCE: 262
gatccacggc ctcctggatt tcttgttcgg tcagcatctc ctcgttgatc 50

<210> SEQ ID NO 263
<211> LENGTH: 49
<212> TYPE: DNA
<213> ORGANISM: Artificial Sequence
<220> FEATURE:
<223> OTHER INFORMATION: Synthetic DNA

<400> SEQUENCE: 263
ccaggaggcc gtggatcgtg gctgtctgcg cattcagtcc ttgatggag 49

<210> SEQ ID NO 264
<211> LENGTH: 50
<212> TYPE: DNA
<213> ORGANISM: Artificial Sequence
<220> FEATURE:
<223> OTHER INFORMATION: Synthetic DNA

<400> SEQUENCE: 264
gcacagcacc agttcacgtt cataatccat ctccatcaag gactgaatgc 50

<210> SEQ ID NO 265
<211> LENGTH: 50
<212> TYPE: DNA
<213> ORGANISM: Artificial Sequence
<220> FEATURE:
<223> OTHER INFORMATION: Synthetic DNA

<400> SEQUENCE: 265
gcattcagtc cttgatggag atggattatg aacgtgaact ggtgctgtgc 50

<210> SEQ ID NO 266
<211> LENGTH: 48
<212> TYPE: DNA
<213> ORGANISM: Artificial Sequence
<220> FEATURE:
<223> OTHER INFORMATION: Synthetic DNA

<400> SEQUENCE: 266
gtttggcgat ttggagcagc acaatttcag agcacagcac cagttcac 48

<210> SEQ ID NO 267
<211> LENGTH: 49
<212> TYPE: DNA
<213> ORGANISM: Artificial Sequence
<220> FEATURE:
<223> OTHER INFORMATION: Synthetic DNA -continued

<400> SEQUENCE: 267
gctccaaatc gccaaacagt tattagagct gacctttgat tacatcgtg 49

<210> SEQ ID NO 268
<211> LENGTH: 50
<212> TYPE: DNA
<213> ORGANISM: Artificial Sequence
<220> FEATURE:
<223> OTHER INFORMATION: Synthetic DNA

<400> SEQUENCE: 268
gcagatcgaa gttgtggccg ttgaacgtca cgatgtaatc aaaggtcagc 50

<210> SEQ ID NO 269
<211> LENGTH: 50
<212> TYPE: DNA
<213> ORGANISM: Artificial Sequence
<220> FEATURE:
<223> OTHER INFORMATION: Synthetic DNA

<400> SEQUENCE: 269
gccacaactt cgatctgcgg tatattacca atcgtctcga gctgttgacc 50

<210> SEQ ID NO 270
<211> LENGTH: 50
<212> TYPE: DNA
<213> ORGANISM: Artificial Sequence
<220> FEATURE:
<223> OTHER INFORMATION: Synthetic DNA

<400> SEQUENCE: 270
cttgtcgggg ctacgaaaga tgattttttc gccggtcaac agctcgagac 50

<210> SEQ ID NO 271
<211> LENGTH: 50
<212> TYPE: DNA
<213> ORGANISM: Artificial Sequence
<220> FEATURE:
<223> OTHER INFORMATION: Synthetic DNA

<400> SEQUENCE: 271
ctttcgtagc cccgacaaga aagaagcggt tcacctgtgc atctatgagc 50

<210> SEQ ID NO 272
<211> LENGTH: 46
<212> TYPE: DNA
<213> ORGANISM: Artificial Sequence
<220> FEATURE:
<223> OTHER INFORMATION: Synthetic DNA

<400> SEQUENCE: 272
caaccccttt gtggctcgac tgattacgct catagatgca caggtg 46

<210> SEQ ID NO 273
<211> LENGTH: 46
<212> TYPE: DNA
<213> ORGANISM: Artificial Sequence
<220> FEATURE:
<223> OTHER INFORMATION: Synthetic DNA

<400> SEQUENCE: 273
gagccacaaa ggggttggag ggatggcgaa tacgaccttc cacgtc 46

<210> SEQ ID NO 274

-continued

<211> LENGTH: 50
<212> TYPE: DNA
<213> ORGANISM: Artificial Sequence
<220> FEATURE:
<223> OTHER INFORMATION: Synthetic DNA

<400> SEQUENCE: 274
ggtcgaaaaa aatggtgcca ttattattat tgacgtggaa ggtcgtattc 50

<210> SEQ ID NO 275
<211> LENGTH: 50
<212> TYPE: DNA
<213> ORGANISM: Artificial Sequence
<220> FEATURE:
<223> OTHER INFORMATION: Synthetic DNA

<400> SEQUENCE: 275
gaatacgacc ttccacgtca ataataataa tggcaccatt tttttcgacc 50

<210> SEQ ID NO 276
<211> LENGTH: 49
<212> TYPE: DNA
<213> ORGANISM: Artificial Sequence
<220> FEATURE:
<223> OTHER INFORMATION: Synthetic DNA

<400> SEQUENCE: 276
gcttctccga tttctggatg aaagaataca ggtcgaaaaa aatggtgcc 49

<210> SEQ ID NO 277
<211> LENGTH: 49
<212> TYPE: DNA
<213> ORGANISM: Artificial Sequence
<220> FEATURE:
<223> OTHER INFORMATION: Synthetic DNA

<400> SEQUENCE: 277
catccagaaa tcggagaagc ttgattctta caaactggac agcatcagc 49

<210> SEQ ID NO 278
<211> LENGTH: 50
<212> TYPE: DNA
<213> ORGANISM: Artificial Sequence
<220> FEATURE:
<223> OTHER INFORMATION: Synthetic DNA

<400> SEQUENCE: 278
gcactttgcc catgcacgaa aaggcgtttt tgctgatgct gtccagtttg 50

<210> SEQ ID NO 279
<211> LENGTH: 49
<212> TYPE: DNA
<213> ORGANISM: Artificial Sequence
<220> FEATURE:
<223> OTHER INFORMATION: Synthetic DNA

<400> SEQUENCE: 279
gtgcatgggc aaagtgctga atcgtggtgt gcgtgagatg acctttatc 49

<210> SEQ ID NO 280
<211> LENGTH: 48
<212> TYPE: DNA
<213> ORGANISM: Artificial Sequence
<220> FEATURE:
<223> OTHER INFORMATION: Synthetic DNA

<400> SEQUENCE: 280

-continued cccttttcgca tcagtggtat catcaccgat aaaggtcatc tcacgcac 48

<210> SEQ ID NO 281
<211> LENGTH: 47
<212> TYPE: DNA
<213> ORGANISM: Artificial Sequence
<220> FEATURE:
<223> OTHER INFORMATION: Synthetic DNA

<400> SEQUENCE: 281
ccactgatgc gaaagggaaa gcggctgtgt ttgcgaaggt cctcacc 47

<210> SEQ ID NO 282
<211> LENGTH: 49
<212> TYPE: DNA
<213> ORGANISM: Artificial Sequence
<220> FEATURE:
<223> OTHER INFORMATION: Synthetic DNA

<400> SEQUENCE: 282
gatatcatcg accgtcacgt aattgcctgt ggtgaggacc ttcgcaaac 49

<210> SEQ ID NO 283
<211> LENGTH: 50
<212> TYPE: DNA
<213> ORGANISM: Artificial Sequence
<220> FEATURE:
<223> OTHER INFORMATION: Synthetic DNA

<400> SEQUENCE: 283
cgtgacggtc gatgatatca tttgtaaagt gattcacaag gacatctggg 50

<210> SEQ ID NO 284
<211> LENGTH: 50
<212> TYPE: DNA
<213> ORGANISM: Artificial Sequence
<220> FEATURE:
<223> OTHER INFORMATION: Synthetic DNA

<400> SEQUENCE: 284
gacagctcaa caccacctta aagccatttt cccagatgtc cttgtgaatc 50

<210> SEQ ID NO 285
<211> LENGTH: 50
<212> TYPE: DNA
<213> ORGANISM: Artificial Sequence
<220> FEATURE:
<223> OTHER INFORMATION: Synthetic DNA

<400> SEQUENCE: 285
gattcacaag gacatctggg aaaatggctt taaggtggtg ttgagctgtc 50

<210> SEQ ID NO 286
<211> LENGTH: 49
<212> TYPE: DNA
<213> ORGANISM: Artificial Sequence
<220> FEATURE:
<223> OTHER INFORMATION: Synthetic DNA

<400> SEQUENCE: 286
ggagagtttg tacgtgtcgt tggtcagagt cggacagctc aacaccacc 49

<210> SEQ ID NO 287
<211> LENGTH: 49
<212> TYPE: DNA

-continued

<213> ORGANISM: Artificial Sequence
<220> FEATURE:
<223> OTHER INFORMATION: Synthetic DNA

<400> SEQUENCE: 287
cgacacgtac aaactctcct ttggtaaaga tgatgtcgac ctggcgcag 49

<210> SEQ ID NO 288
<211> LENGTH: 49
<212> TYPE: DNA
<213> ORGANISM: Artificial Sequence
<220> FEATURE:
<223> OTHER INFORMATION: Synthetic DNA

<400> SEQUENCE: 288
gggcgatgtt caggttatag tctttataca tctgcgccag gtcgacatc 49

<210> SEQ ID NO 289
<211> LENGTH: 47
<212> TYPE: DNA
<213> ORGANISM: Artificial Sequence
<220> FEATURE:
<223> OTHER INFORMATION: Synthetic DNA

<400> SEQUENCE: 289
ctataacctg aacatcgccc ttgatatggc ccgctattgc atccacg 47

<210> SEQ ID NO 290
<211> LENGTH: 49
<212> TYPE: DNA
<213> ORGANISM: Artificial Sequence
<220> FEATURE:
<223> OTHER INFORMATION: Synthetic DNA

<400> SEQUENCE: 290
gtactcccac aggtattggc acagacaggc gtcgtggatg caatagcgg 49

<210> SEQ ID NO 291
<211> LENGTH: 50
<212> TYPE: DNA
<213> ORGANISM: Artificial Sequence
<220> FEATURE:
<223> OTHER INFORMATION: Synthetic DNA

<400> SEQUENCE: 291
gtgccaatac ctgtgggagt actatggtgt agagacgaaa acggatgcgg 50

<210> SEQ ID NO 292
<211> LENGTH: 46
<212> TYPE: DNA
<213> ORGANISM: Artificial Sequence
<220> FEATURE:
<223> OTHER INFORMATION: Synthetic DNA

<400> SEQUENCE: 292
ggactgaggc aacacatagg tagaggcacc cgcatccgtt ttcgtc 46

<210> SEQ ID NO 293
<211> LENGTH: 49
<212> TYPE: DNA
<213> ORGANISM: Artificial Sequence
<220> FEATURE:
<223> OTHER INFORMATION: Synthetic DNA

<400> SEQUENCE: 293
ctatgtgttg cctcagtcca tggtgtttga gtataaagcg agcacggtg 49

-continued

<210> SEQ ID NO 294
<211> LENGTH: 31
<212> TYPE: DNA
<213> ORGANISM: Artificial Sequence
<220> FEATURE:
<223> OTHER INFORMATION: Synthetic DNA

<400> SEQUENCE: 294
gggcccctta atcaccgtgc tcgctttata c 31

<210> SEQ ID NO 295
<211> LENGTH: 50
<212> TYPE: DNA
<213> ORGANISM: Artificial Sequence
<220> FEATURE:
<223> OTHER INFORMATION: Synthetic DNA

<400> SEQUENCE: 295
gggcccctgc tgaaattgct gctggaaacc aagaccatct tagtgcgctc 50

<210> SEQ ID NO 296
<211> LENGTH: 50
<212> TYPE: DNA
<213> ORGANISM: Artificial Sequence
<220> FEATURE:
<223> OTHER INFORMATION: Synthetic DNA

<400> SEQUENCE: 296
cgccttcata ggggaacttt tgtttggttt cagagcgcac taagatggtc 50

<210> SEQ ID NO 297
<211> LENGTH: 46
<212> TYPE: DNA
<213> ORGANISM: Artificial Sequence
<220> FEATURE:
<223> OTHER INFORMATION: Synthetic DNA

<400> SEQUENCE: 297
gttcccctat gaaggcggta aagtttttgc cccgaagcag aagatg 46

<210> SEQ ID NO 298
<211> LENGTH: 50
<212> TYPE: DNA
<213> ORGANISM: Artificial Sequence
<220> FEATURE:
<223> OTHER INFORMATION: Synthetic DNA

<400> SEQUENCE: 298
gttgtagtca aagatcagga cgttgttact aaacatcttc tgcttcgggg 50

<210> SEQ ID NO 299
<211> LENGTH: 50
<212> TYPE: DNA
<213> ORGANISM: Artificial Sequence
<220> FEATURE:
<223> OTHER INFORMATION: Synthetic DNA

<400> SEQUENCE: 299
cgtcctgatc tttgactaca actctctgta tcccaacgtg tgcatctttg 50

<210> SEQ ID NO 300
<211> LENGTH: 50
<212> TYPE: DNA
<213> ORGANISM: Artificial Sequence
<220> FEATURE:

-continued

<223> OTHER INFORMATION: Synthetic DNA

<400> SEQUENCE: 300
cacgccaacc agggtttccg gacttaagtt gccaaagatg cacacgttgg 50

<210> SEQ ID NO 301
<211> LENGTH: 48
<212> TYPE: DNA
<213> ORGANISM: Artificial Sequence
<220> FEATURE:
<223> OTHER INFORMATION: Synthetic DNA

<400> SEQUENCE: 301
gaaaccctgg ttggcgtggt ggtgtcttcg aaccgcttgg aagaagag 48

<210> SEQ ID NO 302
<211> LENGTH: 50
<212> TYPE: DNA
<213> ORGANISM: Artificial Sequence
<220> FEATURE:
<223> OTHER INFORMATION: Synthetic DNA

<400> SEQUENCE: 302
ggtacttttg caggagcagc tggttgttaa tctcttcttc caagcggttc 50

<210> SEQ ID NO 303
<211> LENGTH: 49
<212> TYPE: DNA
<213> ORGANISM: Artificial Sequence
<220> FEATURE:
<223> OTHER INFORMATION: Synthetic DNA

<400> SEQUENCE: 303
ctgctcctgc aaaagtaccc gccgccacgt tacattacgg tgcactgcg 49

<210> SEQ ID NO 304
<211> LENGTH: 50
<212> TYPE: DNA
<213> ORGANISM: Artificial Sequence
<220> FEATURE:
<223> OTHER INFORMATION: Synthetic DNA

<400> SEQUENCE: 304
caatctcgct gatcaggttg ggtaaacgtg gttcgcagtg caccgtaatg 50

<210> SEQ ID NO 305
<211> LENGTH: 49
<212> TYPE: DNA
<213> ORGANISM: Artificial Sequence
<220> FEATURE:
<223> OTHER INFORMATION: Synthetic DNA

<400> SEQUENCE: 305
caacctgatc agcgagattg ccatttttga tcggagcatt gaaggcacc 49

<210> SEQ ID NO 306
<211> LENGTH: 50
<212> TYPE: DNA
<213> ORGANISM: Artificial Sequence
<220> FEATURE:
<223> OTHER INFORMATION: Synthetic DNA

<400> SEQUENCE: 306
ctcggccaga aaggttctca gtaaacgcgg aatggtgcct tcaatgctcc 50

-continued

<210> SEQ ID NO 307
<211> LENGTH: 50
<212> TYPE: DNA
<213> ORGANISM: Artificial Sequence
<220> FEATURE:
<223> OTHER INFORMATION: Synthetic DNA

<400> SEQUENCE: 307
ggagcattga aggcaccatt ccgcgtttac tgagaacctt tctggccgag 50

<210> SEQ ID NO 308
<211> LENGTH: 50
<212> TYPE: DNA
<213> ORGANISM: Artificial Sequence
<220> FEATURE:
<223> OTHER INFORMATION: Synthetic DNA

<400> SEQUENCE: 308
cgcctgtttc agcattttct tataacgcgc acgctcggcc agaaaggttc 50

<210> SEQ ID NO 309
<211> LENGTH: 49
<212> TYPE: DNA
<213> ORGANISM: Artificial Sequence
<220> FEATURE:
<223> OTHER INFORMATION: Synthetic DNA

<400> SEQUENCE: 309
gaaaatgctg aaacaggcga ccagttctac ggaaaaagcc atctacgac 49

<210> SEQ ID NO 310
<211> LENGTH: 50
<212> TYPE: DNA
<213> ORGANISM: Artificial Sequence
<220> FEATURE:
<223> OTHER INFORMATION: Synthetic DNA

<400> SEQUENCE: 310
cgcgatgatc ttgtaggtgt actgcatact gtcgtagatg gctttttccg 50

<210> SEQ ID NO 311
<211> LENGTH: 49
<212> TYPE: DNA
<213> ORGANISM: Artificial Sequence
<220> FEATURE:
<223> OTHER INFORMATION: Synthetic DNA

<400> SEQUENCE: 311
cacctacaag atcatcgcga atagtgtgta tggcttgatg ggttttcgc 49

<210> SEQ ID NO 312
<211> LENGTH: 50
<212> TYPE: DNA
<213> ORGANISM: Artificial Sequence
<220> FEATURE:
<223> OTHER INFORMATION: Synthetic DNA

<400> SEQUENCE: 312
cttagcgctg gcatagctat acaaggcaga gttgcgaaaa cccatcaagc 50

<210> SEQ ID NO 313
<211> LENGTH: 50
<212> TYPE: DNA
<213> ORGANISM: Artificial Sequence
<220> FEATURE:
<223> OTHER INFORMATION: Synthetic DNA -continued

<400> SEQUENCE: 313
gctatgccag cgctaagagt tgtaccagta ttggccgtcg tatgatcctg 50

<210> SEQ ID NO 314
<211> LENGTH: 50
<212> TYPE: DNA
<213> ORGANISM: Artificial Sequence
<220> FEATURE:
<223> OTHER INFORMATION: Synthetic DNA

<400> SEQUENCE: 314
cagttccgct ccattgagta cagattccag atacaggatc atacgacggc 50

<210> SEQ ID NO 315
<211> LENGTH: 48
<212> TYPE: DNA
<213> ORGANISM: Artificial Sequence
<220> FEATURE:
<223> OTHER INFORMATION: Synthetic DNA

<400> SEQUENCE: 315
ctcaatggag cggaactgag taatggcatg cttcgttttg caaacccg 48

<210> SEQ ID NO 316
<211> LENGTH: 48
<212> TYPE: DNA
<213> ORGANISM: Artificial Sequence
<220> FEATURE:
<223> OTHER INFORMATION: Synthetic DNA

<400> SEQUENCE: 316
gcgatcatcc atgtagaacg gattacttaa cgggtttgca aaacgaag 48

<210> SEQ ID NO 317
<211> LENGTH: 48
<212> TYPE: DNA
<213> ORGANISM: Artificial Sequence
<220> FEATURE:
<223> OTHER INFORMATION: Synthetic DNA

<400> SEQUENCE: 317
cgttctacat ggatgatcgc gacattaacc cgattgtgaa gacgtccc 48

<210> SEQ ID NO 318
<211> LENGTH: 47
<212> TYPE: DNA
<213> ORGANISM: Artificial Sequence
<220> FEATURE:
<223> OTHER INFORMATION: Synthetic DNA

<400> SEQUENCE: 318
cctgaagcga aaacggtagt caatcggcag ggacgtcttc acaatcg 47

<210> SEQ ID NO 319
<211> LENGTH: 47
<212> TYPE: DNA
<213> ORGANISM: Artificial Sequence
<220> FEATURE:
<223> OTHER INFORMATION: Synthetic DNA

<400> SEQUENCE: 319
cgattgtgaa gacgtccctg ccgattgact accgttttcg cttcagg 47

<210> SEQ ID NO 320
<211> LENGTH: 46

-continued

<212> TYPE: DNA
<213> ORGANISM: Artificial Sequence
<220> FEATURE:
<223> OTHER INFORMATION: Synthetic DNA

<400> SEQUENCE: 320
cacggagtcg gtatcaccat agacactcct gaagcgaaaa cggtag 46

<210> SEQ ID NO 321
<211> LENGTH: 47
<212> TYPE: DNA
<213> ORGANISM: Artificial Sequence
<220> FEATURE:
<223> OTHER INFORMATION: Synthetic DNA

<400> SEQUENCE: 321
gtgataccga ctccgtgttt accgaaattg acagccagga tgttgac 47

<210> SEQ ID NO 322
<211> LENGTH: 46
<212> TYPE: DNA
<213> ORGANISM: Artificial Sequence
<220> FEATURE:
<223> OTHER INFORMATION: Synthetic DNA

<400> SEQUENCE: 322
ccagctcctt cgctatctca atacttttgt caacatcctg gctgtc 46

<210> SEQ ID NO 323
<211> LENGTH: 46
<212> TYPE: DNA
<213> ORGANISM: Artificial Sequence
<220> FEATURE:
<223> OTHER INFORMATION: Synthetic DNA

<400> SEQUENCE: 323
gatagcgaag gagctggaac gtctgatcaa ctctcgtgtg ctgttc 46

<210> SEQ ID NO 324
<211> LENGTH: 47
<212> TYPE: DNA
<213> ORGANISM: Artificial Sequence
<220> FEATURE:
<223> OTHER INFORMATION: Synthetic DNA

<400> SEQUENCE: 324
cggcctcaaa ctcgatctta aagttgttga acagcacacg agagttg 47

<210> SEQ ID NO 325
<211> LENGTH: 46
<212> TYPE: DNA
<213> ORGANISM: Artificial Sequence
<220> FEATURE:
<223> OTHER INFORMATION: Synthetic DNA

<400> SEQUENCE: 325
gatcgagttt gaggccgtgt ataaaaacct gatcatgcag agcaag 46

<210> SEQ ID NO 326
<211> LENGTH: 49
<212> TYPE: DNA
<213> ORGANISM: Artificial Sequence
<220> FEATURE:
<223> OTHER INFORMATION: Synthetic DNA

<400> SEQUENCE: 326

-continued cgcgctatac ttcatcgtgg tatatttttt cttgctctgc atgatcagg 49

<210> SEQ ID NO 327
<211> LENGTH: 47
<212> TYPE: DNA
<213> ORGANISM: Artificial Sequence
<220> FEATURE:
<223> OTHER INFORMATION: Synthetic DNA

<400> SEQUENCE: 327
cacgatgaag tatagcgcga gttctaactc caaaagtgtg ccggagc 47

<210> SEQ ID NO 328
<211> LENGTH: 44
<212> TYPE: DNA
<213> ORGANISM: Artificial Sequence
<220> FEATURE:
<223> OTHER INFORMATION: Synthetic DNA

<400> SEQUENCE: 328
gggtttcgct agtccccttg ttaatacgct ccggcacact tttg 44

<210> SEQ ID NO 329
<211> LENGTH: 44
<212> TYPE: DNA
<213> ORGANISM: Artificial Sequence
<220> FEATURE:
<223> OTHER INFORMATION: Synthetic DNA

<400> SEQUENCE: 329
caaaagtgtg ccggagcgta ttaacaaggg gactagcgaa accc 44

<210> SEQ ID NO 330
<211> LENGTH: 49
<212> TYPE: DNA
<213> ORGANISM: Artificial Sequence
<220> FEATURE:
<223> OTHER INFORMATION: Synthetic DNA

<400> SEQUENCE: 330
catgtttttg tggaacttgc tgacatcacg acgggtttcg ctagtcccc 49

<210> SEQ ID NO 331
<211> LENGTH: 50
<212> TYPE: DNA
<213> ORGANISM: Artificial Sequence
<220> FEATURE:
<223> OTHER INFORMATION: Synthetic DNA

<400> SEQUENCE: 331
cagcaagttc cacaaaaaca tgattaaaat ttacaagacc cgtttgagcg 50

<210> SEQ ID NO 332
<211> LENGTH: 50
<212> TYPE: DNA
<213> ORGANISM: Artificial Sequence
<220> FEATURE:
<223> OTHER INFORMATION: Synthetic DNA

<400> SEQUENCE: 332
ggttgctgtt catccggcct tcacttaaca tttcgctcaa acgggtcttg 50

<210> SEQ ID NO 333
<211> LENGTH: 44
<212> TYPE: DNA
<213> ORGANISM: Artificial Sequence -continued
<220> FEATURE:
<223> OTHER INFORMATION: Synthetic DNA

<400> SEQUENCE: 333
ccggatgaac agcaaccagg tgtgtatcga cattctgcgt tccc 44

<210> SEQ ID NO 334
<211> LENGTH: 46
<212> TYPE: DNA
<213> ORGANISM: Artificial Sequence
<220> FEATURE:
<223> OTHER INFORMATION: Synthetic DNA

<400> SEQUENCE: 334
gtcgaactcg ctacgaagat ccgtttcaag ggaacgcaga atgtcg 46

<210> SEQ ID NO 335
<211> LENGTH: 45
<212> TYPE: DNA
<213> ORGANISM: Artificial Sequence
<220> FEATURE:
<223> OTHER INFORMATION: Synthetic DNA

<400> SEQUENCE: 335
cttcgtagcg agttcgacag ccgatctagc ccgttggaac tgttc 45

<210> SEQ ID NO 336
<211> LENGTH: 44
<212> TYPE: DNA
<213> ORGANISM: Artificial Sequence
<220> FEATURE:
<223> OTHER INFORMATION: Synthetic DNA

<400> SEQUENCE: 336
gttcaagtgg tgcatgcggc ttaacatgaa cagttccaac gggc 44

<210> SEQ ID NO 337
<211> LENGTH: 48
<212> TYPE: DNA
<213> ORGANISM: Artificial Sequence
<220> FEATURE:
<223> OTHER INFORMATION: Synthetic DNA

<400> SEQUENCE: 337
gcatgcacca cttgaactat aaaagcgccg ataacccgaa catgtacc 48

<210> SEQ ID NO 338
<211> LENGTH: 50
<212> TYPE: DNA
<213> ORGANISM: Artificial Sequence
<220> FEATURE:
<223> OTHER INFORMATION: Synthetic DNA

<400> SEQUENCE: 338
ccgggttgtt tttgttgtac tcggtcacca ggtacatgtt cgggttatcg 50

<210> SEQ ID NO 339
<211> LENGTH: 50
<212> TYPE: DNA
<213> ORGANISM: Artificial Sequence
<220> FEATURE:
<223> OTHER INFORMATION: Synthetic DNA

<400> SEQUENCE: 339
cgataacccg aacatgtacc tggtgaccga gtacaacaaa aacaacccgg 50

-continued

<210> SEQ ID NO 340
<211> LENGTH: 49
<212> TYPE: DNA
<213> ORGANISM: Artificial Sequence
<220> FEATURE:
<223> OTHER INFORMATION: Synthetic DNA

<400> SEQUENCE: 340
gtagtagcgt tcgccaagtt caatagtttc cgggttgttt ttgttgtac 49

<210> SEQ ID NO 341
<211> LENGTH: 50
<212> TYPE: DNA
<213> ORGANISM: Artificial Sequence
<220> FEATURE:
<223> OTHER INFORMATION: Synthetic DNA

<400> SEQUENCE: 341
cttggcgaac gctactactt tgcctatatc tgtccggcga atgttccgtg 50

<210> SEQ ID NO 342
<211> LENGTH: 49
<212> TYPE: DNA
<213> ORGANISM: Artificial Sequence
<220> FEATURE:
<223> OTHER INFORMATION: Synthetic DNA

<400> SEQUENCE: 342
cgtacgtctt gatgttcacg agttttttgg tccacggaac attcgccgg 49

<210> SEQ ID NO 343
<211> LENGTH: 50
<212> TYPE: DNA
<213> ORGANISM: Artificial Sequence
<220> FEATURE:
<223> OTHER INFORMATION: Synthetic DNA

<400> SEQUENCE: 343
cgtgaacatc aagacgtacg aaaccattat tgaccgttcc ttcaagctgg 50

<210> SEQ ID NO 344
<211> LENGTH: 46
<212> TYPE: DNA
<213> ORGANISM: Artificial Sequence
<220> FEATURE:
<223> OTHER INFORMATION: Synthetic DNA

<400> SEQUENCE: 344
cacctcgtaa aaaatgcgct gatctgagcc cagcttgaag gaacgg 46

<210> SEQ ID NO 345
<211> LENGTH: 49
<212> TYPE: DNA
<213> ORGANISM: Artificial Sequence
<220> FEATURE:
<223> OTHER INFORMATION: Synthetic DNA

<400> SEQUENCE: 345
gcgcattttt tacgaggtgt attttaaacg tctgacctcc gaaatcgtg 49

<210> SEQ ID NO 346
<211> LENGTH: 50
<212> TYPE: DNA
<213> ORGANISM: Artificial Sequence
<220> FEATURE:
<223> OTHER INFORMATION: Synthetic DNA -continued

<400> SEQUENCE: 346
gaaatgcaca gcaccttgtt atctaacagg ttcacgattt cggaggtcag 50

<210> SEQ ID NO 347
<211> LENGTH: 49
<212> TYPE: DNA
<213> ORGANISM: Artificial Sequence
<220> FEATURE:
<223> OTHER INFORMATION: Synthetic DNA

<400> SEQUENCE: 347
caaggtgctg tgcatttctt tttttgaacg catgtttggc agcagaccg 49

<210> SEQ ID NO 348
<211> LENGTH: 34
<212> TYPE: DNA
<213> ORGANISM: Artificial Sequence
<220> FEATURE:
<223> OTHER INFORMATION: Synthetic DNA

<400> SEQUENCE: 348
cgcctcatag aaggtcggtc tgctgccaaa catg 34

<210> SEQ ID NO 349
<211> LENGTH: 29
<212> TYPE: DNA
<213> ORGANISM: Artificial Sequence
<220> FEATURE:
<223> OTHER INFORMATION: Synthetic DNA

<400> SEQUENCE: 349
gcggcagcca tagggcccct taatcaccg 29

<210> SEQ ID NO 350
<211> LENGTH: 47
<212> TYPE: DNA
<213> ORGANISM: Artificial Sequence
<220> FEATURE:
<223> OTHER INFORMATION: Synthetic DNA

<400> SEQUENCE: 350
ttaagcgtaa tccggaacat cgtatgggta gggcccctta atcaccg 47

<210> SEQ ID NO 351
<211> LENGTH: 29
<212> TYPE: DNA
<213> ORGANISM: Artificial Sequence
<220> FEATURE:
<223> OTHER INFORMATION: Synthetic DNA

<400> SEQUENCE: 351
gcggcagcca tacgcctcat agaaggtcg 29

<210> SEQ ID NO 352
<211> LENGTH: 47
<212> TYPE: DNA
<213> ORGANISM: Artificial Sequence
<220> FEATURE:
<223> OTHER INFORMATION: Synthetic DNA

<400> SEQUENCE: 352
ttaagcgtaa tccggaacat cgtatgggta cgcctcatag aaggtcg 47

<210> SEQ ID NO 353

-continued

<211> LENGTH: 1542
<212> TYPE: DNA
<213> ORGANISM: Artificial Sequence
<220> FEATURE:
<223> OTHER INFORMATION: Synthetic DNA

<400> SEQUENCE: 353
atggcggatt ctcagccgtt gtctggtgcc ccggaaggcg cggagtatct tcgggcggta 60
ctgcgagctc cagtgtatga agccgcacag gtgaccccgc tgcaaaaaat ggagaaactg 120
agctcccgtc tggataacgt catcctggtc aaacgcgaag atcgtcagcc ggttcacagc 180
ttcaaactgc gcggggccta tgctatgatg gcgggcttaa cggaagagca gaaagcacat 240
ggcgttatta ccgcgtctgc aggcaaccat gcacaggggg tagcgttttc tagtgcgcgt 300
ttaggcgtga aagcgttgat cgtgatgccg accgcaaccg ctgatatcaa agtcgatgcc 360
gtgcgtggct ttggcggaga agtgctgtta cacggcgcaa acttcgatga agcaaaagcc 420
aaagcgatcg aactgtctca gcagcagggg tttacctggg ttccgccgtt cgatcatccg 480
atggtgattg ctggtcaggg cactctggcg ttagaactgc tccagcaaga tgcccacctg 540
gatcgtgtgt ttgtgccggt aggtggagga ggccttgctg caggagtcgc agtgctgatc 600
aaacagttga tgccgcagat caaggttatt gccgtggaag ccgaggatag cgcctgtctg 660
aaagcggcgt tagatgctgg tcatccggtc gatctgccac gtgtaggcct gtttgcggaa 720
ggtgtagcgg tgaagcgtat tggcgacgaa acctttcggc tgtgccagga atatctcgac 780
gacatcatca ccgttgacag cgatgcgatt tgtgccgcga tgaaagacct gttcgaagat 840
gtgcgtgcgg tagctgaacc aagtggtgca ttagcgttgg ccggcatgaa aaagtacatt 900
gccttgcaca acattcgtgg cgaacgcctg gcccatatcc tgagtggagc caacgtcaac 960
ttccatggcc tgcgttacgt tagcgaacgg tgtgaactgg gcgagcaacg tgaagcgctc 1020
ctggccgtta ccatcccaga ggagaagggc agctttctga aattttgcca gctgttaggg 1080
ggccgtagcg tcaccgaatt caactaccgc tttgccgatg cgaaaaatgc gtgcattttc 1140
gtgggcgtcc gtctgtcccg tggcctggaa gagcgcaagg agattctgca gatgctgaac 1200
gatggtggtt attccgtggt ggatctcagc gacgatgaaa tggccaagct gcatgtgcgc 1260
tatatggtgg ggggtcgtcc gagtcacccg ttgcaggaac gcttgtacag cttcgagttt 1320
ccggagtctc ctggtgcact gttacgcttc ctgaacaccc tggggacgta ctggaacatc 1380
agcctgtttc actatcgctc ccatggtact gactacggtc gggtcctggc tgcgtttgaa 1440
ctgggggacc acgaaccgga cttcgaaacc cgcctgaacg aattaggcta cgactgccat 1500
gacgaaacca acaacccggc gtttcgcttt tttctggcag gg 1542

<210> SEQ ID NO 354
<211> LENGTH: 33
<212> TYPE: DNA
<213> ORGANISM: Artificial Sequence
<220> FEATURE:
<223> OTHER INFORMATION: Synthetic DNA

<400> SEQUENCE: 354
atggcggatt ctcagccgtt gtctggtgcc ccg 33

<210> SEQ ID NO 355
<211> LENGTH: 60
<212> TYPE: DNA
<213> ORGANISM: Artificial Sequence
<220> FEATURE:
<223> OTHER INFORMATION: Synthetic DNA -continued

<400> SEQUENCE: 355
atggcggatt ctcagccgtt gtctggtgcc ccggaaggcg cggagtatct tcgggcggta 60

<210> SEQ ID NO 356
<211> LENGTH: 56
<212> TYPE: DNA
<213> ORGANISM: Artificial Sequence
<220> FEATURE:
<223> OTHER INFORMATION: Synthetic DNA

<400> SEQUENCE: 356
gaaggcgcgg agtatcttcg ggcggtactg cgagctccag tgtatgaagc cgcaca 56

<210> SEQ ID NO 357
<211> LENGTH: 60
<212> TYPE: DNA
<213> ORGANISM: Artificial Sequence
<220> FEATURE:
<223> OTHER INFORMATION: Synthetic DNA

<400> SEQUENCE: 357
ctgcgagctc cagtgtatga agccgcacag gtgaccccgc tgcaaaaaat ggagaaactg 60

<210> SEQ ID NO 358
<211> LENGTH: 60
<212> TYPE: DNA
<213> ORGANISM: Artificial Sequence
<220> FEATURE:
<223> OTHER INFORMATION: Synthetic DNA

<400> SEQUENCE: 358
ggtgaccccg ctgcaaaaaa tggagaaact gagctcccgt ctggataacg tcatcctggt 60

<210> SEQ ID NO 359
<211> LENGTH: 60
<212> TYPE: DNA
<213> ORGANISM: Artificial Sequence
<220> FEATURE:
<223> OTHER INFORMATION: Synthetic DNA

<400> SEQUENCE: 359
agctcccgtc tggataacgt catcctggtc aaacgcgaag atcgtcagcc ggttcacagc 60

<210> SEQ ID NO 360
<211> LENGTH: 60
<212> TYPE: DNA
<213> ORGANISM: Artificial Sequence
<220> FEATURE:
<223> OTHER INFORMATION: Synthetic DNA

<400> SEQUENCE: 360
caaacgcgaa gatcgtcagc cggttcacag cttcaaactg cgcggggcct atgctatgat 60

<210> SEQ ID NO 361
<211> LENGTH: 60
<212> TYPE: DNA
<213> ORGANISM: Artificial Sequence
<220> FEATURE:
<223> OTHER INFORMATION: Synthetic DNA

<400> SEQUENCE: 361
ttcaaactgc gcggggccta tgctatgatg gcgggcttaa cggaagagca gaaagcacat 60

<210> SEQ ID NO 362

-continued

<211> LENGTH: 60
<212> TYPE: DNA
<213> ORGANISM: Artificial Sequence
<220> FEATURE:
<223> OTHER INFORMATION: Synthetic DNA

<400> SEQUENCE: 362
ggcgggctta acggaagagc agaaagcaca tggcgttatt accgcgtctg caggcaacca 60

<210> SEQ ID NO 363
<211> LENGTH: 60
<212> TYPE: DNA
<213> ORGANISM: Artificial Sequence
<220> FEATURE:
<223> OTHER INFORMATION: Synthetic DNA

<400> SEQUENCE: 363
ggcgttatta ccgcgtctgc aggcaaccat gcacaggggg tagcgttttc tagtgcgcgt 60

<210> SEQ ID NO 364
<211> LENGTH: 60
<212> TYPE: DNA
<213> ORGANISM: Artificial Sequence
<220> FEATURE:
<223> OTHER INFORMATION: Synthetic DNA

<400> SEQUENCE: 364
tgcacagggg gtagcgtttt ctagtgcgcg tttaggcgtg aaagcgttga tcgtgatgcc 60

<210> SEQ ID NO 365
<211> LENGTH: 60
<212> TYPE: DNA
<213> ORGANISM: Artificial Sequence
<220> FEATURE:
<223> OTHER INFORMATION: Synthetic DNA

<400> SEQUENCE: 365
ttaggcgtga aagcgttgat cgtgatgccg accgcaaccg ctgatatcaa agtcgatgcc 60

<210> SEQ ID NO 366
<211> LENGTH: 60
<212> TYPE: DNA
<213> ORGANISM: Artificial Sequence
<220> FEATURE:
<223> OTHER INFORMATION: Synthetic DNA

<400> SEQUENCE: 366
gaccgcaacc gctgatatca aagtcgatgc cgtgcgtggc tttggcggag aagtgctgtt 60

<210> SEQ ID NO 367
<211> LENGTH: 60
<212> TYPE: DNA
<213> ORGANISM: Artificial Sequence
<220> FEATURE:
<223> OTHER INFORMATION: Synthetic DNA

<400> SEQUENCE: 367
gtgcgtggct ttggcggaga agtgctgtta cacggcgcaa acttcgatga agcaaaagcc 60

<210> SEQ ID NO 368
<211> LENGTH: 60
<212> TYPE: DNA
<213> ORGANISM: Artificial Sequence
<220> FEATURE:
<223> OTHER INFORMATION: Synthetic DNA

<400> SEQUENCE: 368

-continued acacggcgca aacttcgatg aagcaaaagc caaagcgatc gaactgtctc agcagcaggg 60

<210> SEQ ID NO 369
<211> LENGTH: 60
<212> TYPE: DNA
<213> ORGANISM: Artificial Sequence
<220> FEATURE:
<223> OTHER INFORMATION: Synthetic DNA

<400> SEQUENCE: 369
aaagcgatcg aactgtctca gcagcagggg tttacctggg ttccgccgtt cgatcatccg 60

<210> SEQ ID NO 370
<211> LENGTH: 60
<212> TYPE: DNA
<213> ORGANISM: Artificial Sequence
<220> FEATURE:
<223> OTHER INFORMATION: Synthetic DNA

<400> SEQUENCE: 370
gtttacctgg gttccgccgt tcgatcatcc gatggtgatt gctggtcagg gcactctggc 60

<210> SEQ ID NO 371
<211> LENGTH: 58
<212> TYPE: DNA
<213> ORGANISM: Artificial Sequence
<220> FEATURE:
<223> OTHER INFORMATION: Synthetic DNA

<400> SEQUENCE: 371
atggtgattg ctggtcaggg cactctggcg ttagaactgc tccagcaaga tgcccacc 58

<210> SEQ ID NO 372
<211> LENGTH: 56
<212> TYPE: DNA
<213> ORGANISM: Artificial Sequence
<220> FEATURE:
<223> OTHER INFORMATION: Synthetic DNA

<400> SEQUENCE: 372
gttagaactg ctccagcaag atgcccacct ggatcgtgtg tttgtgccgg taggtg 56

<210> SEQ ID NO 373
<211> LENGTH: 54
<212> TYPE: DNA
<213> ORGANISM: Artificial Sequence
<220> FEATURE:
<223> OTHER INFORMATION: Synthetic DNA

<400> SEQUENCE: 373
tggatcgtgt gtttgtgccg gtaggtggag gaggccttgc tgcaggagtc gcag 54

<210> SEQ ID NO 374
<211> LENGTH: 60
<212> TYPE: DNA
<213> ORGANISM: Artificial Sequence
<220> FEATURE:
<223> OTHER INFORMATION: Synthetic DNA

<400> SEQUENCE: 374
gaggaggcct tgctgcagga gtcgcagtgc tgatcaaaca gttgatgccg cagatcaagg 60

<210> SEQ ID NO 375
<211> LENGTH: 60
<212> TYPE: DNA

-continued

<213> ORGANISM: Artificial Sequence
<220> FEATURE:
<223> OTHER INFORMATION: Synthetic DNA

<400> SEQUENCE: 375
tgctgatcaa acagttgatg ccgcagatca aggttattgc cgtggaagcc gaggatagcg 60

<210> SEQ ID NO 376
<211> LENGTH: 60
<212> TYPE: DNA
<213> ORGANISM: Artificial Sequence
<220> FEATURE:
<223> OTHER INFORMATION: Synthetic DNA

<400> SEQUENCE: 376
ttattgccgt ggaagccgag gatagcgcct gtctgaaagc ggcgttagat gctggtcatc 60

<210> SEQ ID NO 377
<211> LENGTH: 60
<212> TYPE: DNA
<213> ORGANISM: Artificial Sequence
<220> FEATURE:
<223> OTHER INFORMATION: Synthetic DNA

<400> SEQUENCE: 377
cctgtctgaa agcggcgtta gatgctggtc atccggtcga tctgccacgt gtaggcctgt 60

<210> SEQ ID NO 378
<211> LENGTH: 60
<212> TYPE: DNA
<213> ORGANISM: Artificial Sequence
<220> FEATURE:
<223> OTHER INFORMATION: Synthetic DNA

<400> SEQUENCE: 378
cggtcgatct gccacgtgta ggcctgtttg cggaaggtgt agcggtgaag cgtattggcg 60

<210> SEQ ID NO 379
<211> LENGTH: 60
<212> TYPE: DNA
<213> ORGANISM: Artificial Sequence
<220> FEATURE:
<223> OTHER INFORMATION: Synthetic DNA

<400> SEQUENCE: 379
ttgcggaagg tgtagcggtg aagcgtattg gcgacgaaac ctttcggctg tgccaggaat 60

<210> SEQ ID NO 380
<211> LENGTH: 59
<212> TYPE: DNA
<213> ORGANISM: Artificial Sequence
<220> FEATURE:
<223> OTHER INFORMATION: Synthetic DNA

<400> SEQUENCE: 380
acgaaacctt tcggctgtgc caggaatatc tcgacgacat catcaccgtt gacagcgat 59

<210> SEQ ID NO 381
<211> LENGTH: 60
<212> TYPE: DNA
<213> ORGANISM: Artificial Sequence
<220> FEATURE:
<223> OTHER INFORMATION: Synthetic DNA

<400> SEQUENCE: 381
atctcgacga catcatcacc gttgacagcg atgcgatttg tgccgcgatg aaagacctgt 60

-continued

<210> SEQ ID NO 382
<211> LENGTH: 60
<212> TYPE: DNA
<213> ORGANISM: Artificial Sequence
<220> FEATURE:
<223> OTHER INFORMATION: Synthetic DNA

<400> SEQUENCE: 382
gcgatttgtg ccgcgatgaa agacctgttc gaagatgtgc gtgcggtagc tgaaccaagt 60

<210> SEQ ID NO 383
<211> LENGTH: 60
<212> TYPE: DNA
<213> ORGANISM: Artificial Sequence
<220> FEATURE:
<223> OTHER INFORMATION: Synthetic DNA

<400> SEQUENCE: 383
tcgaagatgt gcgtgcggta gctgaaccaa gtggtgcatt agcgttggcc ggcatgaaaa 60

<210> SEQ ID NO 384
<211> LENGTH: 60
<212> TYPE: DNA
<213> ORGANISM: Artificial Sequence
<220> FEATURE:
<223> OTHER INFORMATION: Synthetic DNA

<400> SEQUENCE: 384
ggtgcattag cgttggccgg catgaaaaag tacattgcct tgcacaacat tcgtggcgaa 60

<210> SEQ ID NO 385
<211> LENGTH: 60
<212> TYPE: DNA
<213> ORGANISM: Artificial Sequence
<220> FEATURE:
<223> OTHER INFORMATION: Synthetic DNA

<400> SEQUENCE: 385
agtacattgc cttgcacaac attcgtggcg aacgcctggc ccatatcctg agtggagcca 60

<210> SEQ ID NO 386
<211> LENGTH: 55
<212> TYPE: DNA
<213> ORGANISM: Artificial Sequence
<220> FEATURE:
<223> OTHER INFORMATION: Synthetic DNA

<400> SEQUENCE: 386
cgcctggccc atatcctgag tggagccaac gtcaacttcc atggcctgcg ttacg 55

<210> SEQ ID NO 387
<211> LENGTH: 54
<212> TYPE: DNA
<213> ORGANISM: Artificial Sequence
<220> FEATURE:
<223> OTHER INFORMATION: Synthetic DNA

<400> SEQUENCE: 387
acgtcaactt ccatggcctg cgttacgtta gcgaacggtg tgaactgggc gagc 54

<210> SEQ ID NO 388
<211> LENGTH: 54
<212> TYPE: DNA
<213> ORGANISM: Artificial Sequence
<220> FEATURE:

-continued

<223> OTHER INFORMATION: Synthetic DNA

<400> SEQUENCE: 388
ttagcgaacg gtgtgaactg ggcgagcaac gtgaagcgct cctggccgtt acca 54

<210> SEQ ID NO 389
<211> LENGTH: 54
<212> TYPE: DNA
<213> ORGANISM: Artificial Sequence
<220> FEATURE:
<223> OTHER INFORMATION: Synthetic DNA

<400> SEQUENCE: 389
aacgtgaagc gctcctggcc gttaccatcc cagaggagaa gggcagcttt ctga 54

<210> SEQ ID NO 390
<211> LENGTH: 54
<212> TYPE: DNA
<213> ORGANISM: Artificial Sequence
<220> FEATURE:
<223> OTHER INFORMATION: Synthetic DNA

<400> SEQUENCE: 390
tcccagagga gaagggcagc tttctgaaat tttgccagct gttagggggc cgta 54

<210> SEQ ID NO 391
<211> LENGTH: 59
<212> TYPE: DNA
<213> ORGANISM: Artificial Sequence
<220> FEATURE:
<223> OTHER INFORMATION: Synthetic DNA

<400> SEQUENCE: 391
aattttgcca gctgttaggg ggccgtagcg tcaccgaatt caactaccgc tttgccgat 59

<210> SEQ ID NO 392
<211> LENGTH: 60
<212> TYPE: DNA
<213> ORGANISM: Artificial Sequence
<220> FEATURE:
<223> OTHER INFORMATION: Synthetic DNA

<400> SEQUENCE: 392
gcgtcaccga attcaactac cgctttgccg atgcgaaaaa tgcgtgcatt ttcgtgggcg 60

<210> SEQ ID NO 393
<211> LENGTH: 55
<212> TYPE: DNA
<213> ORGANISM: Artificial Sequence
<220> FEATURE:
<223> OTHER INFORMATION: Synthetic DNA

<400> SEQUENCE: 393
gcgaaaaatg cgtgcatttt cgtgggcgtc cgtctgtccc gtggcctgga agagc 55

<210> SEQ ID NO 394
<211> LENGTH: 59
<212> TYPE: DNA
<213> ORGANISM: Artificial Sequence
<220> FEATURE:
<223> OTHER INFORMATION: Synthetic DNA

<400> SEQUENCE: 394
tccgtctgtc ccgtggcctg gaagagcgca aggagattct gcagatgctg aacgatggt 59

-continued

<210> SEQ ID NO 395
<211> LENGTH: 60
<212> TYPE: DNA
<213> ORGANISM: Artificial Sequence
<220> FEATURE:
<223> OTHER INFORMATION: Synthetic DNA

<400> SEQUENCE: 395
gcaaggagat tctgcagatg ctgaacgatg gtggttattc cgtggtggat ctcagcgacg 60

<210> SEQ ID NO 396
<211> LENGTH: 55
<212> TYPE: DNA
<213> ORGANISM: Artificial Sequence
<220> FEATURE:
<223> OTHER INFORMATION: Synthetic DNA

<400> SEQUENCE: 396
ggttattccg tggtggatct cagcgacgat gaaatggcca agctgcatgt gcgct 55

<210> SEQ ID NO 397
<211> LENGTH: 54
<212> TYPE: DNA
<213> ORGANISM: Artificial Sequence
<220> FEATURE:
<223> OTHER INFORMATION: Synthetic DNA

<400> SEQUENCE: 397
atgaaatggc caagctgcat gtgcgctata tggtgggggg tcgtccgagt cacc 54

<210> SEQ ID NO 398
<211> LENGTH: 55
<212> TYPE: DNA
<213> ORGANISM: Artificial Sequence
<220> FEATURE:
<223> OTHER INFORMATION: Synthetic DNA

<400> SEQUENCE: 398
atatggtggg gggtcgtccg agtcacccgt tgcaggaacg cttgtacagc ttcga 55

<210> SEQ ID NO 399
<211> LENGTH: 55
<212> TYPE: DNA
<213> ORGANISM: Artificial Sequence
<220> FEATURE:
<223> OTHER INFORMATION: Synthetic DNA

<400> SEQUENCE: 399
cgttgcagga acgcttgtac agcttcgagt ttccggagtc tcctggtgca ctgtt 55

<210> SEQ ID NO 400
<211> LENGTH: 54
<212> TYPE: DNA
<213> ORGANISM: Artificial Sequence
<220> FEATURE:
<223> OTHER INFORMATION: Synthetic DNA

<400> SEQUENCE: 400
gtttccggag tctcctggtg cactgttacg cttcctgaac accctgggga cgta 54

<210> SEQ ID NO 401
<211> LENGTH: 59
<212> TYPE: DNA
<213> ORGANISM: Artificial Sequence
<220> FEATURE:
<223> OTHER INFORMATION: Synthetic DNA

```
<400> SEQUENCE: 401

acgcttcctg aacaccctgg ggacgtactg aacatcagc ctgtttcact atcgctccc        59

<210> SEQ ID NO 402
<211> LENGTH: 59
<212> TYPE: DNA
<213> ORGANISM: Artificial Sequence
<220> FEATURE:
<223> OTHER INFORMATION: Synthetic DNA

<400> SEQUENCE: 402

ctggaacatc agcctgtttc actatcgctc ccatggtact gactacggtc gggtcctgg       59

<210> SEQ ID NO 403
<211> LENGTH: 54
<212> TYPE: DNA
<213> ORGANISM: Artificial Sequence
<220> FEATURE:
<223> OTHER INFORMATION: Synthetic DNA

<400> SEQUENCE: 403

atggtactga ctacggtcgg gtcctggctg cgtttgaact gggggaccac gaac            54

<210> SEQ ID NO 404
<211> LENGTH: 55
<212> TYPE: DNA
<213> ORGANISM: Artificial Sequence
<220> FEATURE:
<223> OTHER INFORMATION: Synthetic DNA

<400> SEQUENCE: 404

ctgcgtttga actgggggac cacgaaccgg acttcgaaac ccgcctgaac gaatt           55

<210> SEQ ID NO 405
<211> LENGTH: 59
<212> TYPE: DNA
<213> ORGANISM: Artificial Sequence
<220> FEATURE:
<223> OTHER INFORMATION: Synthetic DNA

<400> SEQUENCE: 405

cggacttcga aacccgcctg aacgaattag gctacgactg ccatgacgaa accaacaac      59

<210> SEQ ID NO 406
<211> LENGTH: 58
<212> TYPE: DNA
<213> ORGANISM: Artificial Sequence
<220> FEATURE:
<223> OTHER INFORMATION: Synthetic DNA

<400> SEQUENCE: 406

aggctacgac tgccatgacg aaaccaacaa cccggcgttt cgcttttttc tggcaggg        58

<210> SEQ ID NO 407
<211> LENGTH: 27
<212> TYPE: DNA
<213> ORGANISM: Artificial Sequence
<220> FEATURE:
<223> OTHER INFORMATION: Synthetic DNA

<400> SEQUENCE: 407

ccggcgtttc gcttttttct ggcaggg                                          27

<210> SEQ ID NO 408
<211> LENGTH: 45
```

-continued

<212> TYPE: DNA
<213> ORGANISM: Artificial Sequence
<220> FEATURE:
<223> OTHER INFORMATION: Synthetic DNA

<400> SEQUENCE: 408
tcctcgagca taatggcgga ttctcagccg ttgtctggtg ccccg 45

<210> SEQ ID NO 409
<211> LENGTH: 12
<212> TYPE: DNA
<213> ORGANISM: Artificial Sequence
<220> FEATURE:
<223> OTHER INFORMATION: Synthetic DNA

<400> SEQUENCE: 409
tatgctcgag ga 12

<210> SEQ ID NO 410
<211> LENGTH: 63
<212> TYPE: DNA
<213> ORGANISM: Artificial Sequence
<220> FEATURE:
<223> OTHER INFORMATION: Synthetic DNA

<400> SEQUENCE: 410
gacgacgacg acaagcatat gctcgaggat atggcggatt ctcagccgtt gtctggtgcc 60
ccg 63

<210> SEQ ID NO 411
<211> LENGTH: 30
<212> TYPE: DNA
<213> ORGANISM: Artificial Sequence
<220> FEATURE:
<223> OTHER INFORMATION: Synthetic DNA

<400> SEQUENCE: 411
atcctcgagc atatgcttgt cgtcgtcgtc 30

<210> SEQ ID NO 412
<211> LENGTH: 33
<212> TYPE: DNA
<213> ORGANISM: Artificial Sequence
<220> FEATURE:
<223> OTHER INFORMATION: Synthetic DNA

<400> SEQUENCE: 412
atggcggatt ctcagccgtt gtctggtgcc ccg 33

<210> SEQ ID NO 413
<211> LENGTH: 60
<212> TYPE: DNA
<213> ORGANISM: Artificial Sequence
<220> FEATURE:
<223> OTHER INFORMATION: Synthetic DNA

<400> SEQUENCE: 413
taccgcccga agatactccg cgccttccgg ggcaccagac aacggctgag aatccgccat 60

<210> SEQ ID NO 414
<211> LENGTH: 56
<212> TYPE: DNA
<213> ORGANISM: Artificial Sequence
<220> FEATURE:
<223> OTHER INFORMATION: Synthetic DNA -continued

<400> SEQUENCE: 414
gaaggcgcgg agtatcttcg ggcggtactg cgagctccag tgtatgaagc cgcaca 56

<210> SEQ ID NO 415
<211> LENGTH: 60
<212> TYPE: DNA
<213> ORGANISM: Artificial Sequence
<220> FEATURE:
<223> OTHER INFORMATION: Synthetic DNA

<400> SEQUENCE: 415
cagtttctcc attttttgca gcggggtcac ctgtgcggct tcatacactg gagctcgcag 60

<210> SEQ ID NO 416
<211> LENGTH: 60
<212> TYPE: DNA
<213> ORGANISM: Artificial Sequence
<220> FEATURE:
<223> OTHER INFORMATION: Synthetic DNA

<400> SEQUENCE: 416
ggtgaccccg ctgcaaaaaa tggagaaact gagctcccgt ctggataacg tcatcctggt 60

<210> SEQ ID NO 417
<211> LENGTH: 60
<212> TYPE: DNA
<213> ORGANISM: Artificial Sequence
<220> FEATURE:
<223> OTHER INFORMATION: Synthetic DNA

<400> SEQUENCE: 417
gctgtgaacc ggctgacgat cttcgcgttt gaccaggatg acgttatcca gacgggagct 60

<210> SEQ ID NO 418
<211> LENGTH: 60
<212> TYPE: DNA
<213> ORGANISM: Artificial Sequence
<220> FEATURE:
<223> OTHER INFORMATION: Synthetic DNA

<400> SEQUENCE: 418
caaacgcgaa gatcgtcagc cggttcacag cttcaaactg cgcggggcct atgctatgat 60

<210> SEQ ID NO 419
<211> LENGTH: 60
<212> TYPE: DNA
<213> ORGANISM: Artificial Sequence
<220> FEATURE:
<223> OTHER INFORMATION: Synthetic DNA

<400> SEQUENCE: 419
atgtgctttc tgctcttccg ttaagcccgc catcatagca taggccccgc gcagtttgaa 60

<210> SEQ ID NO 420
<211> LENGTH: 60
<212> TYPE: DNA
<213> ORGANISM: Artificial Sequence
<220> FEATURE:
<223> OTHER INFORMATION: Synthetic DNA

<400> SEQUENCE: 420
ggcgggctta acggaagagc agaaagcaca tggcgttatt accgcgtctg caggcaacca 60

<210> SEQ ID NO 421
<211> LENGTH: 60

-continued

<212> TYPE: DNA
<213> ORGANISM: Artificial Sequence
<220> FEATURE:
<223> OTHER INFORMATION: Synthetic DNA

<400> SEQUENCE: 421
acgcgcacta gaaaacgcta ccccctgtgc atggttgcct gcagacgcgg taataacgcc 60

<210> SEQ ID NO 422
<211> LENGTH: 60
<212> TYPE: DNA
<213> ORGANISM: Artificial Sequence
<220> FEATURE:
<223> OTHER INFORMATION: Synthetic DNA

<400> SEQUENCE: 422
tgcacagggg gtagcgtttt ctagtgcgcg tttaggcgtg aaagcgttga tcgtgatgcc 60

<210> SEQ ID NO 423
<211> LENGTH: 60
<212> TYPE: DNA
<213> ORGANISM: Artificial Sequence
<220> FEATURE:
<223> OTHER INFORMATION: Synthetic DNA

<400> SEQUENCE: 423
ggcatcgact ttgatatcag cggttgcggt cggcatcacg atcaacgctt tcacgcctaa 60

<210> SEQ ID NO 424
<211> LENGTH: 60
<212> TYPE: DNA
<213> ORGANISM: Artificial Sequence
<220> FEATURE:
<223> OTHER INFORMATION: Synthetic DNA

<400> SEQUENCE: 424
gaccgcaacc gctgatatca aagtcgatgc cgtgcgtggc tttggcggag aagtgctgtt 60

<210> SEQ ID NO 425
<211> LENGTH: 60
<212> TYPE: DNA
<213> ORGANISM: Artificial Sequence
<220> FEATURE:
<223> OTHER INFORMATION: Synthetic DNA

<400> SEQUENCE: 425
ggcttttgct tcatcgaagt ttgcgccgtg taacagcact tctccgccaa agccacgcac 60

<210> SEQ ID NO 426
<211> LENGTH: 60
<212> TYPE: DNA
<213> ORGANISM: Artificial Sequence
<220> FEATURE:
<223> OTHER INFORMATION: Synthetic DNA

<400> SEQUENCE: 426
acacggcgca aacttcgatg aagcaaaagc caaagcgatc gaactgtctc agcagcaggg 60

<210> SEQ ID NO 427
<211> LENGTH: 60
<212> TYPE: DNA
<213> ORGANISM: Artificial Sequence
<220> FEATURE:
<223> OTHER INFORMATION: Synthetic DNA

<400> SEQUENCE: 427

-continued cggatgatcg aacggcggaa cccaggtaaa cccctgctgc tgagacagtt cgatcgcttt 60

<210> SEQ ID NO 428
<211> LENGTH: 60
<212> TYPE: DNA
<213> ORGANISM: Artificial Sequence
<220> FEATURE:
<223> OTHER INFORMATION: Synthetic DNA

<400> SEQUENCE: 428
gtttacctgg gttccgccgt tcgatcatcc gatggtgatt gctggtcagg gcactctggc 60

<210> SEQ ID NO 429
<211> LENGTH: 58
<212> TYPE: DNA
<213> ORGANISM: Artificial Sequence
<220> FEATURE:
<223> OTHER INFORMATION: Synthetic DNA

<400> SEQUENCE: 429
ggtgggcatc ttgctggagc agttctaacg ccagagtgcc ctgaccagca atcaccat 58

<210> SEQ ID NO 430
<211> LENGTH: 56
<212> TYPE: DNA
<213> ORGANISM: Artificial Sequence
<220> FEATURE:
<223> OTHER INFORMATION: Synthetic DNA

<400> SEQUENCE: 430
gttagaactg ctccagcaag atgcccacct ggatcgtgtg tttgtgccgg taggtg 56

<210> SEQ ID NO 431
<211> LENGTH: 54
<212> TYPE: DNA
<213> ORGANISM: Artificial Sequence
<220> FEATURE:
<223> OTHER INFORMATION: Synthetic DNA

<400> SEQUENCE: 431
ctgcgactcc tgcagcaagg cctcctccac ctaccggcac aaacacacga tcca 54

<210> SEQ ID NO 432
<211> LENGTH: 60
<212> TYPE: DNA
<213> ORGANISM: Artificial Sequence
<220> FEATURE:
<223> OTHER INFORMATION: Synthetic DNA

<400> SEQUENCE: 432
gaggaggcct tgctgcagga gtcgcagtgc tgatcaaaca gttgatgccg cagatcaagg 60

<210> SEQ ID NO 433
<211> LENGTH: 60
<212> TYPE: DNA
<213> ORGANISM: Artificial Sequence
<220> FEATURE:
<223> OTHER INFORMATION: Synthetic DNA

<400> SEQUENCE: 433
cgctatcctc ggcttccacg gcaataacct tgatctgcgg catcaactgt ttgatcagca 60

<210> SEQ ID NO 434
<211> LENGTH: 60
<212> TYPE: DNA
<213> ORGANISM: Artificial Sequence -continued
<220> FEATURE:
<223> OTHER INFORMATION: Synthetic DNA

<400> SEQUENCE: 434
ttattgccgt ggaagccgag gatagcgcct gtctgaaagc ggcgttagat gctggtcatc 60

<210> SEQ ID NO 435
<211> LENGTH: 60
<212> TYPE: DNA
<213> ORGANISM: Artificial Sequence
<220> FEATURE:
<223> OTHER INFORMATION: Synthetic DNA

<400> SEQUENCE: 435
acaggcctac acgtggcaga tcgaccggat gaccagcatc taacgccgct ttcagacagg 60

<210> SEQ ID NO 436
<211> LENGTH: 60
<212> TYPE: DNA
<213> ORGANISM: Artificial Sequence
<220> FEATURE:
<223> OTHER INFORMATION: Synthetic DNA

<400> SEQUENCE: 436
cggtcgatct gccacgtgta ggcctgtttg cggaaggtgt agcggtgaag cgtattggcg 60

<210> SEQ ID NO 437
<211> LENGTH: 60
<212> TYPE: DNA
<213> ORGANISM: Artificial Sequence
<220> FEATURE:
<223> OTHER INFORMATION: Synthetic DNA

<400> SEQUENCE: 437
attcctggca cagccgaaag gtttcgtcgc caatacgctt caccgctaca ccttccgcaa 60

<210> SEQ ID NO 438
<211> LENGTH: 59
<212> TYPE: DNA
<213> ORGANISM: Artificial Sequence
<220> FEATURE:
<223> OTHER INFORMATION: Synthetic DNA

<400> SEQUENCE: 438
acgaaacctt tcggctgtgc caggaatatc tcgacgacat catcaccgtt gacagcgat 59

<210> SEQ ID NO 439
<211> LENGTH: 60
<212> TYPE: DNA
<213> ORGANISM: Artificial Sequence
<220> FEATURE:
<223> OTHER INFORMATION: Synthetic DNA

<400> SEQUENCE: 439
acaggtcttt catcgcggca caaatcgcat cgctgtcaac ggtgatgatg tcgtcgagat 60

<210> SEQ ID NO 440
<211> LENGTH: 60
<212> TYPE: DNA
<213> ORGANISM: Artificial Sequence
<220> FEATURE:
<223> OTHER INFORMATION: Synthetic DNA

<400> SEQUENCE: 440
gcgatttgtg ccgcgatgaa agacctgttc gaagatgtgc gtgcggtagc tgaaccaagt 60

-continued

<210> SEQ ID NO 441
<211> LENGTH: 60
<212> TYPE: DNA
<213> ORGANISM: Artificial Sequence
<220> FEATURE:
<223> OTHER INFORMATION: Synthetic DNA

<400> SEQUENCE: 441
ttttcatgcc ggccaacgct aatgcaccac ttggttcagc taccgcacgc acatcttcga 60

<210> SEQ ID NO 442
<211> LENGTH: 60
<212> TYPE: DNA
<213> ORGANISM: Artificial Sequence
<220> FEATURE:
<223> OTHER INFORMATION: Synthetic DNA

<400> SEQUENCE: 442
ggtgcattag cgttggccgg catgaaaaag tacattgcct tgcacaacat tcgtggcgaa 60

<210> SEQ ID NO 443
<211> LENGTH: 60
<212> TYPE: DNA
<213> ORGANISM: Artificial Sequence
<220> FEATURE:
<223> OTHER INFORMATION: Synthetic DNA

<400> SEQUENCE: 443
tggctccact caggatatgg gccaggcgtt cgccacgaat gttgtgcaag gcaatgtact 60

<210> SEQ ID NO 444
<211> LENGTH: 55
<212> TYPE: DNA
<213> ORGANISM: Artificial Sequence
<220> FEATURE:
<223> OTHER INFORMATION: Synthetic DNA

<400> SEQUENCE: 444
cgcctggccc atatcctgag tggagccaac gtcaacttcc atggcctgcg ttacg 55

<210> SEQ ID NO 445
<211> LENGTH: 54
<212> TYPE: DNA
<213> ORGANISM: Artificial Sequence
<220> FEATURE:
<223> OTHER INFORMATION: Synthetic DNA

<400> SEQUENCE: 445
gctcgcccag ttcacaccgt tcgctaacgt aacgcaggcc atggaagttg acgt 54

<210> SEQ ID NO 446
<211> LENGTH: 54
<212> TYPE: DNA
<213> ORGANISM: Artificial Sequence
<220> FEATURE:
<223> OTHER INFORMATION: Synthetic DNA

<400> SEQUENCE: 446
ttagcgaacg gtgtgaactg ggcgagcaac gtgaagcgct cctggccgtt acca 54

<210> SEQ ID NO 447
<211> LENGTH: 54
<212> TYPE: DNA
<213> ORGANISM: Artificial Sequence
<220> FEATURE:
<223> OTHER INFORMATION: Synthetic DNA -continued

<400> SEQUENCE: 447
tcagaaagct gcccttctcc tctgggatgg taacggccag gagcgcttca cgtt 54

<210> SEQ ID NO 448
<211> LENGTH: 54
<212> TYPE: DNA
<213> ORGANISM: Artificial Sequence
<220> FEATURE:
<223> OTHER INFORMATION: Synthetic DNA

<400> SEQUENCE: 448
tcccagagga gaagggcagc tttctgaaat tttgccagct gttagggggc cgta 54

<210> SEQ ID NO 449
<211> LENGTH: 59
<212> TYPE: DNA
<213> ORGANISM: Artificial Sequence
<220> FEATURE:
<223> OTHER INFORMATION: Synthetic DNA

<400> SEQUENCE: 449
atcggcaaag cggtagttga attcggtgac gctacggccc cctaacagct ggcaaaatt 59

<210> SEQ ID NO 450
<211> LENGTH: 60
<212> TYPE: DNA
<213> ORGANISM: Artificial Sequence
<220> FEATURE:
<223> OTHER INFORMATION: Synthetic DNA

<400> SEQUENCE: 450
gcgtcaccga attcaactac cgctttgccg atgcgaaaaa tgcgtgcatt ttcgtgggcg 60

<210> SEQ ID NO 451
<211> LENGTH: 55
<212> TYPE: DNA
<213> ORGANISM: Artificial Sequence
<220> FEATURE:
<223> OTHER INFORMATION: Synthetic DNA

<400> SEQUENCE: 451
gctcttccag gccacgggac agacggacgc ccacgaaaat gcacgcattt ttcgc 55

<210> SEQ ID NO 452
<211> LENGTH: 59
<212> TYPE: DNA
<213> ORGANISM: Artificial Sequence
<220> FEATURE:
<223> OTHER INFORMATION: Synthetic DNA

<400> SEQUENCE: 452
tccgtctgtc ccgtggcctg gaagagcgca aggagattct gcagatgctg aacgatggt 59

<210> SEQ ID NO 453
<211> LENGTH: 60
<212> TYPE: DNA
<213> ORGANISM: Artificial Sequence
<220> FEATURE:
<223> OTHER INFORMATION: Synthetic DNA

<400> SEQUENCE: 453
cgtcgctgag atccaccacg gaataaccac catcgttcag catctgcaga atctccttgc 60

<210> SEQ ID NO 454

-continued

<211> LENGTH: 55
<212> TYPE: DNA
<213> ORGANISM: Artificial Sequence
<220> FEATURE:
<223> OTHER INFORMATION: Synthetic DNA

<400> SEQUENCE: 454
ggttattccg tggtggatct cagcgacgat gaaatggcca agctgcatgt gcgct 55

<210> SEQ ID NO 455
<211> LENGTH: 54
<212> TYPE: DNA
<213> ORGANISM: Artificial Sequence
<220> FEATURE:
<223> OTHER INFORMATION: Synthetic DNA

<400> SEQUENCE: 455
ggtgactcgg acgacccccc accatatagc gcacatgcag cttggccatt tcat 54

<210> SEQ ID NO 456
<211> LENGTH: 55
<212> TYPE: DNA
<213> ORGANISM: Artificial Sequence
<220> FEATURE:
<223> OTHER INFORMATION: Synthetic DNA

<400> SEQUENCE: 456
atatggtggg gggtcgtccg agtcacccgt tgcaggaacg cttgtacagc ttcga 55

<210> SEQ ID NO 457
<211> LENGTH: 55
<212> TYPE: DNA
<213> ORGANISM: Artificial Sequence
<220> FEATURE:
<223> OTHER INFORMATION: Synthetic DNA

<400> SEQUENCE: 457
aacagtgcac caggagactc cggaaactcg aagctgtaca agcgttcctg caacg 55

<210> SEQ ID NO 458
<211> LENGTH: 54
<212> TYPE: DNA
<213> ORGANISM: Artificial Sequence
<220> FEATURE:
<223> OTHER INFORMATION: Synthetic DNA

<400> SEQUENCE: 458
gtttccggag tctcctggtg cactgttacg cttcctgaac accctgggga cgta 54

<210> SEQ ID NO 459
<211> LENGTH: 59
<212> TYPE: DNA
<213> ORGANISM: Artificial Sequence
<220> FEATURE:
<223> OTHER INFORMATION: Synthetic DNA

<400> SEQUENCE: 459
gggagcgata gtgaaacagg ctgatgttcc agtacgtccc cagggtgttc aggaagcgt 59

<210> SEQ ID NO 460
<211> LENGTH: 59
<212> TYPE: DNA
<213> ORGANISM: Artificial Sequence
<220> FEATURE:
<223> OTHER INFORMATION: Synthetic DNA

<400> SEQUENCE: 460

-continued ctggaacatc agcctgtttc actatcgctc ccatggtact gactacggtc gggtcctgg 59

<210> SEQ ID NO 461
<211> LENGTH: 54
<212> TYPE: DNA
<213> ORGANISM: Artificial Sequence
<220> FEATURE:
<223> OTHER INFORMATION: Synthetic DNA

<400> SEQUENCE: 461
gttcgtggtc ccccagttca aacgcagcca ggacccgacc gtagtcagta ccat 54

<210> SEQ ID NO 462
<211> LENGTH: 55
<212> TYPE: DNA
<213> ORGANISM: Artificial Sequence
<220> FEATURE:
<223> OTHER INFORMATION: Synthetic DNA

<400> SEQUENCE: 462
ctgcgtttga actgggggac cacgaaccgg acttcgaaac ccgcctgaac gaatt 55

<210> SEQ ID NO 463
<211> LENGTH: 59
<212> TYPE: DNA
<213> ORGANISM: Artificial Sequence
<220> FEATURE:
<223> OTHER INFORMATION: Synthetic DNA

<400> SEQUENCE: 463
gttgttggtt tcgtcatggc agtcgtagcc taattcgttc aggcgggttt cgaagtccg 59

<210> SEQ ID NO 464
<211> LENGTH: 58
<212> TYPE: DNA
<213> ORGANISM: Artificial Sequence
<220> FEATURE:
<223> OTHER INFORMATION: Synthetic DNA

<400> SEQUENCE: 464
aggctacgac tgccatgacg aaaccaacaa cccggcgttt cgctttttc tggcaggg 58

<210> SEQ ID NO 465
<211> LENGTH: 27
<212> TYPE: DNA
<213> ORGANISM: Artificial Sequence
<220> FEATURE:
<223> OTHER INFORMATION: Synthetic DNA

<400> SEQUENCE: 465
ccctgccaga aaaaagcgaa acgccgg 27

<210> SEQ ID NO 466
<211> LENGTH: 42
<212> TYPE: DNA
<213> ORGANISM: Artificial Sequence
<220> FEATURE:
<223> OTHER INFORMATION: Synthetic DNA

<400> SEQUENCE: 466
gcggcagcca tattaccctg ccagaaaaaa gcgaaacgcc gg 42

<210> SEQ ID NO 467
<211> LENGTH: 15
<212> TYPE: DNA

-continued

<213> ORGANISM: Artificial Sequence
<220> FEATURE:
<223> OTHER INFORMATION: Synthetic DNA

<400> SEQUENCE: 467
taatatggct gccgc 15

<210> SEQ ID NO 468
<211> LENGTH: 57
<212> TYPE: DNA
<213> ORGANISM: Artificial Sequence
<220> FEATURE:
<223> OTHER INFORMATION: Synthetic DNA

<400> SEQUENCE: 468
ttaagcgtaa tccggaacat cgtatgggta ccctgccaga aaaaagcgaa acgccgg 57

<210> SEQ ID NO 469
<211> LENGTH: 30
<212> TYPE: DNA
<213> ORGANISM: Artificial Sequence
<220> FEATURE:
<223> OTHER INFORMATION: Synthetic DNA

<400> SEQUENCE: 469
tacccatacg atgttccgga ttacgcttaa 30

<210> SEQ ID NO 470
<211> LENGTH: 31
<212> TYPE: DNA
<213> ORGANISM: Artificial Sequence
<220> FEATURE:
<223> OTHER INFORMATION: Synthetic DNA

<400> SEQUENCE: 470
ctatatctag catatgtcat tcatggacca g 31

<210> SEQ ID NO 471
<211> LENGTH: 36
<212> TYPE: DNA
<213> ORGANISM: Artificial Sequence
<220> FEATURE:
<223> OTHER INFORMATION: Synthetic DNA

<400> SEQUENCE: 471
atgtcattca tggaccagat tccgggcggg ggtaac 36

<210> SEQ ID NO 472
<211> LENGTH: 47
<212> TYPE: DNA
<213> ORGANISM: Artificial Sequence
<220> FEATURE:
<223> OTHER INFORMATION: Synthetic DNA

<400> SEQUENCE: 472
gcaaacattc tactggcaat ttaggatagt tacccccgcc cggaatc 47

<210> SEQ ID NO 473
<211> LENGTH: 46
<212> TYPE: DNA
<213> ORGANISM: Artificial Sequence
<220> FEATURE:
<223> OTHER INFORMATION: Synthetic DNA

<400> SEQUENCE: 473
gccagtagaa tgtttgccga attttcccat tcaaccaagt ctgacc 46

-continued

<210> SEQ ID NO 474
<211> LENGTH: 47
<212> TYPE: DNA
<213> ORGANISM: Artificial Sequence
<220> FEATURE:
<223> OTHER INFORMATION: Synthetic DNA

<400> SEQUENCE: 474
gtttgtggct atcgtttctc ccgcgaaagg tcagacttgg ttgaatg 47

<210> SEQ ID NO 475
<211> LENGTH: 50
<212> TYPE: DNA
<213> ORGANISM: Artificial Sequence
<220> FEATURE:
<223> OTHER INFORMATION: Synthetic DNA

<400> SEQUENCE: 475
gaaacgatag ccacaaactg aagaatttca ttagcgagat tatgctcaac 50

<210> SEQ ID NO 476
<211> LENGTH: 50
<212> TYPE: DNA
<213> ORGANISM: Artificial Sequence
<220> FEATURE:
<223> OTHER INFORMATION: Synthetic DNA

<400> SEQUENCE: 476
catcgttagg ccaagagatc atcgacatgt tgagcataat ctcgctaatg 50

<210> SEQ ID NO 477
<211> LENGTH: 50
<212> TYPE: DNA
<213> ORGANISM: Artificial Sequence
<220> FEATURE:
<223> OTHER INFORMATION: Synthetic DNA

<400> SEQUENCE: 477
ctcttggcct aacgatgcgt ctagaattgt gtactgccgt cgtcatttac 50

<210> SEQ ID NO 478
<211> LENGTH: 50
<212> TYPE: DNA
<213> ORGANISM: Artificial Sequence
<220> FEATURE:
<223> OTHER INFORMATION: Synthetic DNA

<400> SEQUENCE: 478
caaagtcatt agcccactga gcagctggat taagtaaatg acgacggcag 50

<210> SEQ ID NO 479
<211> LENGTH: 50
<212> TYPE: DNA
<213> ORGANISM: Artificial Sequence
<220> FEATURE:
<223> OTHER INFORMATION: Synthetic DNA

<400> SEQUENCE: 479
gtgggctaat gactttgtgc aagaacaggg tattctcgag attacgttcg 50

<210> SEQ ID NO 480
<211> LENGTH: 48
<212> TYPE: DNA
<213> ORGANISM: Artificial Sequence
<220> FEATURE:

-continued

<223> OTHER INFORMATION: Synthetic DNA

<400> SEQUENCE: 480
gttgatacag cccctggata aatgtatcga acgtaatctc gagaatac 48

<210> SEQ ID NO 481
<211> LENGTH: 48
<212> TYPE: DNA
<213> ORGANISM: Artificial Sequence
<220> FEATURE:
<223> OTHER INFORMATION: Synthetic DNA

<400> SEQUENCE: 481
gtattctcga gattacgttc gatacattta tccaggggct gtatcaac 48

<210> SEQ ID NO 482
<211> LENGTH: 49
<212> TYPE: DNA
<213> ORGANISM: Artificial Sequence
<220> FEATURE:
<223> OTHER INFORMATION: Synthetic DNA

<400> SEQUENCE: 482
gattttattg atatcaggcg gtttataaaa gtgttgatac agcccctgg 49

<210> SEQ ID NO 483
<211> LENGTH: 50
<212> TYPE: DNA
<213> ORGANISM: Artificial Sequence
<220> FEATURE:
<223> OTHER INFORMATION: Synthetic DNA

<400> SEQUENCE: 483
ccgcctgata tcaataaaat ctttaacgcc atcacgcagc tgtccgaggc 50

<210> SEQ ID NO 484
<211> LENGTH: 49
<212> TYPE: DNA
<213> ORGANISM: Artificial Sequence
<220> FEATURE:
<223> OTHER INFORMATION: Synthetic DNA

<400> SEQUENCE: 484
ccgttgattc agacgttcaa tgcctaattt tgcctcggac agctgcgtg 49

<210> SEQ ID NO 485
<211> LENGTH: 49
<212> TYPE: DNA
<213> ORGANISM: Artificial Sequence
<220> FEATURE:
<223> OTHER INFORMATION: Synthetic DNA

<400> SEQUENCE: 485
gaacgtctga atcaacggtt tcggaaaatt tgggatcgca tgccaccag 49

<210> SEQ ID NO 486
<211> LENGTH: 46
<212> TYPE: DNA
<213> ORGANISM: Artificial Sequence
<220> FEATURE:
<223> OTHER INFORMATION: Synthetic DNA

<400> SEQUENCE: 486
cataattgcg gccttttctg tcatgaaatc tggtggcatg cgatcc 46

-continued

<210> SEQ ID NO 487
<211> LENGTH: 48
<212> TYPE: DNA
<213> ORGANISM: Artificial Sequence
<220> FEATURE:
<223> OTHER INFORMATION: Synthetic DNA

<400> SEQUENCE: 487
gaaaaggccg caattatgac gtatacccgg ttactgacga aagagacc 48

<210> SEQ ID NO 488
<211> LENGTH: 49
<212> TYPE: DNA
<213> ORGANISM: Artificial Sequence
<220> FEATURE:
<223> OTHER INFORMATION: Synthetic DNA

<400> SEQUENCE: 488
ctccggctta tgcatacgta caatattata ggtctctttc gtcagtaac 49

<210> SEQ ID NO 489
<211> LENGTH: 50
<212> TYPE: DNA
<213> ORGANISM: Artificial Sequence
<220> FEATURE:
<223> OTHER INFORMATION: Synthetic DNA

<400> SEQUENCE: 489
gtatgcataa gccggagacc ctgaaagatg cgatggagga agcctaccag 50

<210> SEQ ID NO 490
<211> LENGTH: 50
<212> TYPE: DNA
<213> ORGANISM: Artificial Sequence
<220> FEATURE:
<223> OTHER INFORMATION: Synthetic DNA

<400> SEQUENCE: 490
cagggaagaa tcgttcggta agggcagtgg tctggtaggc ttcctccatc 50

<210> SEQ ID NO 491
<211> LENGTH: 50
<212> TYPE: DNA
<213> ORGANISM: Artificial Sequence
<220> FEATURE:
<223> OTHER INFORMATION: Synthetic DNA

<400> SEQUENCE: 491
gatggaggaa gcctaccaga ccactgccct taccgaacga ttcttccctg 50

<210> SEQ ID NO 492
<211> LENGTH: 49
<212> TYPE: DNA
<213> ORGANISM: Artificial Sequence
<220> FEATURE:
<223> OTHER INFORMATION: Synthetic DNA

<400> SEQUENCE: 492
gatggtatct ccgtccgcgt ccagttcaaa gccagggaag aatcgttcg 49

<210> SEQ ID NO 493
<211> LENGTH: 50
<212> TYPE: DNA
<213> ORGANISM: Artificial Sequence
<220> FEATURE:
<223> OTHER INFORMATION: Synthetic DNA

<400> SEQUENCE: 493
cggacggaga taccatcata ggcgcaacca ctcacttgca ggaagagtac 50

<210> SEQ ID NO 494
<211> LENGTH: 50
<212> TYPE: DNA
<213> ORGANISM: Artificial Sequence
<220> FEATURE:
<223> OTHER INFORMATION: Synthetic DNA

<400> SEQUENCE: 494
caggttatct tccgaatcgt aatcagaatc gtactcttcc tgcaagtgag 50

<210> SEQ ID NO 495
<211> LENGTH: 49
<212> TYPE: DNA
<213> ORGANISM: Artificial Sequence
<220> FEATURE:
<223> OTHER INFORMATION: Synthetic DNA

<400> SEQUENCE: 495
cgattcggaa gataacctga cccaaaatgg ctacgttcac actgttagg 49

<210> SEQ ID NO 496
<211> LENGTH: 49
<212> TYPE: DNA
<213> ORGANISM: Artificial Sequence
<220> FEATURE:
<223> OTHER INFORMATION: Synthetic DNA

<400> SEQUENCE: 496
gctcatgggc ttattgtatg aacgacgggt cctaacagtg tgaacgtag 49

<210> SEQ ID NO 497
<211> LENGTH: 50
<212> TYPE: DNA
<213> ORGANISM: Artificial Sequence
<220> FEATURE:
<223> OTHER INFORMATION: Synthetic DNA

<400> SEQUENCE: 497
catacaataa gcccatgagc aaccatcgga accgcagaaa caacaacccg 50

<210> SEQ ID NO 498
<211> LENGTH: 50
<212> TYPE: DNA
<213> ORGANISM: Artificial Sequence
<220> FEATURE:
<223> OTHER INFORMATION: Synthetic DNA

<400> SEQUENCE: 498
gcacagacgg tttttgatgc attcttctcg gctcgggttg ttgtttctgc 50

<210> SEQ ID NO 499
<211> LENGTH: 49
<212> TYPE: DNA
<213> ORGANISM: Artificial Sequence
<220> FEATURE:
<223> OTHER INFORMATION: Synthetic DNA

<400> SEQUENCE: 499
catcaaaaac cgtctgtgct tttattgtaa gaaagaaggc catcgactg 49

<210> SEQ ID NO 500
<211> LENGTH: 48

-continued

<212> TYPE: DNA
<213> ORGANISM: Artificial Sequence
<220> FEATURE:
<223> OTHER INFORMATION: Synthetic DNA

<400> SEQUENCE: 500
gagcttgctt tacgggcacg gcattcattc agtcgatggc cttctttc 48

<210> SEQ ID NO 501
<211> LENGTH: 27
<212> TYPE: DNA
<213> ORGANISM: Artificial Sequence
<220> FEATURE:
<223> OTHER INFORMATION: Synthetic DNA

<400> SEQUENCE: 501
gcccgtaaag caagctctaa ccgtagc 27

<210> SEQ ID NO 502
<211> LENGTH: 17
<212> TYPE: DNA
<213> ORGANISM: Artificial Sequence
<220> FEATURE:
<223> OTHER INFORMATION: Synthetic DNA

<400> SEQUENCE: 502
gctacggtta gagcttg 17

<210> SEQ ID NO 503
<211> LENGTH: 34
<212> TYPE: DNA
<213> ORGANISM: Artificial Sequence
<220> FEATURE:
<223> OTHER INFORMATION: Synthetic DNA

<400> SEQUENCE: 503
gtattggatc cttattagct acggttagag cttg 34

<210> SEQ ID NO 504
<211> LENGTH: 1641
<212> TYPE: DNA
<213> ORGANISM: Artificial Sequence
<220> FEATURE:
<223> OTHER INFORMATION: Synthetic DNA

<400> SEQUENCE: 504
ctatatctag catatgacca tcaccccgga aacctctcgc ccgatcgaca ccgaatcttg 60
gaaatcttac tacaaatccg acccgctgtg ctctgctgtt ctgatccaca tgaaagaact 120
gacccagcac aacgttaccc cagaagacat gtccgctttc cgctcctatc agaaaaagct 180
ggaactgtct gagaccttcc gtaaaaacta ctccctggag gacgaaatga tctactacca 240
agatcgcctg gttgtaccga ttaaacaaca aaatgctgtc atgcgtctgt atcacgatca 300
cactctgttt ggtggtcact ttggcgtaac cgttaccctg gcgaaaatct ctccgatcta 360
ctattggccg aaactgcagc actctatcat ccagtacatc cgtacctgcg ttcagtgcca 420
gctgatcaaa tctcaccgcc cacgtctgca tggtctcctg caaccgctcc cgatcgctga 480
aggtcgttgg ctggacatct ctatggactt cgttactggt ttgccgccga cctctaacaa 540
cctgaacatg atcctggtgg tggtggaccg cttctctaaa cgtgctcact tcatcgctac 600
ccgaaaaacc ctggacgcga ctcagctgat cgacctgctc ttccgttaca tcttctctta 660
ccatggcttc ccgcgtacca tcacctctga ccgtgacgtt cgtatgactg cggacaaata 720

-continued

```
ccaagaactg accaaacgtc tgggtatcaa atctaccatg tcttccgcta accacccgca    780

gactgatggt caatccgagc gtaccattca gaccctgaac cgtctcctgc gtgcgtatgc    840

gtctaccaac atccagaact ggcacgttta ccttccgcaa attgaattcg tttacaactc    900

cactccgact cgtactctgg gtaaatctcc gttcgaaatc gacctgggtt acctgccaaa    960

cactccggcg atcaaatctg acgatgaagt taacgctcgt tccttcaccg ctgttgaact   1020

ggctaaacac ctgaaggcgc tgaccatcca gaccaaagaa cagctggaac acgcgcagat   1080

cgaaatggaa accaacaaca accagcgtcg caaaccactg ctgttgaata ttggtgatca   1140

tgttctggta caccgtgatg cctacttcaa aaaaggtgcg tacatgaaag ttcagcagat   1200

ctacgttggt ccattccgtg tcgttaagaa aatcaatgac aacgcgtatg aactggacct   1260

gaactcgcat aagaagaagc accgtgtgat caacgttcag tttctgaaaa aatttgttta   1320

ccgtccggat gcgtacccga aaaacaaacc gatctcttct accgaacgca tcaaacgagc   1380

tcacgaagtt accgcgctga tcggcatcga caccacccac aaaacctatc tgtgccacat   1440

gcaggacgtt gacccgaccc tgtccgttga atactccgaa gctgaattct gccagatccc   1500

agagcgtacc cgtcgttcta tcctggcgaa cttccgtcag ctgtacgaaa cccaagacaa   1560

ccctgaacgt gaagaagatg ttgtttccca gaacgaaatc tgccagtacg acaacacctc   1620

tccgtaataa ggatccaata c                                              1641
```

```
<210> SEQ ID NO 505
<211> LENGTH: 46
<212> TYPE: DNA
<213> ORGANISM: Artificial Sequence
<220> FEATURE:
<223> OTHER INFORMATION: Synthetic DNA

<400> SEQUENCE: 505

ctatatctag catatgacca tcaccccgga aacctctcgc ccgatc                     46


<210> SEQ ID NO 506
<211> LENGTH: 25
<212> TYPE: DNA
<213> ORGANISM: Artificial Sequence
<220> FEATURE:
<223> OTHER INFORMATION: Synthetic DNA

<400> SEQUENCE: 506

accatcaccc cggaaacctc tcgcc                                            25


<210> SEQ ID NO 507
<211> LENGTH: 50
<212> TYPE: DNA
<213> ORGANISM: Artificial Sequence
<220> FEATURE:
<223> OTHER INFORMATION: Synthetic DNA

<400> SEQUENCE: 507

accatcaccc cggaaacctc tcgcccgatc gacaccgaat cttggaaatc                 50


<210> SEQ ID NO 508
<211> LENGTH: 50
<212> TYPE: DNA
<213> ORGANISM: Artificial Sequence
<220> FEATURE:
<223> OTHER INFORMATION: Synthetic DNA

<400> SEQUENCE: 508

cgatcgacac cgaatcttgg aaatcttact acaaatccga cccgctgtgc                 50
```

-continued

<210> SEQ ID NO 509
<211> LENGTH: 50
<212> TYPE: DNA
<213> ORGANISM: Artificial Sequence
<220> FEATURE:
<223> OTHER INFORMATION: Synthetic DNA

<400> SEQUENCE: 509
ttactacaaa tccgacccgc tgtgctctgc tgttctgatc cacatgaaag 50

<210> SEQ ID NO 510
<211> LENGTH: 49
<212> TYPE: DNA
<213> ORGANISM: Artificial Sequence
<220> FEATURE:
<223> OTHER INFORMATION: Synthetic DNA

<400> SEQUENCE: 510
tctgctgttc tgatccacat gaaagaactg acccagcaca acgttaccc 49

<210> SEQ ID NO 511
<211> LENGTH: 45
<212> TYPE: DNA
<213> ORGANISM: Artificial Sequence
<220> FEATURE:
<223> OTHER INFORMATION: Synthetic DNA

<400> SEQUENCE: 511
aactgaccca gcacaacgtt accccagaag acatgtccgc tttcc 45

<210> SEQ ID NO 512
<211> LENGTH: 46
<212> TYPE: DNA
<213> ORGANISM: Artificial Sequence
<220> FEATURE:
<223> OTHER INFORMATION: Synthetic DNA

<400> SEQUENCE: 512
cagaagacat gtccgctttc cgctcctatc agaaaaagct ggaact 46

<210> SEQ ID NO 513
<211> LENGTH: 48
<212> TYPE: DNA
<213> ORGANISM: Artificial Sequence
<220> FEATURE:
<223> OTHER INFORMATION: Synthetic DNA

<400> SEQUENCE: 513
gctcctatca gaaaaagctg gaactgtctg agaccttccg taaaaact 48

<210> SEQ ID NO 514
<211> LENGTH: 48
<212> TYPE: DNA
<213> ORGANISM: Artificial Sequence
<220> FEATURE:
<223> OTHER INFORMATION: Synthetic DNA

<400> SEQUENCE: 514
gctcctatca gaaaaagctg gaactgtctg agaccttccg taaaaact 48

<210> SEQ ID NO 515
<211> LENGTH: 50
<212> TYPE: DNA
<213> ORGANISM: Artificial Sequence
<220> FEATURE:

-continued

<223> OTHER INFORMATION: Synthetic DNA

<400> SEQUENCE: 515
gtctgagacc ttccgtaaaa actactccct ggaggacgaa atgatctact 50

<210> SEQ ID NO 516
<211> LENGTH: 50
<212> TYPE: DNA
<213> ORGANISM: Artificial Sequence
<220> FEATURE:
<223> OTHER INFORMATION: Synthetic DNA

<400> SEQUENCE: 516
actccctgga ggacgaaatg atctactacc aagatcgcct ggttgtaccg 50

<210> SEQ ID NO 517
<211> LENGTH: 49
<212> TYPE: DNA
<213> ORGANISM: Artificial Sequence
<220> FEATURE:
<223> OTHER INFORMATION: Synthetic DNA

<400> SEQUENCE: 517
accaagatcg cctggttgta ccgattaaac aacaaaatgc tgtcatgcg 49

<210> SEQ ID NO 518
<211> LENGTH: 50
<212> TYPE: DNA
<213> ORGANISM: Artificial Sequence
<220> FEATURE:
<223> OTHER INFORMATION: Synthetic DNA

<400> SEQUENCE: 518
attaaacaac aaaatgctgt catgcgtctg tatcacgatc acactctgtt 50

<210> SEQ ID NO 519
<211> LENGTH: 50
<212> TYPE: DNA
<213> ORGANISM: Artificial Sequence
<220> FEATURE:
<223> OTHER INFORMATION: Synthetic DNA

<400> SEQUENCE: 519
tctgtatcac gatcacactc tgtttggtgg tcactttggc gtaaccgtta 50

<210> SEQ ID NO 520
<211> LENGTH: 50
<212> TYPE: DNA
<213> ORGANISM: Artificial Sequence
<220> FEATURE:
<223> OTHER INFORMATION: Synthetic DNA

<400> SEQUENCE: 520
tggtggtcac tttggcgtaa ccgttaccct ggcgaaaatc tctccgatct 50

<210> SEQ ID NO 521
<211> LENGTH: 50
<212> TYPE: DNA
<213> ORGANISM: Artificial Sequence
<220> FEATURE:
<223> OTHER INFORMATION: Synthetic DNA

<400> SEQUENCE: 521
ccctggcgaa aatctctccg atctactatt ggccgaaact gcagcactct 50

-continued

<210> SEQ ID NO 522
<211> LENGTH: 50
<212> TYPE: DNA
<213> ORGANISM: Artificial Sequence
<220> FEATURE:
<223> OTHER INFORMATION: Synthetic DNA

<400> SEQUENCE: 522
ccctggcgaa aatctctccg atctactatt ggccgaaact gcagcactct 50

<210> SEQ ID NO 523
<211> LENGTH: 50
<212> TYPE: DNA
<213> ORGANISM: Artificial Sequence
<220> FEATURE:
<223> OTHER INFORMATION: Synthetic DNA

<400> SEQUENCE: 523
actattggcc gaaactgcag cactctatca tccagtacat ccgtacctgc 50

<210> SEQ ID NO 524
<211> LENGTH: 50
<212> TYPE: DNA
<213> ORGANISM: Artificial Sequence
<220> FEATURE:
<223> OTHER INFORMATION: Synthetic DNA

<400> SEQUENCE: 524
atcatccagt acatccgtac ctgcgttcag tgccagctga tcaaatctca 50

<210> SEQ ID NO 525
<211> LENGTH: 50
<212> TYPE: DNA
<213> ORGANISM: Artificial Sequence
<220> FEATURE:
<223> OTHER INFORMATION: Synthetic DNA

<400> SEQUENCE: 525
gttcagtgcc agctgatcaa atctcaccgc ccacgtctgc atggtctcct 50

<210> SEQ ID NO 526
<211> LENGTH: 50
<212> TYPE: DNA
<213> ORGANISM: Artificial Sequence
<220> FEATURE:
<223> OTHER INFORMATION: Synthetic DNA

<400> SEQUENCE: 526
ccgcccacgt ctgcatggtc tcctgcaacc gctcccgatc gctgaaggtc 50

<210> SEQ ID NO 527
<211> LENGTH: 50
<212> TYPE: DNA
<213> ORGANISM: Artificial Sequence
<220> FEATURE:
<223> OTHER INFORMATION: Synthetic DNA

<400> SEQUENCE: 527
gcaaccgctc ccgatcgctg aaggtcgttg gctggacatc tctatggact 50

<210> SEQ ID NO 528
<211> LENGTH: 47
<212> TYPE: DNA
<213> ORGANISM: Artificial Sequence
<220> FEATURE:
<223> OTHER INFORMATION: Synthetic DNA -continued

<400> SEQUENCE: 528
gttggctgga catctctatg gacttcgtta ctggtttgcc gccgacc 47

<210> SEQ ID NO 529
<211> LENGTH: 50
<212> TYPE: DNA
<213> ORGANISM: Artificial Sequence
<220> FEATURE:
<223> OTHER INFORMATION: Synthetic DNA

<400> SEQUENCE: 529
tcgttactgg tttgccgccg acctctaaca acctgaacat gatcctggtg 50

<210> SEQ ID NO 530
<211> LENGTH: 50
<212> TYPE: DNA
<213> ORGANISM: Artificial Sequence
<220> FEATURE:
<223> OTHER INFORMATION: Synthetic DNA

<400> SEQUENCE: 530
tcgttactgg tttgccgccg acctctaaca acctgaacat gatcctggtg 50

<210> SEQ ID NO 531
<211> LENGTH: 50
<212> TYPE: DNA
<213> ORGANISM: Artificial Sequence
<220> FEATURE:
<223> OTHER INFORMATION: Synthetic DNA

<400> SEQUENCE: 531
tctaacaacc tgaacatgat cctggtggtg gtggaccgct tctctaaacg 50

<210> SEQ ID NO 532
<211> LENGTH: 50
<212> TYPE: DNA
<213> ORGANISM: Artificial Sequence
<220> FEATURE:
<223> OTHER INFORMATION: Synthetic DNA

<400> SEQUENCE: 532
gtggtggacc gcttctctaa acgtgctcac ttcatcgcta cccgaaaaac 50

<210> SEQ ID NO 533
<211> LENGTH: 50
<212> TYPE: DNA
<213> ORGANISM: Artificial Sequence
<220> FEATURE:
<223> OTHER INFORMATION: Synthetic DNA

<400> SEQUENCE: 533
tgctcacttc atcgctaccc gaaaaaccct ggacgcgact cagctgatcg 50

<210> SEQ ID NO 534
<211> LENGTH: 50
<212> TYPE: DNA
<213> ORGANISM: Artificial Sequence
<220> FEATURE:
<223> OTHER INFORMATION: Synthetic DNA

<400> SEQUENCE: 534
cctggacgcg actcagctga tcgacctgct cttccgttac atcttctctt 50

<210> SEQ ID NO 535
<211> LENGTH: 50

-continued

<212> TYPE: DNA
<213> ORGANISM: Artificial Sequence
<220> FEATURE:
<223> OTHER INFORMATION: Synthetic DNA

<400> SEQUENCE: 535
acctgctctt ccgttacatc ttctcttacc atggcttccc gcgtaccatc 50

<210> SEQ ID NO 536
<211> LENGTH: 50
<212> TYPE: DNA
<213> ORGANISM: Artificial Sequence
<220> FEATURE:
<223> OTHER INFORMATION: Synthetic DNA

<400> SEQUENCE: 536
accatggctt cccgcgtacc atcacctctg accgtgacgt tcgtatgact 50

<210> SEQ ID NO 537
<211> LENGTH: 50
<212> TYPE: DNA
<213> ORGANISM: Artificial Sequence
<220> FEATURE:
<223> OTHER INFORMATION: Synthetic DNA

<400> SEQUENCE: 537
acctctgacc gtgacgttcg tatgactgcg gacaaatacc aagaactgac 50

<210> SEQ ID NO 538
<211> LENGTH: 50
<212> TYPE: DNA
<213> ORGANISM: Artificial Sequence
<220> FEATURE:
<223> OTHER INFORMATION: Synthetic DNA

<400> SEQUENCE: 538
acctctgacc gtgacgttcg tatgactgcg gacaaatacc aagaactgac 50

<210> SEQ ID NO 539
<211> LENGTH: 50
<212> TYPE: DNA
<213> ORGANISM: Artificial Sequence
<220> FEATURE:
<223> OTHER INFORMATION: Synthetic DNA

<400> SEQUENCE: 539
gcggacaaat accaagaact gaccaaacgt ctgggtatca aatctaccat 50

<210> SEQ ID NO 540
<211> LENGTH: 50
<212> TYPE: DNA
<213> ORGANISM: Artificial Sequence
<220> FEATURE:
<223> OTHER INFORMATION: Synthetic DNA

<400> SEQUENCE: 540
caaacgtctg ggtatcaaat ctaccatgtc ttccgctaac cacccgcaga 50

<210> SEQ ID NO 541
<211> LENGTH: 50
<212> TYPE: DNA
<213> ORGANISM: Artificial Sequence
<220> FEATURE:
<223> OTHER INFORMATION: Synthetic DNA

<400> SEQUENCE: 541

-continued gtcttccgct aaccacccgc agactgatgg tcaatccgag cgtaccattc 50

<210> SEQ ID NO 542
<211> LENGTH: 50
<212> TYPE: DNA
<213> ORGANISM: Artificial Sequence
<220> FEATURE:
<223> OTHER INFORMATION: Synthetic DNA

<400> SEQUENCE: 542
ctgatggtca atccgagcgt accattcaga ccctgaaccg tctcctgcgt 50

<210> SEQ ID NO 543
<211> LENGTH: 50
<212> TYPE: DNA
<213> ORGANISM: Artificial Sequence
<220> FEATURE:
<223> OTHER INFORMATION: Synthetic DNA

<400> SEQUENCE: 543
agaccctgaa ccgtctcctg cgtgcgtatg cgtctaccaa catccagaac 50

<210> SEQ ID NO 544
<211> LENGTH: 50
<212> TYPE: DNA
<213> ORGANISM: Artificial Sequence
<220> FEATURE:
<223> OTHER INFORMATION: Synthetic DNA

<400> SEQUENCE: 544
gcgtatgcgt ctaccaacat ccagaactgg cacgtttacc ttccgcaaat 50

<210> SEQ ID NO 545
<211> LENGTH: 50
<212> TYPE: DNA
<213> ORGANISM: Artificial Sequence
<220> FEATURE:
<223> OTHER INFORMATION: Synthetic DNA

<400> SEQUENCE: 545
tggcacgttt accttccgca aattgaattc gtttacaact ccactccgac 50

<210> SEQ ID NO 546
<211> LENGTH: 50
<212> TYPE: DNA
<213> ORGANISM: Artificial Sequence
<220> FEATURE:
<223> OTHER INFORMATION: Synthetic DNA

<400> SEQUENCE: 546
tggcacgttt accttccgca aattgaattc gtttacaact ccactccgac 50

<210> SEQ ID NO 547
<211> LENGTH: 50
<212> TYPE: DNA
<213> ORGANISM: Artificial Sequence
<220> FEATURE:
<223> OTHER INFORMATION: Synthetic DNA

<400> SEQUENCE: 547
tgaattcgtt tacaactcca ctccgactcg tactctgggt aaatctccgt 50

<210> SEQ ID NO 548
<211> LENGTH: 50
<212> TYPE: DNA
<213> ORGANISM: Artificial Sequence -continued
<220> FEATURE:
<223> OTHER INFORMATION: Synthetic DNA

<400> SEQUENCE: 548
tcgtactctg ggtaaatctc cgttcgaaat cgacctgggt tacctgccaa 50

<210> SEQ ID NO 549
<211> LENGTH: 50
<212> TYPE: DNA
<213> ORGANISM: Artificial Sequence
<220> FEATURE:
<223> OTHER INFORMATION: Synthetic DNA

<400> SEQUENCE: 549
tcgaaatcga cctgggttac ctgccaaaca ctccggcgat caaatctgac 50

<210> SEQ ID NO 550
<211> LENGTH: 50
<212> TYPE: DNA
<213> ORGANISM: Artificial Sequence
<220> FEATURE:
<223> OTHER INFORMATION: Synthetic DNA

<400> SEQUENCE: 550
acactccggc gatcaaatct gacgatgaag ttaacgctcg ttccttcacc 50

<210> SEQ ID NO 551
<211> LENGTH: 50
<212> TYPE: DNA
<213> ORGANISM: Artificial Sequence
<220> FEATURE:
<223> OTHER INFORMATION: Synthetic DNA

<400> SEQUENCE: 551
gatgaagtta acgctcgttc cttcaccgct gttgaactgg ctaaacacct 50

<210> SEQ ID NO 552
<211> LENGTH: 50
<212> TYPE: DNA
<213> ORGANISM: Artificial Sequence
<220> FEATURE:
<223> OTHER INFORMATION: Synthetic DNA

<400> SEQUENCE: 552
gctgttgaac tggctaaaca cctgaaggcg ctgaccatcc agaccaaaga 50

<210> SEQ ID NO 553
<211> LENGTH: 50
<212> TYPE: DNA
<213> ORGANISM: Artificial Sequence
<220> FEATURE:
<223> OTHER INFORMATION: Synthetic DNA

<400> SEQUENCE: 553
gaaggcgctg accatccaga ccaaagaaca gctggaacac gcgcagatcg 50

<210> SEQ ID NO 554
<211> LENGTH: 50
<212> TYPE: DNA
<213> ORGANISM: Artificial Sequence
<220> FEATURE:
<223> OTHER INFORMATION: Synthetic DNA

<400> SEQUENCE: 554
gaaggcgctg accatccaga ccaaagaaca gctggaacac gcgcagatcg 50

-continued

<210> SEQ ID NO 555
<211> LENGTH: 50
<212> TYPE: DNA
<213> ORGANISM: Artificial Sequence
<220> FEATURE:
<223> OTHER INFORMATION: Synthetic DNA

<400> SEQUENCE: 555
acagctggaa cacgcgcaga tcgaaatgga aaccaacaac aaccagcgtc 50

<210> SEQ ID NO 556
<211> LENGTH: 50
<212> TYPE: DNA
<213> ORGANISM: Artificial Sequence
<220> FEATURE:
<223> OTHER INFORMATION: Synthetic DNA

<400> SEQUENCE: 556
aaatggaaac caacaacaac cagcgtcgca aaccactgct gttgaatatt 50

<210> SEQ ID NO 557
<211> LENGTH: 50
<212> TYPE: DNA
<213> ORGANISM: Artificial Sequence
<220> FEATURE:
<223> OTHER INFORMATION: Synthetic DNA

<400> SEQUENCE: 557
gcaaaccact gctgttgaat attggtgatc atgttctggt acaccgtgat 50

<210> SEQ ID NO 558
<211> LENGTH: 50
<212> TYPE: DNA
<213> ORGANISM: Artificial Sequence
<220> FEATURE:
<223> OTHER INFORMATION: Synthetic DNA

<400> SEQUENCE: 558
ggtgatcatg ttctggtaca ccgtgatgcc tacttcaaaa aaggtgcgta 50

<210> SEQ ID NO 559
<211> LENGTH: 50
<212> TYPE: DNA
<213> ORGANISM: Artificial Sequence
<220> FEATURE:
<223> OTHER INFORMATION: Synthetic DNA

<400> SEQUENCE: 559
gcctacttca aaaaaggtgc gtacatgaaa gttcagcaga tctacgttgg 50

<210> SEQ ID NO 560
<211> LENGTH: 50
<212> TYPE: DNA
<213> ORGANISM: Artificial Sequence
<220> FEATURE:
<223> OTHER INFORMATION: Synthetic DNA

<400> SEQUENCE: 560
catgaaagtt cagcagatct acgttggtcc attccgtgtc gttaagaaaa 50

<210> SEQ ID NO 561
<211> LENGTH: 47
<212> TYPE: DNA
<213> ORGANISM: Artificial Sequence
<220> FEATURE:
<223> OTHER INFORMATION: Synthetic DNA -continued

<400> SEQUENCE: 561
tccattccgt gtcgttaaga aaatcaatga caacgcgtat gaactgg 47

<210> SEQ ID NO 562
<211> LENGTH: 47
<212> TYPE: DNA
<213> ORGANISM: Artificial Sequence
<220> FEATURE:
<223> OTHER INFORMATION: Synthetic DNA

<400> SEQUENCE: 562
tccattccgt gtcgttaaga aaatcaatga caacgcgtat gaactgg 47

<210> SEQ ID NO 563
<211> LENGTH: 50
<212> TYPE: DNA
<213> ORGANISM: Artificial Sequence
<220> FEATURE:
<223> OTHER INFORMATION: Synthetic DNA

<400> SEQUENCE: 563
tcaatgacaa cgcgtatgaa ctggacctga actcgcataa gaagaagcac 50

<210> SEQ ID NO 564
<211> LENGTH: 50
<212> TYPE: DNA
<213> ORGANISM: Artificial Sequence
<220> FEATURE:
<223> OTHER INFORMATION: Synthetic DNA

<400> SEQUENCE: 564
acctgaactc gcataagaag aagcaccgtg tgatcaacgt tcagtttctg 50

<210> SEQ ID NO 565
<211> LENGTH: 49
<212> TYPE: DNA
<213> ORGANISM: Artificial Sequence
<220> FEATURE:
<223> OTHER INFORMATION: Synthetic DNA

<400> SEQUENCE: 565
cgtgtgatca acgttcagtt tctgaaaaaa tttgtttacc gtccggatg 49

<210> SEQ ID NO 566
<211> LENGTH: 50
<212> TYPE: DNA
<213> ORGANISM: Artificial Sequence
<220> FEATURE:
<223> OTHER INFORMATION: Synthetic DNA

<400> SEQUENCE: 566
aaaaaatttg tttaccgtcc ggatgcgtac ccgaaaaaca aaccgatctc 50

<210> SEQ ID NO 567
<211> LENGTH: 50
<212> TYPE: DNA
<213> ORGANISM: Artificial Sequence
<220> FEATURE:
<223> OTHER INFORMATION: Synthetic DNA

<400> SEQUENCE: 567
cgtacccgaa aaacaaaccg atctcttcta ccgaacgcat caaacgagct 50

<210> SEQ ID NO 568

-continued

<211> LENGTH: 50
<212> TYPE: DNA
<213> ORGANISM: Artificial Sequence
<220> FEATURE:
<223> OTHER INFORMATION: Synthetic DNA

<400> SEQUENCE: 568
cgtacccgaa aaacaaaccg atctcttcta ccgaacgcat caaacgagct 50

<210> SEQ ID NO 569
<211> LENGTH: 50
<212> TYPE: DNA
<213> ORGANISM: Artificial Sequence
<220> FEATURE:
<223> OTHER INFORMATION: Synthetic DNA

<400> SEQUENCE: 569
ttctaccgaa cgcatcaaac gagctcacga agttaccgcg ctgatcggca 50

<210> SEQ ID NO 570
<211> LENGTH: 50
<212> TYPE: DNA
<213> ORGANISM: Artificial Sequence
<220> FEATURE:
<223> OTHER INFORMATION: Synthetic DNA

<400> SEQUENCE: 570
cacgaagtta ccgcgctgat cggcatcgac accacccaca aaacctatct 50

<210> SEQ ID NO 571
<211> LENGTH: 50
<212> TYPE: DNA
<213> ORGANISM: Artificial Sequence
<220> FEATURE:
<223> OTHER INFORMATION: Synthetic DNA

<400> SEQUENCE: 571
tcgacaccac ccacaaaacc tatctgtgcc acatgcagga cgttgacccg 50

<210> SEQ ID NO 572
<211> LENGTH: 50
<212> TYPE: DNA
<213> ORGANISM: Artificial Sequence
<220> FEATURE:
<223> OTHER INFORMATION: Synthetic DNA

<400> SEQUENCE: 572
gtgccacatg caggacgttg acccgaccct gtccgttgaa tactccgaag 50

<210> SEQ ID NO 573
<211> LENGTH: 50
<212> TYPE: DNA
<213> ORGANISM: Artificial Sequence
<220> FEATURE:
<223> OTHER INFORMATION: Synthetic DNA

<400> SEQUENCE: 573
accctgtccg ttgaatactc cgaagctgaa ttctgccaga tcccagagcg 50

<210> SEQ ID NO 574
<211> LENGTH: 50
<212> TYPE: DNA
<213> ORGANISM: Artificial Sequence
<220> FEATURE:
<223> OTHER INFORMATION: Synthetic DNA

<400> SEQUENCE: 574

-continued accctgtccg ttgaatactc cgaagctgaa ttctgccaga tcccagagcg 50

<210> SEQ ID NO 575
<211> LENGTH: 50
<212> TYPE: DNA
<213> ORGANISM: Artificial Sequence
<220> FEATURE:
<223> OTHER INFORMATION: Synthetic DNA

<400> SEQUENCE: 575
ctgaattctg ccagatccca gagcgtaccc gtcgttctat cctggcgaac 50

<210> SEQ ID NO 576
<211> LENGTH: 50
<212> TYPE: DNA
<213> ORGANISM: Artificial Sequence
<220> FEATURE:
<223> OTHER INFORMATION: Synthetic DNA

<400> SEQUENCE: 576
tacccgtcgt tctatcctgg cgaacttccg tcagctgtac gaaacccaag 50

<210> SEQ ID NO 577
<211> LENGTH: 47
<212> TYPE: DNA
<213> ORGANISM: Artificial Sequence
<220> FEATURE:
<223> OTHER INFORMATION: Synthetic DNA

<400> SEQUENCE: 577
ttccgtcagc tgtacgaaac ccaagacaac cctgaacgtg aagaaga 47

<210> SEQ ID NO 578
<211> LENGTH: 46
<212> TYPE: DNA
<213> ORGANISM: Artificial Sequence
<220> FEATURE:
<223> OTHER INFORMATION: Synthetic DNA

<400> SEQUENCE: 578
acaaccctga acgtgaagaa gatgttgttt cccagaacga aatctg 46

<210> SEQ ID NO 579
<211> LENGTH: 46
<212> TYPE: DNA
<213> ORGANISM: Artificial Sequence
<220> FEATURE:
<223> OTHER INFORMATION: Synthetic DNA

<400> SEQUENCE: 579
tgttgtttcc cagaacgaaa tctgccagta cgacaacacc tctccg 46

<210> SEQ ID NO 580
<211> LENGTH: 22
<212> TYPE: DNA
<213> ORGANISM: Artificial Sequence
<220> FEATURE:
<223> OTHER INFORMATION: Synthetic DNA

<400> SEQUENCE: 580
ccagtacgac aacacctctc cg 22

<210> SEQ ID NO 581
<211> LENGTH: 47
<212> TYPE: DNA

-continued

<213> ORGANISM: Artificial Sequence
<220> FEATURE:
<223> OTHER INFORMATION: Synthetic DNA

<400> SEQUENCE: 581
gaaatctgcc agtacgacaa cacctctccg taataaggat ccaatac 47

<210> SEQ ID NO 582
<211> LENGTH: 46
<212> TYPE: DNA
<213> ORGANISM: Artificial Sequence
<220> FEATURE:
<223> OTHER INFORMATION: Synthetic DNA

<400> SEQUENCE: 582
ctatatctag catatgacca tcaccccgga aacctctcgc ccgatc 46

<210> SEQ ID NO 583
<211> LENGTH: 25
<212> TYPE: DNA
<213> ORGANISM: Artificial Sequence
<220> FEATURE:
<223> OTHER INFORMATION: Synthetic DNA

<400> SEQUENCE: 583
accatcaccc cggaaacctc tcgcc 25

<210> SEQ ID NO 584
<211> LENGTH: 50
<212> TYPE: DNA
<213> ORGANISM: Artificial Sequence
<220> FEATURE:
<223> OTHER INFORMATION: Synthetic DNA

<400> SEQUENCE: 584
gatttccaag attcggtgtc gatcgggcga gaggtttccg gggtgatggt 50

<210> SEQ ID NO 585
<211> LENGTH: 50
<212> TYPE: DNA
<213> ORGANISM: Artificial Sequence
<220> FEATURE:
<223> OTHER INFORMATION: Synthetic DNA

<400> SEQUENCE: 585
cgatcgacac cgaatcttgg aaatcttact acaaatccga cccgctgtgc 50

<210> SEQ ID NO 586
<211> LENGTH: 50
<212> TYPE: DNA
<213> ORGANISM: Artificial Sequence
<220> FEATURE:
<223> OTHER INFORMATION: Synthetic DNA

<400> SEQUENCE: 586
ctttcatgtg gatcagaaca gcagagcaca gcgggtcgga tttgtagtaa 50

<210> SEQ ID NO 587
<211> LENGTH: 49
<212> TYPE: DNA
<213> ORGANISM: Artificial Sequence
<220> FEATURE:
<223> OTHER INFORMATION: Synthetic DNA

<400> SEQUENCE: 587
tctgctgttc tgatccacat gaaagaactg acccagcaca acgttaccc 49

-continued

<210> SEQ ID NO 588
<211> LENGTH: 45
<212> TYPE: DNA
<213> ORGANISM: Artificial Sequence
<220> FEATURE:
<223> OTHER INFORMATION: Synthetic DNA

<400> SEQUENCE: 588
ggaaagcgga catgtcttct ggggtaacgt tgtgctgggt cagtt 45

<210> SEQ ID NO 589
<211> LENGTH: 46
<212> TYPE: DNA
<213> ORGANISM: Artificial Sequence
<220> FEATURE:
<223> OTHER INFORMATION: Synthetic DNA

<400> SEQUENCE: 589
cagaagacat gtccgctttc cgctcctatc agaaaaagct ggaact 46

<210> SEQ ID NO 590
<211> LENGTH: 48
<212> TYPE: DNA
<213> ORGANISM: Artificial Sequence
<220> FEATURE:
<223> OTHER INFORMATION: Synthetic DNA

<400> SEQUENCE: 590
agtttttacg gaaggtctca gacagttcca gctttttctg ataggagc 48

<210> SEQ ID NO 591
<211> LENGTH: 48
<212> TYPE: DNA
<213> ORGANISM: Artificial Sequence
<220> FEATURE:
<223> OTHER INFORMATION: Synthetic DNA

<400> SEQUENCE: 591
gctcctatca gaaaaagctg gaactgtctg agaccttccg taaaaact 48

<210> SEQ ID NO 592
<211> LENGTH: 50
<212> TYPE: DNA
<213> ORGANISM: Artificial Sequence
<220> FEATURE:
<223> OTHER INFORMATION: Synthetic DNA

<400> SEQUENCE: 592
agtagatcat ttcgtcctcc agggagtagt ttttacggaa ggtctcagac 50

<210> SEQ ID NO 593
<211> LENGTH: 50
<212> TYPE: DNA
<213> ORGANISM: Artificial Sequence
<220> FEATURE:
<223> OTHER INFORMATION: Synthetic DNA

<400> SEQUENCE: 593
actccctgga ggacgaaatg atctactacc aagatcgcct ggttgtaccg 50

<210> SEQ ID NO 594
<211> LENGTH: 49
<212> TYPE: DNA
<213> ORGANISM: Artificial Sequence
<220> FEATURE:

-continued

<223> OTHER INFORMATION: Synthetic DNA

<400> SEQUENCE: 594
cgcatgacag cattttgttg tttaatcggt acaaccaggc gatcttggt 49

<210> SEQ ID NO 595
<211> LENGTH: 50
<212> TYPE: DNA
<213> ORGANISM: Artificial Sequence
<220> FEATURE:
<223> OTHER INFORMATION: Synthetic DNA

<400> SEQUENCE: 595
attaaacaac aaaatgctgt catgcgtctg tatcacgatc acactctgtt 50

<210> SEQ ID NO 596
<211> LENGTH: 50
<212> TYPE: DNA
<213> ORGANISM: Artificial Sequence
<220> FEATURE:
<223> OTHER INFORMATION: Synthetic DNA

<400> SEQUENCE: 596
taacggttac gccaaagtga ccaccaaaca gagtgtgatc gtgatacaga 50

<210> SEQ ID NO 597
<211> LENGTH: 50
<212> TYPE: DNA
<213> ORGANISM: Artificial Sequence
<220> FEATURE:
<223> OTHER INFORMATION: Synthetic DNA

<400> SEQUENCE: 597
tggtggtcac tttggcgtaa ccgttaccct ggcgaaaatc tctccgatct 50

<210> SEQ ID NO 598
<211> LENGTH: 50
<212> TYPE: DNA
<213> ORGANISM: Artificial Sequence
<220> FEATURE:
<223> OTHER INFORMATION: Synthetic DNA

<400> SEQUENCE: 598
agagtgctgc agtttcggcc aatagtagat cggagagatt ttcgccaggg 50

<210> SEQ ID NO 599
<211> LENGTH: 50
<212> TYPE: DNA
<213> ORGANISM: Artificial Sequence
<220> FEATURE:
<223> OTHER INFORMATION: Synthetic DNA

<400> SEQUENCE: 599
ccctggcgaa aatctctccg atctactatt ggccgaaact gcagcactct 50

<210> SEQ ID NO 600
<211> LENGTH: 50
<212> TYPE: DNA
<213> ORGANISM: Artificial Sequence
<220> FEATURE:
<223> OTHER INFORMATION: Synthetic DNA

<400> SEQUENCE: 600
gcaggtacgg atgtactgga tgatagagtg ctgcagtttc ggccaatagt 50

-continued

<210> SEQ ID NO 601
<211> LENGTH: 50
<212> TYPE: DNA
<213> ORGANISM: Artificial Sequence
<220> FEATURE:
<223> OTHER INFORMATION: Synthetic DNA

<400> SEQUENCE: 601
atcatccagt acatccgtac ctgcgttcag tgccagctga tcaaatctca 50

<210> SEQ ID NO 602
<211> LENGTH: 50
<212> TYPE: DNA
<213> ORGANISM: Artificial Sequence
<220> FEATURE:
<223> OTHER INFORMATION: Synthetic DNA

<400> SEQUENCE: 602
aggagaccat gcagacgtgg gcggtgagat ttgatcagct ggcactgaac 50

<210> SEQ ID NO 603
<211> LENGTH: 50
<212> TYPE: DNA
<213> ORGANISM: Artificial Sequence
<220> FEATURE:
<223> OTHER INFORMATION: Synthetic DNA

<400> SEQUENCE: 603
ccgcccacgt ctgcatggtc tcctgcaacc gctcccgatc gctgaaggtc 50

<210> SEQ ID NO 604
<211> LENGTH: 50
<212> TYPE: DNA
<213> ORGANISM: Artificial Sequence
<220> FEATURE:
<223> OTHER INFORMATION: Synthetic DNA

<400> SEQUENCE: 604
agtccataga gatgtccagc caacgacctt cagcgatcgg gagcggttgc 50

<210> SEQ ID NO 605
<211> LENGTH: 47
<212> TYPE: DNA
<213> ORGANISM: Artificial Sequence
<220> FEATURE:
<223> OTHER INFORMATION: Synthetic DNA

<400> SEQUENCE: 605
gttggctgga catctctatg gacttcgtta ctggtttgcc gccgacc 47

<210> SEQ ID NO 606
<211> LENGTH: 50
<212> TYPE: DNA
<213> ORGANISM: Artificial Sequence
<220> FEATURE:
<223> OTHER INFORMATION: Synthetic DNA

<400> SEQUENCE: 606
caccaggatc atgttcaggt tgttagaggt cggcggcaaa ccagtaacga 50

<210> SEQ ID NO 607
<211> LENGTH: 50
<212> TYPE: DNA
<213> ORGANISM: Artificial Sequence
<220> FEATURE:
<223> OTHER INFORMATION: Synthetic DNA -continued

<400> SEQUENCE: 607
tcgttactgg tttgccgccg acctctaaca acctgaacat gatcctggtg 50

<210> SEQ ID NO 608
<211> LENGTH: 50
<212> TYPE: DNA
<213> ORGANISM: Artificial Sequence
<220> FEATURE:
<223> OTHER INFORMATION: Synthetic DNA

<400> SEQUENCE: 608
cgtttagaga agcggtccac caccaccagg atcatgttca ggttgttaga 50

<210> SEQ ID NO 609
<211> LENGTH: 50
<212> TYPE: DNA
<213> ORGANISM: Artificial Sequence
<220> FEATURE:
<223> OTHER INFORMATION: Synthetic DNA

<400> SEQUENCE: 609
gtggtggacc gcttctctaa acgtgctcac ttcatcgcta cccgaaaaac 50

<210> SEQ ID NO 610
<211> LENGTH: 50
<212> TYPE: DNA
<213> ORGANISM: Artificial Sequence
<220> FEATURE:
<223> OTHER INFORMATION: Synthetic DNA

<400> SEQUENCE: 610
cgatcagctg agtcgcgtcc agggtttttc gggtagcgat gaagtgagca 50

<210> SEQ ID NO 611
<211> LENGTH: 50
<212> TYPE: DNA
<213> ORGANISM: Artificial Sequence
<220> FEATURE:
<223> OTHER INFORMATION: Synthetic DNA

<400> SEQUENCE: 611
cctggacgcg actcagctga tcgacctgct cttccgttac atcttctctt 50

<210> SEQ ID NO 612
<211> LENGTH: 50
<212> TYPE: DNA
<213> ORGANISM: Artificial Sequence
<220> FEATURE:
<223> OTHER INFORMATION: Synthetic DNA

<400> SEQUENCE: 612
gatggtacgc gggaagccat ggtaagagaa gatgtaacgg aagagcaggt 50

<210> SEQ ID NO 613
<211> LENGTH: 50
<212> TYPE: DNA
<213> ORGANISM: Artificial Sequence
<220> FEATURE:
<223> OTHER INFORMATION: Synthetic DNA

<400> SEQUENCE: 613
accatggctt cccgcgtacc atcacctctg accgtgacgt tcgtatgact 50

<210> SEQ ID NO 614
<211> LENGTH: 50

-continued

<212> TYPE: DNA
<213> ORGANISM: Artificial Sequence
<220> FEATURE:
<223> OTHER INFORMATION: Synthetic DNA

<400> SEQUENCE: 614
gtcagttctt ggtatttgtc cgcagtcata cgaacgtcac ggtcagaggt 50

<210> SEQ ID NO 615
<211> LENGTH: 50
<212> TYPE: DNA
<213> ORGANISM: Artificial Sequence
<220> FEATURE:
<223> OTHER INFORMATION: Synthetic DNA

<400> SEQUENCE: 615
acctctgacc gtgacgttcg tatgactgcg gacaaatacc aagaactgac 50

<210> SEQ ID NO 616
<211> LENGTH: 50
<212> TYPE: DNA
<213> ORGANISM: Artificial Sequence
<220> FEATURE:
<223> OTHER INFORMATION: Synthetic DNA

<400> SEQUENCE: 616
atggtagatt tgatacccag acgtttggtc agttcttggt atttgtccgc 50

<210> SEQ ID NO 617
<211> LENGTH: 50
<212> TYPE: DNA
<213> ORGANISM: Artificial Sequence
<220> FEATURE:
<223> OTHER INFORMATION: Synthetic DNA

<400> SEQUENCE: 617
caaacgtctg ggtatcaaat ctaccatgtc ttccgctaac cacccgcaga 50

<210> SEQ ID NO 618
<211> LENGTH: 50
<212> TYPE: DNA
<213> ORGANISM: Artificial Sequence
<220> FEATURE:
<223> OTHER INFORMATION: Synthetic DNA

<400> SEQUENCE: 618
gaatggtacg ctcggattga ccatcagtct gcgggtggtt agcggaagac 50

<210> SEQ ID NO 619
<211> LENGTH: 50
<212> TYPE: DNA
<213> ORGANISM: Artificial Sequence
<220> FEATURE:
<223> OTHER INFORMATION: Synthetic DNA

<400> SEQUENCE: 619
ctgatggtca atccgagcgt accattcaga ccctgaaccg tctcctgcgt 50

<210> SEQ ID NO 620
<211> LENGTH: 50
<212> TYPE: DNA
<213> ORGANISM: Artificial Sequence
<220> FEATURE:
<223> OTHER INFORMATION: Synthetic DNA

<400> SEQUENCE: 620

-continued gttctggatg ttggtagacg catacgcacg caggagacgg ttcagggtct 50

<210> SEQ ID NO 621
<211> LENGTH: 50
<212> TYPE: DNA
<213> ORGANISM: Artificial Sequence
<220> FEATURE:
<223> OTHER INFORMATION: Synthetic DNA

<400> SEQUENCE: 621
gcgtatgcgt ctaccaacat ccagaactgg cacgtttacc ttccgcaaat 50

<210> SEQ ID NO 622
<211> LENGTH: 50
<212> TYPE: DNA
<213> ORGANISM: Artificial Sequence
<220> FEATURE:
<223> OTHER INFORMATION: Synthetic DNA

<400> SEQUENCE: 622
gtcggagtgg agttgtaaac gaattcaatt tgcggaaggt aaacgtgcca 50

<210> SEQ ID NO 623
<211> LENGTH: 50
<212> TYPE: DNA
<213> ORGANISM: Artificial Sequence
<220> FEATURE:
<223> OTHER INFORMATION: Synthetic DNA

<400> SEQUENCE: 623
tggcacgttt accttccgca aattgaattc gtttacaact ccactccgac 50

<210> SEQ ID NO 624
<211> LENGTH: 50
<212> TYPE: DNA
<213> ORGANISM: Artificial Sequence
<220> FEATURE:
<223> OTHER INFORMATION: Synthetic DNA

<400> SEQUENCE: 624
acggagattt acccagagta cgagtcggag tggagttgta aacgaattca 50

<210> SEQ ID NO 625
<211> LENGTH: 50
<212> TYPE: DNA
<213> ORGANISM: Artificial Sequence
<220> FEATURE:
<223> OTHER INFORMATION: Synthetic DNA

<400> SEQUENCE: 625
tcgtactctg ggtaaatctc cgttcgaaat cgacctgggt tacctgccaa 50

<210> SEQ ID NO 626
<211> LENGTH: 50
<212> TYPE: DNA
<213> ORGANISM: Artificial Sequence
<220> FEATURE:
<223> OTHER INFORMATION: Synthetic DNA

<400> SEQUENCE: 626
gtcagatttg atcgccggag tgtttggcag gtaacccagg tcgatttcga 50

<210> SEQ ID NO 627
<211> LENGTH: 50
<212> TYPE: DNA
<213> ORGANISM: Artificial Sequence -continued
<220> FEATURE:
<223> OTHER INFORMATION: Synthetic DNA

<400> SEQUENCE: 627
acactccggc gatcaaatct gacgatgaag ttaacgctcg ttccttcacc 50

<210> SEQ ID NO 628
<211> LENGTH: 50
<212> TYPE: DNA
<213> ORGANISM: Artificial Sequence
<220> FEATURE:
<223> OTHER INFORMATION: Synthetic DNA

<400> SEQUENCE: 628
aggtgtttag ccagttcaac agcggtgaag gaacgagcgt taacttcatc 50

<210> SEQ ID NO 629
<211> LENGTH: 50
<212> TYPE: DNA
<213> ORGANISM: Artificial Sequence
<220> FEATURE:
<223> OTHER INFORMATION: Synthetic DNA

<400> SEQUENCE: 629
gctgttgaac tggctaaaca cctgaaggcg ctgaccatcc agaccaaaga 50

<210> SEQ ID NO 630
<211> LENGTH: 50
<212> TYPE: DNA
<213> ORGANISM: Artificial Sequence
<220> FEATURE:
<223> OTHER INFORMATION: Synthetic DNA

<400> SEQUENCE: 630
cgatctgcgc gtgttccagc tgttctttgg tctggatggt cagcgccttc 50

<210> SEQ ID NO 631
<211> LENGTH: 50
<212> TYPE: DNA
<213> ORGANISM: Artificial Sequence
<220> FEATURE:
<223> OTHER INFORMATION: Synthetic DNA

<400> SEQUENCE: 631
gaaggcgctg accatccaga ccaaagaaca gctggaacac gcgcagatcg 50

<210> SEQ ID NO 632
<211> LENGTH: 50
<212> TYPE: DNA
<213> ORGANISM: Artificial Sequence
<220> FEATURE:
<223> OTHER INFORMATION: Synthetic DNA

<400> SEQUENCE: 632
gacgctggtt gttgttggtt tccatttcga tctgcgcgtg ttccagctgt 50

<210> SEQ ID NO 633
<211> LENGTH: 50
<212> TYPE: DNA
<213> ORGANISM: Artificial Sequence
<220> FEATURE:
<223> OTHER INFORMATION: Synthetic DNA

<400> SEQUENCE: 633
aaatggaaac caacaacaac cagcgtcgca aaccactgct gttgaatatt 50

-continued

<210> SEQ ID NO 634
<211> LENGTH: 50
<212> TYPE: DNA
<213> ORGANISM: Artificial Sequence
<220> FEATURE:
<223> OTHER INFORMATION: Synthetic DNA

<400> SEQUENCE: 634
atcacggtgt accagaacat gatcaccaat attcaacagc agtggtttgc 50

<210> SEQ ID NO 635
<211> LENGTH: 50
<212> TYPE: DNA
<213> ORGANISM: Artificial Sequence
<220> FEATURE:
<223> OTHER INFORMATION: Synthetic DNA

<400> SEQUENCE: 635
ggtgatcatg ttctggtaca ccgtgatgcc tacttcaaaa aaggtgcgta 50

<210> SEQ ID NO 636
<211> LENGTH: 50
<212> TYPE: DNA
<213> ORGANISM: Artificial Sequence
<220> FEATURE:
<223> OTHER INFORMATION: Synthetic DNA

<400> SEQUENCE: 636
ccaacgtaga tctgctgaac tttcatgtac gcaccttttt tgaagtaggc 50

<210> SEQ ID NO 637
<211> LENGTH: 50
<212> TYPE: DNA
<213> ORGANISM: Artificial Sequence
<220> FEATURE:
<223> OTHER INFORMATION: Synthetic DNA

<400> SEQUENCE: 637
catgaaagtt cagcagatct acgttggtcc attccgtgtc gttaagaaaa 50

<210> SEQ ID NO 638
<211> LENGTH: 47
<212> TYPE: DNA
<213> ORGANISM: Artificial Sequence
<220> FEATURE:
<223> OTHER INFORMATION: Synthetic DNA

<400> SEQUENCE: 638
ccagttcata cgcgttgtca ttgattttct taacgacacg gaatgga 47

<210> SEQ ID NO 639
<211> LENGTH: 47
<212> TYPE: DNA
<213> ORGANISM: Artificial Sequence
<220> FEATURE:
<223> OTHER INFORMATION: Synthetic DNA

<400> SEQUENCE: 639
tccattccgt gtcgttaaga aaatcaatga caacgcgtat gaactgg 47

<210> SEQ ID NO 640
<211> LENGTH: 50
<212> TYPE: DNA
<213> ORGANISM: Artificial Sequence
<220> FEATURE:
<223> OTHER INFORMATION: Synthetic DNA -continued

<400> SEQUENCE: 640
gtgcttcttc ttatgcgagt tcaggtccag ttcatacgcg ttgtcattga 50

<210> SEQ ID NO 641
<211> LENGTH: 50
<212> TYPE: DNA
<213> ORGANISM: Artificial Sequence
<220> FEATURE:
<223> OTHER INFORMATION: Synthetic DNA

<400> SEQUENCE: 641
acctgaactc gcataagaag aagcaccgtg tgatcaacgt tcagtttctg 50

<210> SEQ ID NO 642
<211> LENGTH: 49
<212> TYPE: DNA
<213> ORGANISM: Artificial Sequence
<220> FEATURE:
<223> OTHER INFORMATION: Synthetic DNA

<400> SEQUENCE: 642
catccggacg gtaaacaaat tttttcagaa actgaacgtt gatcacacg 49

<210> SEQ ID NO 643
<211> LENGTH: 50
<212> TYPE: DNA
<213> ORGANISM: Artificial Sequence
<220> FEATURE:
<223> OTHER INFORMATION: Synthetic DNA

<400> SEQUENCE: 643
aaaaaatttg tttaccgtcc ggatgcgtac ccgaaaaaca aaccgatctc 50

<210> SEQ ID NO 644
<211> LENGTH: 50
<212> TYPE: DNA
<213> ORGANISM: Artificial Sequence
<220> FEATURE:
<223> OTHER INFORMATION: Synthetic DNA

<400> SEQUENCE: 644
agctcgtttg atgcgttcgg tagaagagat cggtttgttt ttcgggtacg 50

<210> SEQ ID NO 645
<211> LENGTH: 50
<212> TYPE: DNA
<213> ORGANISM: Artificial Sequence
<220> FEATURE:
<223> OTHER INFORMATION: Synthetic DNA

<400> SEQUENCE: 645
cgtacccgaa aaacaaaccg atctcttcta ccgaacgcat caaacgagct 50

<210> SEQ ID NO 646
<211> LENGTH: 50
<212> TYPE: DNA
<213> ORGANISM: Artificial Sequence
<220> FEATURE:
<223> OTHER INFORMATION: Synthetic DNA

<400> SEQUENCE: 646
tgccgatcag cgcggtaact tcgtgagctc gtttgatgcg ttcggtagaa 50

<210> SEQ ID NO 647

-continued

<211> LENGTH: 50
<212> TYPE: DNA
<213> ORGANISM: Artificial Sequence
<220> FEATURE:
<223> OTHER INFORMATION: Synthetic DNA

<400> SEQUENCE: 647
cacgaagtta ccgcgctgat cggcatcgac accacccaca aaacctatct 50

<210> SEQ ID NO 648
<211> LENGTH: 50
<212> TYPE: DNA
<213> ORGANISM: Artificial Sequence
<220> FEATURE:
<223> OTHER INFORMATION: Synthetic DNA

<400> SEQUENCE: 648
cgggtcaacg tcctgcatgt ggcacagata ggttttgtgg gtggtgtcga 50

<210> SEQ ID NO 649
<211> LENGTH: 50
<212> TYPE: DNA
<213> ORGANISM: Artificial Sequence
<220> FEATURE:
<223> OTHER INFORMATION: Synthetic DNA

<400> SEQUENCE: 649
gtgccacatg caggacgttg acccgaccct gtccgttgaa tactccgaag 50

<210> SEQ ID NO 650
<211> LENGTH: 50
<212> TYPE: DNA
<213> ORGANISM: Artificial Sequence
<220> FEATURE:
<223> OTHER INFORMATION: Synthetic DNA

<400> SEQUENCE: 650
cgctctggga tctggcagaa ttcagcttcg gagtattcaa cggacagggt 50

<210> SEQ ID NO 651
<211> LENGTH: 50
<212> TYPE: DNA
<213> ORGANISM: Artificial Sequence
<220> FEATURE:
<223> OTHER INFORMATION: Synthetic DNA

<400> SEQUENCE: 651
accctgtccg ttgaatactc cgaagctgaa ttctgccaga tcccagagcg 50

<210> SEQ ID NO 652
<211> LENGTH: 50
<212> TYPE: DNA
<213> ORGANISM: Artificial Sequence
<220> FEATURE:
<223> OTHER INFORMATION: Synthetic DNA

<400> SEQUENCE: 652
gttcgccagg atagaacgac gggtacgctc tgggatctgg cagaattcag 50

<210> SEQ ID NO 653
<211> LENGTH: 50
<212> TYPE: DNA
<213> ORGANISM: Artificial Sequence
<220> FEATURE:
<223> OTHER INFORMATION: Synthetic DNA

<400> SEQUENCE: 653

-continued tacccgtcgt tctatcctgg cgaacttccg tcagctgtac gaaacccaag 50

<210> SEQ ID NO 654
<211> LENGTH: 47
<212> TYPE: DNA
<213> ORGANISM: Artificial Sequence
<220> FEATURE:
<223> OTHER INFORMATION: Synthetic DNA

<400> SEQUENCE: 654
tcttcttcac gttcagggtt gtcttgggtt tcgtacagct gacggaa 47

<210> SEQ ID NO 655
<211> LENGTH: 46
<212> TYPE: DNA
<213> ORGANISM: Artificial Sequence
<220> FEATURE:
<223> OTHER INFORMATION: Synthetic DNA

<400> SEQUENCE: 655
acaaccctga acgtgaagaa gatgttgttt cccagaacga aatctg 46

<210> SEQ ID NO 656
<211> LENGTH: 46
<212> TYPE: DNA
<213> ORGANISM: Artificial Sequence
<220> FEATURE:
<223> OTHER INFORMATION: Synthetic DNA

<400> SEQUENCE: 656
cggagaggtg ttgtcgtact ggcagatttc gttctgggaa acaaca 46

<210> SEQ ID NO 657
<211> LENGTH: 22
<212> TYPE: DNA
<213> ORGANISM: Artificial Sequence
<220> FEATURE:
<223> OTHER INFORMATION: Synthetic DNA

<400> SEQUENCE: 657
ccagtacgac aacacctctc cg 22

<210> SEQ ID NO 658
<211> LENGTH: 21
<212> TYPE: DNA
<213> ORGANISM: Artificial Sequence
<220> FEATURE:
<223> OTHER INFORMATION: Synthetic DNA

<400> SEQUENCE: 658
cggagaggtg ttgtcgtact g 21

<210> SEQ ID NO 659
<211> LENGTH: 47
<212> TYPE: DNA
<213> ORGANISM: Artificial Sequence
<220> FEATURE:
<223> OTHER INFORMATION: Synthetic DNA

<400> SEQUENCE: 659
gtattggatc cttattacgg agaggtgttg tcgtactggc agatttc 47